(12) United States Patent  (10) Patent No.: US 7,696,229 B2
Dunn et al.  (45) Date of Patent: Apr. 13, 2010

(54) COMPOUNDS HAVING 5-HT6 RECEPTOR AFFINITY

(75) Inventors: Robert Dunn, Towaco, NJ (US); Truc Minh Nguyen, Des Moines, IA (US); Wenge Xie, Mahwah, NJ (US); Ashok Tehim, Ridgewood, NJ (US)

(73) Assignee: Memory Pharmaceuticals Corporation, Montvale, NJ (US)

( * ) Notice: Subject to any disclaimer, the term of this patent is extended or adjusted under 35 U.S.C. 154(b) by 469 days.

(21) Appl. No.: 11/676,203

(22) Filed: Feb. 16, 2007

(65) Prior Publication Data

US 2008/0039462 A1 Feb. 14, 2008

Related U.S. Application Data

(60) Provisional application No. 60/774,399, filed on Feb. 17, 2006.

(51) Int. Cl.
*C07D 471/02* (2006.01)
*C07D 413/00* (2006.01)
*C07D 401/00* (2006.01)
*A61K 31/497* (2006.01)

(52) U.S. Cl. .................. 514/323; 514/254.09; 546/201; 544/373

(58) Field of Classification Search ................. 544/373; 546/201; 514/323, 254.09
See application file for complete search history.

(56) References Cited

U.S. PATENT DOCUMENTS

| 4,670,447 | A  | 6/1987  | Strupczewski |
| 4,954,503 | A  | 9/1990  | Strupczewski et al. |
| 5,041,445 | A  | 8/1991  | Hrib et al. |
| 5,077,405 | A  | 12/1991 | Strupczewski et al. |
| 5,364,866 | A  | 11/1994 | Strupczewski et al. |
| 5,776,963 | A  | 7/1998  | Strupczewski et al. |
| 6,100,291 | A  | 8/2000  | Slassi et al. |
| 6,133,287 | A  | 10/2000 | Slassi et al. |
| 6,191,141 | B1 | 2/2001  | Edwards et al. |
| 6,251,893 | B1 | 6/2001  | Maddaford et al. |
| 6,255,306 | B1 | 7/2001  | Macor |
| 6,686,374 | B1 | 2/2004  | Edwards et al. |
| 6,767,912 | B2 | 7/2004  | Zhou et al. |
| 6,790,848 | B2 | 9/2004  | Briggs et al. |
| 6,818,639 | B2 | 11/2004 | Sukhwinder et al. |
| 6,897,215 | B1 | 5/2005  | Xin et al. |
| 6,903,112 | B2 | 6/2005  | Zhou et al. |
| 6,916,818 | B2 | 7/2005  | Edwards et al. |
| 6,951,871 | B2 | 10/2005 | Aslanian et al. |
| 7,034,029 | B2 | 4/2006  | Kelly et al. |
| 2002/0115670 | A1 | 8/2002  | Kelly et al. |
| 2002/0165251 | A1 | 11/2002 | Caldirola et al. |
| 2004/0087595 | A1 | 5/2004  | Kelly et al. |
| 2004/0132741 | A1 | 7/2004  | Kelly et al. |
| 2004/0220177 | A1 | 11/2004 | Kath et al. |
| 2004/0242589 | A1 | 12/2004 | Bromidge et al. |
| 2005/0090496 | A1 | 4/2005  | Ahmed et al. |
| 2005/0124603 | A1 | 6/2005  | Zhou et al. |
| 2005/0171118 | A1 | 8/2005  | Beard et al. |
| 2005/0176705 | A1 | 8/2005  | Bromidge |
| 2005/0182072 | A1 | 8/2005  | Cao et al. |
| 2005/0245540 | A1 | 11/2005 | Takeshita et al. |
| 2005/0256106 | A1 | 11/2005 | Caldirola et al. |
| 2006/0069094 | A1 | 3/2006  | Bonhaus et al. |
| 2006/0106012 | A1 | 5/2006  | Sethofer et al. |
| 2006/0116384 | A1 | 6/2006  | Kelly et al. |

FOREIGN PATENT DOCUMENTS

| EP | 0402644 | | 12/1990 |
| EP | 0623618 | | 11/1994 |
| EP | 0812826 | | 12/1997 |
| EP | 0875513 | A1 | 11/1998 |
| JP | 7033744 | | 2/1995 |
| WO | WO 92/13856 | | 8/1992 |
| WO | 9511680 | | 5/1995 |
| WO | 9639397 | | 12/1996 |
| WO | 98/22457 | | 5/1998 |
| WO | 00/17198 | | 3/2000 |
| WO | WO 00/63203 | | 10/2000 |
| WO | 0078716 | | 12/2000 |
| WO | WO 01/12629 | | 2/2001 |
| WO | WO-01/32660 | | 5/2001 |
| WO | WO-02/36562 | | 5/2002 |
| WO | WO 02/051837 | | 7/2002 |

(Continued)

OTHER PUBLICATIONS

Vippagunta et al, "Crystalline Solids" Advanced Drug Delivery Reviews, vol. 48, pp. 3-26 (2001).*

(Continued)

*Primary Examiner*—Kahsay T Habte
(74) *Attorney, Agent, or Firm*—Darby & Darby P.C.; Lydia G. Olson

(57) ABSTRACT

The present disclosure provides compounds having affinity for the 5HT6 receptor which are of the formula (I):

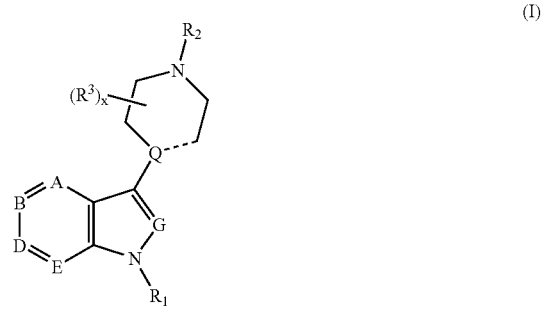

wherein $R^1$-$R^3$ A, B, D, E, G, Q, and x are as defined herein. The disclosure also relates to methods of preparing such compounds, compositions containing such compounds, and methods of use thereof.

30 Claims, No Drawings

FOREIGN PATENT DOCUMENTS

| WO | 02060871 | 8/2002 |
|---|---|---|
| WO | 2004069828 | 8/2004 |
| WO | 2005013974 | 2/2005 |
| WO | 2005014000 | 2/2005 |
| WO | 2005014045 | 2/2005 |
| WO | 2005066126 | 7/2005 |
| WO | WO-2006/101745 | 5/2006 |

OTHER PUBLICATIONS

Gavezzotti, "Are Crystal Structures Predictable?" Accounts of Chemical Research, vol. 27, pp. 309-314 (1994).*

Blier et al. (Biol. Psychiatry 2003; 53: 193-203).*

"Developments In The Treatment Of Parkinson's Disease," Drug and Therapeutics Bulletin, May 1999, 37(5):33, 36-40.

Al-Chalabi, Ammar et al., "Recent Advances in Amyotrophic Lateral Sclerosis," Current Opinion in Neurology, 2000, 13:397-405.

Bartus, Raymond T., "On Neurodegenerative Diseases, Models, and Treatment Strategies: Lessons Learned and Lessons Forgotten a Generation Following the Cholinergic Hypothesis," Experimental Neurology, 2000, 163:495-529.

Bentley, J. C. et al., "5-HT6 Antisense Oligonucleotide I.C.V. Affects Rat Performance in the Water Maze and Feeding," Journal of Psychopharmacology, Supplement to vol. 11 No. 3, 1997, p. A64, abstract 255.

Bentley, Jane C. et al., "Investigation of Stretching Behaviour Induced by the Selective 5-HT6 Receptor Antagonist, Ro 04-6790, in Rats," British Journal of Pharmacology, 1999, 126:1537-1542.

Lindner, Mark D., "Reliability, Distribution, and Validity of Age-Related Cognitive Deficits in the Morris Water Maze," Neurobiology of Learning and Memory, 1997, 68:203-220.

Miller, Vaughn P. et al., "Flourometric High-Throughput Screening for Inhibitors of Cytochrome P450," Annals New York Academy of Sciences, 2000, 919:26-32.

Robichaud, Albert J. et al., "Recent Advances in Selective Serotonin Receptor Modulation," Annual Reports in Medicinal Chemistry, 2000, chapter 2, 35: title page, bibliography page, pp. 11-20.

Rogers, D. C. et al., "5-HT6 Receptor Antagonists Enhance Retention of a Water Maze Task in the Rat," Psychopharmacology, 2001, 158:114-119.

Rowland, Lewis P. et al., "Amyotrophic Lateral Sclerosis," The New England Journal of Medicine, May 2001, 344 (22):1688-1700.

Shannon, Kathleen M., "Chorea," Current Opinion in Neurology, Aug. 1996, 9(4): bibliography page, pp. 298-302.

Sleight, Andrew J. et al., "The 5-ht6 Receptor: A New Target for the Treatment of CNS Disorders," Serotonin: ID Research Alert, 1997, 2(3):115-118.

Cole, D.C. et al. Biorg. Med. Chem. Lett. 15 (2005) 379-383.

Cole, Derek C. et al. J. Med. Chem. 48 (2005) 353-356.

Isaac, Methvin et al. Biorg. Med. Chem. Lett. 10 (2000) 1719-1721.

Hoyer, D. et al., Neuropharmacology, 1997, 36(4/5):419-428.

Ward, R.P. et al., Neuroscience, 1995, 64(4):1105-1111.

Roth, Bryan L. et al., J. Pharmacol. Exp. Ther., 1994, 268(3):1403-1410.

Bourson, Anne et al., J. Pharmacol. Exp. Ther., 1995, 274(1):173-180.

Monsma, Jr., Frederick J. et al., Mol. Pharmacol., 1993, 43, 320-327.

Sleight, Andrew J. et al., Serotonin ID Research Alert, 1997, 2(3), 115-118.

Bentley, Jane C. et al., Brit. Journal of Pharmacology, 1999, 126:1537-1542.

Bentley, J.C. et al., J. Psychopharmacol Suppl. A64, 1997, p. 255.

\* cited by examiner

COMPOUNDS HAVING 5-HT6 RECEPTOR AFFINITY

This application claims priority to U.S. Provisional Application 60/774,399 which was filed Feb. 17, 2006, and is hereby incorporated by reference in its entirety.

FIELD OF THE INVENTION

The present invention relates generally to the field of serotonin 5-HT6 affinity. More specifically, this invention relates to novel compounds having affinity for the 5-HT6 receptor, in particular to compounds having selective 5-HT6 affinity, methods of preparing such compounds, compositions containing such compounds, and methods of use thereof.

BACKGROUND OF THE INVENTION

The human 5-hydroxytryptamine-6 (5HT6) receptor, one of the most recently cloned serotonergic receptors, is a 440-amino acid polypeptide with seven transmembrane spanning domains typical of the G-protein-coupled receptors. It is one of the 14 receptors that mediate the effects of the neurotransmitter 5-hydroxytryptamine (5-HT, serotonin) (Hoyer et al., *Neuropharmacology*, 1997, 36:419). Within the transmembrane region, the human 5HT6 receptor shows about 30-40% homology to other human 5-HT receptors and is found to be positively coupled to adenylyl cyclase.

The prominent localization of 5HT6 receptor mRNA in the nucleus accumbens, striatum, olfactory tubercle, substantia nigra, and hippocampus of the brain (Ward et al., *Neuroscience*, 1995, 64:1105) together with its high affinity for several therapeutically important antipsychotics and antidepressants, suggest a possible role for this receptor in the treatment of schizophrenia and depression. In fact, the prototypic atypical antipsychotic agent clozapine exhibits greater affinity for the 5HT6 receptor than for any other receptor subtype (Monsma et al., *J. Pharmacol. Exp. Ther.*, 1994, 268:1403).

Although the 5HT6 receptor has a distinct pharmacological profile, in vivo investigation of receptor function has been hindered by the lack of selective agonists and antagonists. Recent experiments demonstrated that chronic intracerebroventricular treatment with an antisense oligonucleotide, directed at 5HT6 receptor mRNA, elicited a behavioral syndrome in rats consisting of yawning, stretching, and chewing. This syndrome in the antisense-treated rats was dose-dependently antagonized by atropine (a muscarinic antagonist), implicating 5HT6 receptor in the control of cholinergic neurotransmission. Therefore, 5HT6 receptor antagonists may be useful for the treatment of memory dysfunction (Bourson et al., *J. Pharmacol. Exp. Ther.*, 1995, 274:173), and to treat other central nervous system (CNS) disorders.

The high affinity of a number of antipsychotic agents for the 5-HT6 receptor, in addition to its mRNA localization in striatum, olfactory tubercle and nucleus accumbens suggests that some of the clinical actions of these compounds may be mediated through this receptor. Compounds which interact with, stimulate, or inhibit the 5-HT6 receptor are commonly referred to as 5-HT6 ligands. In particular, 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, migraine, Alzheimer's disease (enhancement of cognitive memory), sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, schizophrenia, bipolar disorder, and also disorders associated with spinal trauma and/or head injury such as hydrocephalus. Such compounds are also expected to be of use in the treatment of certain gastrointestinal (GI) disorders such as functional bowel disorder and irritable bowel syndrome (See for ex. B. L. Roth et al., *J. Pharmacol. Exp. Ther.*, 1994, 268, pages 1403-14120, D. R. Sibley et al., *Mol. Pharmacol.*, 1993, 43, 320-327, A. J. Sleight et al., *Neurotransmission*, 1995, 11, 1-5, and A. J. Sleight et al. *Serotonin ID Research Alert*, 1997, 2 (3), 115-8). Furthermore, the effect of 5-HT6 antagonist and 5-HT6 antisense oligonucleotides to reduce food intake in rats has been reported (*Br. J. Pharmac.*, 1999 Suppl. 126, page 66 and *J. Psychopharmacol Suppl.* A64, 1997, page 255).

Therefore, it is an object of this invention to provide compounds which are useful as therapeutic agents in the treatment of a variety of central nervous system disorders related to or affected by the 5-HT6 receptor.

It is another object of this invention to provide therapeutic methods and pharmaceutical compositions useful for the treatment of central nervous system disorders related to or affected by the 5-HT6 receptor.

The following patents and publications also provide relevant background to the present invention. All references cited below are incorporated herein by reference in their entirety and to the same extent as if each reference was individually incorporated by reference. U.S. Pat. Nos. 6,100,291, 6,133,287, 6,191,141, 6,251,893, 6,686,374, 6,767,912, 6,897,215, 6,903,112, and 6,916,818; Published U.S. Application Nos. 2005/0124603, and 2005/0171118.

SUMMARY OF THE INVENTION

The present invention relates to novel compounds that have affinity, preferably selectively, for the serotonin 5-HT$_6$ receptor, methods of use thereof, and the synthesis thereof.

Still further, the present invention provides methods for synthesizing compounds with such activity and selectivity, as well as methods of and corresponding pharmaceutical compositions for treating a disorder (e.g. a mood disorder and/or a cognitive disorder) in a patient, wherein the disorder is related to or affected by the 5HT6 receptor.

DETAILED DESCRIPTION OF THE INVENTION

The present invention includes compounds of formula I:

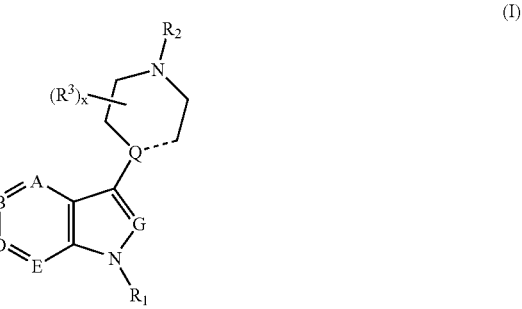

wherein
A, B, D, E and G, are each independently CH, CR$^4$ or N;
----- represents a single bond or a double bond;

Q is C when ---- is a double bond, and Q is CH or N when ----- is a single bond;
x is 0, 1, 2, 3, or 4;
$R^1$ is $SO_2Ar$, wherein
Ar is selected from formulas (a)-(r):

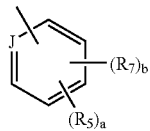
(a)

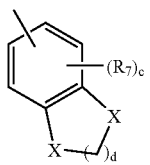
(b)

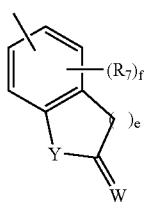
(c)

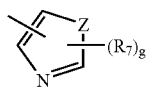
(d)

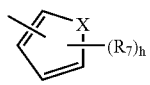
(e)

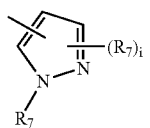
(f)

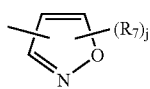
(g)

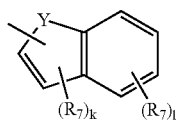
(h)

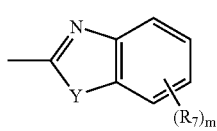
(i)

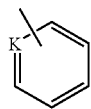
(j)

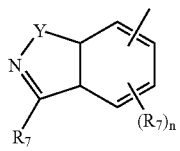
(k)

-continued

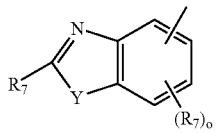
(l)

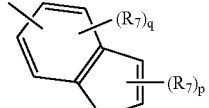
(m)

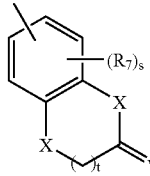
(n)

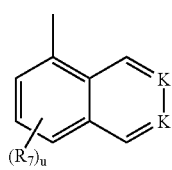
(o)

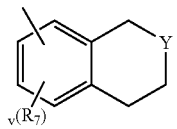
(p)

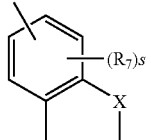
(q)

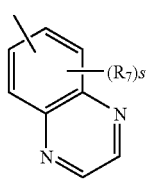
(r)

wherein
J is $CR^7$ (e.g., CH) or N;
K is, in each instance independently, CH or N;
W is O, S, or is absent;
X is, in each instance independently, O or $NR^7$;
Y is O, N7 or S;
Z is S or $NR^7$;
a is 1, 2, 3, 4 or 5;
b, l, m and v are independently 0, 1, 2, 3 or 4;
c, f, h, n, o, q, s, and u are independently 0, 1, 2 or 3;
d and e are independently 1, 2 or 3;
g, i, j, and p are independently 0, 1 or 2;
k and t are 0 or 1;
$R^2$ is H or alkyl having 1 to 8, preferably 1 to 4 carbon atoms (e.g., $CH_3$), cycloalkyl having 3 to 12, preferably 3 to 8 carbon atoms, or cycloalkylalkyl having 4 to 12, preferably 4 to 8 carbon atoms, each of which is branched or unbranched and each of which is unsubstituted or substituted one or more times with halogen, $C_{1-4}$-alkyl, $C_{1-4}$-alkoxy, oxo, or any combination thereof;

$R^3$ is H or alkyl having 1 to 8, preferably 1 to 4 carbon atoms, which is unsubstituted or substituted one or more times by halogen, $C_{1-4}$-alkyl, $C_{1-4}$-alkoxy, oxo, or any combination thereof;

$R^4$ is halogen (e.g., F), nitro,
alkyl having 1 to 8, preferably 1 to 4 carbon atoms, cycloalkyl having 3 to 12, preferably 3 to 8 carbon atoms, or cycloalkylalkyl having 4 to 12, preferably 4 to 8 carbon atoms, each of which is branched or unbranched and which is unsubstituted or substituted one or more times with halogen, $C_{1-4}$-alkyl, $C_{1-4}$-alkoxy, oxo, or any combination thereof (e.g., $CHF_2$, or $CF_3$),
an alkoxy having 1 to 8, preferably 1 to 4 carbon atoms, or
a heterocyclic group, which is saturated, partially saturated or unsaturated, having 5 to 10 ring atoms in which at least 1 ring atom is an N, O or S atom, which is unsubstituted or substituted one or more times by halogen, hydroxy, $C_{5-7}$-aryl, $C_{1-4}$-alkyl, $C_{1-4}$-alkoxy, cyano, halogenated $C_{1-4}$-alkyl (e.g., trifluoromethyl), nitro, or any combination thereof (e.g., substituted or unsubstituted morpholinyl, substituted or unsubstituted pyrrolyl, substituted or unsubstituted pyrrolidinyl, substituted or unsubstituted piperidinyl, substituted or unsubstituted pyridyl), $R^5$ is amino ($NH_2$), $C_{1-4}$-alkylamino, $C_{1-4}$-dialkylamino (e.g., $NMe_2$), or $NR^6C(O)R^8$ (e.g., —$NHC(O)CH_3$, or —$N(CH_3)C(O)CH_3$)),
a heterocyclic group, which is saturated, partially saturated or unsaturated, having 5 to 10 ring atoms in which at least 1 ring atom is an N, O or S atom, which is unsubstituted or substituted one or more times by halogen, hydroxy, $C_{5-7}$-aryl, $C_{1-4}$-alkyl, $C_{1-4}$-alkoxy, cyano, halogenated $C_{1-4}$-alkyl (e.g., trifluoromethyl), nitro, or any combination thereof (e.g., substituted or unsubstituted morpholinyl, substituted or unsubstituted pyrimidinyl, substituted or unsubstituted pyrrolidinyl), or
—O—Ar', wherein Ar' is an aryl, $R^6$ is H or alkyl having 1 to 8, preferably 1 to 4 carbon atoms, which is branched or unbranched and which is unsubstituted or substituted one or more times with halogen, $C_{1-4}$-alkyl, $C_{1-4}$-alkoxy, oxo, or any combination thereof;

$R^7$ is, in each case, independently
H, halogen (e.g., F, Cl, Br), $C(O)R^8$ (e.g., $COCH_3$), $CO_2R^8$ (e.g., $CO_2CH_3$), $NR^6COR^8$ (e.g., $NHCOCH_3$),
alkyl having 1 to 12, preferably 1 to 8 carbon atoms, which is branched or unbranched and which is unsubstituted or substituted one or more times by halogen, hydroxy, cyano, $C_{1-4}$-alkoxy, oxo or any combination thereof (e.g., $CH_3$, $CH_2CH_3$, $CHF_2$, $CF_3$, etc.), and wherein optionally one or more —$CH_2CH_2$— groups is replaced in each case by —CH=CH— or —C≡C—,
alkoxy having 1 to 8, preferably 1 to 4 carbon atoms, which is branched or unbranched and which is unsubstituted or substituted one or more times by halogen (e.g., $OCHF_2$, or $OCF_3$),
cycloalkyl having 3 to 10, preferably 3 to 8 carbon atoms, which is unsubstituted or substituted one or more times by halogen, hydroxy, oxo, cyano, $C_{1-4}$-alkyl, $C_{1-4}$-alkoxy, or any combination thereof (e.g., cyclopentyl),
cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, $C_{1-4}$-alkyl, $C_{1-4}$-alkoxy or any combination thereof (e.g., cyclopentylmethyl or cyclopropylmethyl), aryl having 6 to 14 carbon atoms, which is unsubstituted or substituted one or more times by halogen, $CF_3$, $OCF_3$, $C_{1-4}$-alkyl, hydroxy, $C_{1-4}$-alkoxy, nitro, methylenedioxy, ethylenedioxy, cyano, or any combination thereof (e.g., substituted or unsubstituted phenyl, or substituted or unsubstituted pyridinyl.), arylalkyl in which the aryl portion has 6 to 14 carbon atoms and the alkyl portion, which is branched or unbranched, has 1 to 5 carbon atoms, wherein the arylalkyl radical is unsubstituted, substituted in the aryl portion one or more times by halogen, $CF_3$, $OCF_3$, $C_{1-4}$-alkyl, hydroxy, $C_{1-4}$-alkoxy, nitro, cyano, methylenedioxy, ethylenedioxy, or any combination thereof, and/or substituted in the alkyl portion one or more times by halogen, oxo, hydroxy, cyano, or any combination thereof, and wherein in the alkyl portion one or more —$CH_2CH_2$— groups are each optionally replaced by —CH=CH— or —C≡C—, and one or more —$CH_2$— groups are each optionally replaced by —O— or —NH— (e.g., phenylethyl, phenylpropyl, phenylbutyl, methoxyphenylethyl, methoxyphenylpropyl, chlorophenylethyl, chlorophenylpropyl, phenylethenyl, phenoxyethyl, phenoxybutyl, chlorophenoxyethyl, or chlorophenylaminoethyl.), a heterocyclic group, which is saturated, partially saturated or unsaturated, having 5 to 10 ring atoms in which at least 1 ring atom is an N, O or S atom, which is unsubstituted or substituted one or more times by halogen, hydroxy, $C_{5-7}$-aryl, $C_{1-4}$-alkyl, $C_{1-4}$-alkoxy, cyano, trifluoromethyl, nitro, oxo, or any combination thereof (e.g., substituted or unsubstituted morpholinyl), or a heterocycle-alkyl group, wherein the heterocyclic portion is saturated, partially saturated or unsaturated, and has 5 to 10 ring atoms in which at least 1 ring atom is an N, O or S atom, and the alkyl portion is branched or unbranched and has 1 to 5 carbon atoms, the heterocycle-alkyl group is unsubstituted, substituted one or more times in the heterocyclic portion by halogen, $OCF_3$, hydroxy, $C_{5-7}$-aryl, $C_{1-4}$-alkyl, $C_{1-4}$-alkoxy, cyano, trifluoromethyl, nitro, oxo, or any combination thereof, and/or substituted in the alkyl portion one or more times by halogen, oxo, hydroxy, cyano, or any combination thereof, and wherein in the alkyl portion one or more —$CH_2CH_2$— groups are each optionally replaced by —CH=CH— or —C≡C—, and one or more —$CH_2$— groups are each optionally replaced by —O— or —NH—;

$R^8$ is in each instance, independently, H or alkyl having 1 to 8, carbon atoms, preferably 1 to 4 carbon atoms, which is branched or unbranched and which is unsubstituted or substituted one or more times by halogen (e.g., $CH_3$, $CH_2CH_3$, $CHF_2$, or $CF_3$);

and pharmaceutically acceptable salts or solvates (e.g., hydrates) thereof, or solvates of pharmaceutically acceptable salts thereof;

with the following provisos:

(i) when Ar is represented by formula 0) and G is CH or $CR^4$, then at least one of A, B, D, or E represents $CR^4$ in which $R^4$ is other than H, halogen, alkyl, halogenated alkyl, or alkoxy;

when Ar is represented by formula 0) and G is N, then at least one of A, B, D, or E represents CR$^4$ in which R$^4$ is other than H, halogen, alkyl, halogenated alkyl, alkoxy, —OH, —NH$_2$, or NO$_2$;

(ii) when A, B, D, E and G are CH, and Ar is represented by formula (b), and each X is O, then d is 3;

(iii) when one of A, B, D, or E represents N and the rest are CH, G is CH, and Ar is represented by one of formulas (d)-(i), then at least one R$^7$ substituent on said formula (d)-(i) is other than H, halogen, hydroxyl, alkyl, alkoxy, halogenated alkyl, halogenated alkoxy;

(iv) when G is N and A, B, and D are CH or CR$^4$, then:
  (1) R$_2$ is alkyl having 1 to 8 carbon atoms,
  (2) Q is N,
  (3) Ar is selected from formulas (d)-(g) (preferably formula (d)), or
  (4) a combination of at least two of (1)-(3) (preferably a combination of (1) and (3));

(v) when Ar is represented by the formula (o), one K is N and the other K is CH;

(vi) said compound is not:
1-[(4-aminophenyl)sulfonyl]-5-nitro-3-(1,2,3,6-tetrahydro-4-pyridinyl)-1H indole,
1-[(4-aminophenyl)sulfonyl]-5-bromo-3-(1,2,3,6-tetrahydro-4-pyridinyl)-1H indole,
1-[(4-aminophenyl)sulfonyl]-5-fluoro-3-(1,2,3,6-tetrahydro-4-pyridinyl)-1H indole,
1-[(4-aminophenyl)sulfonyl]-6-chloro-3-(1,2,3,6-tetrahydro-4-pyridinyl)-1H indole,
1-[(4-aminophenyl)sulfonyl]-6-nitro-3-(1,2,3,6-tetrahydro-4-pyridinyl)-1H indole,
1-[(4-aminophenyl)sulfonyl]-3-(1,2,3,6-tetrahydro-4-pyridinyl)-1H indole,
5-(4-methyl-2-thiazolyl)-1-(phenylsulfonyl)-3-(1,2,3,6-tetrahydro-4-pyridinyl)-1H indole,
1-[(4-aminophenyl)sulfonyl]-5-fluoro-3-(4-piperidinyl)-1H indole,
1-[(4-aminophenyl)sulfonyl]-6-chloro-3-(4-piperidinyl)-1H indole, or
3,6-dihydro-4-[5(4-methyl-2-thiazolyl)-1-(phenylsulfonyl)-1H-indol-3-yl)-1,1-dimethylethylester;

or a pharmaceutically acceptable salt thereof, or a solvate thereof, or a solvate of a pharmaceutically acceptable salt thereof.

In one embodiment of the present invention, the invention includes compounds of formula I:

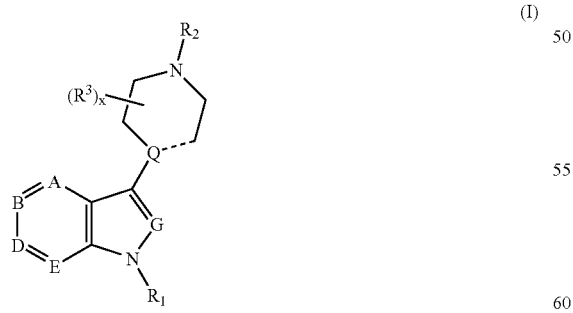

wherein
A, B, D, E and G, are each independently CH, CR$^4$ or N;
----- represents a single bond or a double bond;
Q is C when ---- is a double bond, and Q is CH when ----- is a single bond;

x is 0, 1, 2, 3, or 4;
R$^1$ is SO$_2$Ar, wherein
Ar is selected from formulas (a)-(n):

 (a)

 (b)

 (c)

 (d)

 (e)

 (f)

 (g)

 (h)

 (i)

 (j)

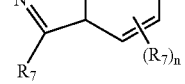 (k)

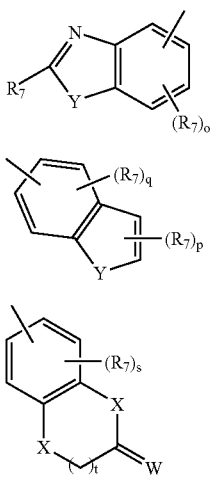

wherein
J is CR⁷ (e.g., CH) or N;
K is CH or N;
W is O, S, or is absent;
X is O or NR⁷;
Y is O, NR⁷ or S;
Z is S or NR⁷;
a is 1, 2, 3, 4 or 5;
b, l and m are independently 0, 1, 2, 3 or 4;
c, f, h, n, o, q and s are independently 0, 1, 2 or 3;
d and e are independently 1, 2 or 3;
g, i, j, and p are independently 0, 1 or 2;
k and t are 0 or 1;
R² is H or alkyl having 1 to 8, preferably 1 to 4 carbon atoms (e.g., CH₃), cycloalkyl having 3 to 12, preferably 3 to 8 carbon atoms, or cycloalkylalkyl having 4 to 12, preferably 4 to 8 carbon atoms, each of which is branched or unbranched and each of which is unsubstituted or substituted one or more times with halogen, C₁₋₄-alkyl, C₁₋₄-alkoxy, oxo, or combinations thereof;
R³ is H or alkyl having 1 to 8, preferably 1 to 4 carbon atoms, which is unsubstituted or substituted one or more times by halogen, C₁₋₄-alkyl, C₁₋₄-alkoxy, oxo, or combinations thereof;
R⁴ is halogen (e.g., F), nitro,
  alkyl having 1 to 8, preferably 1 to 4 carbon atoms, cycloalkyl having 3 to 12, preferably 3 to 8 carbon atoms, or cycloalkylalkyl having 4 to 12, preferably 4 to 8 carbon atoms, each of which is branched or unbranched and which is unsubstituted or substituted one or more times with halogen, C₁₋₄-alkyl, C₁₋₄-alkoxy, oxo, or combinations thereof (e.g., CHF₂, CF₃), or
  a heterocyclic group, which is saturated, partially saturated or unsaturated, having 5 to 10 ring atoms in which at least 1 ring atom is an N, O or S atom, which is unsubstituted or substituted one or more times by halogen, hydroxy, aryl, alkyl, alkoxy, cyano, halogenated alkyl (e.g., trifluoromethyl), nitro, or combinations thereof (e.g., substituted or unsubstituted morpholinyl, substituted or unsubstituted pyrrolyl, substituted or unsubstituted pyrrolidinyl, substituted or unsubstituted piperidinyl, substituted or unsubstituted pyridyl), R⁵ is amino (NH₂), alkylamino, dialkylamino (e.g., NMe₂), NR⁶C(O)R⁸ (e.g., —NHC(O)CH₃, —N(CH₃)C(O)CH₃)) or
  a heterocyclic group, which is saturated, partially saturated or unsaturated, having 5 to 10 ring atoms in which at least 1 ring atom is an N, O or S atom, which is unsubstituted or substituted one or more times by halogen, hydroxy, aryl, alkyl, alkoxy, cyano, halogenated alkyl (e.g., trifluoromethyl), nitro, or combinations thereof (e.g., substituted or unsubstituted morpholinyl, substituted or unsubstituted pyrimidinyl, substituted or unsubstituted pyrrolidinyl),
R⁶ is H or alkyl having 1 to 8, preferably 1 to 4 carbon atoms, which is branched or unbranched and which is unsubstituted or substituted one or more times with halogen, C₁₋₄-alkyl, C₁₋₄-alkoxy, oxo, or combinations thereof;
R⁷ is, in each case, independently
  H, halogen (e.g., F, Cl, Br), C(O)R⁸ (e.g., COCH₃), CO₂R⁸ (e.g., CO₂CH₃), NR⁶COR⁸ (e.g., NHCOCH₃),
  alkyl having 1 to 12, preferably 1 to 8 carbon atoms, which is branched or unbranched and which is unsubstituted or substituted one or more times by halogen, hydroxy, cyano, C₁₋₄-alkoxy, oxo or combinations thereof, and wherein optionally one or more —CH₂CH₂— groups is replaced in each case by —CH=CH— or —C≡C— (e.g., CH₃, CH₂CH₃, CHF₂, CF₃, etc.),
  alkoxy having 1 to 8, preferably 1 to 4 carbon atoms, which is branched or unbranched and which is unsubstituted or substituted one or more times by halogen (e.g., OCHF₂, OCF₃),
  cycloalkyl having 3 to 10, preferably 3 to 8 carbon atoms, which is unsubstituted or substituted one or more times by halogen, hydroxy, oxo, cyano, alkyl having 1 to 4 carbon atoms, alkoxy having 1 to 4 carbon atoms, or combinations thereof (e.g., cyclopentyl),
  cycloalkylalkyl having 4 to 16, preferably 4 to 12 carbon atoms, which is unsubstituted or substituted in the cycloalkyl portion and/or the alkyl portion one or more times by halogen, oxo, cyano, hydroxy, C₁₋₄-alkyl, C₁₋₄-alkoxy or combinations thereof (e.g., cyclopentylmethyl, cyclopropylmethyl, etc.),
  aryl having 6 to 14 carbon atoms, which is unsubstituted or substituted one or more times by halogen, CF₃, OCF₃, alkyl, hydroxy, alkoxy, nitro, methylenedioxy, ethylenedioxy, cyano, or combinations thereof (e.g., substituted or unsubstituted phenyl, substituted or unsubstituted pyridinyl, etc.),
  arylalkyl in which the aryl portion has 6 to 14 carbon atoms and the alkyl portion, which is branched or unbranched, has 1 to 5 carbon atoms, wherein the arylalkyl radical is unsubstituted, substituted in the aryl portion one or more times by halogen, CF₃, OCF₃, alkyl, hydroxy, alkoxy, nitro, cyano, methylenedioxy, ethylenedioxy, or combinations thereof, and/or substituted in the alkyl portion one or more times by halogen, oxo, hydroxy, cyano, or combinations thereof, and wherein in the alkyl portion one or more —CH₂CH₂— groups are each optionally replaced by —CH=CH— or —C≡C—, and one or more —CH₂— groups are each optionally replaced by —O— or —NH— (e.g., phenylethyl, phenylpropyl, phenylbutyl, methoxyphenylethyl, methoxyphenylpropyl, chlorophenylethyl, chlorophenylpropyl, phenylethenyl, phenoxyethyl, phenoxybutyl, chlorophenoxyethyl, chlorophenylaminoethyl, etc.), a heterocyclic group, which is saturated, partially saturated or unsaturated, having 5 to 10 ring atoms in which at least 1 ring atom is an N, O or S atom, which is unsubstituted or substituted one or more times by halogen, hydroxy, aryl, alkyl, alkoxy, cyano, trifluoromethyl, nitro, oxo, or combinations thereof (e.g., substituted or unsubstituted morpholinyl), or a heterocycle-alkyl group, wherein the heterocyclic portion is saturated, partially saturated or unsaturated, and has 5 to 10 ring atoms in which at least 1 ring atom is an N, O or S atom, and the alkyl portion is branched or unbranched and has 1 to 5 carbon atoms, the heterocycle-alkyl group is unsubstituted, substituted one or more times in the heterocyclic portion by halogen, $OCF_3$, hydroxy, aryl, alkyl, alkoxy, cyano, trifluoromethyl, nitro, oxo, or combinations thereof, and/or substituted in the alkyl portion one or more times by halogen, oxo, hydroxy, cyano, or combinations thereof, and wherein in the alkyl portion one or more —$CH_2CH_2$— groups are each optionally replaced by —CH=CH— or —C≡C—, and one or more —$CH_2$— groups are each optionally replaced by —O— or —NH—;

$R^8$ is in each case, independently, H or alkyl having 1 to 8, carbon atoms, preferably 1 to 4 carbon atoms, which is branched or unbranched and which is unsubstituted or substituted one or more times by halogen (e.g., $CH_3$, $CH_2CH_3$, $CHF_2$, $CF_3$, etc.);

and pharmaceutically acceptable salts or solvates (e.g., hydrates) thereof, or solvates of pharmaceutically acceptable salts thereof;

with the following provisos:

(i) when Ar is represented by formula (j), then at least one of A, B, D, or E represents $CR^4$ in which $R^4$ is other than H, halogen, alkyl, or halogenated alkyl;

(ii) when A, B, D, E and G are CH, and Ar is represented by formula (b), and each X is O, then d is 3;

(iii) when one of A, B, D, or E represents N and the rest are CH, G is CH, and Ar is represented by one of formulas (d)-(i), then at least one $R^7$ substituent on said formula (d)-(i) is other than H, halogen, hydroxyl, alkyl, alkoxy, halogenated alkyl, halogenated alkoxy;

(iv) when G is N and A, B, and D are CH or $CR^4$, then:
 (a) $R_2$ is alkyl having 1 to 8 carbon atoms,
 (b) Q is N,
 (c) Ar is selected from formulas (d)-(g) (preferably formula (d)), or
 (d) a combination of at least two of (a)-(c) (preferably a combination of (a) and (c);

(v) said compound is not:
1-[(4-aminophenyl)sulfonyl]-5-nitro-3-(1,2,3,6-tetrahydro-4-pyridinyl)-1H indole,
1-[(4-aminophenyl)sulfonyl]-5-bromo-3-(1,2,3,6-tetrahydro-4-pyridinyl)-1H indole,
1-[(4-aminophenyl)sulfonyl]-5-fluoro-3-(1,2,3,6-tetrahydro-4-pyridinyl)-1H indole,
1-[(4-aminophenyl)sulfonyl]-6-chloro-3-(1,2,3,6-tetrahydro-4-pyridinyl)-1H indole,
1-[(4-aminophenyl)sulfonyl]-6-nitro-3-(1,2,3,6-tetrahydro-4-pyridinyl)-1H indole,
1-[(4-aminophenyl)sulfonyl]-3-(1,2,3,6-tetrahydro-4-pyridinyl)-1H indole,
5-(4-methyl-2-thiazolyl)-1-phenylsulfonyl-3-(1,2,3,6-tetrahydro-4-pyridinyl)-1H indole,
1-[(4-aminophenyl)sulfonyl]-5-fluoro-3-(4-piperidinyl)-1H indole,
1-[(4-aminophenyl)sulfonyl]-6-chloro-3-(4-piperidinyl)-1H indole, or
3,6-dihydro-4-[5 (4-methyl-2-thiazolyl)-1-(phenylsulfonyl)-1H-indol-3-yl)-1,1-dimethylethylester;

or a pharmaceutically acceptable salt thereof, or a solvate thereof, or a solvate of a pharmaceutically acceptable salt thereof.

According to a further embodiment, the compound of formula (I) is represented by subformulas (Ia)-(Ix):

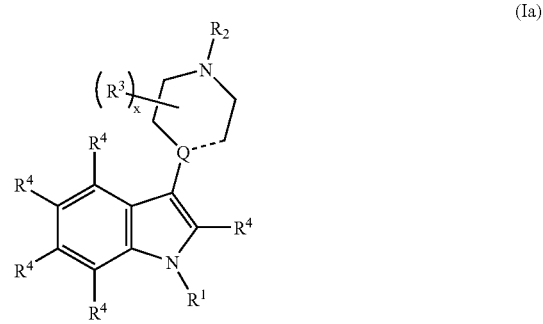
(Ia)

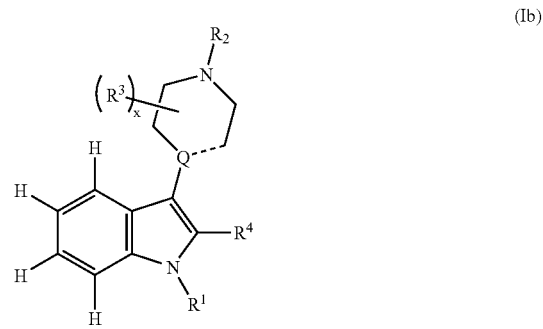
(Ib)

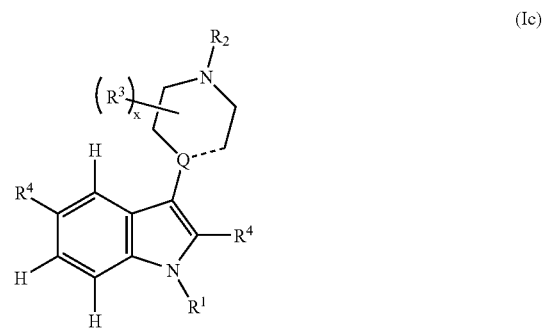
(Ic)

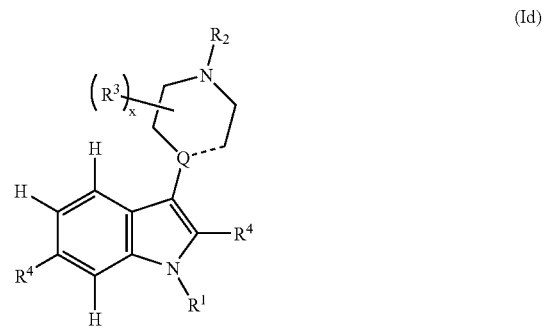
(Id)

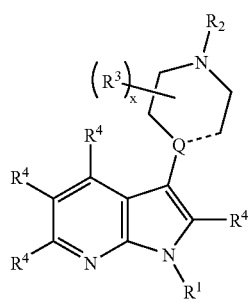 (Ie)
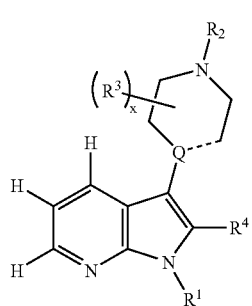 (If)
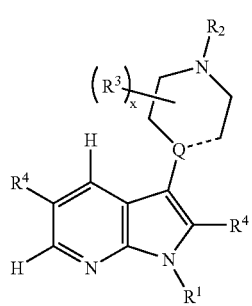 (Ig)
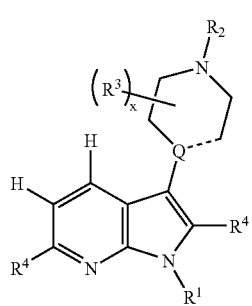 (Ih)
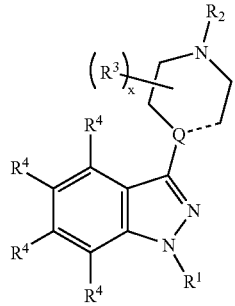 (Ii)
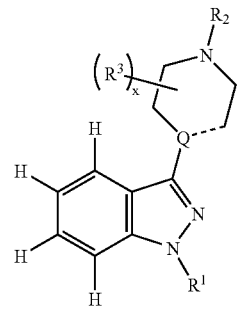 (Ij)
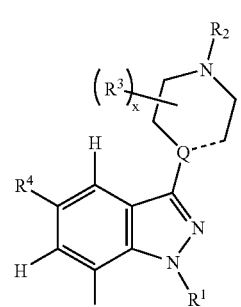 (Ik)
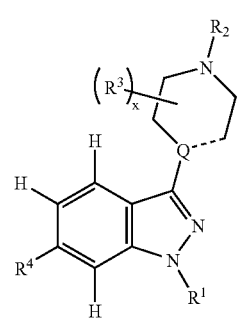 (Il)
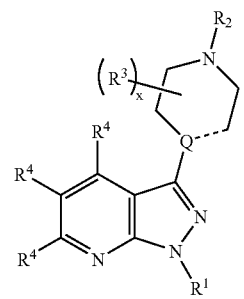 (Im)
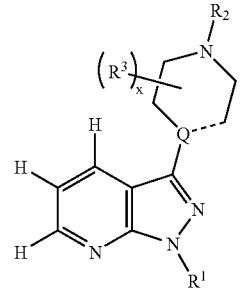 (In)

-continued
(Io) 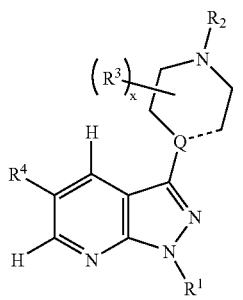
(Ip) 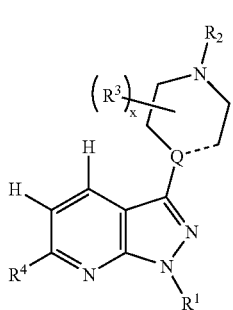
(Iq) 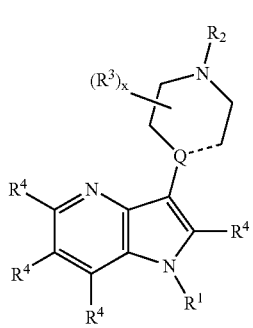
(Ir) 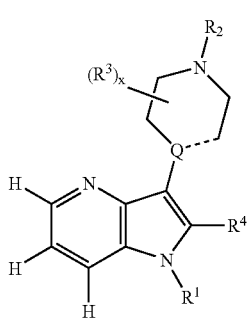
(Is) 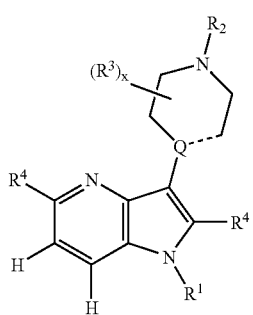
(It) 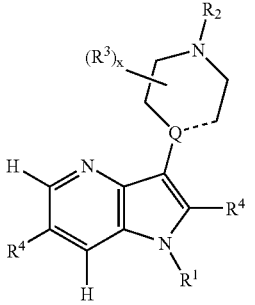
(Iu) 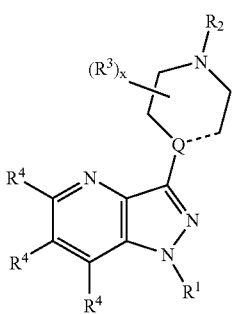
(Iv) 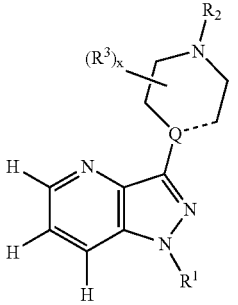
(Iw) 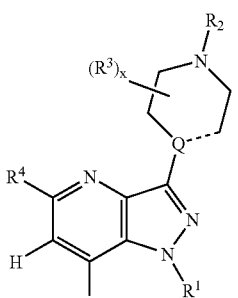
(Ix) 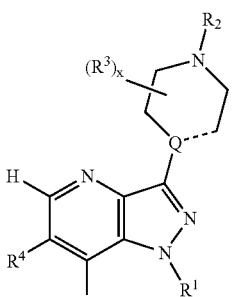
According to a preferred embodiment, the compound of formula (I) is represented by subformulas Ib), Ic, Id, If, Ig, Ih, Ij, Ik, Il, In, Io, Ip, Iq, Ir, Is, It, Iu, Iv, Iw or Ix, for example, subformulas Ib, Ic, Id, If, Ij, Ik, or In.

In another preferred embodiment, the compound of formula (I) is represented by one or more of the following subformulas:

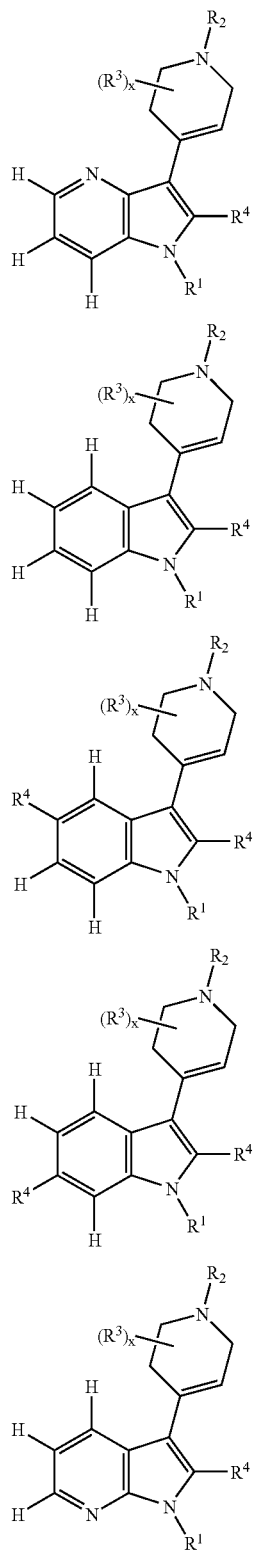

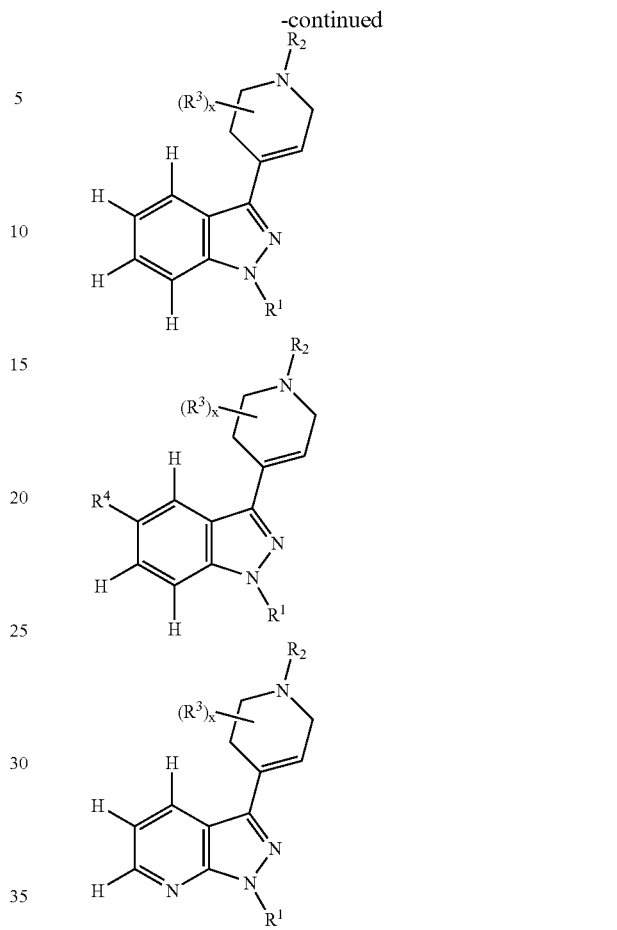

According to a further aspect of the present invention, when —Ar is aminophenyl, then at least one of A, B, D, or E is $CR^4$ in which $R^4$ is other than H, halogen or nitro.

According to a further aspect of the present invention, when —Ar is unsubstituted phenyl or unsubstituted pyridinyl, then at least one of A, B, D, or E is $CR^4$ in which $R^4$ is nitro or a substituted or unsubstituted heterocyclic group.

According to a further aspect of the present invention, when —Ar is unsubstituted phenyl or unsubstituted pyridinyl, then at least one of A, B, D, or E is $CR^4$ in which $R^4$ is nitro or a substituted or unsubstituted heterocyclic group other than thiazolyl (e.g., substituted or unsubstituted pyridyl, substituted or unsubstituted pyrrolyl (e.g., 2,5-dimethylpyrrol-1-yl).

According to a further aspect of the present invention, when A, B, D, E and G are CH, and Ar is represented by formula (b), then d is 3.

In a preferred embodiment $R_2$ is H.

In another preferred embodiment, the bond between Q and CH (i.e., ----- in Formula I) represents a single bond and Q is CH or N.

Halogen herein refers to F, Cl, Br, and I. Preferred halogens are F and Cl.

Alkyl means a straight-chain or branched-chain aliphatic hydrocarbon radical. Suitable alkyl groups include, but are not limited to, methyl, ethyl, propyl, isopropyl, butyl, sec-butyl, tert-butyl, pentyl, hexyl, heptyl, octyl, nonyl, decyl, undecyl, and dodecyl. Other examples of suitable alkyl groups include, but are not limited to, 1-, 2- or 3-methylbutyl, 1,1-, 1,2- or 2,2-dimethylpropyl, 1-ethylpropyl, 1-, 2-, 3- or 4-methylpentyl, 1,1-, 1,2-, 1,3-, 2,2-, 2,3- or 3,3-dimethylbutyl, 1- or 2-ethylbutyl, ethylmethylpropyl, trimethylpropyl, methylhexyl, dimethylpentyl, ethylpentyl, ethylmethylbutyl, dimethylbutyl, and the like.

These alkyl radicals can optionally have one or more —$CH_2CH_2$— groups replaced in each case by —CH═CH— or —C≡C— groups. Suitable alkenyl or alkynyl groups include, but are not limited to, 1-propenyl, 2-propenyl, 1-propynyl, 1-butenyl, 2-butenyl, 3-butenyl, 1-butynyl, 1,3-butadienyl, and 3-methyl-2-butenyl.

The alkyl groups include cycloalkyl groups, e.g., monocyclic, bicyclic or tricyclic saturated hydrocarbon radical having 3 to 8 carbon atoms, preferably 3 to 6 carbon atoms. Suitable cycloalkyl groups include, but are not limited to, cyclopropyl, cyclobutyl, cyclopentyl, cyclohexyl, cycloheptyl, cyclooctyl, and norbornyl. Other suitable cycloalkyl groups include, but are not limited to, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, and bicyclo[4.2.0]octyl.

The alkyl groups also include cycloalkylalkyl in which the cycloalkyl portions have preferably 3 to 8 carbon atoms, preferably 4 to 6 carbon atoms and alkyl the portions have preferably 1 to 8 carbon atoms, preferably 1 to 4 carbon atoms. Suitable examples include, but are not limited to, cyclopentylethyl and cyclopropylmethyl.

In the arylalkyl groups and heteroalkyl groups, "alkyl" refers to a divalent alkylene group preferably having 1 to 4 carbon atoms.

In the cases where alkyl is a substituent (e.g., alkyl substituents on aryl and heteroaryl groups) or is part of a substituent (e.g., in the alkylamino, dialkylamino, hydroxyalkyl, hydroxyalkoxy, alkylthio, alkylsulphinyl, and alkylsulphonyl substituents), the alkyl portion preferably has 1 to 12 carbon atoms, especially 1 to 8 carbon atoms, in particular 1 to 4 carbon atoms.

Aryl, as a group or substituent per se or as part of a group or substituent, refers to an aromatic carbocyclic radical containing 6 to 14 carbon atoms, preferably 6 to 12 carbon atoms, especially 6 to 10 carbon atoms. Suitable aryl groups include, but are not limited to, phenyl, naphthyl and biphenyl. Substituted aryl groups include the above-described aryl groups which are substituted one or more times by, for example, halogen, alkyl, hydroxy, alkoxy, nitro, methylenedioxy, ethylenedioxy, amino, alkylamino, dialkylamino, hydroxyalkyl, hydroxyalkoxy, carboxy, cyano, acyl, alkoxycarbonyl, alkylthio, alkylsulphinyl, alkylsulphonyl, phenoxy, and acyloxy (e.g., acetoxy).

Arylalkyl refers to an aryl-alkyl-radical in which the aryl and alkyl portions are in accordance with the previous descriptions. Suitable examples include, but are not limited to, benzyl, 1-phenethyl, 2-phenethyl, phenpropyl, phenbutyl, phenpentyl, and naphthalenemethyl.

Heteroaryl groups refer to unsaturated heterocyclic groups having one or two rings and a total number of 5 to 10 ring atoms wherein at least one of the ring atoms is preferably an N, O or S atom. Preferably, the heteroaryl group contains 1 to 3, especially 1 or 2, hetero-ring atoms selected from N, O and S. Suitable heteroaryl groups include, for example, furyl, benzothienyl, benzofuranyl, pyrrolyl, pyrazolyl, imidazolyl, pyridyl, pyrimidinyl, isoxazolyl, quinolinyl, azaindolyl, naphthyridinyl, thiazolyl, and the like. Preferred heteroaryl groups include, but are not limited to, furyl, benzothienyl, benzofuranyl, pyrrolyl, pyrazolyl, imidazolyl, pyridyl, pyrimidinyl, isoxazolyl, and thiazolyl.

Substituted heteroaryl groups refer to the heteroaryl groups described above which are substituted in one or more places by preferably halogen, aryl, alkyl, alkoxy, cyano, halogenated alkyl (e.g., trifluoromethyl), nitro, oxo, amino, alkylamino, and dialkylamino.

Hetereocycles are non-aromatic, saturated or partially unsaturated, cyclic groups containing at least one hetero-ring atom, preferably selected from N, S, and O, for example, 1,2,3,4,-tetrahydroquinolyl, dihydrobenzofuranyl, dihydrobenzodioxepinyl, dihydrobenzodioxinyl, dihydroindolyl, benzodioxolyl, 3-tetrahydrofuranyl, piperidinyl, imidazolinyl, imidazolidinyl, pyrrolinyl, pyrrolidinyl, morpholinyl, piperazinyl, oxazolidinyl, and indolinyl.

Heteroarylalkyl refers to a heteroaryl-alkyl-group wherein the heteroaryl and alkyl portions are in accordance with the previous discussions. Suitable examples include, but are not limited to, pyridylmethyl, thienylmethyl, pyrimidinylmethyl, pyrazinylmethyl, isoquinolinylmethyl, pyridylethyl and thienylethyl.

Carbocyclic structures are non-aromatic monocyclic or bicyclic structures containing 5 to 14 carbon atoms, preferably 6 to 10 carbon atoms, wherein the ring structure(s) optionally contain at least one C═C bond.

Acyl refers to alkanoyl radicals having 2 to 4 carbon atoms. Suitable acyl groups include, but are not limited to, formyl, acetyl, propionyl, and butanoyl.

Substituted radicals preferably have 1 to 3 substituents, especially 1 or 2 substituents.

$R^2$ is preferably H or alkyl having 1 to 4 carbon atoms, e.g., methyl, ethyl, propyl, isopropyl, n-butyl, especially methyl.

$R^3$ is preferably H or alkyl having 1 to 4 carbon atoms, e.g., methyl, ethyl, propyl, isopropyl, n-butyl, especially methyl. More preferably, $R^3$ is H.

$R^4$ is preferably halogen (e.g., F, Cl, Br, more preferably F), nitro, alkyl having 1 to 4 carbon atoms, which is branched or unbranched and which is unsubstituted or substituted one or more times with halogen, $C_{1-4}$-alkyl, $C_{1-4}$-alkoxy, oxo, or any combination thereof (e.g., $CF_3$) or heterocyclic group (e.g., substituted or unsubstituted pyrrolyl, pyridinyl, pyrrolidinyl, morpholinyl, piperidinyl). In one preferred embodiment, $R^4$ is halogen, fluorinated $C_{1-4}$-alkyl, or heterocyclic group. In another preferred embodiment, $R^4$ is halogen (e.g., F), or fluorinated $C_{1-4}$-alkyl (e.g. $CF_3$).

When $R^5$ is a heterocyclic group, it is preferably unsubstituted or substituted pyrrolyl (e.g., 2,5-dimethyl-1H-pyrrol-1-yl), pyridinyl (e.g., pyridin-4-yl, pyridine-3-yl, pyridine-2-yl), pyrrolidinyl (e.g., pyrrolidin-1-yl), or morpholinyl (e.g., morpholin-4-yl).

$R^6$ is preferably H or alkyl having 1 to 4 carbon atoms, e.g., methyl, ethyl, propyl, isopropyl, n-butyl, especially H or methyl.

$R^7$ is preferably $C_{1-4}$-alkyl (e.g., methyl, ethyl), halogenated $C_{1-4}$-alkyl (e.g., $CHF_2$, $CF_3$), aryl (e.g., unsubstituted or substituted phenyl), $CO_2R^8$ (e.g., $CO_2CH_3$), $NR^6COR^8$ (e.g., NHCOCH3, $N(CH_3)COCH_3$), halogen (e.g., F, Cl), or C(O)$R^8$ (e.g., $COCH_3$).

$R^8$ is preferably alkyl having 1 to 4 carbon atoms, e.g., $CH_3$, $CH_2CH_3$, especially $CH_3$.

Q is preferably C or CH or N.

Y is preferably O or $NR^7$.

W is preferably absent, or when present, is preferably O.

Preferred examples of Ar represented by formulas (a)-(r) include, but are not limited to, phenyl substituted at least once by amino, dialkylamino (e.g. $N(CH_3)_2$), $NR^6COR^8$ (e.g., $NHCOCH_3$), $N(CH_3)COCH_3$), or substituted or unsubstituted heterocyclic group (e.g., pyrimidinyl, pyrrolidinyl, morpholinyl); pyridinyl substituted at least once by substituted or unsubstituted heterocyclic group (e.g., morpholinyl); unsubstituted or substituted dihydrobenzofuranyl (e.g., 2,3-dihydrobenzofuran-5-yl); unsubstituted or substituted dihydrobenzodioxepinyl (e.g., 3,4-dihydro-2H-1,5-benzodioxepm-7-yl); unsubstituted or substituted thiazolyl (e.g., 4-alkyl-2-aryl-substituted thiazolyl); unsubstituted or substituted pyrazolyl (e.g., 5-methyl-1-phenyl-1H-pyrazol-4-yl, 1-methyl-3-trifluoromethyl-1H-pyrazol-4-yl, 1,3,5-trimethyl-1-H-pyrazol-4-yl, 1-ethyl-3-methyl-1H-pyrazol-4-yl, 1-difluoromethyl-5-methyl-1H-pyrazol-4-yl, 1-difluoromethyl-3-methyl-1H-pyrazol-4-yl, 1-ethyl-5-methyl-1H-pyrazol-4-yl, 1-ethyl-1H-pyrazol-4-yl, 1-ethyl-3,5-dimethyl-1H-pyrazol-4-yl, 1-methyl-1H-pyrazol-4-yl, 1,5-dimethyl-1H-pyrazol-4-yl); unsubstituted or substituted benzothienyl (e.g., 1-benzothien-2-yl, 1-benzothien-3-yl); unsubstituted or substituted furanyl (e.g., 5-acetoxy-furan-2-yl, 2,5-dimethyl-furan-3-yl); unsubstituted or substituted benzofuranyl (e.g., 1-benzofuran-2-yl); unsubstituted or substituted oxazolyl (e.g., 3,5-dimethyloxazol-4-yl); unsubstituted or substituted benzothiazolyl (e.g., 1,3-benzothiazol-6-yl); unsubstituted or substituted pyrrolyl (e.g., 4-chloro-1,2-dimethyl-1-H-pyrrol-3-yl); unsubstituted or substituted imidazolyl (e.g., 1-methyl-1H-imidazol-4-yl, 1,2-dimethyl-1H-imidazol-4-yl); unsubstituted or substituted dihydroindolyl (e.g., 2,3,dihydro-1-H-indol-5-yl, 1-acetyl-2,3,dihydro-1-H-indol-5-yl, 1-methyl-2,3,dihydro-1-H-indol-5-yl, 1-ethyl-2,3,dihydro-1-H-indol-5-yl); unsubstituted or substituted indazolyl (e.g., 1-(2,2-dimethylpropanoyl)indazol-5-yl); and unsubstituted or substituted tetrahydroisoquinolinyl (e.g., 1,2,3,4-tetrahydroisoquinolin-7-yl, 1-methyl-1,2,3,4-tetrahydroisoquinolin-7-yl, 1-methyl-1,2,3,4-tetrahydroisoquinolin-7-yl).

In addition, preferred compounds in accordance with the invention are described by subformulas (i)-(xix), which correspond to formula I, but exhibit the following preferred groups:

(i) A, D, E, and G are CH,
B is $CR^4$ wherein $R^4$ is H, halogen or halogenated alkyl, and
$R^1$ is $SO_2Ar$ wherein Ar is phenyl substituted at least once by amino, dialkylamino (e.g. $N(CH_3)_2$), $NR^6COR^8$ (e.g., $NHCOCH_3$), $N(CH_3)COCH_3$), or substituted or unsubstituted heterocyclic group (e.g., pyrimidinyl, pyrrolidinyl, morpholinyl),
pyridinyl substituted at least once by substituted or unsubstituted heterocyclic group (e.g., morpholinyl) unsubstituted or substituted dihydrobenzofuranyl (e.g., 2,3-dihydrobenzofuran-5-yl),
unsubstituted or substituted dihydrobenzodioxepinyl (e.g., 3,4-dihydro-2H-1,5-benzodioxepin-7-yl),
unsubstituted or substituted thiazolyl (e.g., 4-alkyl-2-aryl-substituted thiazolyl),
unsubstituted or substituted pyrazolyl (e.g., 5-methyl-1-phenyl-1H-pyrazol-4-yl, 1-methyl-3-trifluoromethyl-1H-pyrazol-4-yl, 1,3,5-trimethyl-1-H-pyrazol-4-yl, 1-ethyl-3-methyl-1H-pyrazol-4-yl, 1-difluoromethyl-5-methyl-1H-pyrazol-4-yl, 1-difluoromethyl-3-methyl-1H-pyrazol-4-yl, 1-ethyl-5-methyl-1H-pyrazol-4-yl, 1-ethyl-1H-pyrazol-4-yl, 1-ethyl-3,5-dimethyl-1H-pyrazol-4-yl, 1-methyl-1H-pyrazol-4-yl, 1,5-dimethyl-1H-pyrazol-4-yl),
unsubstituted or substituted benzothienyl (e.g., 1-benzothien-2-yl, 1-benzothien-3-yl),
unsubstituted or substituted furanyl (e.g., 5-acetoxy-furan-2-yl, 2,5-dimethyl-furan-3-yl),
unsubstituted or substituted benzofuranyl (e.g., 1-benzofuran-2-yl), unsubstituted or substituted oxazolyl (e.g., 3,5-dimethyloxazol-4-yl),
unsubstituted or substituted benzothiazolyl (e.g., 1,3-benzothiazol-6-yl),
unsubstituted or substituted pyrrolyl (e.g., 4-chloro-1,2-dimethyl-1-H-pyrrol-3-yl),
unsubstituted or substituted dihydroindolyl (e.g., 2,3,dihydro-1-H-indol-5-yl, 1-acetyl-2,3,dihydro-1-H-indol-5-yl, 1-methyl-2,3,dihydro-1-H-indol-5-yl, 1-ethyl-2,3,dihydro-1-H-indol-5-yl),
unsubstituted or substituted indazolyl (e.g., 1-(2,2-dimethylpropanoyl) indazol-5-yl), or
unsubstituted or substituted tetrahydroisoquinolinyl (e.g., 1,2,3,4-tetrahydroisoquinolin-7-yl, 1-methyl-1,2,3,4-tetrahydroisoquinolin-7-yl, 1-methyl-1,2,3,4-tetrahydroisoquinolin-7-yl).

(ii) A, D, E, and G are CH,
B is $CR^4$ wherein $R^4$ is H, halogen or halogenated alkyl, and
$R^1$ is $SO_2Ar$ wherein Ar is phenyl substituted at least once by amino, dimethylamino, $NHCOCH_3$, $N(CH_3)COCH_3$, unsubstituted or substituted pyrimidinyl, unsubstituted or substituted pyrrolidinyl or unsubstituted or substituted morpholinyl,
pyridinyl substituted at least once by substituted or unsubstituted heterocyclic group,
unsubstituted or substituted dihydrobenzofuranyl,
unsubstituted or substituted dihydrobenzodioxepinyl,
unsubstituted thiazolyl or thiazolyl substituted by one or more alkyl and/or aryl groups,
unsubstituted pyrazolyl or pyrazolyl substituted by one or more alkyl, aryl, halogenated alkyl groups,
unsubstituted or substituted benzothienyl,
unsubstituted furanyl or furanyl substituted by one or more acetoxy and/or alkyl groups,
unsubstituted or substituted benzofuranyl,
unsubstituted oxazolyl or oxazolyl substituted by one or more alkyl groups,
unsubstituted or substituted benzothiazolyl,
unsubstituted pyrrolyl or pyrrolyl substituted by one or more halogen and/or alkyl groups,
unsubstituted dihydroindolyl or dihydroindolyl substituted by one or more acetyl, and/or alkyl groups,
unsubstituted indazolyl or indazolyl substituted by one or more $C(O)R^8$ groups, or
unsubstituted tetrahydroisoquinolinyl or tetrahydroisoquinolinyl substituted by one or more alkyl groups.

(iii) A, D, E, and G are CH,
B is $CR^4$ wherein $R^4$ is H, F, or $CF_3$, and
$R^1$ is $SO_2Ar$ wherein Ar is 4-aminophenyl, 4-dimethylaminophenyl, 3-dimethylaminophenyl, p-$C_6H_4$(NHCOCH$_3$), p-$C_6H_4$(N(CH$_3$)COCH$_3$), 3-(2-methylpyrimidin-4-yl)phenyl, 4-morpholin-4-ylphenyl, 4-pyrrolidin-1-ylphenyl, 3-pyrrolidin-1-ylphenyl, 4-morpholin-4-yl-pyridin-3-yl, 2,3-dihydrobenzofuran-5-yl, 3,4-dihydro-2H-1,5-benzodioxepin-7-yl, 4-methyl-2-phenyl-1,3-thiazol-5-yl, 5-methyl-1-phenyl-1H-pyrazol-4-yl, 1-methyl-3-trifluoromethyl-1H-pyrazol-4-yl, 1,3,5-trimethyl-1-H-pyrazol-4-yl, 1-ethyl-3-methyl-1H-pyrazol-4-yl, 1-difluoromethyl-5-methyl-1H-pyrazol-4-yl, 1-difluoromethyl-3-methyl-1H-pyrazol-4-yl, 1-ethyl-5-methyl-1H-pyrazol-4-yl, 1-ethyl-1H-pyrazol-4-yl, 1-ethyl-3,5-dimethyl-1H-pyrazol-4-yl, 1-methyl-1H-pyrazol-4-yl, 1,5-dimethyl-1H-pyrazol-4-yl, 1-benzothien-2-yl, 1-benzothien-3-yl, 5-acetoxy-furan-2-yl, 2,5-dimethyl-furan-3-yl, 1-benzofuran-2-yl, 3,5-dimethyloxazol-4-yl), 1,3-benzothiazol-6-yl), 4-chloro-1,2-dimethyl-1-H-pyrrol-3-yl), 2,3-dihydro-1-H-indol-5-yl, 1-acetyl-2,3,dihydro-1-H-indol-5-yl, 1-methyl-2,3,dihydro-1-H-indol-5-yl, 1-ethyl-2,3,dihydro-1-H-indol-5-yl), 1,2,3,4-tetrahydroisoquinolin-7-yl, 1-methyl-1,2,3,4-tetrahydroisoquinolin-7-yl, 1-(2,2-dimethylpropanoyl)indazol-5-yl, or 1-methyl-1,2,3,4-tetrahydroisoquinolin-7-yl.

(iv) A, B, D, and E are CH or $CR^4$,
$R^1$ is $SO_2Ar$ wherein Ar is an unsubstituted phenyl, and
at least one of A, B, D and E is $CR^4$ in which $R^4$ is $NO_2$ or heterocyclic group (e.g., substituted or unsubstituted pyrrolyl, pyridinyl, pyrrolidinyl, morpholinyl).

(v) A, and E are CH,
$R^1$ is $SO_2Ar$ wherein Ar is an unsubstituted phenyl, and
at least one of B or D is $CR^4$ in which $R^4$ is $NO_2$ or heterocyclic group (e.g., substituted or unsubstituted pyrrolyl, pyridinyl, pyrrolidinyl, morpholinyl).

(vi) A, and E are CH,
$R^1$ is $SO_2Ar$ wherein Ar is an unsubstituted phenyl, and
at least one of B or D is $CR^4$ in which $R^4$ is $NO_2$, 2,5-dimethylpyrrol-1-yl, pyridin-4-yl, pyridine-3-yl, pyridine-2-yl, pyrrolidin-1-yl, or morpholin-4-yl.

(vii) A, D, and G are CH,
E is N,
B is $CR^4$ wherein $R^4$ is H, halogen (e.g., F) or halogenated alkyl (e.g., $CF_3$), and
$R^1$ is $SO_2Ar$ wherein Ar is phenyl substituted at least once by amino, dialkylamino (e.g. $N(CH_3)_2$), $NR^6COR^8$ (e.g., $NHCOCH_3$), $N(CH_3)COCH_3$), or substituted or unsubstituted heterocyclic group (e.g., pyrimidinyl, pyrrolidinyl, morpholinyl),
pyridinyl substituted at least once by substituted or unsubstituted heterocyclic group (e.g., morpholinyl)
unsubstituted or substituted dihydrobenzofuranyl (e.g., 2,3-dihydrobenzofuran-5-yl),
unsubstituted or substituted dihydrobenzodioxepinyl (e.g., 3,4-dihydro-2H-1,5-benzodioxepin-7-yl),
thiazolyl substituted at least once by aryl (e.g., 4-alkyl-2-aryl-substituted thiazolyl),
unsubstituted or substituted dihydroindolyl (e.g., 2,3,dihydro-1-H-indol-5-yl, 1-acetyl-2,3,dihydro-1-H-indol-5-yl, 1-methyl-2,3,dihydro-1-H-indol-5-yl, 1-ethyl-2,3,dihydro-1-H-indol-5-yl), or
unsubstituted or substituted tetrahydroisoquinolinyl (e.g., 1,2,3,4-tetrahydroisoquinolin-7-yl, 1-methyl-1,2,3,4-tetrahydroisoquinolin-7-yl, 1-methyl-1,2,3,4-tetrahydroisoquinolin-7-yl).

(viii) A, D, and G are CH,
E is N,
B is $CR^4$ wherein $R^4$ is H, halogen (e.g., F) or halogenated alkyl (e.g., $CF_3$), and
$R^1$ is $SO_2Ar$ wherein Ar is phenyl substituted at least once by amino, dialkylamino (e.g. $N(CH_3)_2$), $NR^6COR^8$ (e.g., $NHCOCH_3$), $N(CH_3)COCH_3$), or substituted or unsubstituted heterocyclic group (e.g., pyrimidinyl, pyrrolidinyl, morpholinyl),
pyridinyl substituted at least once by substituted or unsubstituted heterocyclic group,
unsubstituted or substituted dihydrobenzofuranyl,
unsubstituted or substituted dihydrobenzodioxepinyl,
thiazolyl substituted at least once by aryl,
unsubstituted dihydroindolyl or dihydroindolyl substituted by one or more acetyl and/or alkyl groups, or
unsubstituted tetrahydroisoquinolinyl or tetrahydroisoquinolinyl substituted by one or more alkyl groups.

(ix) A, B, D, and & are CH,
E is N, and
$R^1$ is $SO_2Ar$ wherein Ar is 4-aminophenyl, 4-dimethylaminophenyl, 3-dimethylaminophenyl, p-$C_6H_4$(NH-$COCH_3$), p-$C_6H_4$(N($CH_3$)$COCH_3$), 3-(2-methylpyrimidin-4-yl)phenyl, 4-morpholin-4-ylphenyl, 4-pyrrolidin-1-ylphenyl, 3-pyrrolidin-1-ylphenyl, 4-morpholin-4-yl-pyridin-3-yl, 2,3-dihydrobenzofuran-5-yl, 3,4-dihydro-2H-1,5-benzodioxepin-7-yl, 4-methyl-2-phenyl-1,3-thiazol-5-yl, 2,3,dihydro-1-H-indol-5-yl, 1-acetyl-2,3,dihydro-1-H-indol-5-yl, 1-methyl-2,3,dihydro-1-H-indol-5-yl, 1-ethyl-2,3,dihydro-1-H-indol-5-yl), 1,2,3,4-tetrahydroisoquinolin-7-yl, 1-methyl-1,2,3,4-tetrahydroisoquinolin-7-yl, or 1-methyl-1,2,3,4-tetrahydroisoquinolin-7-yl.

(x) A, D, and E are CH,
G is N,
B is $CR^4$ wherein $R^4$ is H, halogen or halogenated alkyl, and
$R^1$ is $SO_2Ar$ wherein Ar is unsubstituted or substituted imidazolyl (e.g., 1,2-dimethyl-1H-imidazol-4-yl), or unsubstituted or substituted furyl (e.g., 2,5-dimethyl-fur-3-yl).

(xi) A, B and D are CH or $CR^4$,
E and G are N,
$R^1$ is $SO_2Ar$ wherein Ar is unsubstituted or substituted imidazolyl (e.g., 1,2-dimethyl-1H-imidazol-4-yl), or unsubstituted or substituted furyl (e.g., 2,5-dimethyl-fur-3-yl).

(xii) A, D and G are CH,
B is $CR^4$ wherein $R^4$ is H, halogen, halogenated alkyl, nitro, pyridine, dimethyl pyrrole, tetrahydropyrrole, tetrahydropyridine, or tetrahydrooxazine,
E is CH or N,
$R_2$ is $CH_3$,
$R_3$ is H,
--- is a double bond and Q is C.

(xiii) Ar is a heterocycle selected from formulas (b)-(i) and (k)-(l).

(xiv) G is CH or $CR^4$.

(xv) $R^4$ is halogen (e.g., F), nitro,
alkyl having 1 to 8, preferably 1 to 4 carbon atoms, cycloalkyl having 3 to 12, preferably 3 to 8 carbon atoms, or cycloalkylalkyl having 4 to 12, preferably 4 to 8 carbon atoms, each of which is branched or unbranched and which is unsubstituted or substituted one or more times with halogen, $C_{1-4}$-alkyl, $C_{1-4}$-alkoxy, oxo, or any combination thereof, or
a heterocyclic group, which is saturated, partially saturated or unsaturated, having 5 to 10 ring atoms in which at least 1 ring atom is an N, O or S atom, which is unsubstituted or substituted one or more times by halogen, hydroxy, aryl, alkyl, alkoxy, cyano, halogenated alkyl, nitro, or any combination thereof.

(xvi) Q is N,
A, B, and D are CH,
E is CH or NH,
$R_2$ is H or $CH_3$,
$R_3$ is H, and
$R^1$ is $SO_2Ar$ wherein Ar is a heterocycle selected from formulas (a), (c) and (n).

(xvii) A, D, and E are CH,
B is $CR^4$ and $R^4$ is F

R¹ is SO₂Ar wherein Ar is a heterocycle having the formula (o),
R₂ is H or CH₃, and
R₃ is H.
(xviii) R¹ is SO₂Ar wherein Ar is 2,3-dihydrobenzo[b][1,4]dioxine, 3,4-dihydroquinolin-2(1H)-one, 4-methyl-3,4-dihydro-2H-benzo[b][1,4]oxazine, or 2H-benzo[b][1,4]oxazin-3(4H)-one.
(xix) Q is N
A, B, D, E and G are CH,
R¹ is SO₂Ar wherein Ar is 2H-benzo[b][1,4]oxazin-3(4H)-one,
R₂ is H,
R₃ is H,
and ----- represents a single bond.

According to a compound and/or method aspect of the present invention, the compounds are selected from:

2) N-(4-{[3-(1-methyl-1,2,3,6-tetrahydropyridin-4-yl)-1H-indol-1-yl]sulfonyl}phenyl)acetamide,
3) N-(4-{[3-(1-methyl-1,2,3,6-tetrahydropyridin-4-yl)-1H-pyrrolo[2,3-b]pyridin-1-yl]sulfonyl}phenyl)acetamide,
4) N-(4-{[5-fluoro-3-(1-methyl-1,2,3,6-tetrahydropyridin-4-yl)-1H-indol-1-yl]sulfonyl}phenyl)acetamide,
5) N-(4-{[3-(1-methyl-1,2,3,6-tetrahydropyridin-4-yl)-5-(trifluoromethyl)-1H-indol-1-yl]sulfonyl}phenyl)acetamide,
6) 1-(2,3-dihydro-1-benzofuran-5-ylsulfonyl)-3-(1-methyl-1,2,3,6-tetrahydropyridin-4-yl)-1H-indole,
7) 1-(2,3-dihydro-1-benzofuran-5-ylsulfonyl)-3-(1-methyl-1,2,3,6-tetrahydropyridin-4-yl)-1H-pyrrolo[2,3-b]pyridine,
8) 1-(2,3-dihydro-1-benzofuran-5-ylsulfonyl)-5-fluoro-3-(1-methyl-1,2,3,6-tetrahydropyridin-4-yl)-1H-indole,
9) 1-(2,3-dihydro-1-benzofuran-5-ylsulfonyl)-3-(1-methyl-1,2,3,6-tetrahydropyridin-4-yl)-5-(trifluoromethyl)-1H-indole,
10) 1-(3,4-dihydro-2H-1,5-benzodioxepin-7-ylsulfonyl)-3-(1-methyl-1,2,3,6-tetrahydropyridin-4-yl)-1H-indole,
11) 1-(3,4-dihydro-2H-1,5-benzodioxepin-7-ylsulfonyl)-3-(1-methyl-1,2,3,6-tetrahydropyridin-4-yl)-1H-pyrrolo[2,3-b]pyridine,
12) 1-(3,4-dihydro-2H-1,5-benzodioxepin-7-ylsulfonyl)-5-fluoro-3-(1-methyl-1,2,3,6-tetrahydropyridin-4-yl)-1H-indole,
13) 1-(3,4-dihydro-2H-1,5-benzodioxepin-7-ylsulfonyl)-3-(1-methyl-1,2,3,6-tetrahydropyridin-4-yl)-5-(trifluoromethyl)-1H-indole,
14) 1-[(4-methyl-2-phenyl-1,3-thiazol-5-yl)sulfonyl]-3-(1-methyl-1,2,3,6-tetrahydropyridin-4-yl)-1H-indole,
15) 1-[(4-methyl-2-phenyl-1,3-thiazol-5-yl)sulfonyl]-3-(1-methyl-1,2,3,6-tetrahydropyridin-4-yl)-1H-pyrrolo[2,3-b]pyridine,
16) 5-fluoro-1-[(4-methyl-2-phenyl-1,3-thiazol-5-yl)sulfonyl]-3-(1-methyl-1,2,3,6-tetrahydropyridin-4-yl)-1H-indole,
17) 1-[(4-methyl-2-phenyl-1,3-thiazol-5-yl)sulfonyl]-3-(1-methyl-1,2,3,6-tetrahydropyridin-4-yl)-5-(trifluoromethyl)-1H-indole,
18) 1-[(5-methyl-1-phenyl-1H-pyrazol-4-yl)sulfonyl]-3-(1-methyl-1,2,3,6-tetrahydropyridin-4-yl)-1H-indole,
19) 1-[(5-methyl-1-phenyl-1H-pyrazol-4-yl)sulfonyl]-3-(1-methyl-1,2,3,6-tetrahydropyridin-4-yl)-1H-pyrrolo[2,3-b]pyridine,
20) 5-fluoro-1-[(5-methyl-1-phenyl-1H-pyrazol-4-yl)sulfonyl]-3-(1-methyl-1,2,3,6-tetrahydropyridin-4-yl)-1H-indole,
21) 1-[(5-methyl-1-phenyl-1H-pyrazol-4-yl)sulfonyl]-3-(1-methyl-1,2,3,6-tetrahydropyridin-4-yl)-5-(trifluoromethyl)-1H-indole,
22) 1-(1-benzothien-2-ylsulfonyl)-3-(1-methyl-1,2,3,6-tetrahydropyridin-4-yl)-1H-indole,
23) 1-(1-benzothien-2-ylsulfonyl)-5-fluoro-3-(1-methyl-1,2,3,6-tetrahydropyridin-4-yl)-1H-indole,
24) 1-(1-benzothien-2-ylsulfonyl)-3-(1-methyl-1,2,3,6-tetrahydropyridin-4-yl)-5-(trifluoromethyl)-1H-indole,
25) 3-(1-methyl-1,2,3,6-tetrahydropyridin-4-yl)-1-{[1-methyl-3-(trifluoromethyl)-1H-pyrazol-4-yl]sulfonyl}-1H-indole,
26) 5-fluoro-3-(1-methyl-1,2,3,6-tetrahydropyridin-4-yl)-1-{[1-methyl-3-(trifluoromethyl)-1H-pyrazol-4-yl]sulfonyl}-1H-indole,
27) 3-(1-methyl-1,2,3,6-tetrahydropyridin-4-yl)-1-{[1-methyl-3-(trifluoromethyl)-1H-pyrazol 4-yl]sulfonyl}-5-(trifluoromethyl)-1H-indole,
28) Methyl 5-{[3-(1-methyl-1,2,3,6-tetrahydropyridin-4-yl)-1H-indol-1-yl]sulfonyl}-2-furoate,
29) Methyl 5-{[5-fluoro-3-(1-methyl-1,2,3,6-tetrahydropyridin-4-yl)-1H-indol-1-yl]sulfonyl}-2-furoate,
30) Methyl 5-{[3-(1-methyl-1,2,3,6-tetrahydropyridin-4-yl)-5-(trifluoromethyl)-1H-indol-1-yl]sulfonyl}-2-furoate,
31) Methyl 5-{[3-(1-methyl-1,2,3,6-tetrahydropyridin-4-yl)-1H-pyrrolo[2,3-b]pyridin-1-yl]sulfonyl}-2-furoate,
32) 1-[(1-methyl-1H-imidazol-4-yl)sulfonyl]-3-(1-methyl-1,2,3,6-tetrahydropyridin-4-yl)-1H-indole,
33) 5-fluoro-1-[(1-methyl-1H-imidazol-4-yl)sulfonyl]-3-(1-methyl-1,2,3,6-tetrahydropyridin-4-yl)-1H-indole,
34) 1-[(1-methyl-1H-imidazol-4-yl)sulfonyl]-3-(1-methyl-1,2,3,6-tetrahydropyridin-4-yl)-5-(trifluoromethyl)-1H-indole,
35) 1-(2,3-dihydro-1,4-benzodioxin-6-ylsulfonyl)-3-(1-methyl-1,2,3,6-tetrahydropyridin-4-yl)-1H-pyrrolo[2,3-b]pyridine,
36) 1-[(1,2-dimethyl-1H-imidazol-4-yl)sulfonyl]-3-(1-methyl-1,2,3,6-tetrahydropyridin-4-yl)-1H-indazole,
37) 1-[(1,2-dimethyl-1H-imidazol-4-yl)sulfonyl]-5-fluoro-3-(1-methyl-1,2,3,6-tetrahydropyridin-4-yl)-1H-indazole,
38) 1-[(1,2-dimethyl-1H-imidazol-4-yl)sulfonyl]-3-(1-methyl-1,2,3,6-tetrahydropyridin-4-yl)-5-(trifluoromethyl)-1H-indazole,
39) 1-[(2,5-dimethyl-3-furyl)sulfonyl]-3-(1-methyl-1,2,3,6-tetrahydropyridin-4-yl)-1H-indole,
40) 1-[(2,5-dimethyl-3-furyl)sulfonyl]-5-fluoro-3-(1-methyl-1,2,3,6-tetrahydropyridin-4-yl)-1H-indole,
41) 1-[(2,5-dimethyl-3-furyl)sulfonyl]-3-(1-methyl-1,2,3,6-tetrahydropyridin-4-yl)-5-(trifluoromethyl)-1H-indole,
42) 1-(1-benzothien-3-ylsulfonyl)-3-(1-methyl-1,2,3,6-tetrahydropyridin-4-yl)-1H-indole,
43) 1-(1-benzothien-3-ylsulfonyl)-5-fluoro-3-(1-methyl-1,2,3,6-tetrahydropyridin-4-yl)-1H-indole,
44) 1-(1-benzothien-3-ylsulfonyl)-3-(1-methyl-1,2,3,6-tetrahydropyridin-4-yl)-5-(trifluoromethyl)-1H-indole,
45) 1-(1,3-benzodioxol-5-ylsulfonyl)-3-(1-methyl-1,2,3,6-tetrahydropyridin-4-yl)-1H-pyrrolo[2,3-b]pyridine,
46) 1-(1-benzofuran-2-ylsulfonyl)-3-(1-methyl-1,2,3,6-tetrahydropyridin-4-yl)-1H-indole,
47) 1-(1-benzofuran-2-ylsulfonyl)-5-fluoro-3-(1-methyl-1,2,3,6-tetrahydropyridin-4-yl)-1H-indole,
48) 1-(1-benzofuran-2-ylsulfonyl)-3-(1-methyl-1,2,3,6-tetrahydropyridin-4-yl)-5-(trifluoromethyl)-1H-indole,
49) 1-{[3-(2-methylpyrimidin-4-yl)phenyl]sulfonyl}-3-(1-methyl-1,2,3,6-tetrahydropyridin-4-yl)-1H-indole, 50) 5-fluoro-1-{[3-(2-methylpyrimidin-4-yl)phenyl]sulfonyl}-3-(1-methyl-1,2,3,6-tetrahydropyridin-4-yl)-1H-indole,
51) 1-{[3-(2-methylpyrimidin-4-yl)phenyl]sulfonyl}-3-(1-methyl-1,2,3,6-tetrahydropyridin-4-yl)-5-(trifluoromethyl)-1H-indole,
52) 1-{[3-(2-methylpyrimidin-4-yl)phenyl]sulfonyl}-3-(1-methyl-1,2,3,6-tetrahydropyridin-4-yl)-1H-pyrrolo[2,3-b]pyridine,
53) 1-[(3,5-dimethylisoxazol-4-yl)sulfonyl]-3-(1-methyl-1,2,3,6-tetrahydropyridin-4-yl)-1H-indole,
54) 1-[(3,5-dimethylisoxazol-4-yl)sulfonyl]-5-fluoro-3-(1-methyl-1,2,3,6-tetrahydropyridin-4-yl)-1H-indole,
55) 1-[(3,5-dimethylisoxazol-4-yl)sulfonyl]-3-(1-methyl-1,2,3,6-tetrahydropyridin-4-yl)-5-(trifluoromethyl)-1H-indole,
56) 6-{[3-(1-methyl-1,2,3,6-tetrahydropyridin-4-yl)-1H-indol-1-yl]sulfonyl}-1,3-benzothiazole,
57) 6-{[5-fluoro-3-(1-methyl-1,2,3,6-tetrahydropyridin-4-yl)-1H-indol-1-yl]sulfonyl}-1,3-benzothiazole,
58) 6-{[3-(1-methyl-1,2,3,6-tetrahydropyridin-4-yl)-5-(trifluoromethyl)-1H-indol-1-yl]sulfonyl}-1,3-benzothiazole,
59) 3-(1-methyl-1,2,3,6-tetrahydropyridin-4-yl)-1-[(1,3,5-trimethyl-1H-pyrazol-4-yl)sulfonyl]-1H-indole,
60) 5-fluoro-3-(1-methyl-1,2,3,6-tetrahydropyridin-4-yl)-1-[(1,3,5-trimethyl-1H-pyrazol-4-yl)sulfonyl]-1H-indole,
61) 3-(1-methyl-1,2,3,6-tetrahydropyridin-4-yl)-5-(trifluoromethyl)-1-[(1,3,5-trimethyl-1H-pyrazol-4-yl)sulfonyl]-1H-indole,
62) 1-[(4-chloro-1,2-dimethyl-1H-pyrrol-3-yl)sulfonyl]-3-(1-methyl-1,2,3,6-tetrahydropyridin-4-yl)-1H-indole,
63) 1-[(4-chloro-1,2-dimethyl-1H-pyrrol-3-yl)sulfonyl]-5-fluoro-3-(1-methyl-1,2,3,6-tetrahydropyridin-4-yl)-1H-indole,
64) 1-[(4-chloro-1,2-dimethyl-1H-pyrrol-3-yl)sulfonyl]-3-(1-methyl-1,2,3,6-tetrahydropyridin-4-yl)-5-(trifluoromethyl)-1H-indole,
65) 1-[(1-acetyl-2,3-dihydro-1H-indol-5-yl)sulfonyl]-3-(1-methyl-1,2,3,6-tetrahydropyridin-4-yl)-1H-indole,
66) 1-[(1-acetyl-2,3-dihydro-1H-indol-5-yl)sulfonyl]-5-fluoro-3-(1-methyl-1,2,3,6-tetrahydropyridin-4-yl)-1H-indole,
67) 1-[(1-acetyl-2,3-dihydro-1H-indol-5-yl)sulfonyl]-3-(1-methyl-1,2,3,6-tetrahydropyridin-4-yl)-5-(trifluoromethyl)-1H-indole,
68) 1-[(1-acetyl-2,3-dihydro-1H-indol-5-yl)sulfonyl]-3-(1-methyl-1,2,3,6-tetrahydropyridin-4-yl)-1H-pyrrolo[2,3-b]pyridine,
69) 3-(1-methyl-1,2,3,6-tetrahydropyridin-4-yl)-1-[(6-morpholin-4-ylpyridin-3-yl)sulfonyl]-1H-indole,
70) 5-fluoro-3-(1-methyl-1,2,3,6-tetrahydropyridin-4-yl)-1-[(6-morpholin-4-ylpyridin-3-yl)sulfonyl]-1H-indole,
71) 3-(1-methyl-1,2,3,6-tetrahydropyridin-4-yl)-1-[(6-morpholin-4-ylpyridin-3-yl)sulfonyl]-5-(trifluoromethyl)-1H-indole,
72) 3-(1-methyl-1,2,3,6-tetrahydropyridin-4-yl)-1-[(6-morpholin-4-ylpyridin-3-yl)sulfonyl]-1H-pyrrolo[2,3-b]pyridine,
73) 1-(2,3-dihydro-1H-indol-5-ylsulfonyl)-3-(1-methyl-1,2,3,6-tetrahydropyridin-4-yl)-1H-indole,
74) 1-(2,3-dihydro-1H-indol-5-ylsulfonyl)-5-fluoro-3-(1-methyl-1,2,3,6-tetrahydropyridin-4-yl)-1H-indole,
75) 1-(2,3-dihydro-1H-indol-5-ylsulfonyl)-3-(1-methyl-1,2,3,6-tetrahydropyridin-4-yl)-5-(trifluoromethyl)-1H-indole,
76) 1-(2,3-dihydro-1H-indol-5-ylsulfonyl)-3-(1-methyl-1,2,3,6-tetrahydropyridin-4-yl)-1H-pyrrolo[2,3-b]pyridine,
77) 3-(1-methyl-1,2,3,6-tetrahydropyridin-4-yl)-5-nitro-1-(phenylsulfonyl)-1H-indole,
78) 3-(1-methyl-1,2,3,6-tetrahydropyridin-4-yl)-6-nitro-1-(phenylsulfonyl)-1H-indole,
79) 5-(2,5-dimethyl-1H-pyrrol-1-yl)-3-(1-methyl-1,2,3,6-tetrahydropyridin-4-yl)-1-(phenylsulfonyl)-1H-indole,
80) 6-(2,5-dimethyl-1H-pyrrol-1-yl)-3-(1-methyl-1,2,3,6-tetrahydropyridin-4-yl)-1-(phenylsulfonyl)-1H-indole,
81) 3-(1-methyl-1,2,3,6-tetrahydropyridin-4-yl)-1-{phenylsulfonyl)-5-pyridin-4-yl-1H-indole,
82) 4-{[3-(1-methyl-1,2,3,6-tetrahydropyridin-4-yl)-5-(trifluoromethyl)-1H-indol-1-yl]sulfonyl}aniline,
83) 4-{[3-(1-methyl-1,2,3,6-tetrahydropyridin-4-yl)-1H-pyrrolo[2,3-b]pyridin-1-yl]sulfonyl}aniline,
84) 3-(1-methyl-1,2,3,6-tetrahydropyridin-4-yl)-1-(phenylsulfonyl)-5-pyridin-3-yl-1H-indole,
85) 3-(1-methyl-1,2,3,6-tetrahydropyridin-4-yl)-1-(phenylsulfonyl)-6-pyridin-3-yl-1H-indole,
86) 3-(1-methyl-1,2,3,6-tetrahydropyridin-4-yl)-1-phenylsulfonyl)-6-pyridin-4-yl-1H-indole,
87) 3-(1-methyl-1,2,3,6-tetrahydropyridin-4-yl)-1-[(4-morpholin-4-ylphenyl)sulfonyl]-1H-indole,
88) 5-fluoro-3-(1-methyl-1,2,3,6-tetrahydropyridin-4-yl)-1-[(4-morpholin-4-ylphenyl)sulfonyl]-1H-indole,
89) 3-(1-methyl-1,2,3,6-tetrahydropyridin-4-yl)-1-[(4-morpholin-4-ylphenyl)sulfonyl]-5-(trifluoromethyl)-1H-indole,
90) 3-(1-methyl-1,2,3,6-tetrahydropyridin-4-yl)-1-[(4-morpholin-4-ylphenyl)sulfonyl]-1H-pyrrolo[2,3-b]pyridine,
91) N,N-dimethyl-4-{[3-(1-methyl-1,2,3,6-tetrahydropyridin-4-yl)-1H-indol-1-yl]sulfonyl}aniline,
92) 4-{[5-fluoro-3-(1-methyl-1,2,3,6-tetrahydropyridin-4-yl)-1H-indol-1-yl]sulfonyl}-N,N-dimethylaniline,
93) N,N-dimethyl-4-{[3-(1-methyl-1,2,3,6-tetrahydropyridin-4-yl)-5-(trifluoromethyl)-1H-indol-1-yl]sulfonyl}aniline,
94) N,N-dimethyl-4-{[3-(1-methyl-1,2,3,6-tetrahydropyridin-4-yl)-1H-pyrrolo[2,3-b]pyridin-1-yl]sulfonyl}aniline,
95) N,N-dimethyl-3-{[3-(1-methyl-1,2,3,6-tetrahydropyridin-4-yl)-1H-indol-1-yl]sulfonyl}aniline,
96) 3-{[5-fluoro-3-(1-methyl-1,2,3,6-tetrahydropyridin-4-yl)-1H-indol-1-yl]sulfonyl}-N,N-dimethylaniline,
97) N,N-dimethyl-3-{[3-(1-methyl-1,2,3,6-tetrahydropyridin-4-yl)-5-(trifluoromethyl)-1H-indol-1-yl]sulfonyl}aniline,
98) N,N-dimethyl-3-{[3-(1-methyl-1,2,3,6-tetrahydropyridin-4-yl)-1H-pyrrolo[2,3-b]pyridin-1-yl]sulfonyl}aniline,
99) 3-(1-methyl-1,2,3,6-tetrahydropyridin-4-yl)-1-(phenylsulfonyl)-5-pyrrolidin-1-yl-1H-indole,
100) 3-(1-methyl-1,2,3,6-tetrahydropyridin-4-yl)-1-(phenylsulfonyl)-6-pyrrolidin-1-yl-1H-indole,
101) 3-(1-methyl-1,2,3,6-tetrahydropyridin-4-yl)-1-(phenylsulfonyl)-5-piperidin-1-yl-1H-indole,
102) 3-(1-methyl-1,2,3,6-tetrahydropyridin-4-yl)-1-(phenylsulfonyl)-6-piperidin-1-yl-1H-indole,
103) 3-(1-methyl-1,2,3,6-tetrahydropyridin-4-yl)-5-morpholin-4-yl-1-(phenylsulfonyl)-1H-indole,
104) 3-(1-methyl-1,2,3,6-tetrahydropyridin-4-yl)-6-morpholin-4-yl-1-(phenylsulfonyl)-1H-indole,
105) 3-(1-methyl-1,2,3,6-tetrahydropyridin-4-yl)-1-(phenylsulfonyl)-5-pyridin-2-yl-1H-indole dihydrochloride,
106) 3-(1-methyl-1,2,3,6-tetrahydropyridin-4-yl)-1-(phenylsulfonyl)-6-pyridin-2-yl-1H-indole dihydrochloride,
107) 1-[(1-methyl-2,3-dihydro-1H-indol-6-yl)sulfonyl]-3-(1-methyl-1,2,3,6-tetrahydropyridin-4-yl)-1H-indole, 108) 5-fluoro-1-[(1-methyl-2,3-dihydro-1H-indol-6-yl)sulfonyl]-3-(1-methyl-1,2,3,6-tetrahydropyridin-4-yl)-1H-indole,
109) 1-[(1-methyl-2,3-dihydro-1H-indol-6-yl)sulfonyl]-3-(1-methyl-1,2,3,6-tetrahydropyridin-4-yl)-5-(trifluoromethyl)-1H-indole,
110) 1-[(1-methyl-2,3-dihydro-1H-indol-6-yl)sulfonyl]-3-(1-methyl-1,2,3,6-tetrahydropyridin-4-yl)-1H-pyrrolo[2,3-b]pyridine,
111) 1-[(1-ethyl-2,3-dihydro-1H-indol-6-yl)sulfonyl]-3-(1-methyl-1,2,3,6-tetrahydropyridin-4-yl)-1H-indole,
112) 1-[(1-ethyl-2,3-dihydro-1H-indol-6-yl)sulfonyl]-5-fluoro-3-(1-methyl-1,2,3,6-tetrahydropyridin-4-yl)-1H-indole,
113) 1-[(1-ethyl-2,3-dihydro-1H-indol-6-yl)sulfonyl]-3-(1-methyl-1,2,3,6-tetrahydropyridin-4-yl)-5-(trifluoromethyl)-1H-indole,
114) 1-[(1-ethyl-2,3-dihydro-1H-indol-6-yl)sulfonyl]-3-(1-methyl-1,2,3,6-tetrahydropyridin-4-yl)-1H-pyrrolo[2,3-b]pyridine,
115) N-methyl-N-(4-{[3-(1-methyl-1,2,3,6-tetrahydropyridin-4-yl)-1H-indol-1-yl]sulfonyl}phenyl)acetamide,
116) N-(4-{[5-fluoro-3-(1-methyl-1,2,3,6-tetrahydropyridin-4-yl)-1H-indol-1-yl]sulfonyl}phenyl)-N-methyl acetamide,
117) N-methyl-N-(4-{[3-(1-methyl-1,2,3,6-tetrahydropyridin-4-yl)-5-(trifluoromethyl)-1H-indol-1-yl]sulfonyl}phenyl)acetamide,
118) N-methyl-N-(4-{[3-(1-methyl-1,2,3,6-tetrahydropyridin-4-yl)-1H-pyrrolo[2,3-b]pyridin-1-yl]sulfonyl}phenyl)acetamide,
119) 7-{[3-(1-methyl-1,2,3,6-tetrahydropyridin-4-yl)-1H-indol-1-yl]sulfonyl}-1,2,3,4-tetrahydroquinoline,
120) 7-{[5-fluoro-3-(1-methyl-1,2,3,6-tetrahydropyridin-4-yl)-1H-indol-1-yl]sulfonyl}-1,2,3,4-tetrahydroquinoline,
121) 7-{[3-(1-methyl-1,2,3,6-tetrahydropyridin-4-yl)-5-(trifluoromethyl)-1H-indol-1-yl]sulfonyl}-1,2,3,4-tetrahydroquinoline,
122) 7-{[3-(1-methyl-1,2,3,6-tetrahydropyridin-4-yl)-1H-pyrrolo[2,3-b]pyridin-1-yl]sulfonyl}-1,2,3,4-tetrahydroquinoline,
123) 1-methyl-7-{[3-(1-methyl-1,2,3,6-tetrahydropyridin-4-yl)-1H-indol-1-yl]sulfonyl}-1,2,3,4-tetrahydroquinoline,
124) 7-{[5-fluoro-3-(1-methyl-1,2,3,6-tetrahydropyridin-4-yl)-1H-indol-1-yl]sulfonyl}-1-methyl-1,2,3,4-tetrahydroquinoline,
125) 1-methyl-7-{[3-(1-methyl-1,2,3,6-tetrahydropyridin-4-yl)-5-(trifluoromethyl)-1H-indol-1-yl]sulfonyl}-1,2,3,4-tetrahydroquinoline,
126) 1-methyl-7-{[3-(1-methyl-1,2,3,6-tetrahydropyridin-4-yl)-1H-pyrrolo[2,3-b]pyridin-1-yl]sulfonyl}-1,2,3,4-tetrahydroquinoline,
127) 1-methyl-6-{[3-(1-methyl-1,2,3,6-tetrahydropyridin-4-yl)-1H-indol-1-yl]sulfonyl}-1,2,3,4-tetrahydroquinoline,
128) 6-{[5-fluoro-3-(1-methyl-1,2,3,6-tetrahydropyridin-4-yl)-1H-indol-1-yl]sulfonyl}-1-methyl-1,2,3,4-tetrahydroquinoline,
129) 1-methyl-6-{[3-(1-methyl-1,2,3,6-tetrahydropyridin-4-yl)-5-(trifluoromethyl)-1H-indol-1-yl]sulfonyl}-1,2,3,4-tetrahydroquinoline,
130) 1-methyl-6-{[3-(1-methyl-1,2,3,6-tetrahydropyridin-4-yl)-1H-pyrrolo[2,3-b]pyridin-1-yl]sulfonyl}-1,2,3,4-tetrahydroquinoline,
131) 3-(1-methyl-1,2,3,6-tetrahydropyridin-4-yl)-1-[(4-pyrrolidin-1-ylphenyl)sulfonyl]-1H-indole,
132) 5-fluoro-3-(1-methyl-1,2,3,6-tetrahydropyridin-4-yl)-1-[(4-pyrrolidin-1-ylphenyl)sulfonyl]-1H-indole,
133) 3-(1-methyl-1,2,3,6-tetrahydropyridin-4-yl)-1-[(4-pyrrolidin-1-ylphenyl)sulfonyl]-5-(trifluoromethyl)-1H-indole,
134) 3-(1-methyl-1,2,3,6-tetrahydropyridin-4-yl)-1-[(4-pyrrolidin-1-ylphenyl)sulfonyl]-1H-pyrrolo[2,3-b]pyridine,
135) 3-(1-methyl-1,2,3,6-tetrahydropyridin-4-yl)-1-[(3-pyrrolidin-1-ylphenyl)sulfonyl]-1H-indole,
136) 5-fluoro-3-(1-methyl-1,2,3,6-tetrahydropyridin-4-yl)-1-[(3-pyrrolidin-1-ylphenyl)sulfonyl]-1H-indole,
137) 3-(1-methyl-1,2,3,6-tetrahydropyridin-4-yl)-1-[(3-pyrrolidin-1-ylphenyl)sulfonyl]-5-(trifluoromethyl)-1H-indole,
138) 3-(1-methyl-1,2,3,6-tetrahydropyridin-4-yl)-1-[(3-pyrrolidin-1-ylphenyl)sulfonyl]-1H-pyrrolo[2,3-b]pyridine,
139) 1-[(1-ethyl-3-methyl-1H-pyrazol-4-yl)sulfonyl]-3-(1-methyl-1,2,3,6-tetrahydropyridin-4-yl)-1H-indole,
140) 1-[(1-ethyl-3-methyl-1H-pyrazol-4-yl)sulfonyl]-5-fluoro-3-(1-methyl-1,2,3,6-tetrahydropyridin-4-yl)-1H-indole,
141) 1-[(1-ethyl-3-methyl-1H-pyrazol-4-yl)sulfonyl]-3-(1-methyl-1,2,3,6-tetrahydropyridin-4-yl)-5-(trifluoromethyl)-1H-indole,
142) 1-{[1-(difluoromethyl)-5-methyl-1H-pyrazol-4-yl]sulfonyl}-3-(1-methyl-1,2,3,6-tetrahydropyridin-4-yl)-1H-indole,
143) 1-{[1-(difluoromethyl)-5-methyl-1H-pyrazol-4-yl]sulfonyl}-5-fluoro-3-(1-methyl-1,2,3,6-tetrahydropyridin-4-yl)-1H-indole,
144) 1-{[1-(difluoromethyl)-5-methyl-1H-pyrazol-4-yl]sulfonyl}-3-(1-methyl-1,2,3,6-tetrahydropyridin-4-yl)-5-(trifluoromethyl)-1H-indole,
145) 1-[(1-ethyl-5-methyl-1H-pyrazol-4-yl)sulfonyl]-3-(1-methyl-1,2,3,6-tetrahydropyridin-4-yl)-1H-indole,
146) 1-[(1-ethyl-5-methyl-1H-pyrazol-4-yl)sulfonyl]-5-fluoro-3-(1-methyl-1,2,3,6-tetrahydropyridin-4-yl)-1H-indole,
147) 1-[(1-ethyl-5-methyl-1H-pyrazol-4-yl)sulfonyl]-3-(1-methyl-1,2,3,6-tetrahydropyridin-4-yl)-5-(trifluoromethyl)-1H-indole,
148) 1-[(1-ethyl-1H-pyrazol-4-yl)sulfonyl]-3-(1-methyl-1,2,3,6-tetrahydropyridin-4-yl)-1H-indole
149) 1-[(1-ethyl-1H-pyrazol-4-yl)sulfonyl]-5-fluoro-3-(1-methyl-1,2,3,6-tetrahydropyridin-4-yl)-1H-indole,
150) 1-[(1-ethyl-1H-pyrazol-4-yl)sulfonyl]-3-(1-methyl-1,2,3,6-tetrahydropyridin-4-yl)-5-(trifluoromethyl)-1H-indole,
151) 1-[(1-ethyl-3,5-dimethyl-1H-pyrazol-4-yl)sulfonyl]-3-(1-methyl-1,2,3,6-tetrahydropyridin-4-yl)-1H-indole,
152) 1-[(1-ethyl-3,5-dimethyl-1H-pyrazol-4-yl)sulfonyl]-5-fluoro-3-(1-methyl-1,2,3,6-tetrahydropyridin-4-yl)-1H-indole,
153) 1-[(1-ethyl-3,5-dimethyl-1H-pyrazol-4-yl)sulfonyl]-3-(1-methyl-1,2,3,6-tetrahydropyridin-4-yl)-5-(trifluoromethyl)-1H-indole,
154) 1-[(1-methyl-1H-pyrazol-4-yl)sulfonyl]-3-(1-methyl-1,2,3,6-tetrahydropyridin-4-yl)-1H-indole,
155) 5-fluoro-1-[(1-methyl-1H-pyrazol-4-yl)sulfonyl]-3-(1-methyl-1,2,3,6-tetrahydropyridin-4-yl)-1H-indole,
156) 1-[(1-methyl-1H-pyrazol-4-yl)sulfonyl]-3-(1-methyl-1,2,3,6-tetrahydropyridin-4-yl)-5-(trifluoromethyl)-1H-indole,
157) 1-[(1,5-dimethyl-1H-pyrazol-4-yl)sulfonyl]-3-(1-methyl-1,2,3,6-tetrahydropyridin-4-yl)-1H-indole,
158) 1-[(1,5-dimethyl-1H-pyrazol-4-yl)sulfonyl]-5-fluoro-3-(1-methyl-1,2,3,6-tetrahydropyridin-4-yl)-1H-indole, 159) 1-[(1,5-dimethyl-1H-pyrazol-4-yl)sulfonyl]-3-(1-methyl-1,2,3,6-tetrahydropyridin-4-yl)-5-(trifluoromethyl)-1H-indole,
160) 1-[(1,3-dimethyl-1H-pyrazol-4-yl)sulfonyl]-3-(1-methyl-1,2,3,6-tetrahydropyridin-4-yl)-1H-indole,
161) 1-[(1,3-dimethyl-1H-pyrazol-4-yl)sulfonyl]-5-fluoro-3-(1-methyl-1,2,3,6-tetrahydropyridin-4-yl)-1H-indole,
162) 1-[(1,3-dimethyl-1H-pyrazol-4-yl)sulfonyl]-3-(1-methyl-1,2,3,6-tetrahydropyridin-4-yl)-5-(trifluoromethyl)-1H-indole,
163) 1-[(1-methyl-2,3-dihydro-1H-indol-5-yl)sulfonyl]-3-(1-methyl-1,2,3,6-tetrahydropyridin-4-yl)-1H-indole,
164) 5-fluoro-1-[(1-methyl-2,3-dihydro-1H-indol-5-yl)sulfonyl]-3-(1-methyl-1,2,3,6-tetrahydropyridin-4-yl)-1H-indole,
165) 1-[(1-methyl-2,3-dihydro-1H-indol-5-yl)sulfonyl]-3-(1-methyl-1,2,3,6-tetrahydropyridin-4-yl)-5-(trifluoromethyl)-1H-indole,
166) 1-[(1-methyl-2,3-dihydro-1H-indol-5-yl)sulfonyl]-3-(1-methyl-1,2,3,6-tetrahydropyridin-4-yl)-1H-pyrrolo[2,3-b]pyridine,
167) 1-(2,2-dimethylpropanoyl)-5-{[3-(1-methyl-1,2,3,6-tetrahydropyridin-4-yl)-1H-indol-1-yl]sulfonyl}-1H-indazole,
168) 1-(2,2-dimethylpropanoyl)-5-{[5-fluoro-3-(1-methyl-1,2,3,6-tetrahydropyridin-4-yl)-1H-indol-1-yl]sulfonyl}-1H-indazole,
169) 1-(2,2-dimethylpropanoyl)-5-{[3-(1-methyl-1,2,3,6-tetrahydropyridin-4-yl)-5-(trifluoromethyl)-1H-indol-1-yl]sulfonyl}-1H-indazole,
170) 1-{[1-(difluoromethyl)-3-methyl-1H-pyrazol-4-yl]sulfonyl}-3-(1-methyl-1,2,3,6-tetrahydropyridin-4-yl)-1H-indole,
171) 1-{[1-(difluoromethyl)-3-methyl-1H-pyrazol-4-yl]sulfonyl}-5-fluoro-3-(1-methyl-1,2,3,6-tetrahydropyridin-4-yl)-1H-indole,
172) 1-{[1-(difluoromethyl)-3-methyl-1H-pyrazol-4-yl]sulfonyl}-3-(1-methyl-1,2,3,6-tetrahydropyridin-4-yl)-5-(trifluoromethyl)-1H-indole,
173) 1-(2,3-dihydro-1,4-benzodioxin-6-ylsulfonyl)-3-(1-methyl-1,2,3,6-tetrahydropyridin-4-yl)-1H-indole,
174) 1-(2,3-dihydro-1,4-benzodioxin-6-ylsulfonyl)-5-fluoro-3-(1-methyl-1,2,3,6-tetrahydropyridin-4-yl)-1H-indole,
175) 1-(2,3-dihydro-1,4-benzodioxin-6-ylsulfonyl)-3-(1-methyl-1,2,3,6-tetrahydropyridin-4-yl)-5-(trifluoromethyl)-1H-indole,
176) 4-{[3-(1-methyl-1,2,3,6-tetrahydropyridin-4-yl)-1H-indol-1-yl]sulfonyl}aniline,
177) 4-{[5-fluoro-3-(1-methyl-1,2,3,6-tetrahydropyridin-4-yl)-1H-indol-1-yl]sulfonyl}aniline,
178) 1-(2,2-dimethylpropanoyl)-5-{[3-(1-methyl-1,2,3,6-tetrahydropyridin-4-yl)-1H-pyrrolo[2,3-b]pyridin-1-yl]sulfonyl}-1H-indazole
179) 6-{[3-(1-methyl-1,2,3,6-tetrahydropyridin-4-yl)-1H-pyrrolo[2,3-b]pyridin-1-yl]sulfonyl}-3,4-dihydroquinolin-2(1H)-one,
180) 1-methyl-6-{[3-(1-methyl-1,2,3,6-tetrahydropyridin-4-yl)-1H-pyrrolo[2,3-b]pyridin-1-yl]sulfonyl}-3,4-dihydroquinolin-2(1H)-one,
181) 1-methyl-6-{[3-(1-methyl-1,2,3,6-tetrahydropyridin-4-yl)-5-(trifluoromethyl)-1H-indol-1-yl]sulfonyl}-3,4-dihydroquinolin-2(1H)-one,
182) 6-{[5-fluoro-3-(1-methyl-1,2,3,6-tetrahydropyridin-4-yl)-1H-indol-1-yl]sulfonyl}-1-methyl-3,4-dihydroquinolin-2(1H)-one,
183) 1-methyl-6-{[3-(1-methyl-1,2,3,6-tetrahydropyridin-4-yl)-1H-indol-1-yl]sulfonyl}-3,4-dihydroquinolin-2(1H)-one,
184) 1-(2,3-dihydro-1,4-benzodioxin-6-ylsulfonyl)-3-(1-methylpiperidin-4-yl)-1H-pyrrolo[2,3-b]pyridine,
185) 1-(2,3-dihydro-1,4-benzodioxin-6-ylsulfonyl)-3-(1,2,3,6-tetrahydropyridin-4-yl)-1H-pyrrolo[2,3-b]pyridine,
186) 5-fluoro-1-[(1-methyl-1H-indol-5-yl)sulfonyl]-3-(1-methyl-1,2,3,6-tetrahydropyridin-4-yl)-1H-indole,
187) 3-(1-methyl-1,2,3,6-tetrahydropyridin-4-yl)-6-(1,3-oxazol-2-yl)-1-(pyridin-3-ylsulfonyl)-1H-indole,
188) 1-(2,3-dihydro-1,4-benzodioxin-6-ylsulfonyl)-3-(1-methyl-1,2,3,6-tetrahydropyridin-4-yl)-6-(1,3-oxazol-2-yl)-1H-indole,
189) 1-[(1-ethyl-1H-pyrazol-4-yl)sulfonyl]-3-(1-methyl-1,2,3,6-tetrahydropyridin-4-yl)-6-(1,3-oxazol-2-yl)-1H-indole,
190) 1-[(1-ethyl-1H-pyrazol-4-yl)sulfonyl]-3-(1-methyl-1,2,3,6-tetrahydropyridin-4-yl)-5-(1,3-oxazol-2-yl)-1H-indole,
191) 1-(2,3-dihydro-1,4-benzodioxin-6-ylsulfonyl)-3-(1-methyl-1,2,3,6-tetrahydropyridin-4-yl)-5-(1,3-oxazol-2-yl)-1H-indole,
192) 5-(3,6-dihydro-2H-pyran-4-yl)-3-(1-methyl-1,2,3,6-tetrahydropyridin-4-yl)-1-(phenylsulfonyl)-1H-indole,
193) 3-(1-methyl-1,2,3,6-tetrahydropyridin-4-yl)-1-(phenylsulfonyl)-6-(1,3-thiazol-2-yl)-1H-indole,
194) 5-fluoro-1-{[6-(3-methoxypyrrolidin-1-yl)pyridin-3-yl]sulfonyl}-3-(1-methyl-1,2,3,6-tetrahydropyridin-4-yl)-1H-indole,
195) 1-{[6-(3-methoxypyrrolidin-1-yl)pyridin-3-yl]sulfonyl}-3-(1-methyl-1,2,3,6-tetrahydropyridin-4-yl)-1H-pyrrolo[2,3-b]pyridine,
196) 7-{[5-fluoro-3-(1-methyl-1,2,3,6-tetrahydropyridin-4-yl)-1H-indol-1-yl]sulfonyl}-2H-1,4-benzoxazin-3(4H)-one,
197) 7-{[3-(1-methyl-1,2,3,6-tetrahydropyridin-4-yl)-1H-pyrrolo[2,3-b]pyridin-1-yl]sulfonyl}-2H-1,4-benzoxazin-3(4H)-one,
198) 1-[(1-acetyl-2,3-dihydro-1H-indol-6-yl)sulfonyl]-5-fluoro-3-(1-methyl-1,2,3,6-tetrahydropyridin-4-yl)-1H-indole,
199) 1-[(1-acetyl-2,3-dihydro-1H-indol-6-yl)sulfonyl]-3-(1-methyl-1,2,3,6-tetrahydropyridin-4-yl)-1H-pyrrolo[2,3-b]pyridine,
200) 4-methyl-7-{[3-(1-methyl-1,2,3,6-tetrahydropyridin-4-yl)-1H-pyrrolo[2,3-b]pyridin-1-yl]sulfonyl}-3,4->dihydro-2H-1,4-benzoxazine,
201) 1-(2,3-dihydro-1,4-benzodioxin-6-ylsulfonyl)-5-fluoro-3-(1-methylpiperidin-4-yl)-1H-indole hydroformate,
202) 1-(2,3-dihydro-1,4-benzodioxin-6-ylsulfonyl)-3-(1-methyl-1,2,3,6-tetrahydropyridin-4-yl)-1H-pyrrolo[3,2-b]pyridine,
203) 4-methyl-7-{[3-(1-methyl-1,2,3,6-tetrahydropyridin-4-yl)-1H-pyrrolo[3,2-b]pyridin-1-yl]sulfonyl}-3,4-dihydro-2H-1,4-benzoxazine,
204) 3-(1-methyl-1,2,3,6-tetrahydropyridin-4-yl)-5-(1,3-oxazol-2-yl)-1-(pyridin-3-ylsulfonyl)-1H-indole,
205) 1-(2,3-dihydro-1,4-benzodioxin-6-ylsulfonyl)-3-(1-methyl-1,2,3,6-tetrahydropyridin-4-yl)-5-(1,3-thiazol-2-yl)-1H-indole,
206) 3-(1-methyl-1,2,3,6-tetrahydropyridin-4-yl)-1-(pyridin-3-ylsulfonyl)-5-(1,3-thiazol-2-yl)-1H-indole,
207) 1-[(1-ethyl-1H-pyrazol-4-yl)sulfonyl]-3-(1-methyl-1,2,3,6-tetrahydropyridin-4-yl)-5-(1,3-thiazol-2-yl)-1H-indole, 208) 1-[(1-methyl-2,3-dihydro-1H-indol-5-yl)sulfonyl]-3-(1-methyl-1,2,3,6-tetrahydropyridin-4-yl)-1H-pyrrolo[3,2-b]pyridine,
209) 1-[(1-acetyl-2,3-dihydro-1H-indol-5-yl)sulfonyl]-3-(1-methyl-1,2,3,6-tetrahydropyridin-4-yl)-1H-pyrrolo[3,2-b]pyridine,
210) 1-(4-{[3-(1-methyl-1,2,3,6-tetrahydropyridin-4-yl)-1H-pyrrolo[2,3-b]pyridin-1-yl]sulfonyl}phenyl)pyrrolidin-2-one,
211) 3-methyl-6-{[3-(1-methyl-1,2,3,6-tetrahydropyridin-4-yl)-1H-pyrrolo[2,3-b]pyridin-1-yl]sulfonyl}-1,3-benzoxazol-2(3H)-one,
212) 1-[(1-methyl-2,3-dihydro-1H-indol-5-yl)sulfonyl]-3-(1-methyl-1,2,3,6-tetrahydropyridin-4-yl)-1H-pyrrolo[2,3-b]pyridine,
213) 1-[(1-acetyl-2,3-dihydro-1H-indol-5-yl)sulfonyl]-3-(1-methyl-1,2,3,6-tetrahydropyridin-4-yl)-1H-pyrrolo[2,3-b]pyridine,
214) 1-(4-{[3-(1-methyl-1,2,3,6-tetrahydropyridin-4-yl)-1H-pyrrolo[3,2-b]pyridin-1-yl]sulfonyl}phenyl)pyrrolidin-2-one,
215) 3-methyl-6-{[3-(1-methyl-1,2,3,6-tetrahydropyridin-4-yl)-1H-pyrrolo[3,2-b]pyridin-1-yl]sulfonyl}-1,3-benzoxazol-2(3H)-one,
216) 7-{[5-fluoro-3-(1-methyl-1,2,3,6-tetrahydropyridin-4-yl)-1H-indol-1-yl]sulfonyl}-4-methyl-3,4-dihydro-2H-1,4-benzoxazine; compound with formic acid,
217) 7-{[5-fluoro-3-(1-methylpiperidin-4-yl)-1H-indol-1-yl]sulfonyl}-4-methyl-3,4-dihydro-2H-1,4-benzoxazine; compound with formic acid,
218) 1-(2,3-dihydro-1,4-benzodioxin-6-ylsulfonyl)-5-fluoro-3-(1,2,3,6-tetrahydropyridin-4-yl)-1H-indole hydroformate,
219) 6-{[3-(1-methyl-1,2,3,6-tetrahydropyridin-4-yl)-1H-pyrrolo[2,3-b]pyridin-1-yl]sulfonyl}-2H-1,4-benzoxazin-3(4H)-one,
220) 5-{[3-(1-methyl-1,2,3,6-tetrahydropyridin-4-yl)-1H-pyrrolo[3,2-b]pyridin-1-yl]sulfonyl}-1,3-dihydro-2H-benzimidazol-2-one,
221) 7-{[3-(1-methyl-1,2,3,6-tetrahydropyridin-4-yl)-1H-pyrrolo[3,2-b]pyridin-1-yl]sulfonyl}-2H-1,4-benzoxazin-3(4H)-one,
222) 6-{[3-(1-methyl-1,2,3,6-tetrahydropyridin-4-yl)-1H-pyrrolo[3,2-b]pyridin-1-yl]sulfonyl}-2H-1,4-benzoxazin-3(4H)-one,
223) 6-{[5-fluoro-3-(1-methyl-1,2,3,6-tetrahydropyridin-4-yl)-1H-indol-1-yl]sulfonyl}-2H-1,4-benzoxazin-3(4H)-one; compound with formic acid,
224) 6-{[5-fluoro-3-(1-methyl-1,2,3,6-tetrahydropyridin-4-yl)-1H-indol-1-yl]sulfonyl}-3-methyl-1,3-benzoxazol-2(3H)-one; compound with formic acid,
225) 7-{[6-(3-methoxypyrrolidin-1-yl)-3-(1-methyl-1,2,3,6-tetrahydropyridin-4-yl)-1H-indol-1-yl]sulfonyl}-4-methyl-3,4-dihydro-2H-1,4-benzoxazine,
226) 6-(3-methoxypyrrolidin-1-yl)-3-(1-methyl-1,2,3,6-tetrahydropyridin-4-yl)-1-(pyridin-3-ylsulfonyl)-1H-indole,
227) 6-(3-methoxypyrrolidin-1-yl)-1-[(1-methyl-1H-indol-5-yl)sulfonyl]-3-(1-methyl-1,2,3,6-tetrahydropyridin-4-yl)-1H-indole,
228) 7-{[4-fluoro-3-(1-methyl-1,2,3,6-tetrahydropyridin-4-yl)-1H-indol-1-yl]sulfonyl}-4-methyl-3,4-dihydro-2H-1,4-benzoxazine; compound with formic acid,
229) 7-[5-Fluoro-3-(1-methyl-1,2,3,6-tetrahydro-pyridin-4-yl)-indole-1-sulfonyl]-4-methyl-3,4-dihydro-2H-benzo[1,4]oxazine,
230) 7-{[6-fluoro-3-(1-methyl-1,2,3,6-tetrahydropyridin-4-yl)-1H-indol-1-yl]sulfonyl}-4-methyl-3,4-dihydro-2H-1,4-benzoxazine; compound with formic acid,
231) 7-{[7-fluoro-3-(1-methyl-1,2,3,6-tetrahydropyridin-4-yl)-1H-indol-1-yl]sulfonyl}-4-methyl-3,4-dihydro-2H-1,4-benzoxazine; compound with formic acid,
232) 1-[(1-acetyl-2,3-dihydro-1H-indol-5-yl)sulfonyl]-3-(1,2,3,6-tetrahydropyridin-4-yl)-1H-pyrrolo[2,3-b]pyridine,
233) 1-(3,4-dihydro-2H-1,5-benzodioxepin-7-ylsulfonyl)-3-(1-methyl-1,2,3,6-tetrahydropyridin-4-yl)-1H-pyrrolo[3,2-b]pyridine,
234) 4-methyl-6-{[3-(1-methyl-1,2,3,6-tetrahydropyridin-4-yl)-1H-pyrrolo[3,2-b]pyridin-1-yl]sulfonyl}-3,4-dihydro-2H-1,4-benzoxazine,
235) 1-[(1-acetyl-2,3-dihydro-1H-indol-5-yl)sulfonyl]-3-(1-methylpiperidin-4-yl)-1H-pyrrolo[2,3-b]pyridine,
236) 7-{[3,5-bis(1-methyl-1,2,3,6-tetrahydropyridin-4-yl)-1H-indol-1-yl]sulfonyl}-4-methyl-3,4-dihydro-2H-1,4-benzoxazine,
237) 7-{[3-(1-methyl-1,2,3,6-tetrahydropyridin-4-yl)-1H-indazol-1-yl]sulfonyl}-2H-1,4-benzoxazin-3(4H)-one,
238) 1-[(1-methyl-1H-indol-5-yl)sulfonyl]-3-(1-methyl-1,2,3,6-tetrahydropyridin-4-yl)-1H-indazole,
239) 1-[(1-methyl-1H-indol-5-yl)sulfonyl]-3,5-bis(1-methyl-1,2,3,6-tetrahydropyridin-4-yl)-1H-indole,
240) 1-(2,3-dihydro-1,4-benzodioxin-6-ylsulfonyl)-3-piperidin-4-yl-1H-pyrrolo[2,3-b]pyridine; compound with formic acid,
241) 1-(2,3-dihydro-1,4-benzodioxin-6-ylsulfonyl)-5-fluoro-3-piperidin-4-yl-1H-indole hydroformate,
242) 7-{[3,5-bis(1-methylpiperidin-4-yl)-1H-indol-1-yl]sulfonyl}-4-methyl-3,4-dihydro-2H-1,4-benzoxazine,
243) 1-[(1-acetyl-2,3-dihydro-1H-indol-5-yl)sulfonyl]-3-(1-methyl-1,2,3,6-tetrahydropyridin-4-yl)-1H-pyrrolo[2,3-b]pyridine,
244) 1-[(1-acetyl-2,3-dihydro-1H-indol-5-yl)sulfonyl]-3-piperidin-4-yl-1H-pyrrolo[2,3-b]pyridine,
245) 4-methyl-7-{[3-(1-methylpiperidin-4-yl)-1H-pyrrolo[3,2-b]pyridin-1-yl]sulfonyl}-3,4-dihydro-2H-1,4-benzoxazine; compound with formic acid,
246) 4-methyl-7-{[3-(1,2,3,6-tetrahydropyridin-4-yl)-1H-pyrrolo[3,2-b]pyridin-1-yl]sulfonyl}-3,4-dihydro-2H-1,4-benzoxazine; compound with formic acid,
247) 4-methyl-7-[(3-piperidin-4-yl-1H-pyrrolo[3,2-b]pyridin-1-yl)sulfonyl]-3,4-dihydro-2H-1,4-benzoxazine; compound with formic acid,
248) 4-methyl-7-{[3-(1-methyl-1,2,3,6-tetrahydropyridin-4-yl)-1H-indazol-1-yl]sulfonyl}-3,4-dihydro-2H-1,4-benzoxazine; compound with formic acid,
249) 1-{[3-(3-methoxypyrrolidin-1-yl)phenyl]sulfonyl}-3-(1-methyl-1,2,3,6-tetrahydropyridin-4-yl)-1H-pyrrolo[2,3-b]pyridine,
250) 1-(3-{[3-(1-methyl-1,2,3,6-tetrahydropyridin-4-yl)-1H-pyrrolo[2,3-b]pyridin-1-yl]sulfonyl}phenyl)pyrrolidin-2-one,
251) 1-[(5-bromo-2,3-dihydro-1-benzofuran-7-yl)sulfonyl]-3-(1-methyl-1,2,3,6-tetrahydropyridin-4-yl)-1H-pyrrolo[2,3-b]pyridine,
252) 1-{[3-(3-methoxypyrrolidin-1-yl)phenyl]sulfonyl}-3-(1-methyl-1,2,3,6-tetrahydropyridin-4-yl)-1H-pyrrolo[3,2-b]pyridine,
253) 1-(3-{[3-(1-methyl-1,2,3,6-tetrahydropyridin-4-yl)-1H-pyrrolo[3,2-b]pyridin-1-yl]sulfonyl}phenyl)pyrrolidin-2-one,
254) 1-[(5-bromo-2,3-dihydro-1-benzofuran-7-yl)sulfonyl]-3-(1-methyl-1,2,3,6-tetrahydropyridin-4-yl)-1H-pyrrolo[3,2-b]pyridine, 255) 6-ethyl-1-[(1-methyl-1H-indol-5-yl)sulfonyl]-3-(1-methyl-1,2,3,6-tetrahydropyridin-4-yl)-1H-pyrrolo[2,3-b]pyridine,
256) 6-ethyl-1-[(1-methyl-1H-indol-6-yl)sulfonyl]-3-(1-methyl-1,2,3,6-tetrahydropyridin-4-yl)-1H-pyrrolo[2,3-b]pyridine,
257) 6-ethyl-3-(1-methyl-1,2,3,6-tetrahydropyridin-4-yl)-1-[(3-pyrrolidin-1-ylphenyl)sulfonyl]-1H-pyrrolo[2,3-b]pyridine,
258) 6-ethyl-1-{[3-(3-methoxypyrrolidin-1-yl)phenyl]sulfonyl}-3-(1-methyl-1,2,3,6-tetrahydropyridin-4-yl)-1H-pyrrolo[2,3-b]pyridine,
259) 1-(3-{[6-ethyl-3-(1-methyl-1,2,3,6-tetrahydropyridin-4-yl)-1H-pyrrolo[2,3-b]pyridin-1-yl]sulfonyl}phenyl)pyrrolidin-2-one,
260) 1-[(5-bromo-2,3-dihydro-1-benzofuran-7-yl)sulfonyl]-6-ethyl-3-(1-methyl-1,2,3,6-tetrahydropyridin-4-yl)-1H-pyrrolo[2,3-b]pyridine,
261) 3-(1-methyl-1,2,3,6-tetrahydropyridin-4-yl)-5-(1H-pyrazol-1-yl)-1-(pyridin-3-ylsulfonyl)-1H-indole; compound with formic acid,
262) 4-methyl-7-{[3-(1-methyl-1,2,3,6-tetrahydropyridin-4-yl)-5-(1H-pyrazol-1-yl)-1H-indol-1-yl]sulfonyl}-3,4-dihydro-2H-1,4-benzoxazine; compound with formic acid,
263) 5-(1H-imidazol-1-yl)-3-(1-methyl-1,2,3,6-tetrahydropyridin-4-yl)-1-(pyridin-3-ylsulfonyl)-1H-indole; compound with formic acid,
264) 7-{[5-(1H-imidazol-1-yl)-3-(1-methyl-1,2,3,6-tetrahydropyridin-4-yl)-1H-indol-1-yl]sulfonyl}-4-methyl-3,4-dihydro-2H-1,4-benzoxazine; compound with formic acid,
265) 1-[(1-acetyl-2,3-dihydro-1H-indol-5-yl)sulfonyl]-3-(1-methyl-1,2,3,6-tetrahydropyridin-4-yl)-1H-indazole,
266) 4-acetyl-6-{[3-(1-methyl-1,2,3,6-tetrahydropyridin-4-yl)-1H-indazol-1-yl]sulfonyl}-3,4-dihydro-2H-1,4-benzoxazine,
267) 5-{[3-(1-methyl-1,2,3,6-tetrahydropyridin-4-yl)-1H-indazol-1-yl]sulfonyl}-1,2-benzisoxazole,
268) 1-(1-benzothien-5-ylsulfonyl)-3-(1-methyl-1,2,3,6-tetrahydropyridin-4-yl)-1H-indazole,
269) 1-(1-benzofuran-5-ylsulfonyl)-3-(1-methyl-1,2,3,6-tetrahydropyridin-4-yl)-1H-indazole,
270) 1-[(1-acetyl-2,3-dihydro-1H-indol-5-yl)sulfonyl]-6-ethyl-3-(1-methyl-1,2,3,6-tetrahydropyridin-4-yl)-1H-pyrrolo[2,3-b]pyridine,
271) 6-{[3-(1-methyl-1,2,3,6-tetrahydropyridin-4-yl)-1H-indazol-1-yl]sulfonyl}-2H-1,4-benzoxazin-3(4H)-one,
272) 1-(1-benzofuran-5-ylsulfonyl)-3-(1-methyl-1,2,3,6-tetrahydropyridin-4-yl)-1H-pyrazolo[4,3-b]pyridine,
273) 1-(1-benzothien-5-ylsulfonyl)-3-(1-methyl-1,2,3,6-tetrahydropyridin-4-yl)-1H-pyrazolo[4,3-b]pyridine,
274) 1-(1-benzofuran-5-ylsulfonyl)-3-(1-methyl-1,2,3,6-tetrahydropyridin-4-yl)-1H-pyrazolo[3,4-b]pyridine,
275) 1-(1-benzothien-5-ylsulfonyl)-3-(1-methyl-1,2,3,6-tetrahydropyridin-4-yl)-1H-pyrazolo[3,4-b]pyridine,
276) 1-[(1-acetyl-2,3-dihydro-1H-indol-5-yl)sulfonyl]-5-fluoro-3-(1-methyl-1,2,3,6-tetrahydropyridin-4-yl)-1H-indazole; compound with formic acid,
277) 5-fluoro-1-[(1-methyl-1H-indol-5-yl)sulfonyl]-3-(1-methyl-1,2,3,6-tetrahydropyridin-4-yl)-1H-indazole; compound with formic acid,
278) 5-fluoro-1-[(1-methyl-1H-indol-6-yl)sulfonyl]-3-(1-methyl-1,2,3,6-tetrahydropyridin-4-yl)-1H-indazole; compound with formic acid,
279) 1-{[3-(3-methoxypyrrolidin-1-yl)phenyl]sulfonyl}-3-(1-methyl-1,2,3,6-tetrahydropyridin-4-yl)-1H-pyrazolo[4,3-b]pyridine,
280) 1-{[3-(3-methoxypyrrolidin-1-yl)phenyl]sulfonyl}-3-(1-methyl-1,2,3,6-tetrahydropyridin-4-yl)-1H-pyrazolo[3,4-b]pyridine,
281) 7-{[3-(1-methyl-1,2,3,6-tetrahydropyridin-4-yl)-1H-pyrazolo[4,3-b]pyridin-1-yl]sulfonyl}-2H-1,4-benzoxazin-3(4H)-one,
282) 7-{[3-(1-methyl-1,2,3,6-tetrahydropyridin-4-yl)-1H-pyrazolo[3,4-b]pyridin-1-yl]sulfonyl}-2H-1,4-benzoxazin-3(4H)-one,
283) 1-[(1-acetyl-2,3-dihydro-1H-indol-5-yl)sulfonyl]-3-(1-methyl-1,2,3,6-tetrahydropyridin-4-yl)-1H-pyrazolo[3,4-b]pyridine,
284) 1-[(1-acetyl-2,3-dihydro-1H-indol-5-yl)sulfonyl]-3-(1-methyl-1,2,3,6-tetrahydropyridin-4-yl)-1H-pyrazolo[4,3-b]pyridine,
285) 4-Methyl-7-(3-piperidin-4-yl-pyrrolo[3,2-b]pyridine-1-sulfonyl)-3,4-dihydro-2H-benzo[1,4]oxazine,
286) 1-(3-{[3-(1-methyl-1,2,3,6-tetrahydropyridin-4-yl)-1H-pyrrolo[3,2-b]pyridin-1-yl]sulfonyl}-phenyl)pyrrolidin-3-ol,
287) 1-[(1-acetyl-2,3-dihydro-1H-indol-6-yl)sulfonyl]-3-(1-methyl-1,2,3,6-tetrahydropyridin-4-yl)-1H-pyrrolo[2,3-b]pyridine,
288) 1-[(6-morpholin-4-ylpyridin-3-yl)sulfonyl]-3-(1,2,3,6-tetrahydropyridin-4-yl)-1H-pyrrolo[3,2-b]pyridine; compound with formic acid,
289) 1-{[6-(3-methoxypyrrolidin-1-yl)pyridin-3-yl]sulfonyl}-3-(1,2,3,6-tetrahydropyridin-4-yl)-1H-pyrrolo[3,2-b]pyridine; compound with formic acid,
290) 1-[(5-methoxypyridin-3-yl)sulfonyl]-3-(1,2,3,6-tetrahydropyridin-4-yl)-1H-pyrrolo[3,2-b]pyridine; compound with formic acid,
291) 1-{[5-(3-methoxypyrrolidin-1-yl)pyridin-3-yl]sulfonyl}-3-(1,2,3,6-tetrahydropyridin-4-yl)-1H-pyrrolo[3,2-b]pyridine; compound with formic acid,
292) 1-[(1-acetyl-2,3-dihydro-1H-indol-5-yl)sulfonyl]-3-(1,2,3,6-tetrahydropyridin-4-yl)-1H-pyrrolo[3,2-b]pyridine,
293) 5-methoxy-1-{[3-(3-methoxypyrrolidin-1-yl)phenyl]sulfonyl}-3-(1-methyl-1,2,3,6-tetrahydropyridin-4-yl)-1H-indole,
294) 7-{[3-(1,2,3,6-tetrahydropyridin-4-yl)-1H-pyrrolo[3,2-b]pyridin-1-yl]sulfonyl}-2H-1,4-benzoxazin-3(4H)-one,
295) 7-{[3-(1,2,3,6-tetrahydropyridin-4-yl)-1H-pyrrolo[3,2-b]pyridin-1-yl]sulfonyl}-3,4-dihydroquinolin-2(1H)-one,
296) 4-methyl-6-{[3-(1,2,3,6-tetrahydropyridin-4-yl)-1H-pyrrolo[3,2-b]pyridin-1-yl]sulfonyl}-3,4-dihydro-2H-1,4-benzoxazine,
297) 6-{[3-(1,2,3,6-tetrahydropyridin-4-yl)-1H-pyrrolo[3,2-b]pyridin-1-yl]sulfonyl}-2H-1,4-benzoxazin-3(4H)-one,
298) 7-{[5-methoxy-3-(1-methyl-1,2,3,6-tetrahydropyridin-4-yl)-1H-indol-1-yl]sulfonyl}-2H-1,4-benzoxazin-3(4H)-one,
299) 7-{[5-methoxy-3-(1-methyl-1,2,3,6-tetrahydropyridin-4-yl)-1H-indol-1-yl]sulfonyl}-4-methyl-3,4-dihydro-2H-1,4-benzoxazine,
300) 5-methoxy-3-(1-methyl-1,2,3,6-tetrahydropyridin-4-yl)-1-(pyridin-3-ylsulfonyl)-1H-indole,
301) 1-{[3-(3-methoxypyrrolidin-1-yl)phenyl]sulfonyl}-3-(4-methylpiperazin-1-yl)-1H-indazole,
302) 1-{[3-(3-methoxypyrrolidin-1-yl)phenyl]sulfonyl}-3-piperazin-1-yl-1H-indazole,
303) 7-[(3-piperazin-1-yl-1H-indazol-1-yl)sulfonyl]-2H-1,4-benzoxazin-3(4H)-one,
304) 7-{[3-(4-methylpiperazin-1-yl)-1H-indazol-1-yl]sulfonyl}-2H-1,4-benzoxazin-3(4H)-one,
305) 7-{[3-(4-methylpiperazin-1-yl)-1H-indol-1-yl]sulfonyl}-2H-1,4-benzoxazin-3 (4H)-one, 306) 7-[(3-piperazin-1-yl-1H-indol-1-yl)sulfonyl]-2H-1,4-benzoxazin-3(4H)-one,
307) 1-{[3-(3-methoxypyrrolidin-1-yl)phenyl]sulfonyl}-3-(4-methylpiperazin-1-yl)-1H-indole,
308) 1-{[3-(3-methoxypyrrolidin-1-yl)phenyl]sulfonyl}-3-piperazin-1-yl-1H-indole,
309) 1-[(1-acetyl-2,3-dihydro-1H-indol-5-yl)sulfonyl]-3-piperazin-1-yl-1H-pyrrolo[2,3-b]pyridine; compound with formic acid,
310) 1-{[3-(3-methoxypyrrolidin-1-yl)phenyl]sulfonyl}-3-piperazin-1-yl-1H-pyrrolo[2,3-b]pyridine; compound with formic acid,
311) 1-[(1-acetyl-2,3-dihydro-1H-indol-5-yl)sulfonyl]-3-(4-methylpiperazin-1-yl)-1H-indazole,
312) 1-[(1-acetyl-2,3-dihydro-1H-indol-5-yl)sulfonyl]-3-piperazin-1-yl-1H-indazole,
313) 3-piperazin-1-yl-1-(pyridin-3-ylsulfonyl)-1H-indazole,
314) 1-[(1-acetyl-2,3-dihydro-1H-indol-5-yl)sulfonyl]-3-(4-methylpiperazin-1-yl)-1H-indole,
315) 4-methyl-7-{[3-(4-methylpiperazin-1-yl)-1H-indazol-1-yl]sulfonyl}-3,4-dihydro-2H-1,4-benzoxazine,
316) 1-[(1-acetyl-2,3-dihydro-1H-indol-5-yl)sulfonyl]-3-piperazin-1-yl-1H-indole,
317) 7-[(3-piperazin-1-yl-1H-indol-1-yl)sulfonyl]-2H-1,4-benzoxazin-3(4H)-one,
318) 4-methyl-7-[(3-piperazin-1-yl-1H-indol-1-yl)sulfonyl]-3,4-dihydro-2H-1,4-benzoxazine; compound with formic acid,
319) 4-methyl-7-[(3-piperazin-1-yl-1H-indazol-1-yl)sulfonyl]-3,4-dihydro-2H-1,4-benzoxazine,
320) 7-[(3-piperazin-1-yl-1H-indol-1-yl)sulfonyl]-2H-1,4-benzoxazin-3(4H)-one,
321) 7-[(3-piperazin-1-yl-1H-indazol-1-yl)sulfonyl]-2H-1,4-benzoxazin-3(4H)-one,
322) 5-{[5-fluoro-3-(1-methyl-1,2,3,6-tetrahydropyridin-4-yl)-1H-indol-1-yl]sulfonyl} isoquinoline hydroformate,
323) 5-{[5-fluoro-3-(1-methylpiperidin-4-yl)-1H-indol-1-yl]sulfonyl}isoquinoline hydroformate,
324) 5-{[5-fluoro-3-(1,2,3,6-tetrahydropyridin-4-yl)-1H-indol-1-yl]sulfonyl} isoquinoline hydroformate,
325) 8-[5-Fluoro-3-(1-methyl-1,2,3,6-tetrahydro-pyridin-4-yl)-indole-1-sulfonyl]-isoquinoline; compound with formic acid,
326) 1-(1,2-benzisoxazol-5-ylsulfonyl)-3-(1-methyl-1,2,3,6-tetrahydropyridin-4-yl)-1H-pyrazolo[4,3-b]pyridine,
327) 1-(1,2-benzisoxazol-5-ylsulfonyl)-3-(1-methyl-1,2,3,6-tetrahydropyridin-4-yl)-1H-pyrazolo[3,4-b]pyridine,
328) 3-(1-methyl-1,2,3,6-tetrahydropyridin-4-yl)-1-[(6-phenoxypyridin-3-yl)sulfonyl]-1H-pyrrolo[3,2-b]pyridine,
329) 2-methyl-8-{[3-(1-methyl-1,2,3,6-tetrahydropyridin-4-yl)-1H-pyrrolo[3,2-b]pyridin-1-yl]sulfonyl}-1,2,3,4-tetrahydroisoquinoline,
330) 1-[(1-acetyl-2,3-dihydro-1H-indol-5-yl)sulfonyl]-5-methoxy-3-(1-methyl-1,2,3,6-tetrahydropyridin-4-yl)-1H-indole, wherein salts listed above can also be in free base form or in the form of another pharmaceutically acceptable salt, and free base forms listed above can also be in the form of a pharmaceutically acceptable salt, wherein a compound listed above (either in a free base form or in the form of a pharmaceutically acceptable salt) can also be in the form of a solvate (such as a hydrate), wherein a compound listed above (in a free base form or solvate thereof, or in the form of a pharmaceutically acceptable salt or solvate thereof) can also be in the form of a polymorph, and wherein if the compound exhibits chirality it can be in the form of a mixture of enantiomers such as a racemate or a mixture of diastereomers, or can be in the form of a single enantiomer or a single diastereomer.

The following table presents structures for selected compounds of the present invention:

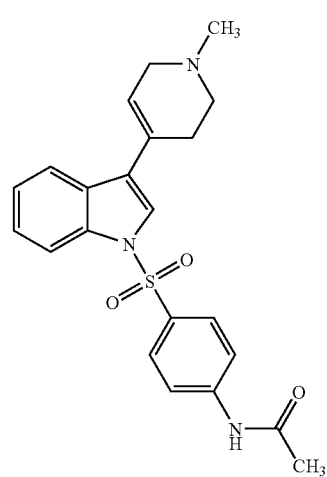

2)

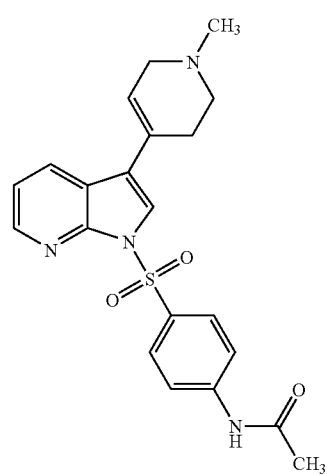

3)

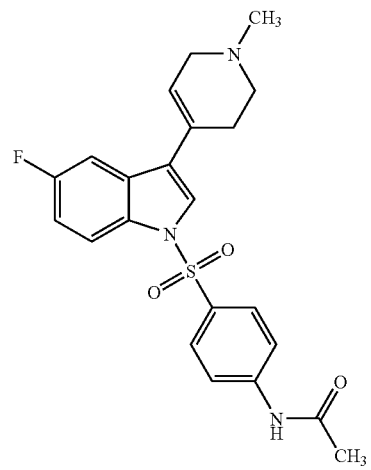

4)

5)
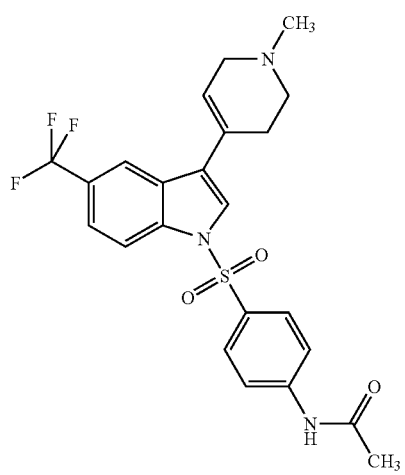
6)
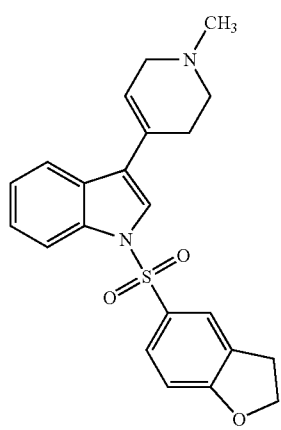
7)
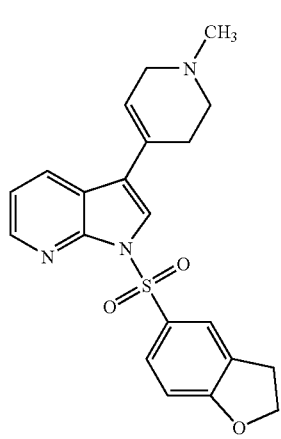
8)
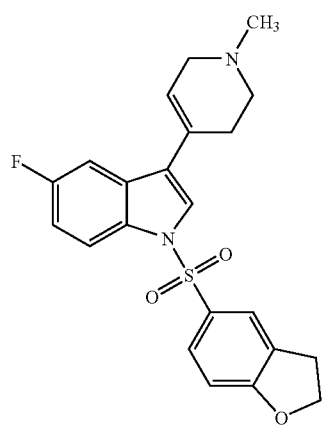
9)
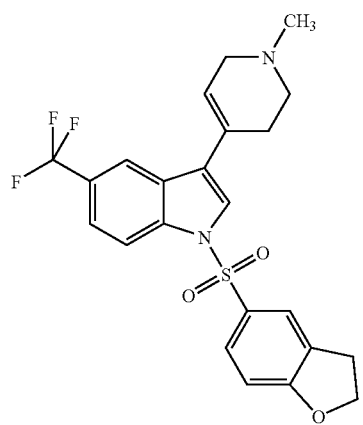
10)
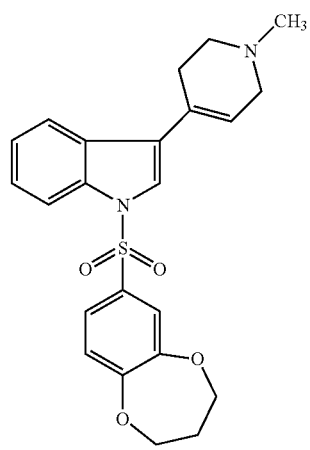

11)
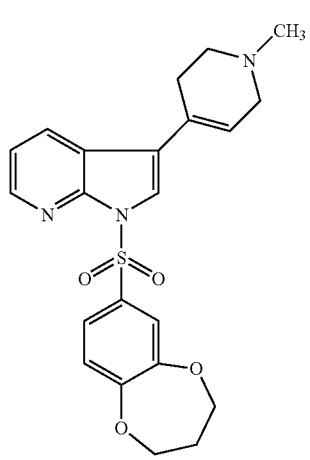
12)
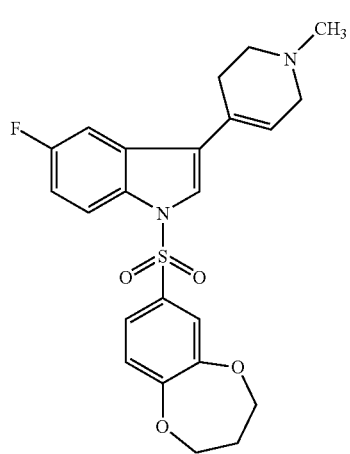
13)
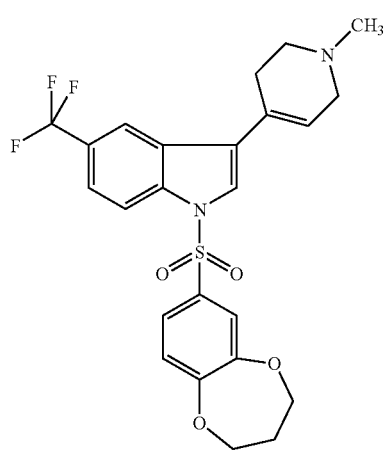
14)
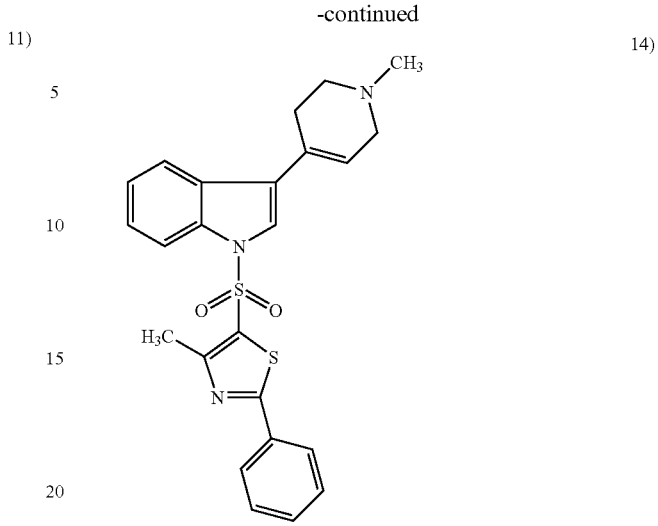
15)
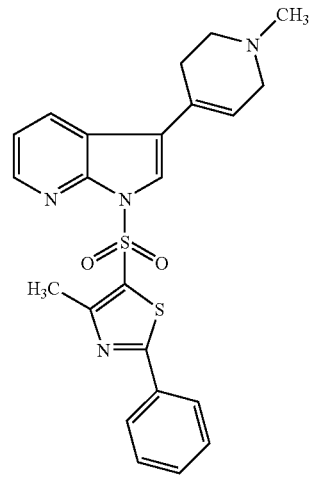
16)
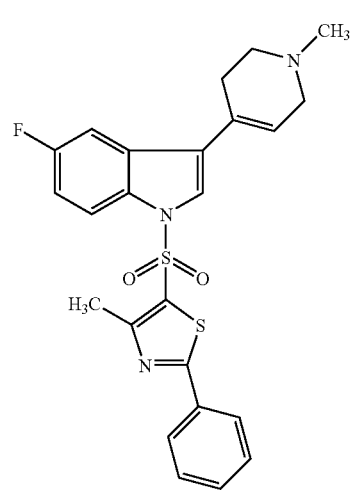

-continued
17)
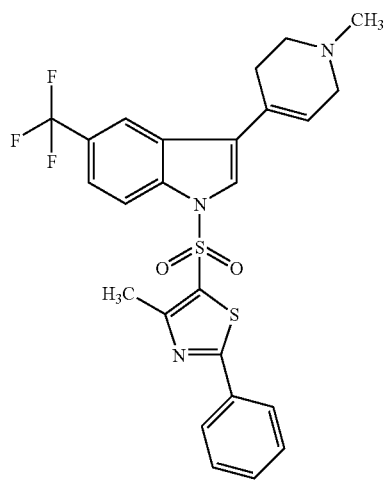
18)
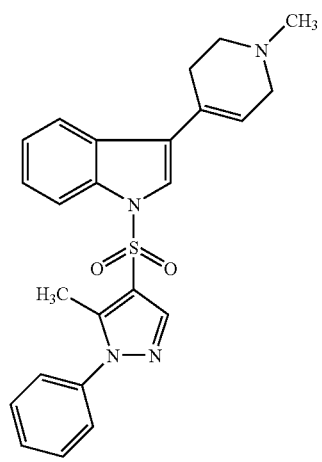
19)
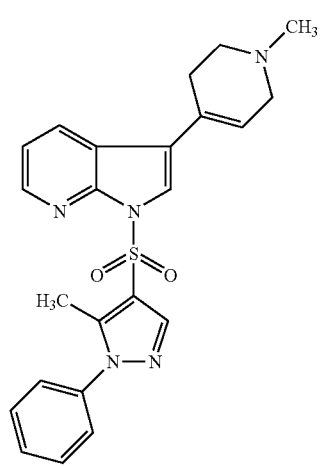
-continued
20)
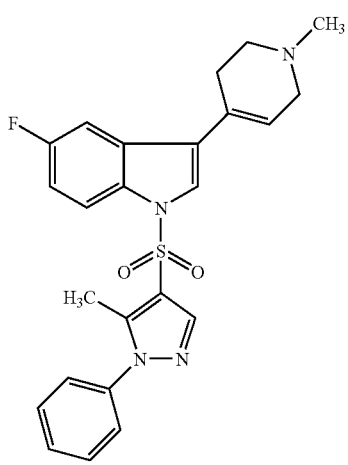
21)
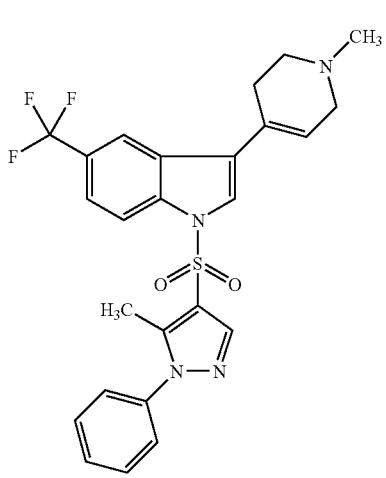
22)
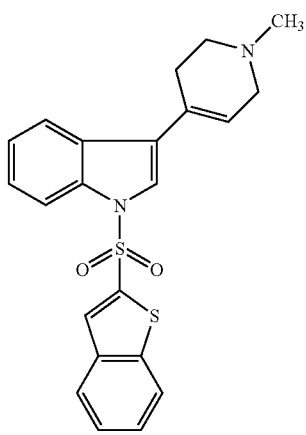

-continued
23)
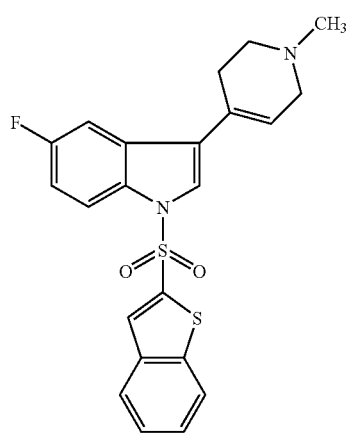
24)
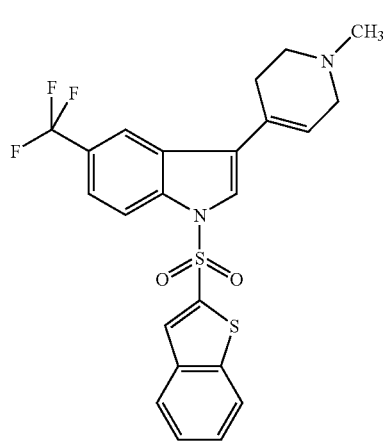
25)
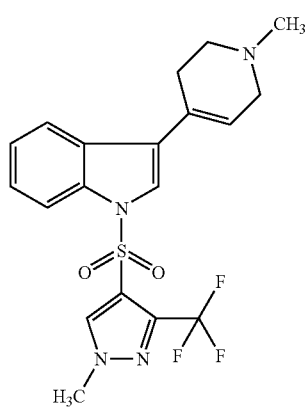
-continued
26)
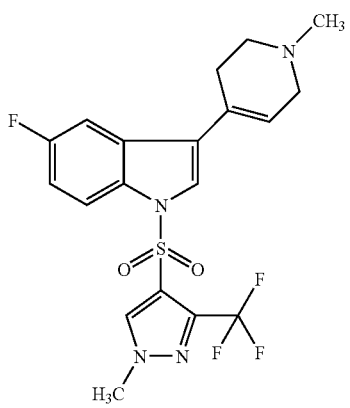
27)
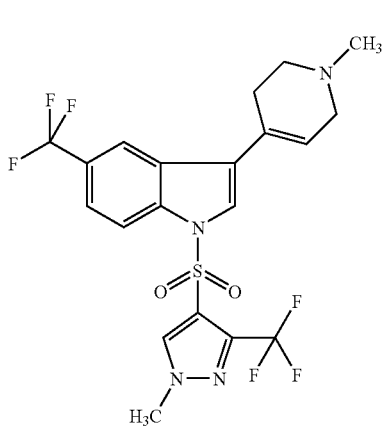
28)
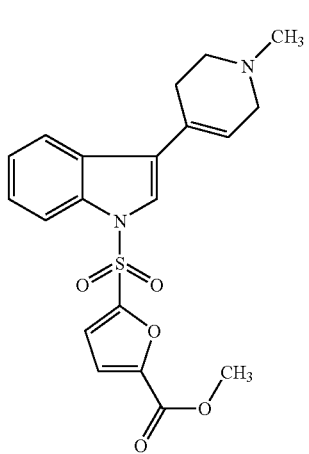

-continued
29)
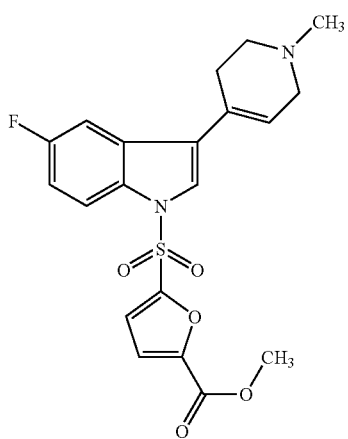
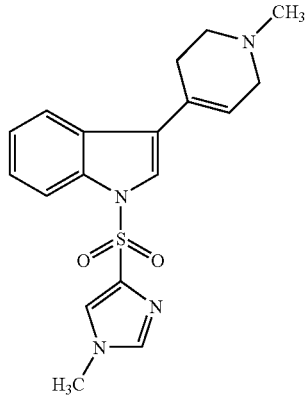
32)
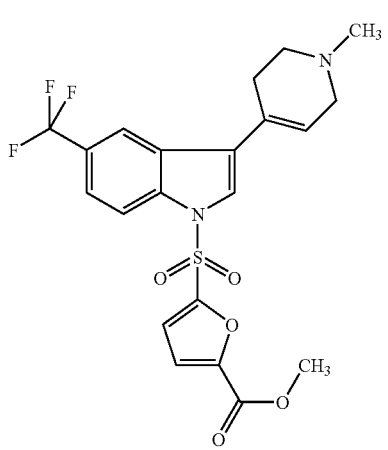
30)
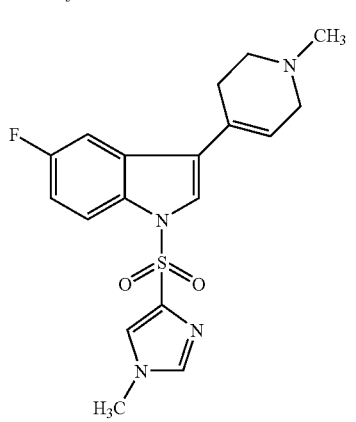
33)
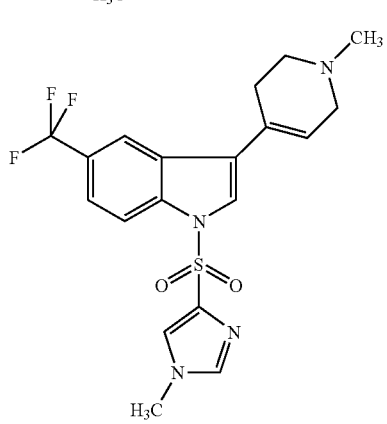
34)
31)
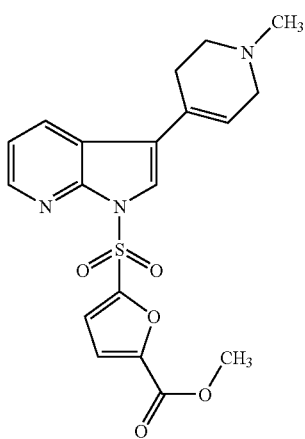
35)

36) 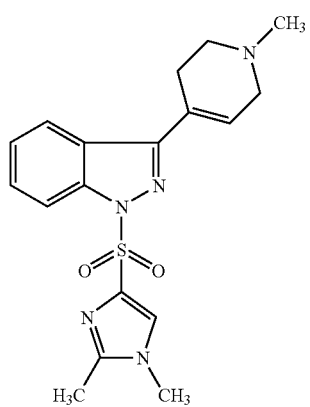
37) 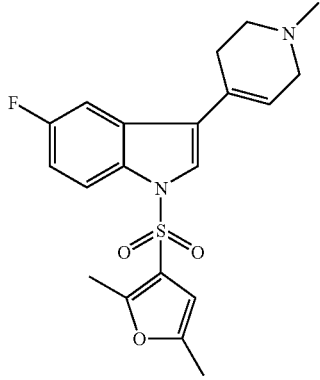
38) 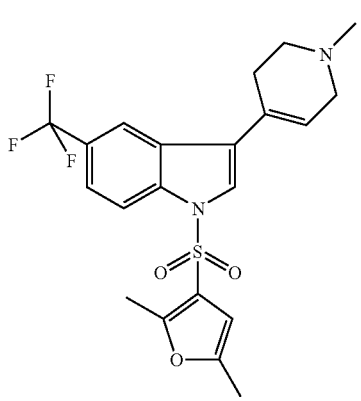
39) 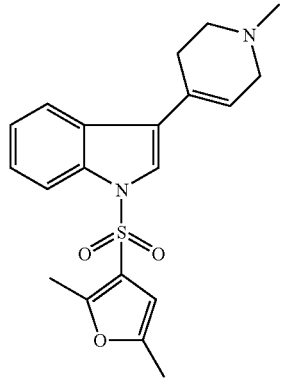
40) 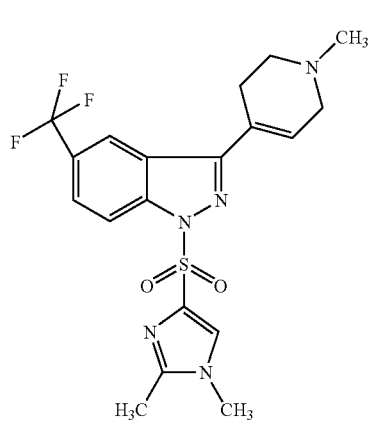
41)
42)
43)

-continued
44) 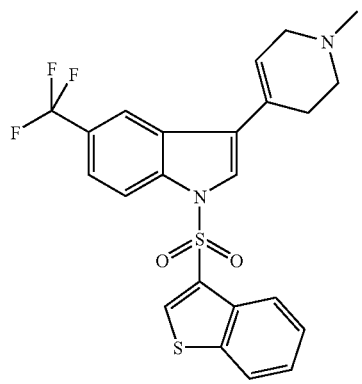
45) 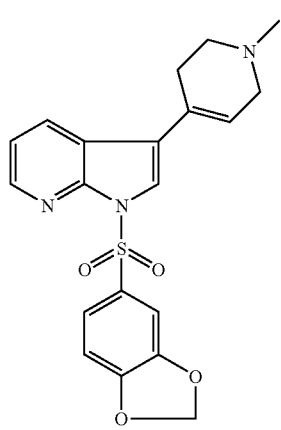
46) 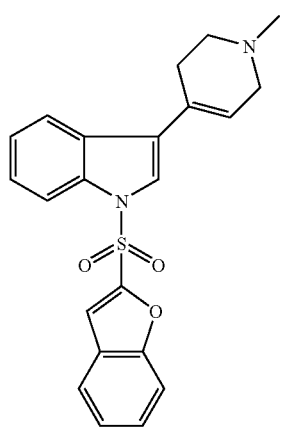
47) 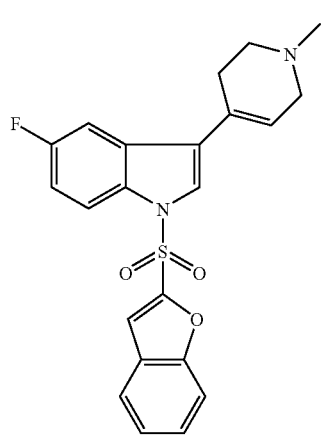
-continued
48) 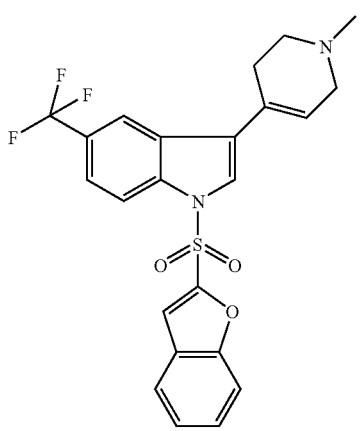
49) 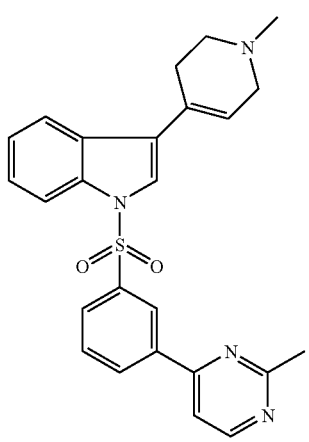
50) 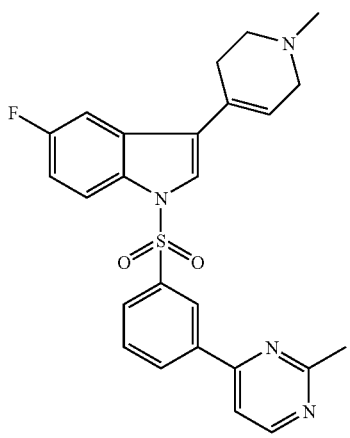

51) 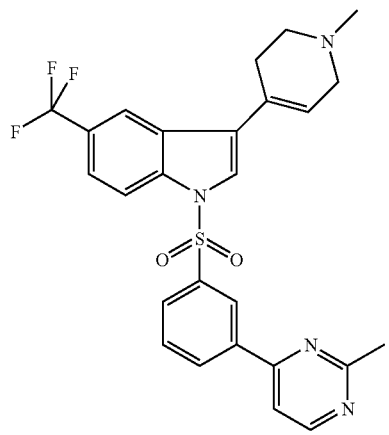
52) 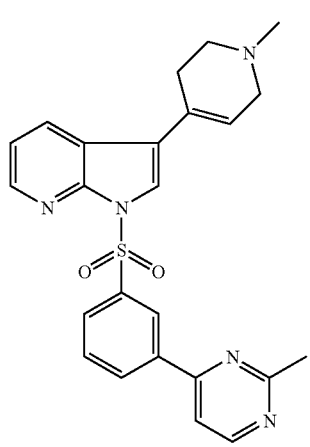
53) 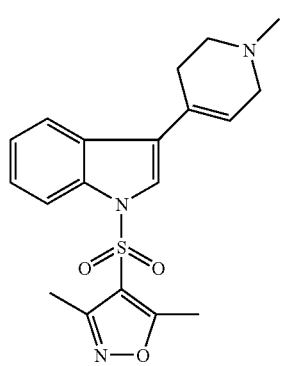
54) 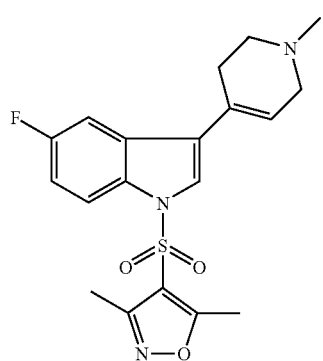
55) 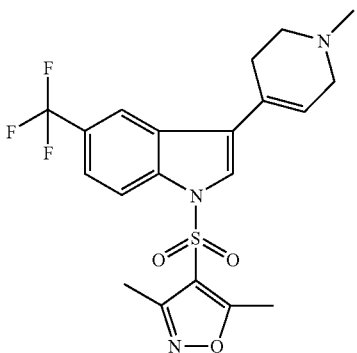
56) 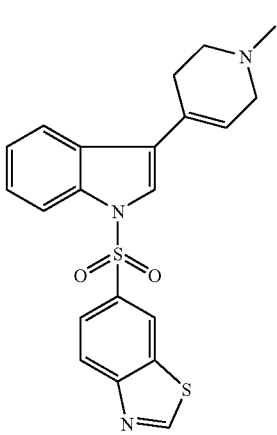
57) 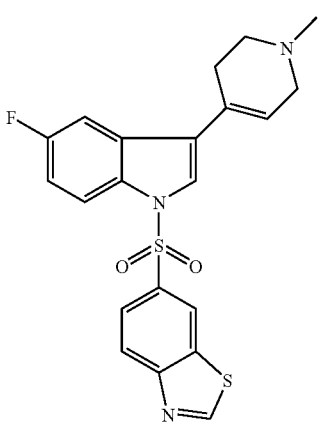
58) 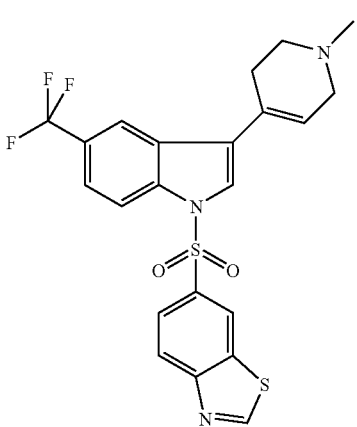

-continued
59) 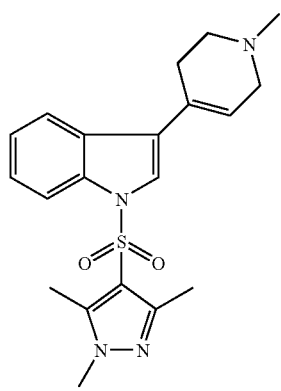
60) 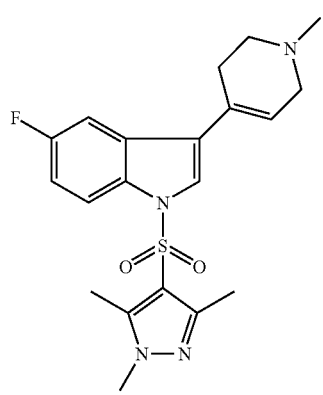
61) 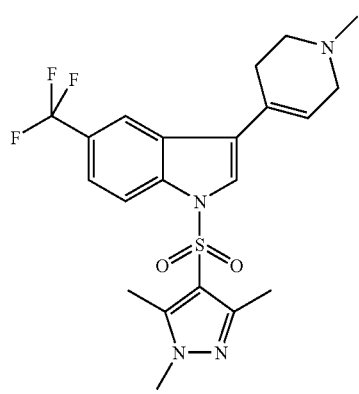
62) 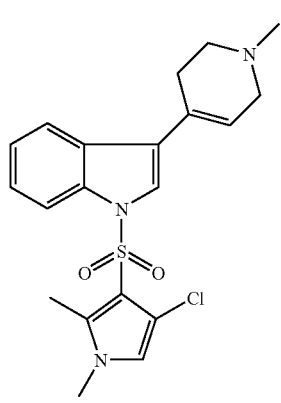
-continued
63) 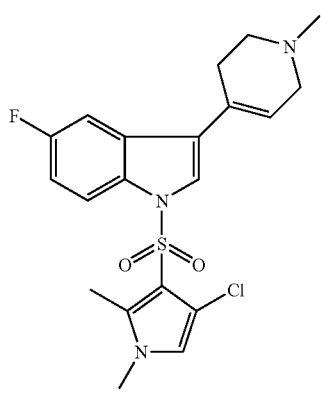
64) 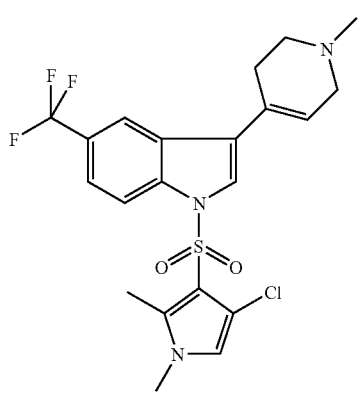
65) 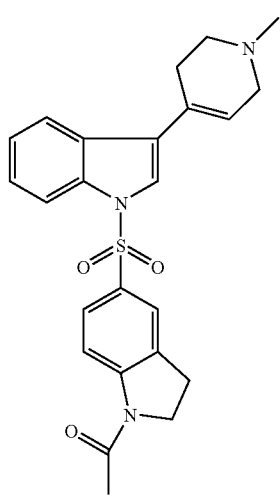

-continued
66)
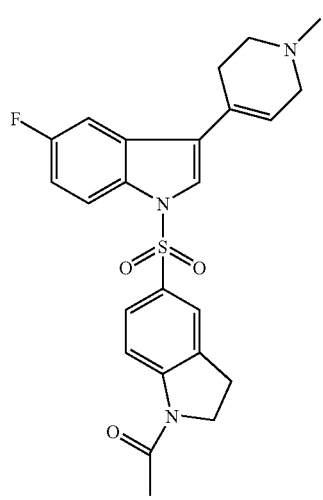
67)
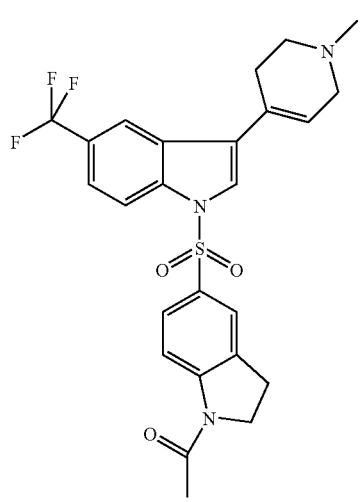
68)
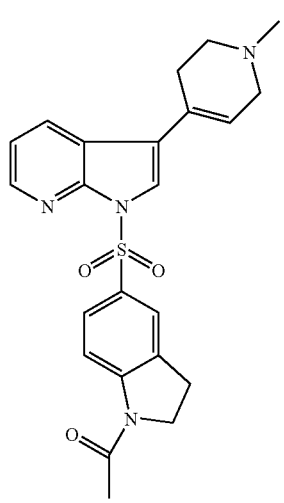
-continued
69)
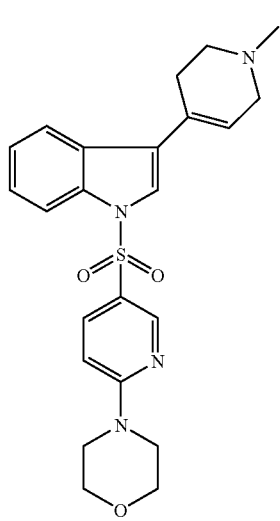
70)
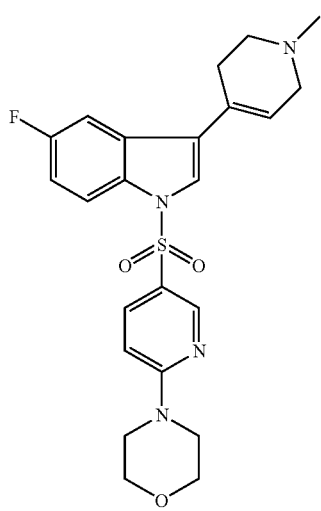
71)
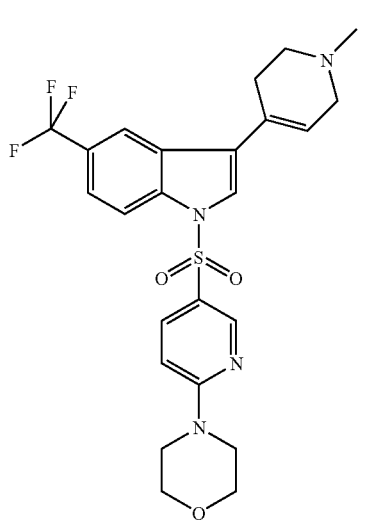

72) 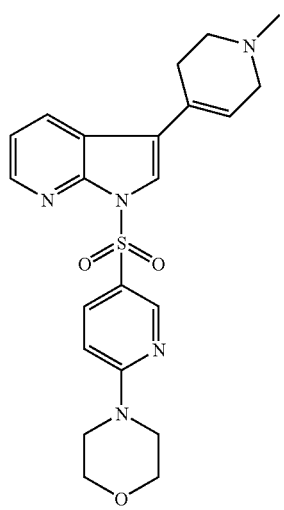
73) 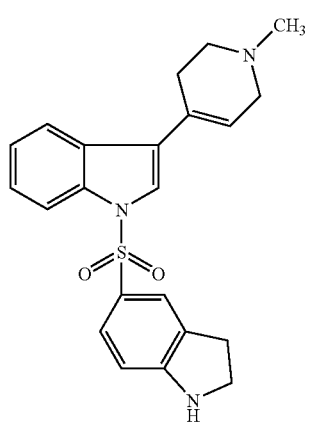
74) 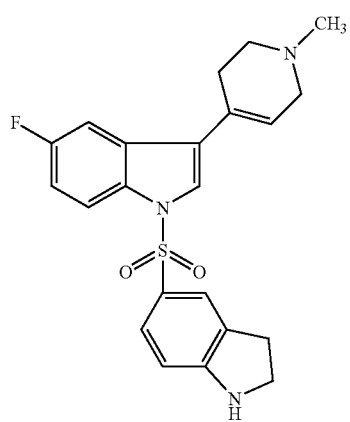
75) 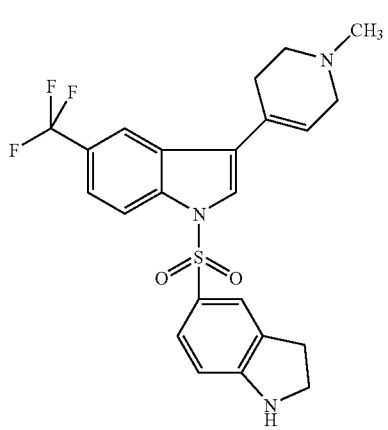
76) 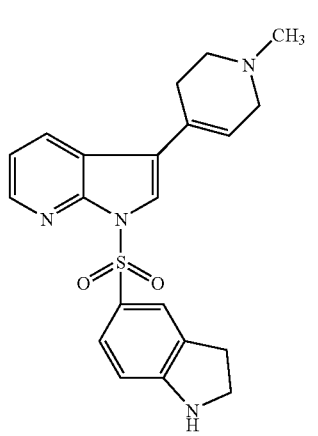
77) 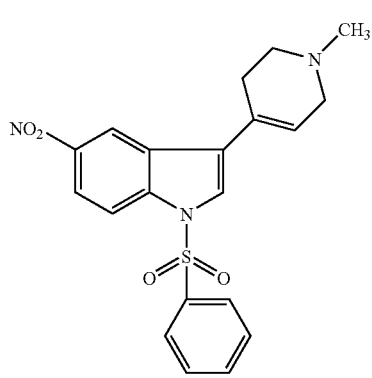
78) 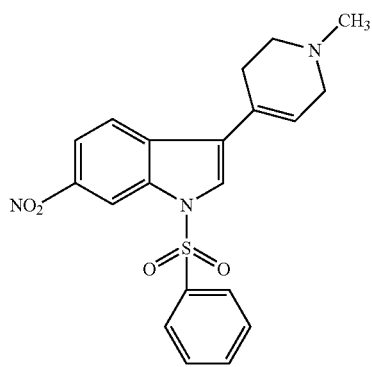

61
-continued
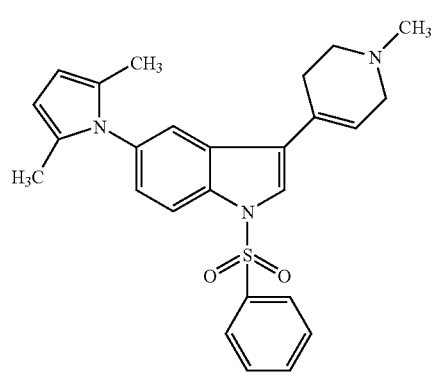
79)
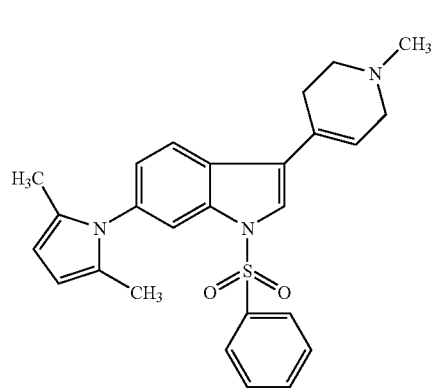
80)
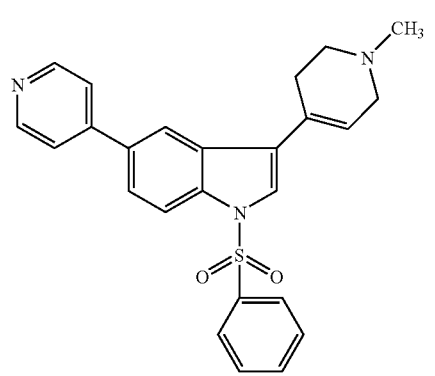
81)
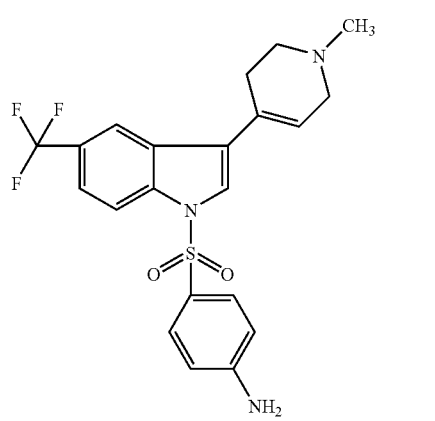
82)
62
-continued
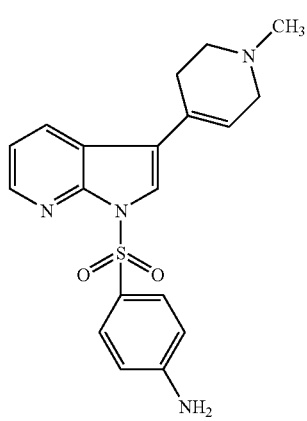
83)
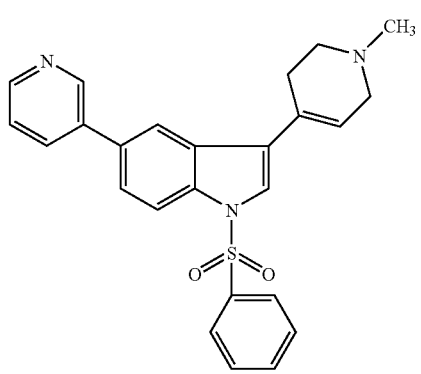
84)
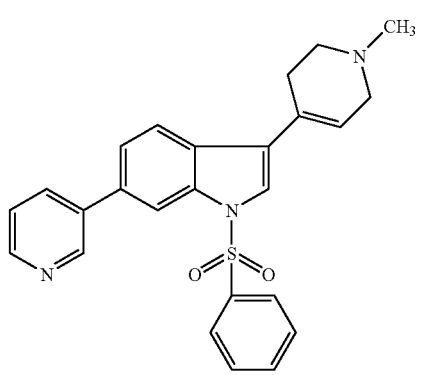
85)
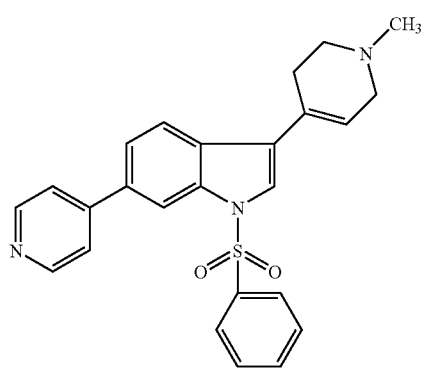
86)

87) 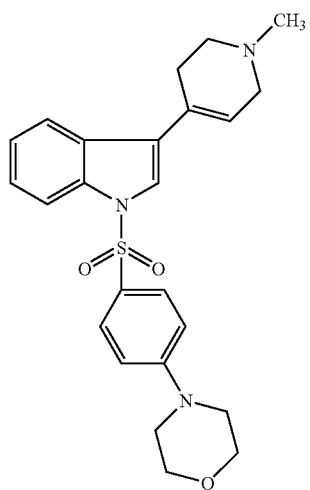
88) 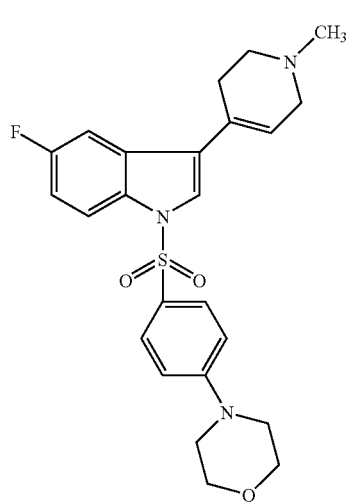
89) 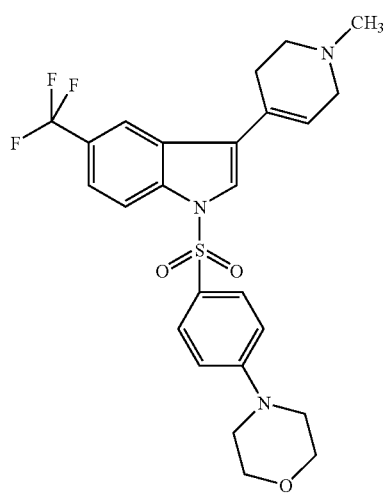
90) 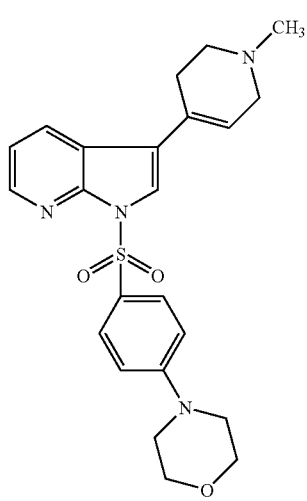
91) 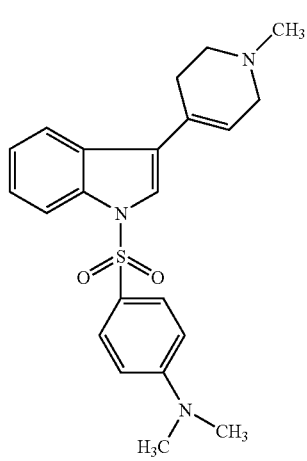
92) 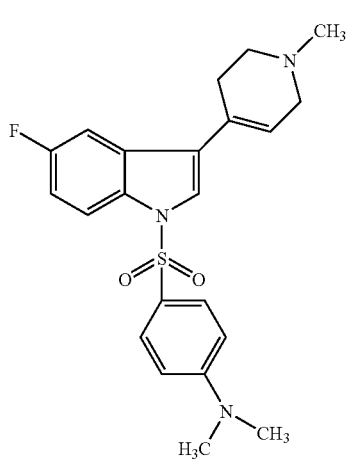

-continued
93) 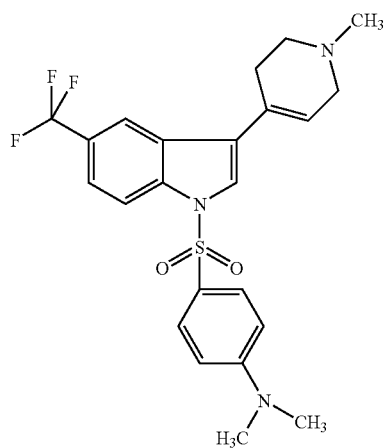
94) 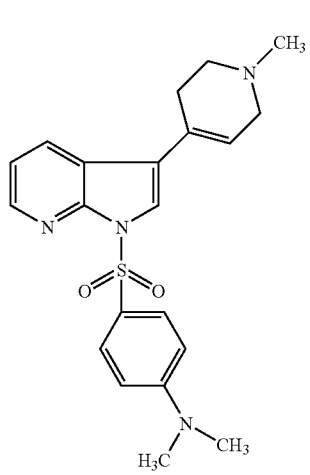
95) 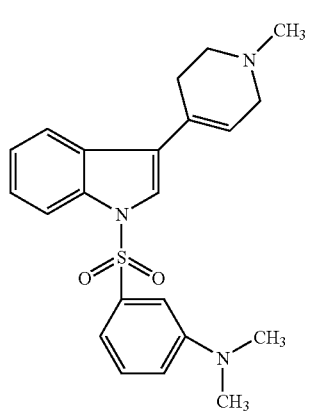
-continued
96) 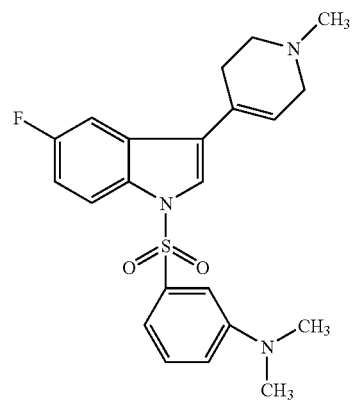
97) 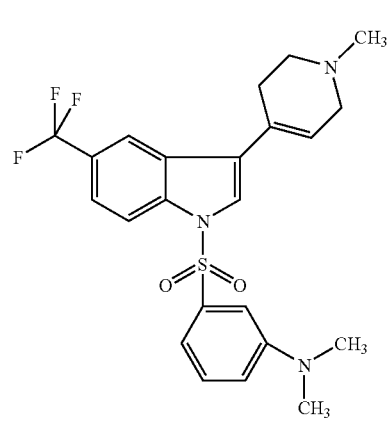
98) 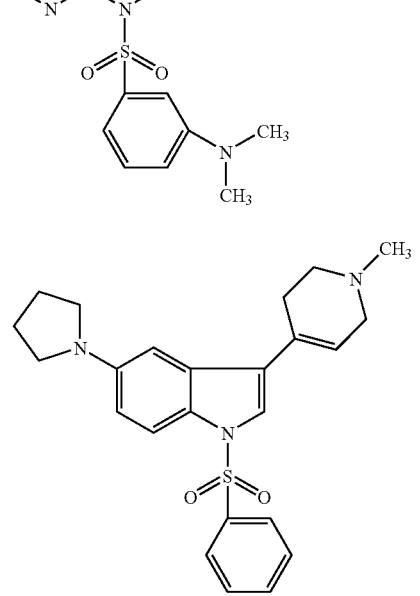
99)

-continued
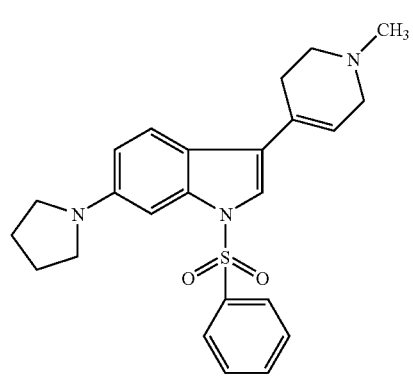
100)
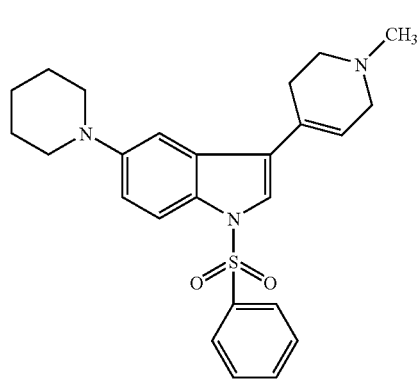
101)
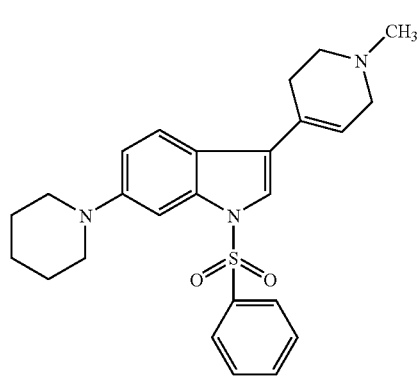
102)
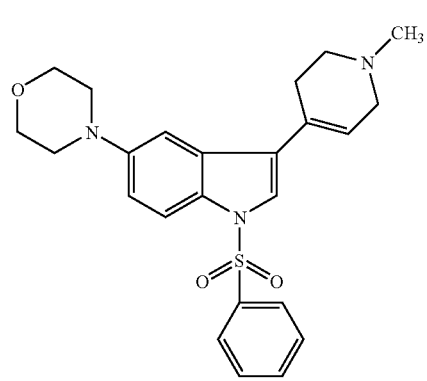
103)
-continued
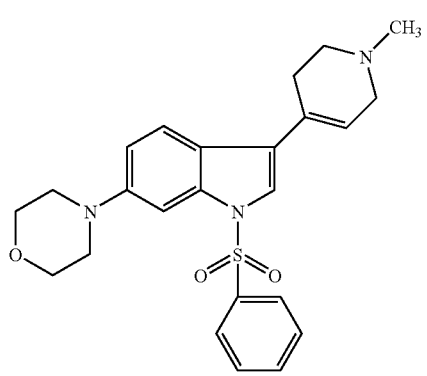
104)
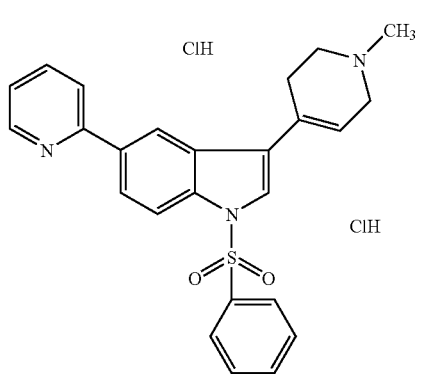
105)
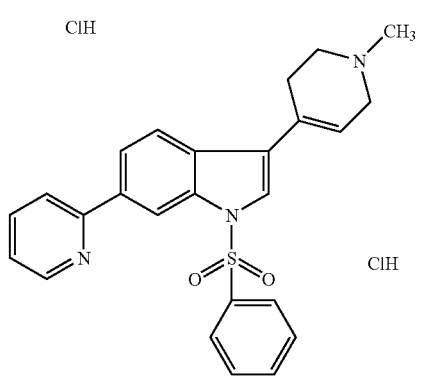
106)
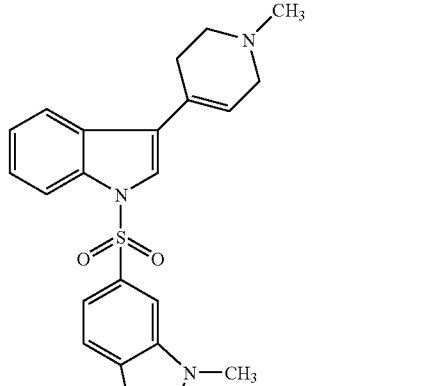
107)

-continued
108) 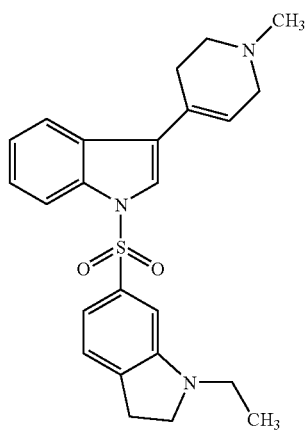
109) 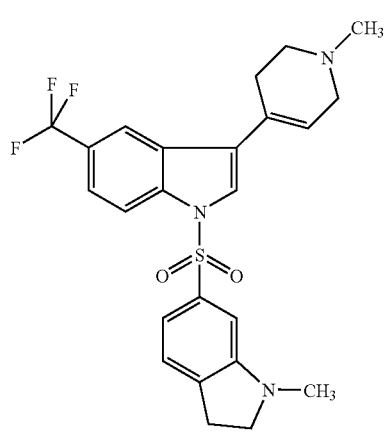
110) 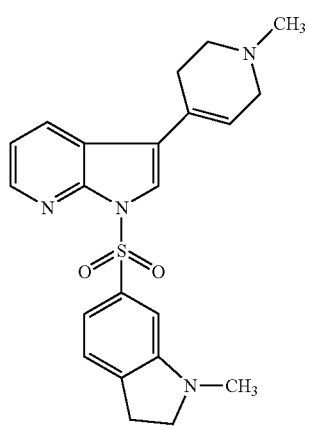
-continued
111) 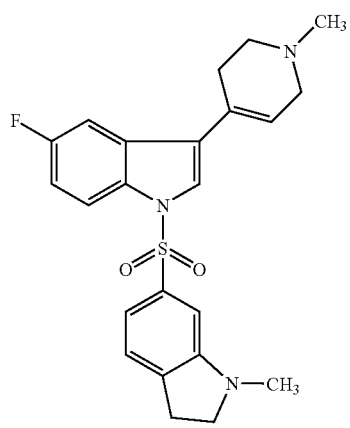
112) 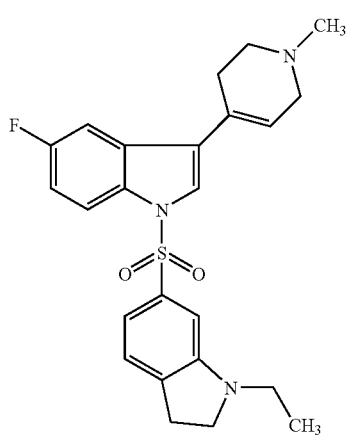
113) 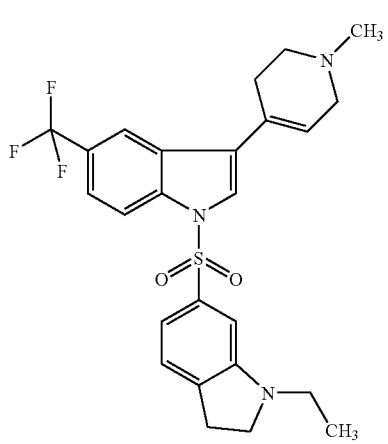

-continued
114)
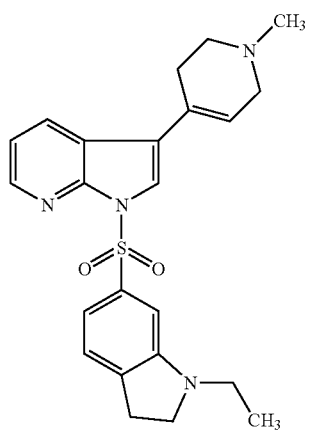
115)
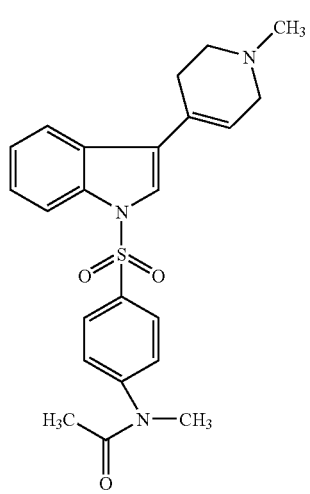
116)
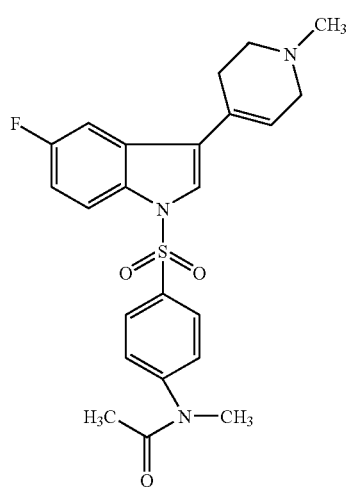
-continued
117)
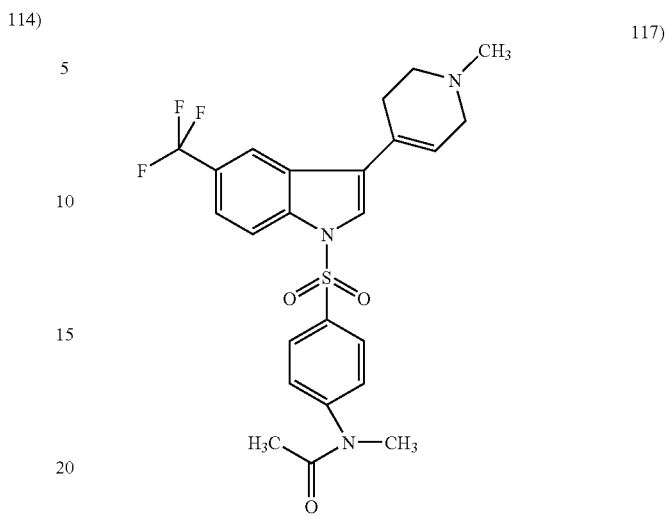
118)
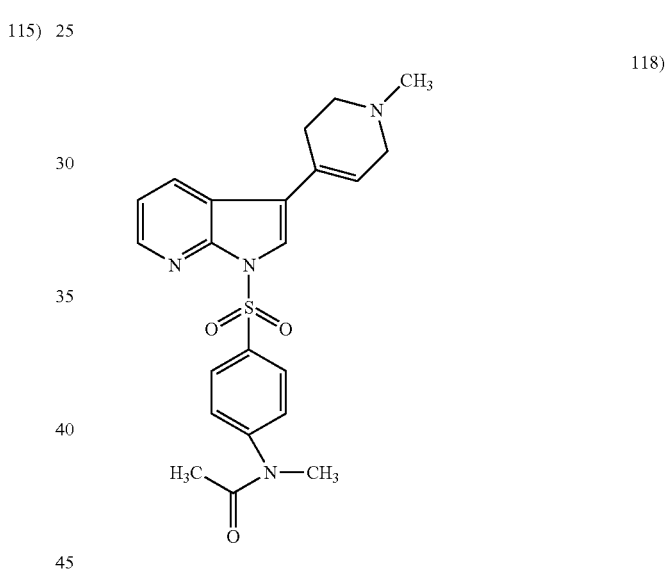
119)
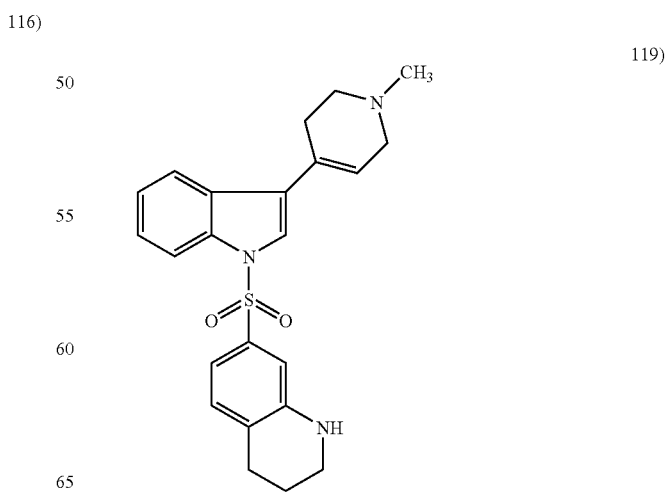

-continued
120)
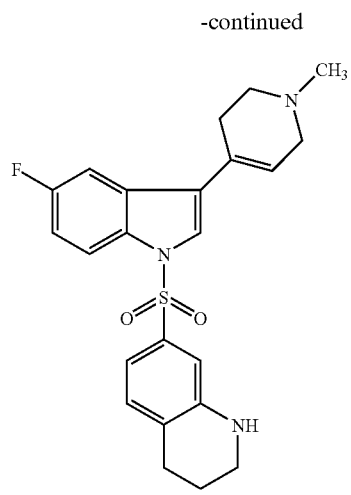
121)
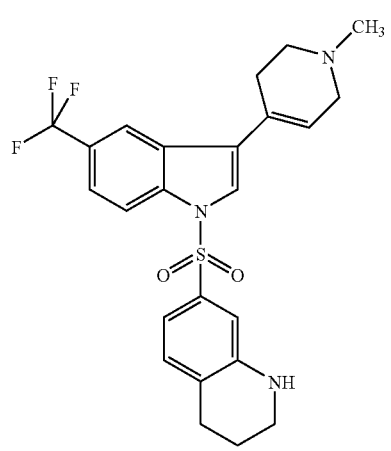
122)
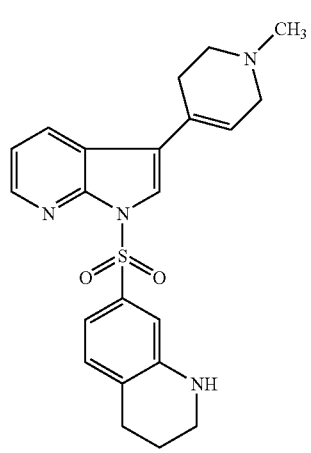
-continued
123)
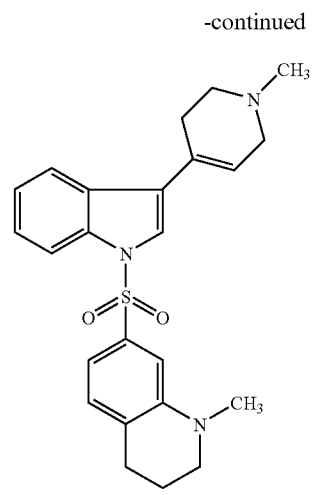
124)
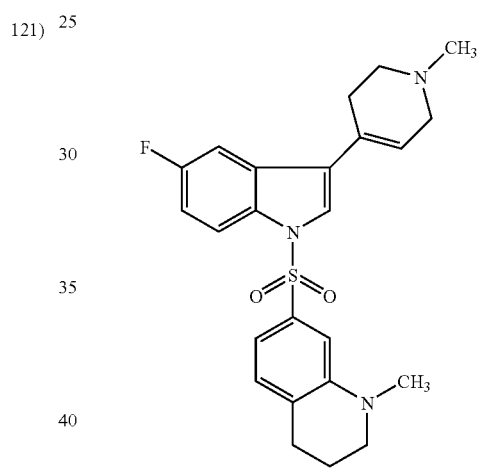
125)
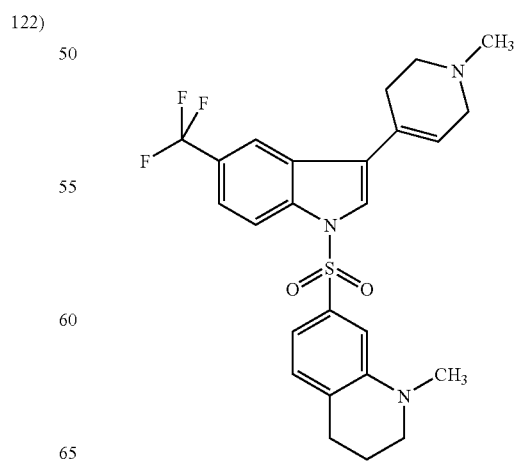

-continued
126)
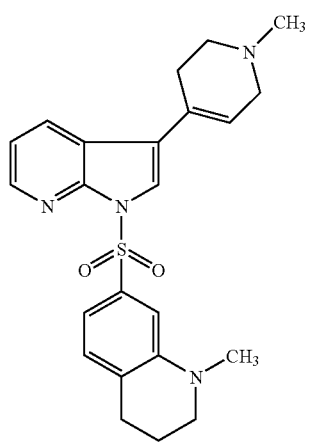
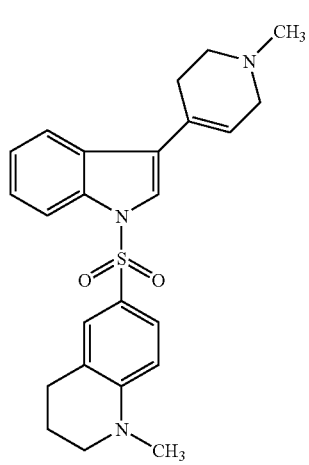
128)
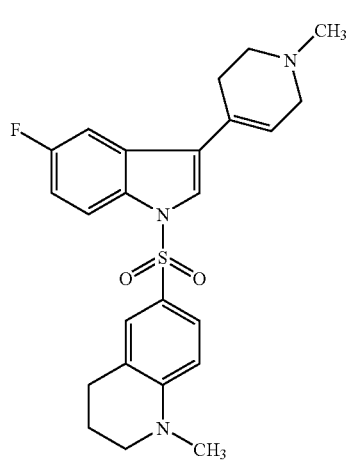
-continued
129)
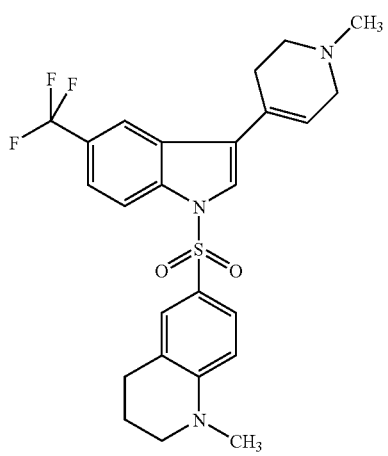
130)
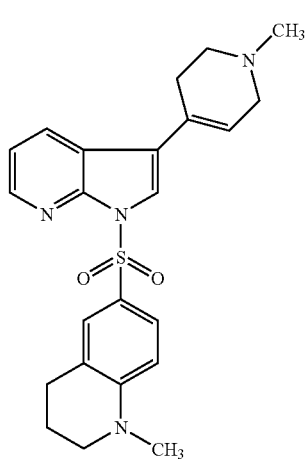
131)
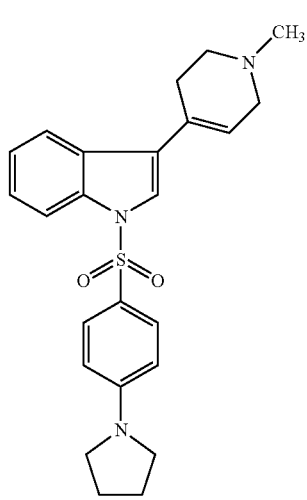

132) 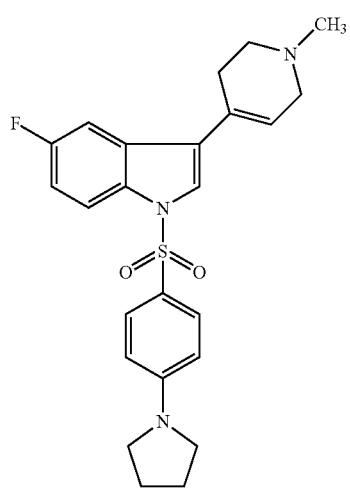
133) 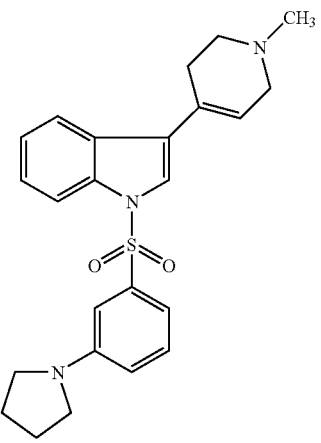
135) 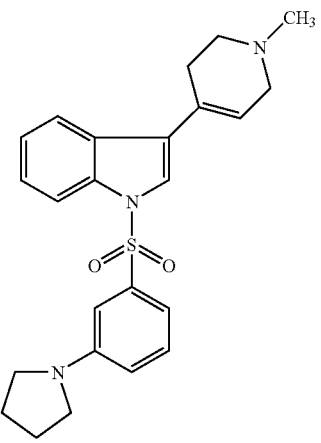
134) 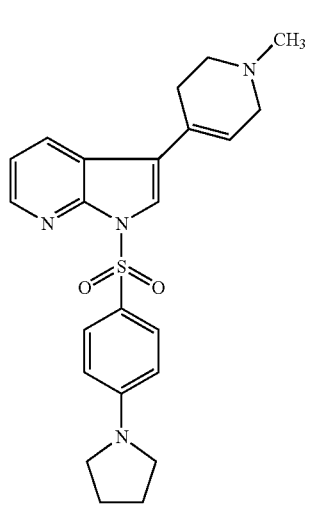
136) 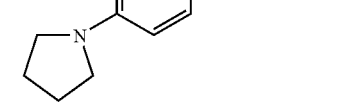
137) 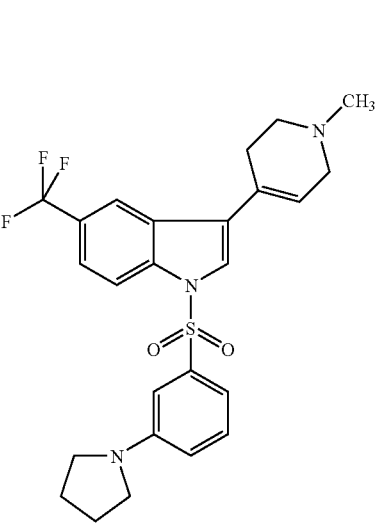

138)
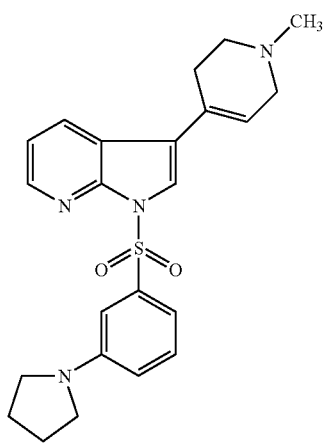
139)
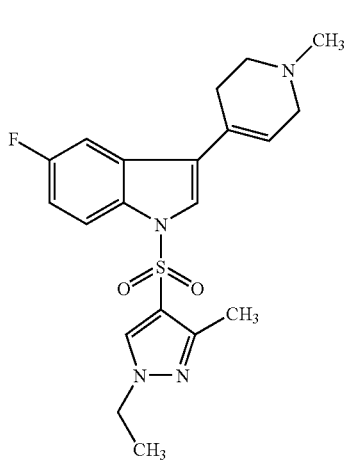
141)
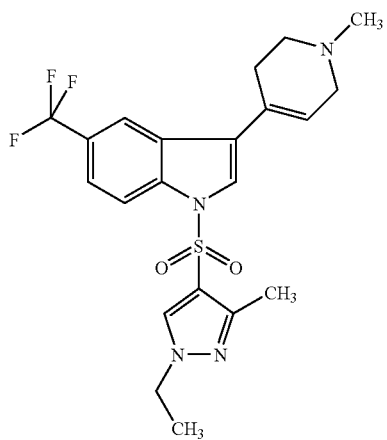
142)
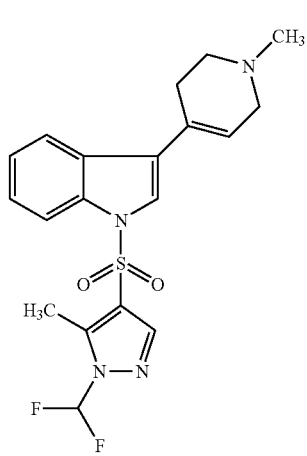
143)
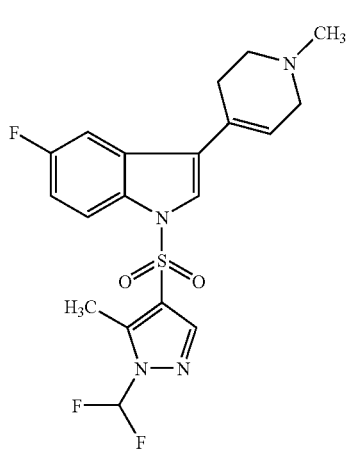

144) 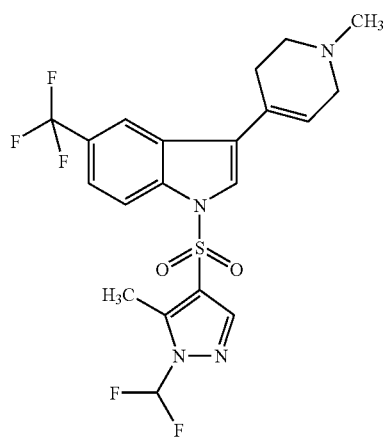
147) 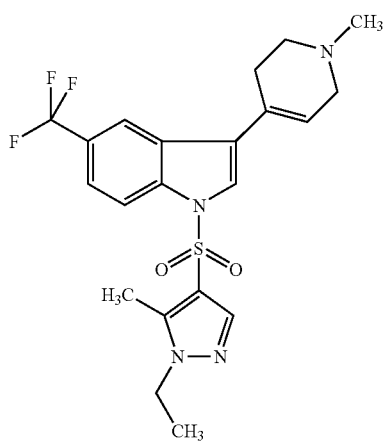
145) 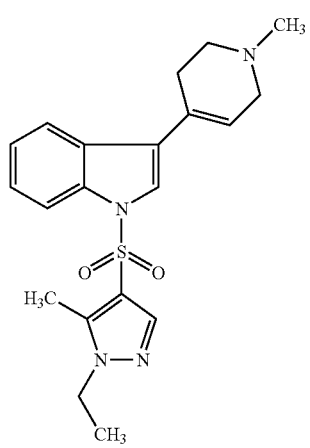
148) 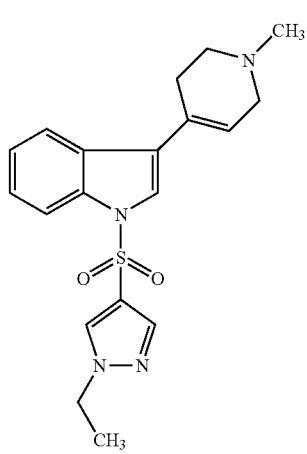
146) 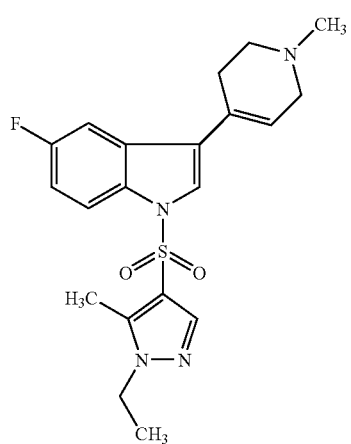
149) 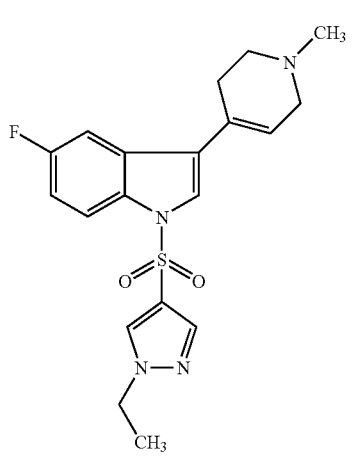

150)
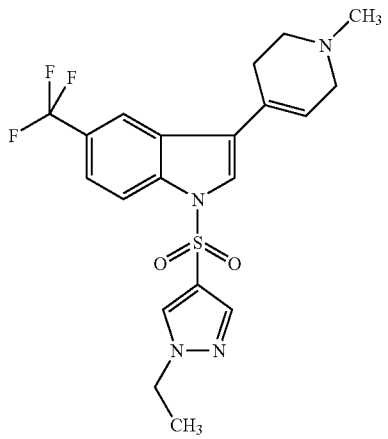
151)
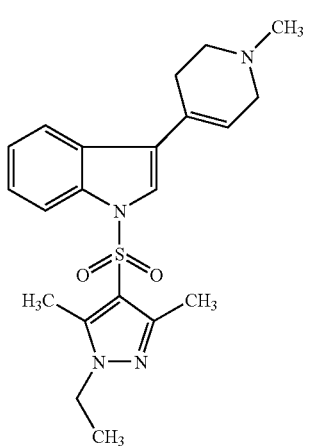
152)
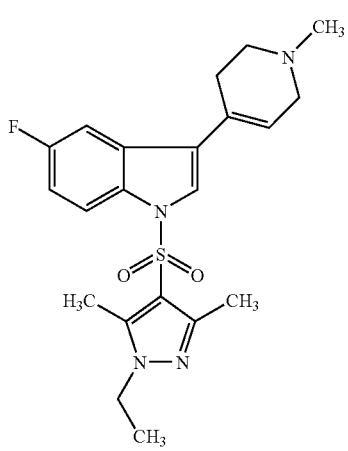
153)
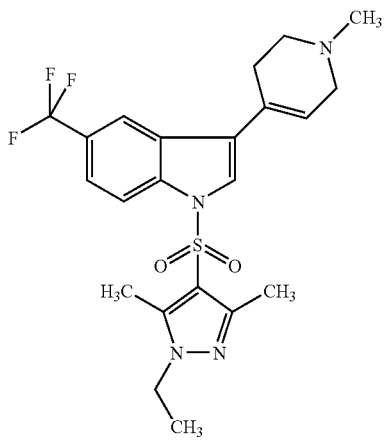
154)
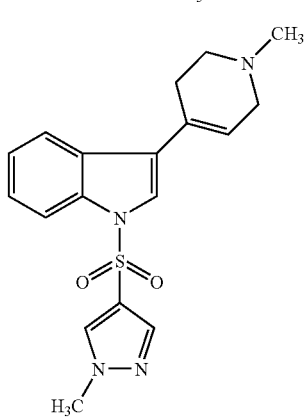
155)
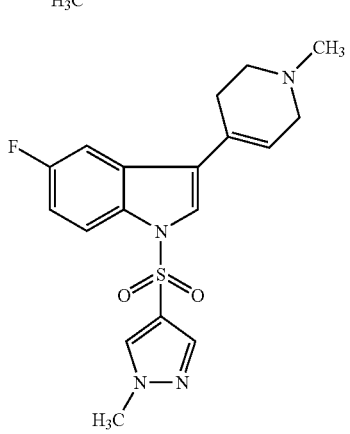
156)
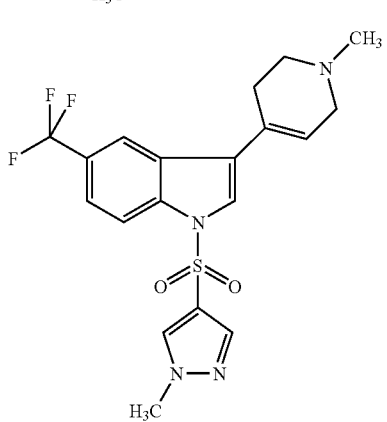

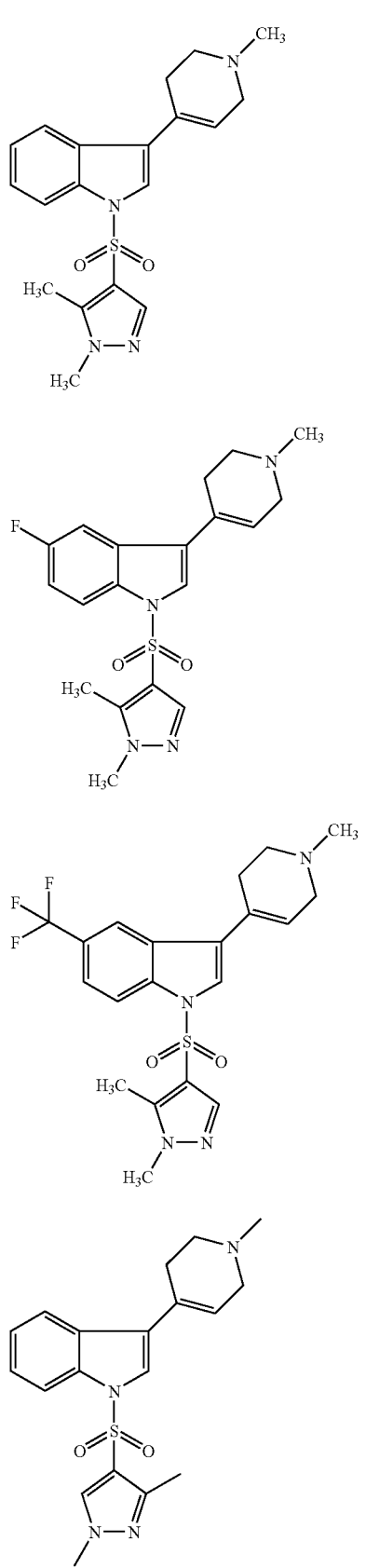
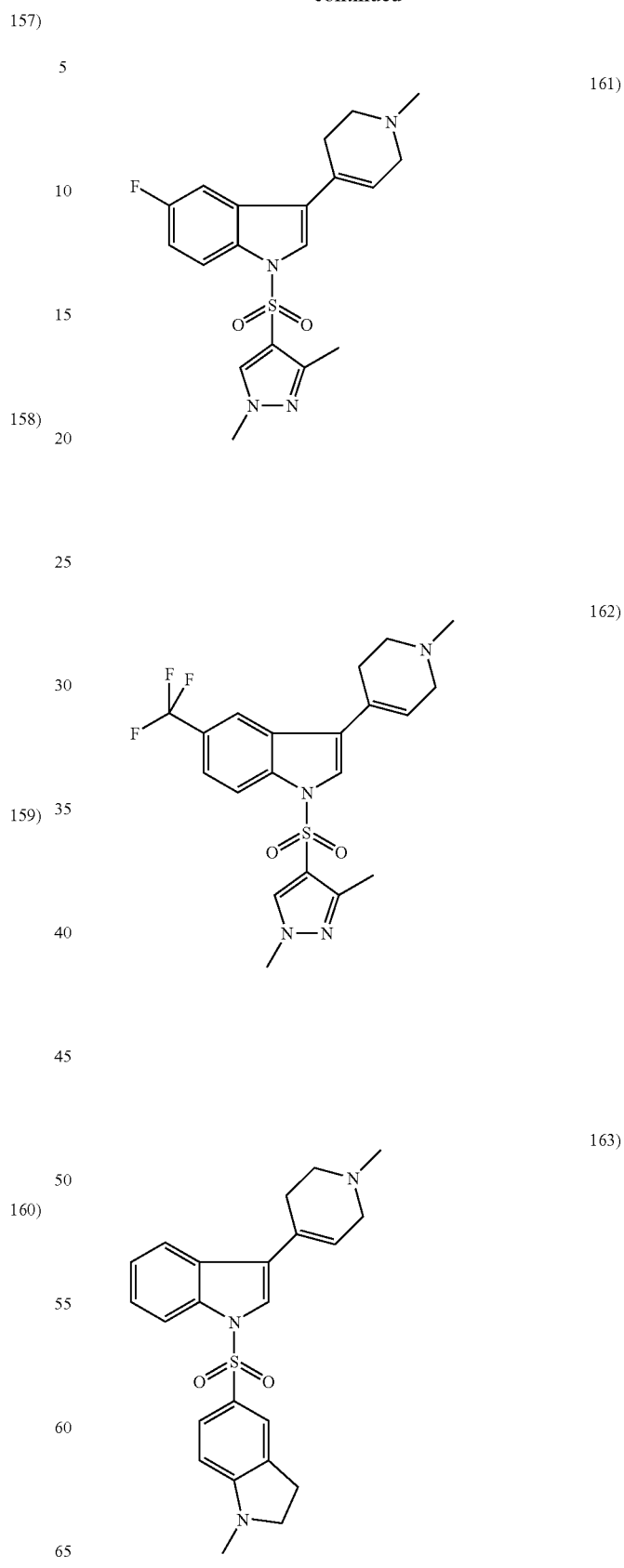

164) 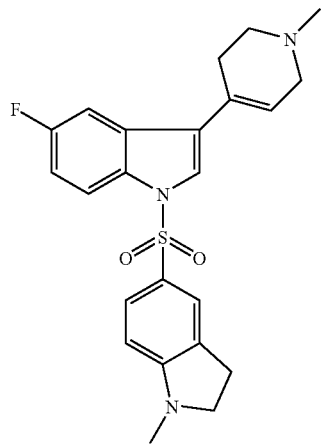
165) 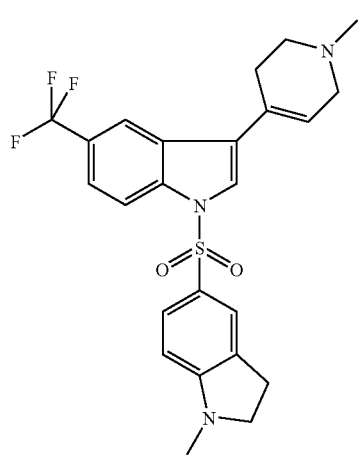
166) 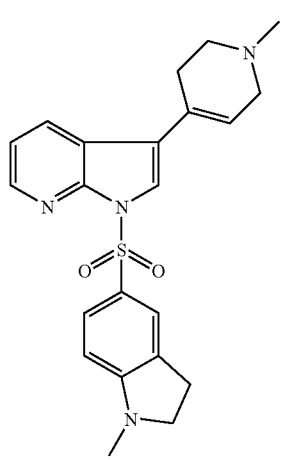
167) 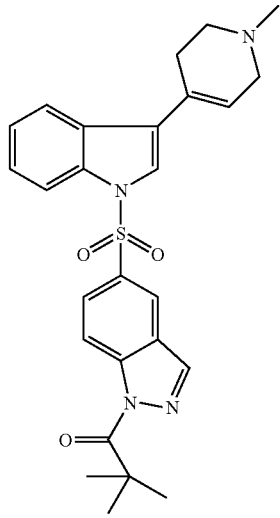
168)
169)

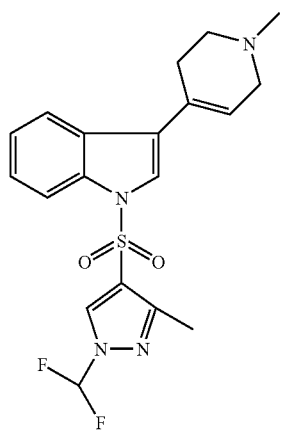
170)
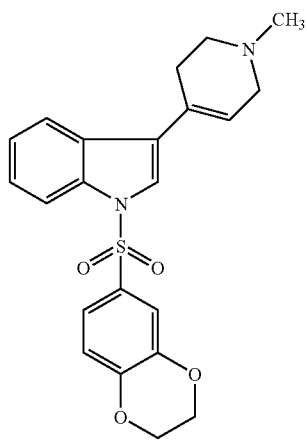
173)
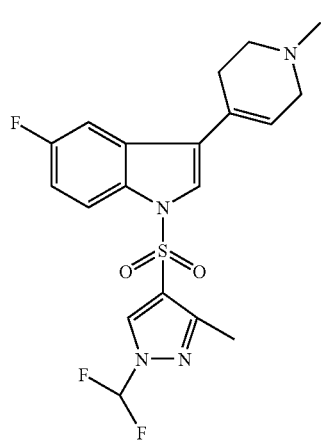
171)
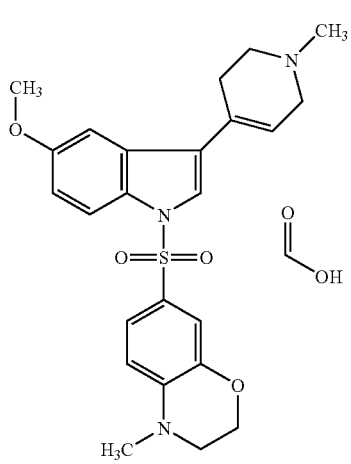
174)
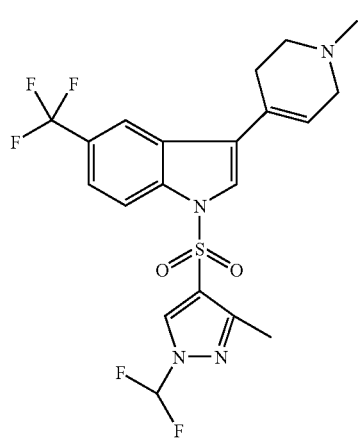
172)
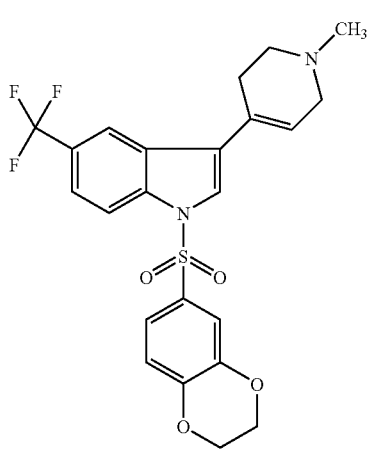
175)

176) 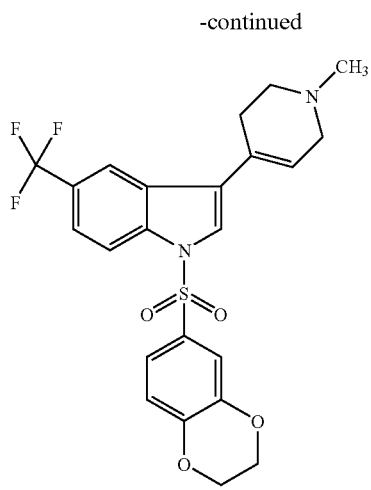
177) 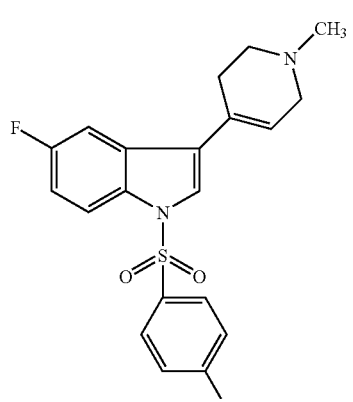
178) 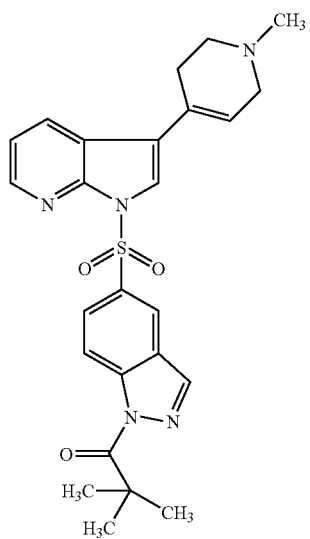
179) 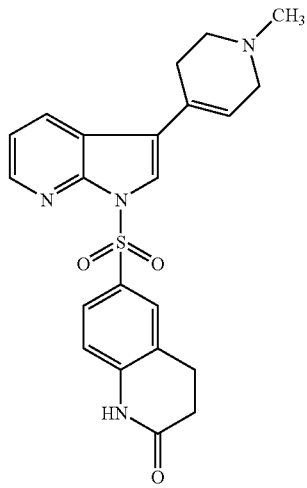
180) 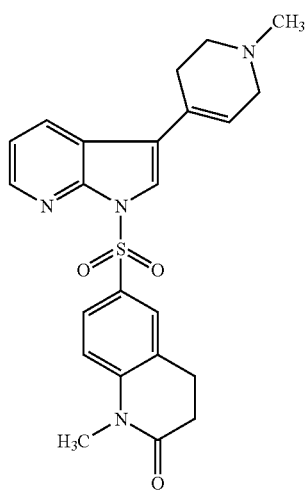
181) 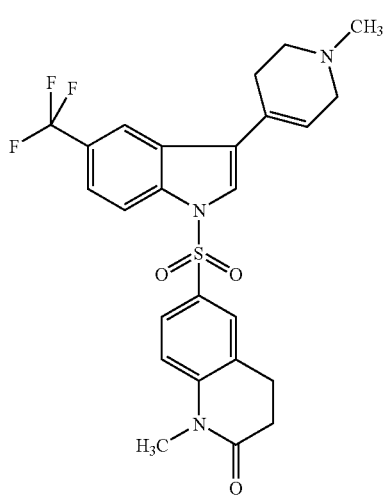

-continued
182) 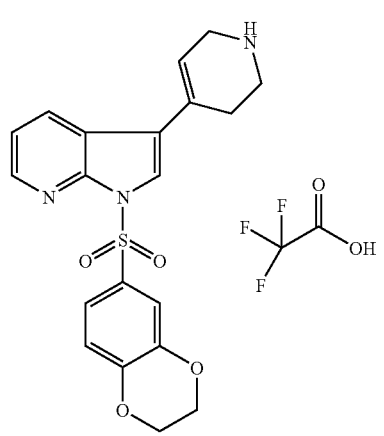
183) 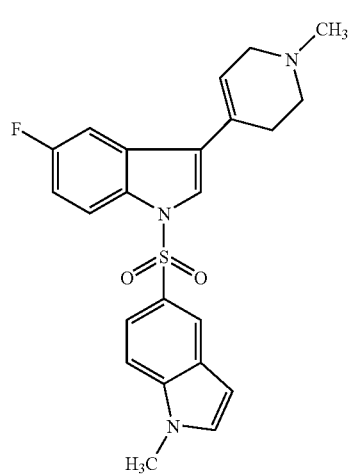
185) 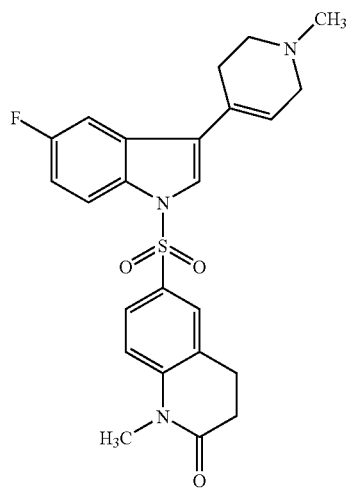
186) 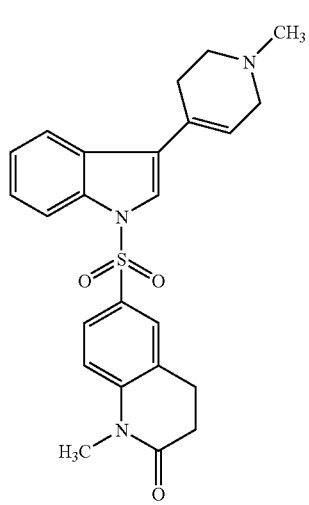
184) 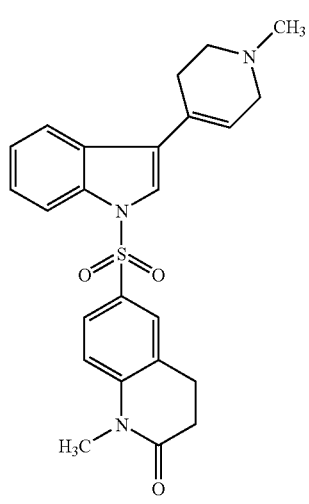
187) 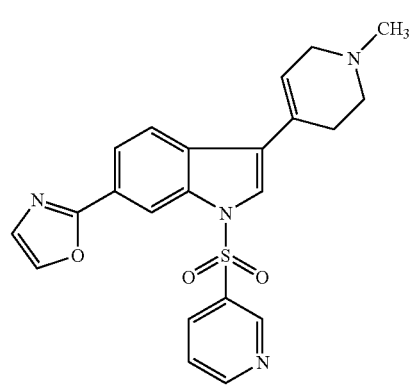

188)
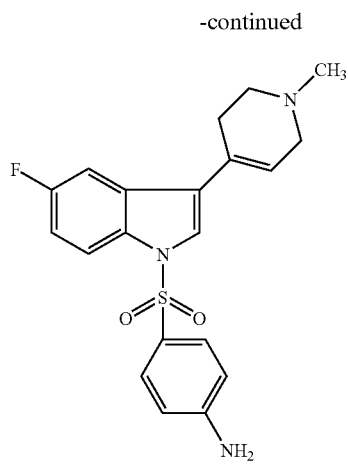
189)
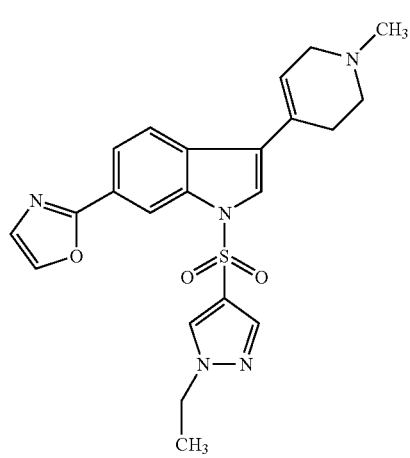
190)
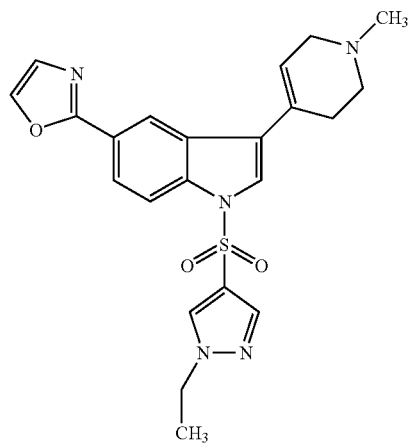
191)
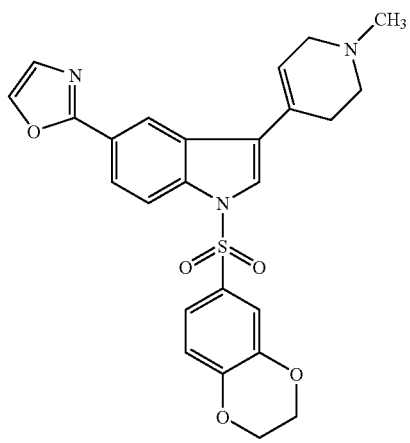
192)
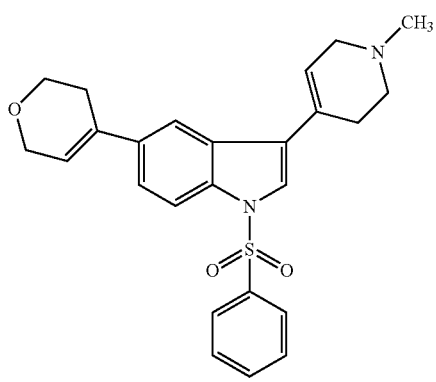
193)
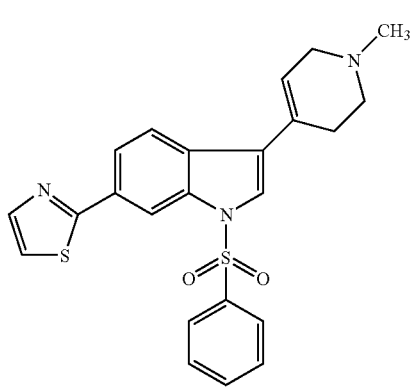

194)
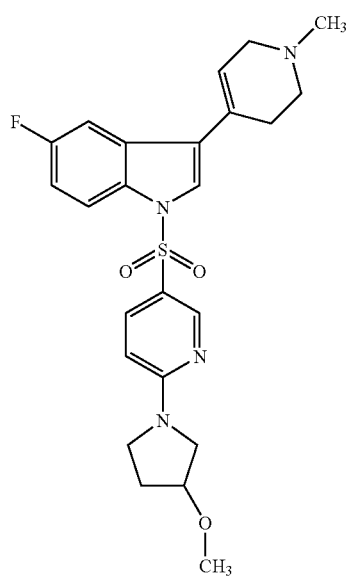
195)
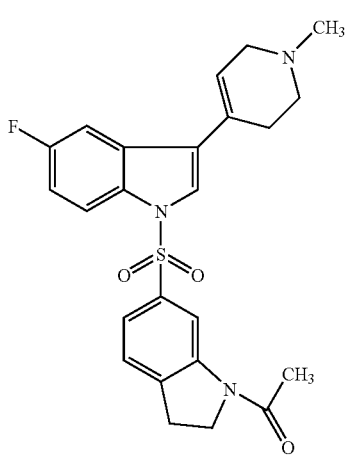
196)
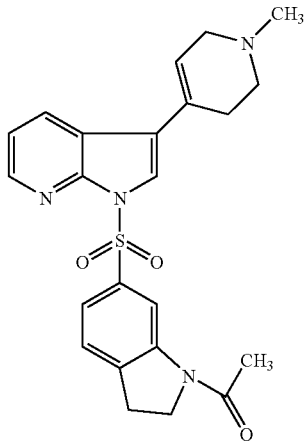
197)
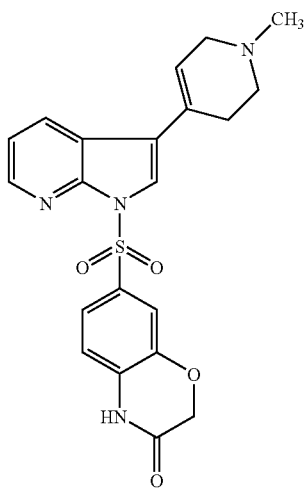
198)
199)

-continued
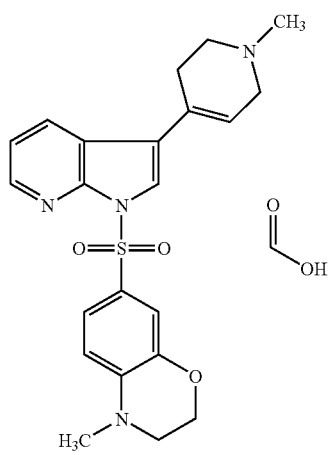
199)
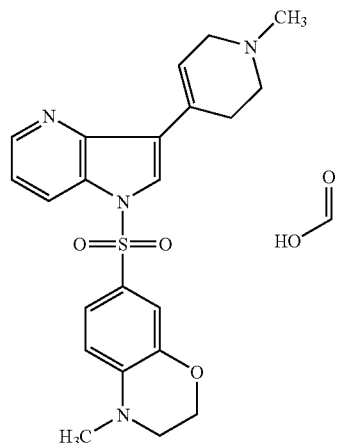
200)
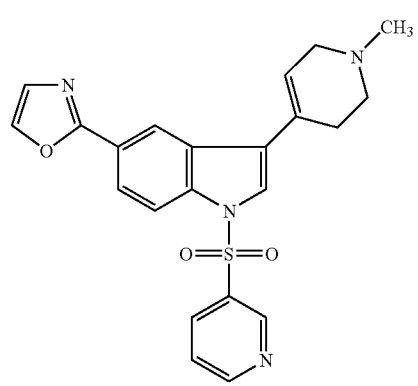
203)
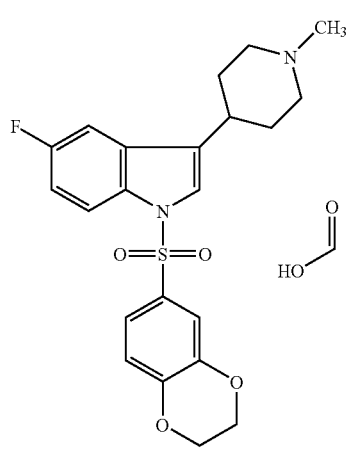
200)
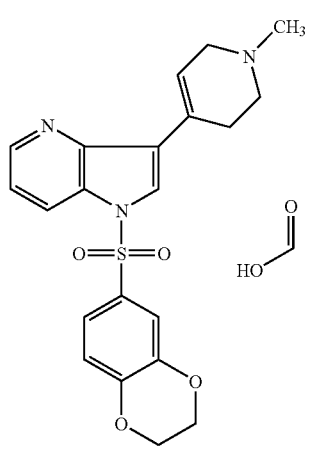
202)
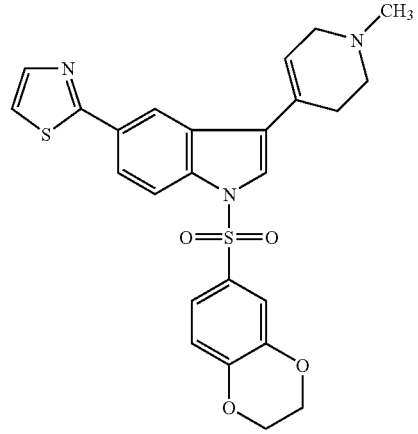
204)
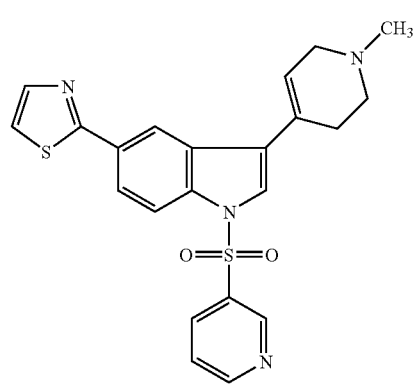
205)
206)

207)
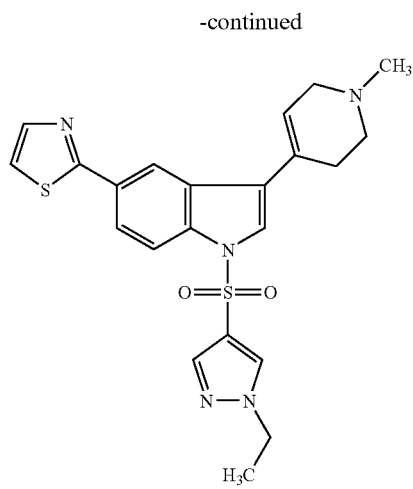
208)
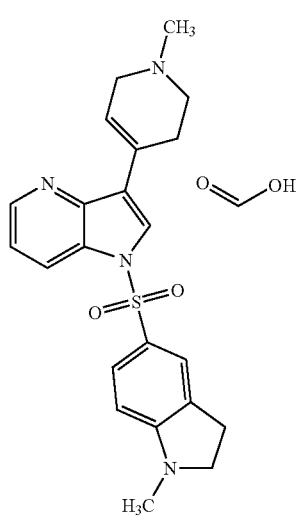
209)
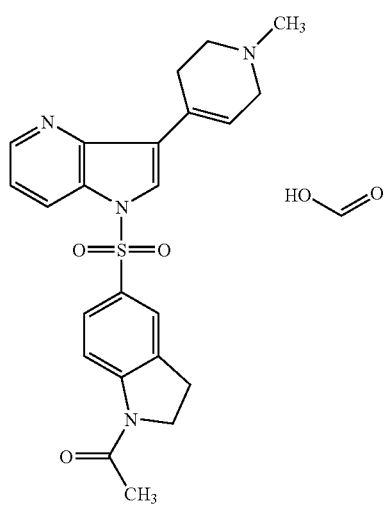
210)
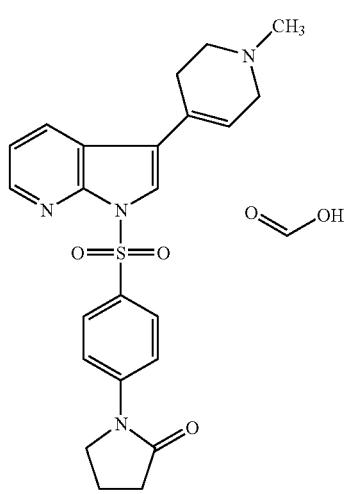
211)
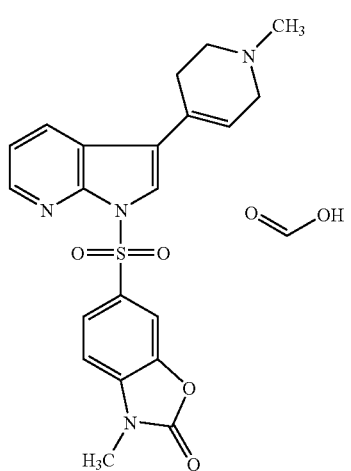
212)
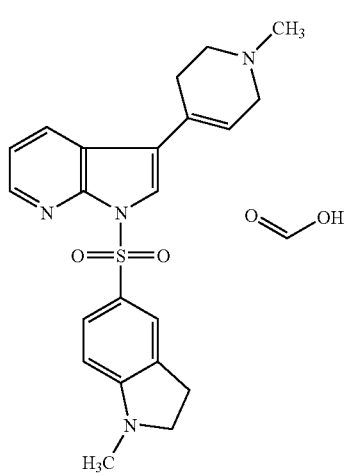

103
-continued
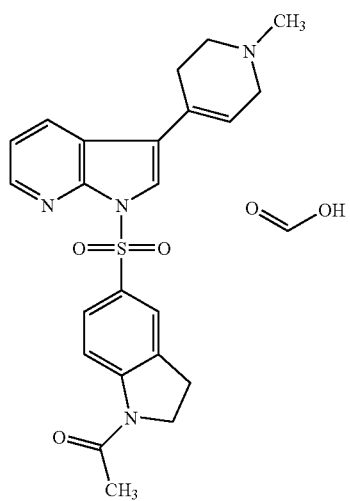
213)
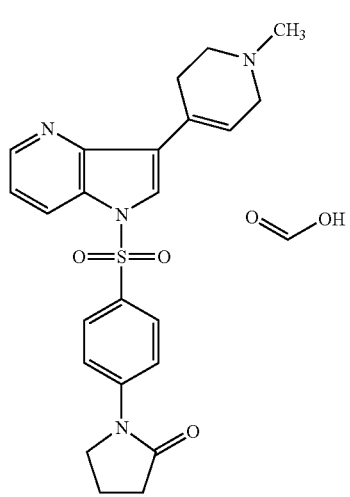
214)
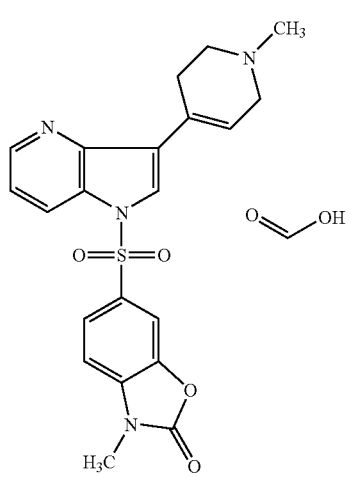
215)
104
-continued
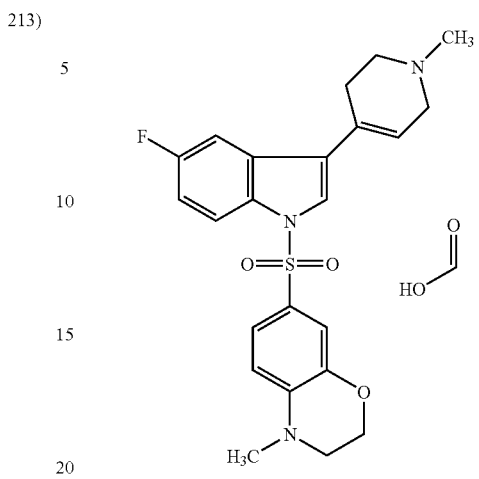
216)
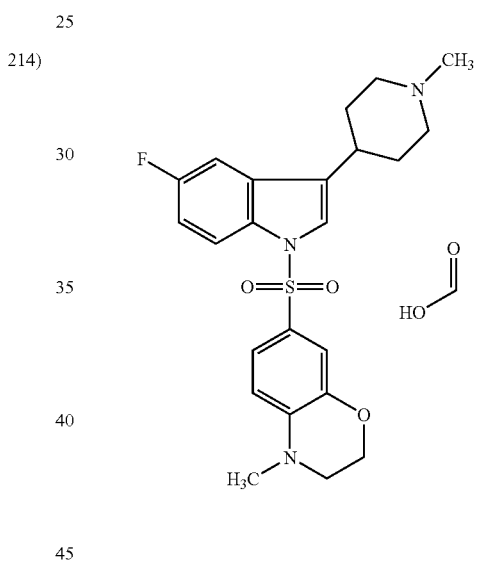
217)
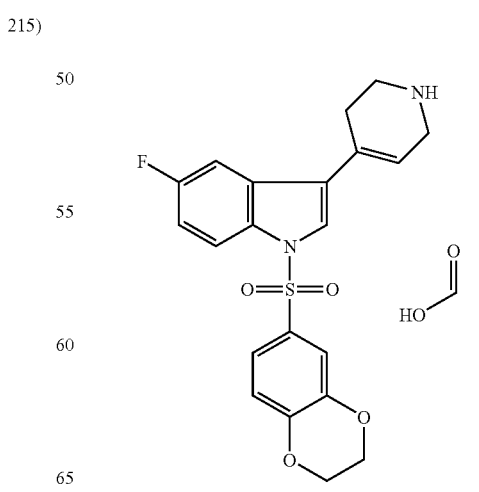
218

219) 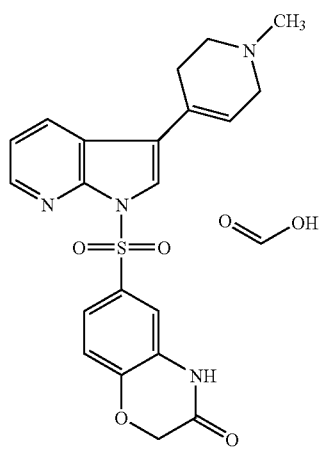
220) 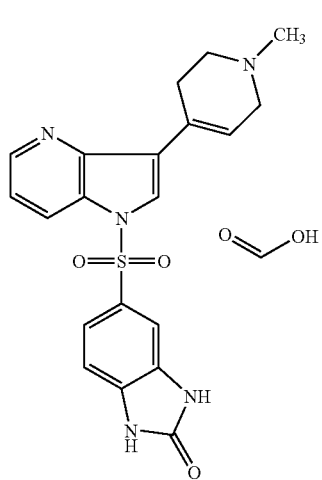
221) 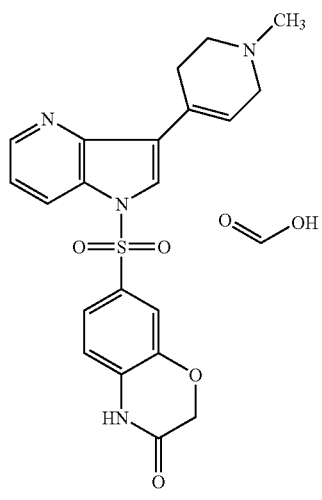
222) 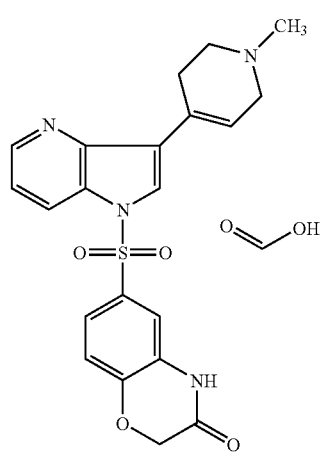
223) 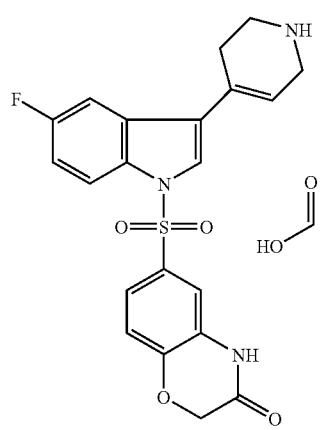
224) 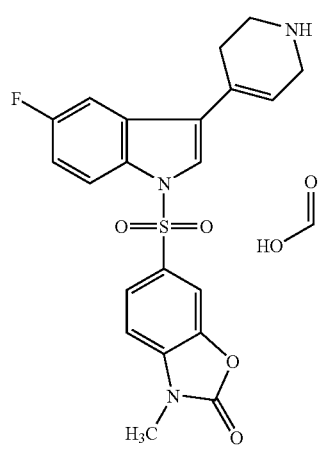

225) 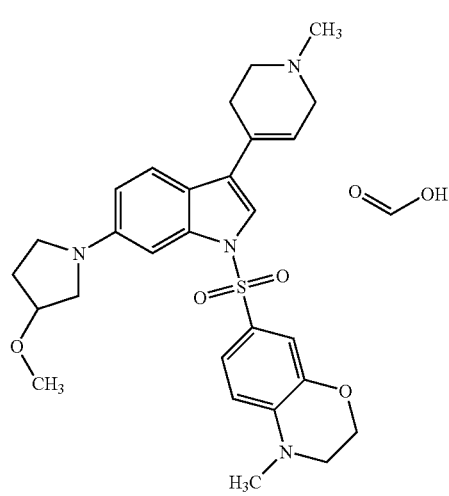
226) 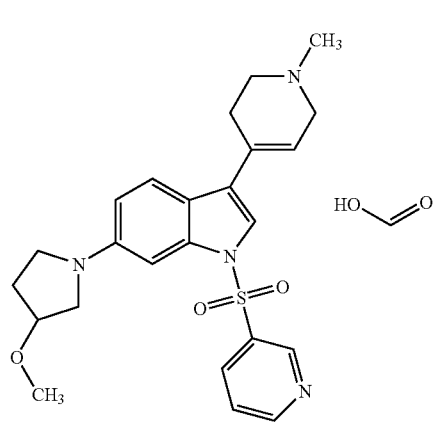 
227)
228) 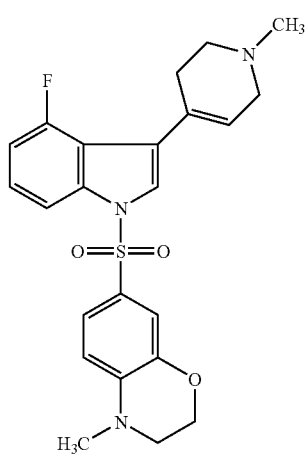
229) 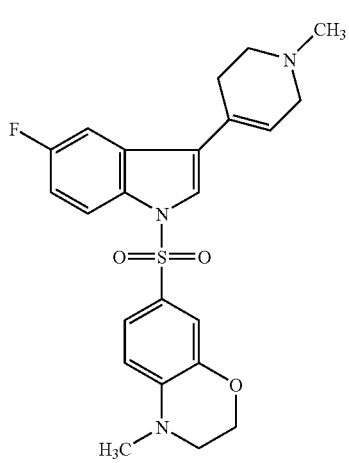
230) 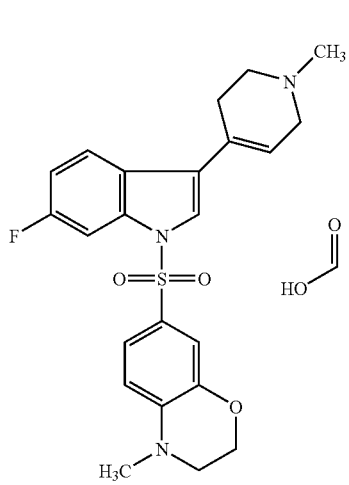

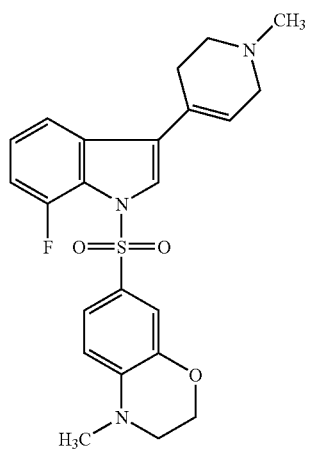
231)
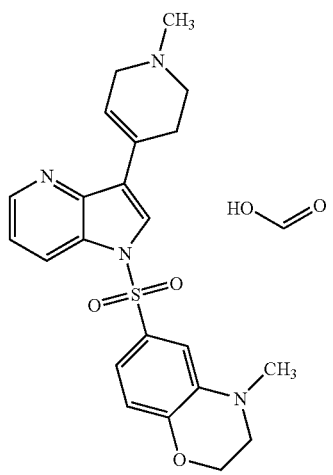
234)
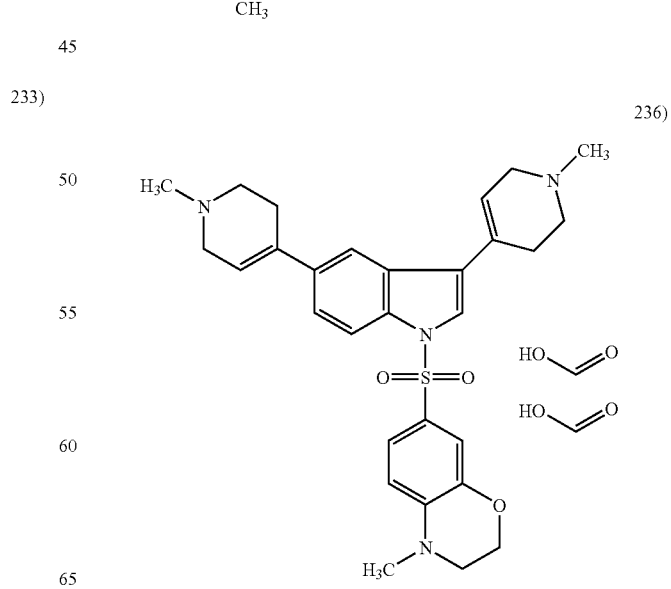

111
-continued
237)
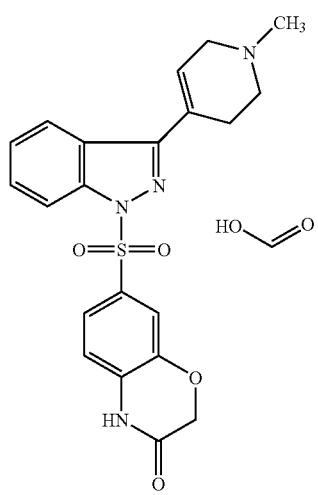
238)
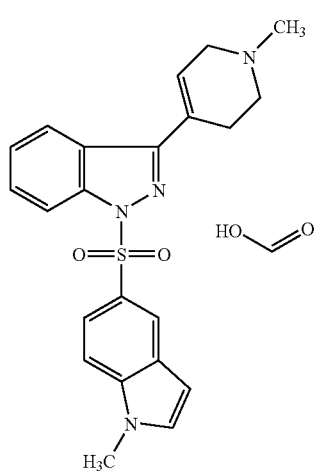
239)
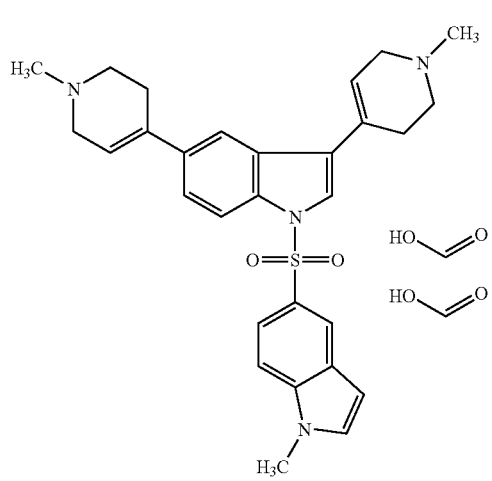
112
-continued
240)
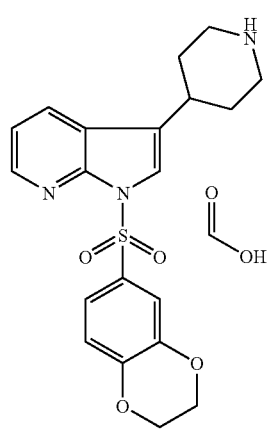
241)
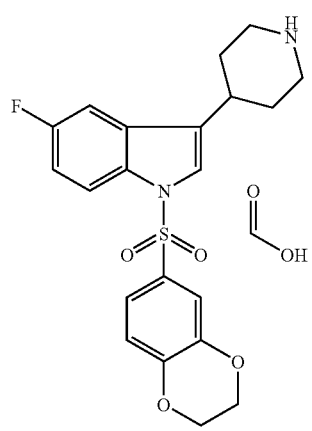
242)
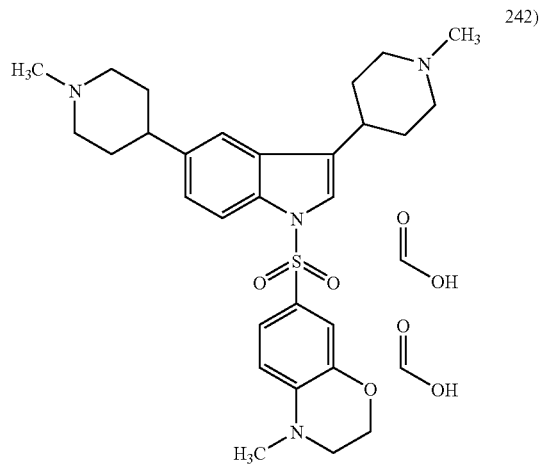

-continued
113)
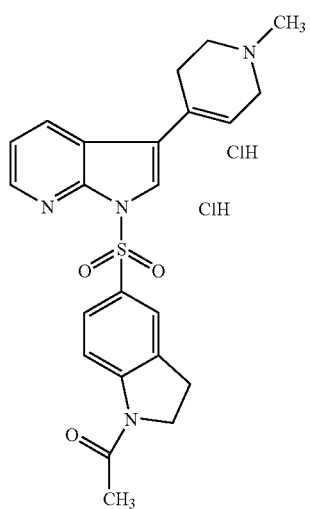
ClH
ClH
244)
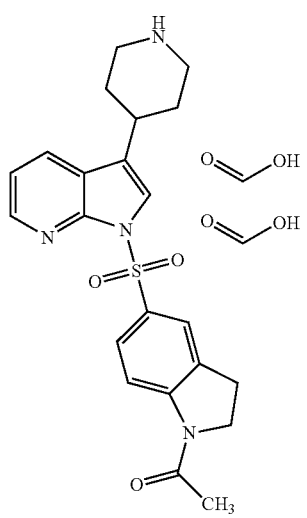
245)
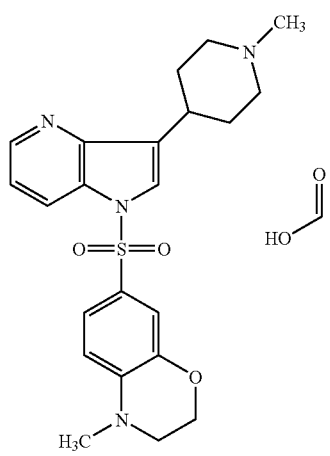
-continued
243)
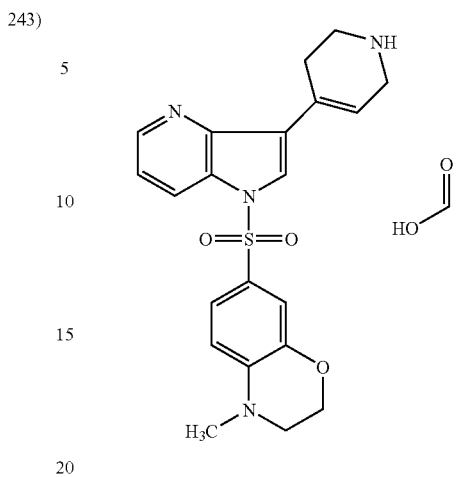
246)
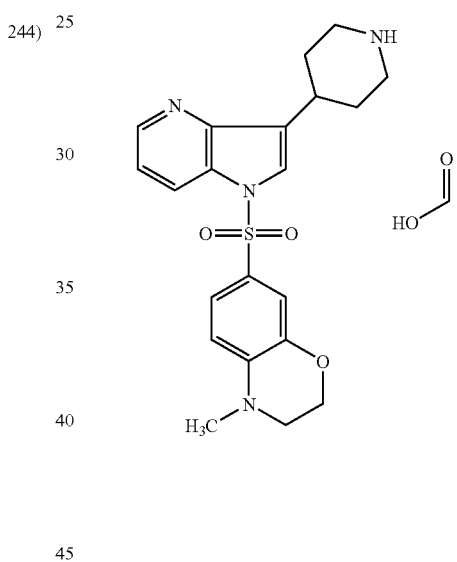
247)
248)
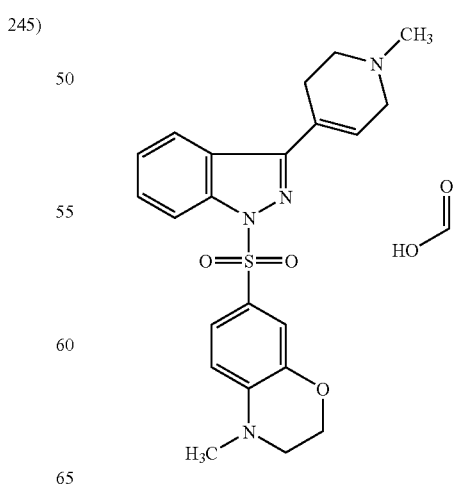

249)
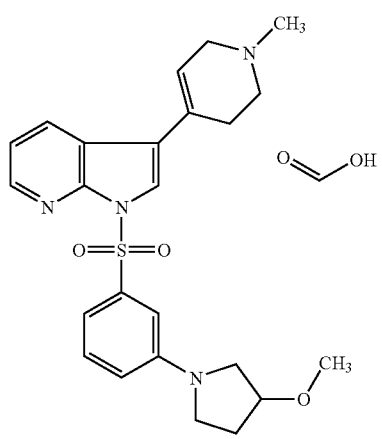
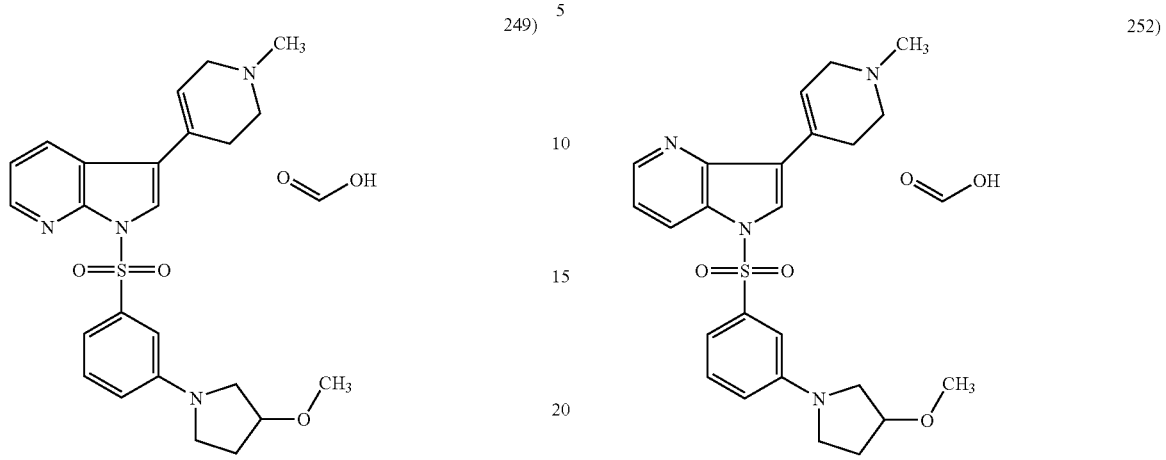
250)
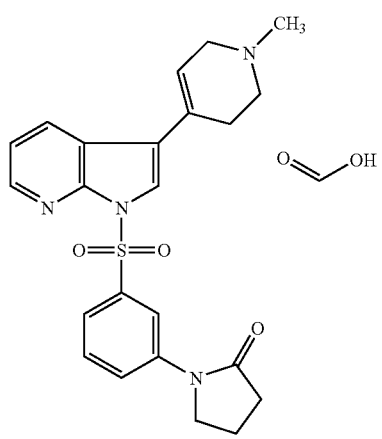
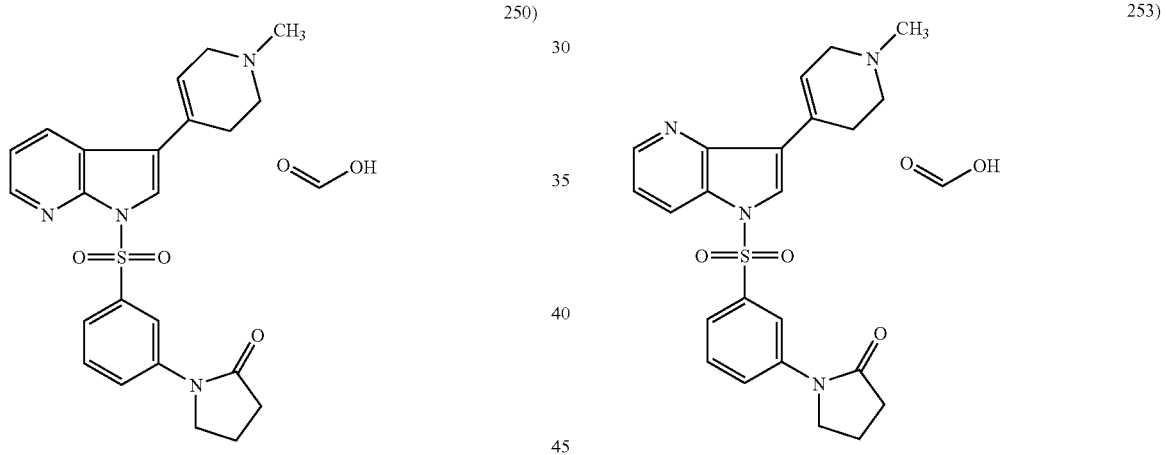
251)
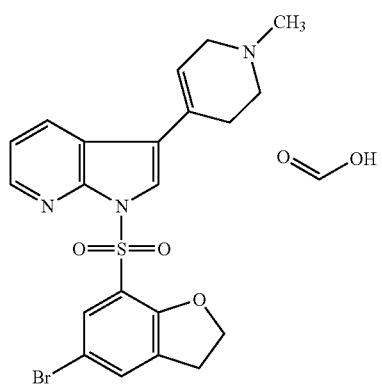
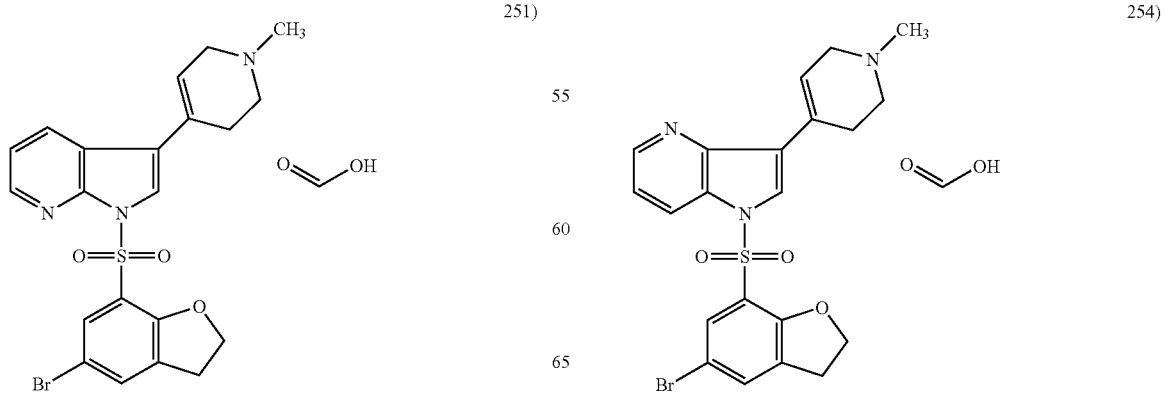
252)
253)
254)

255) 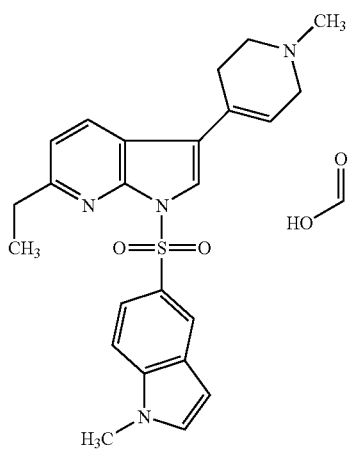
256) 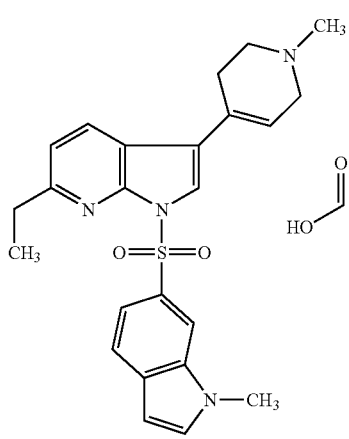
257) 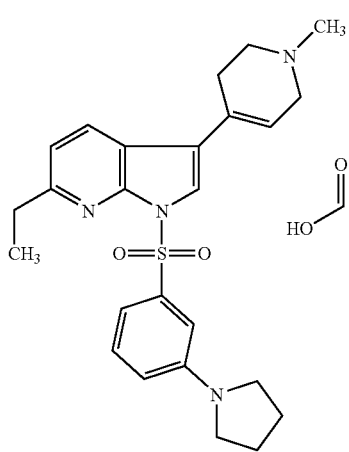
258) 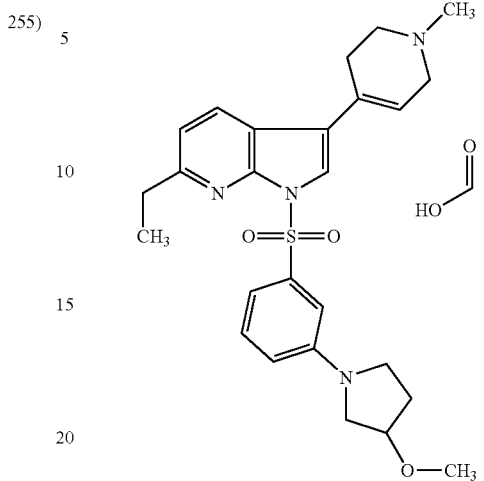
259) 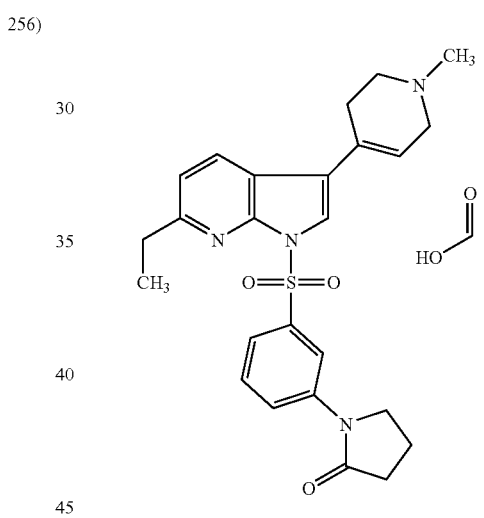
260) 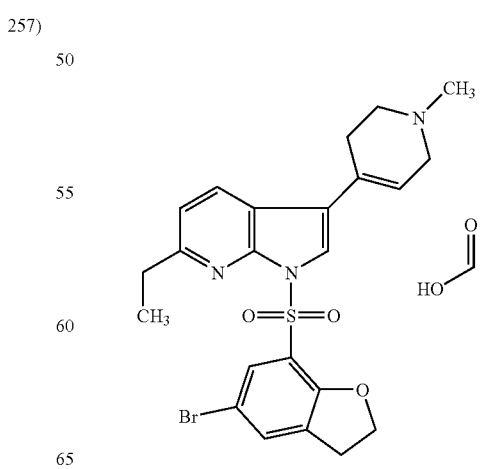

-continued
261)
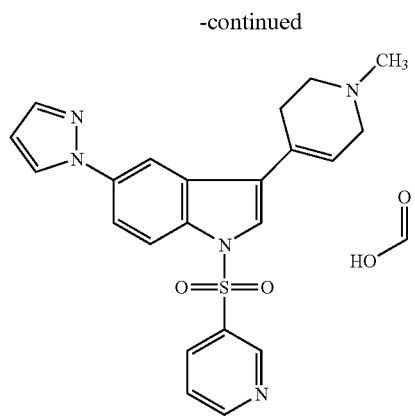
262)
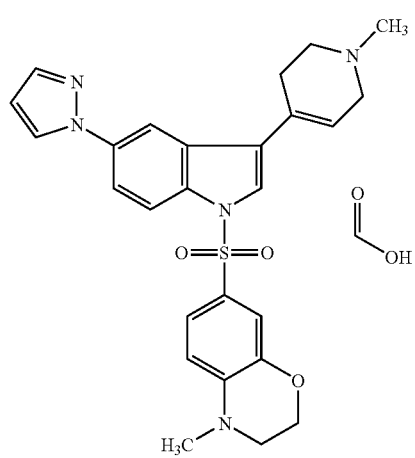
263)
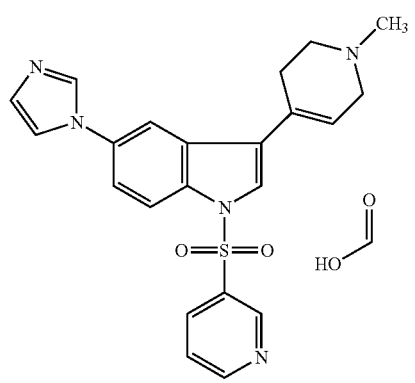
264)
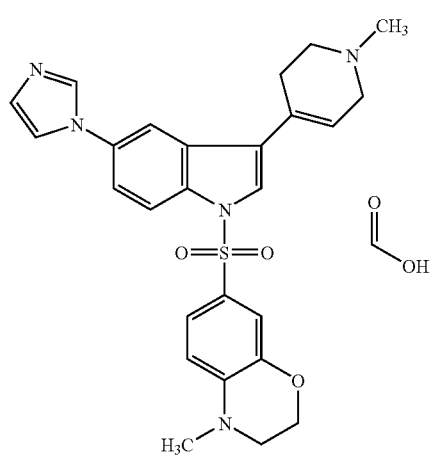
-continued
265)
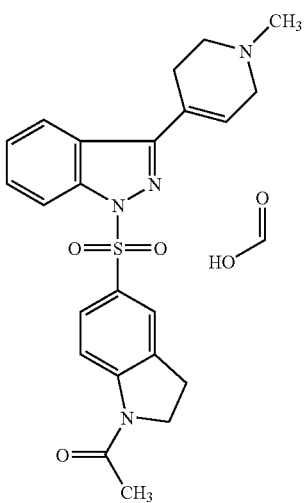
266)
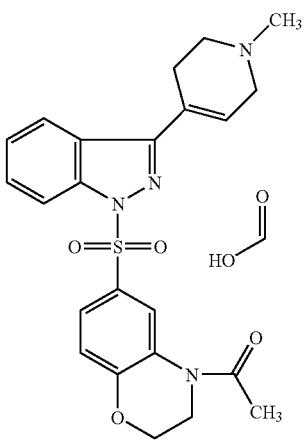
267)
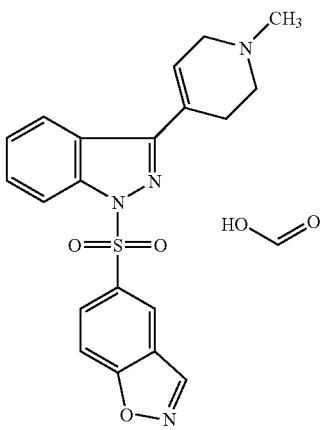

-continued
268)
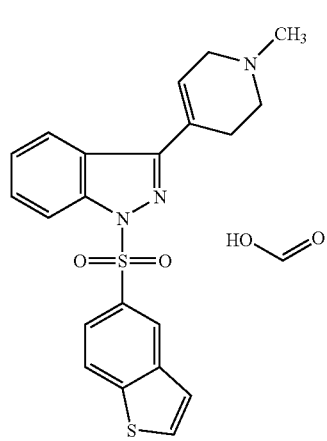
269)
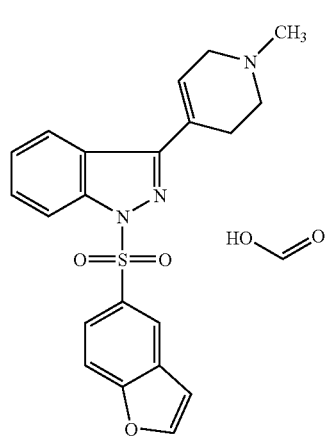
270)
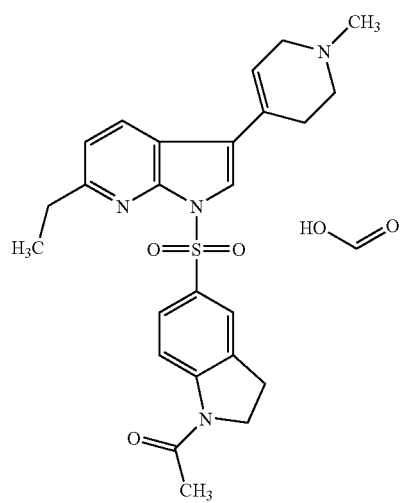
-continued
271)
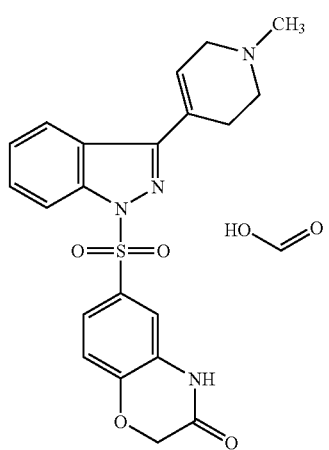
272)
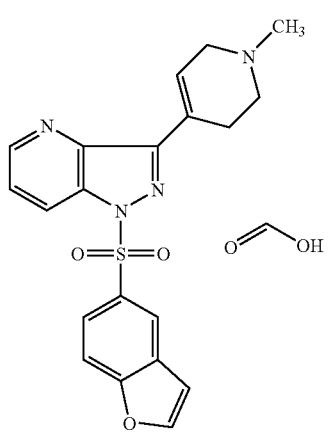
273)
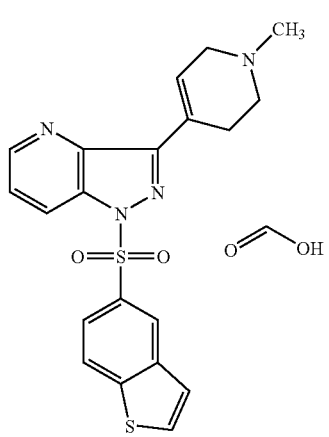

274)
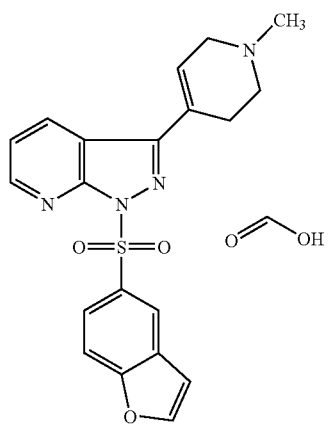
275)
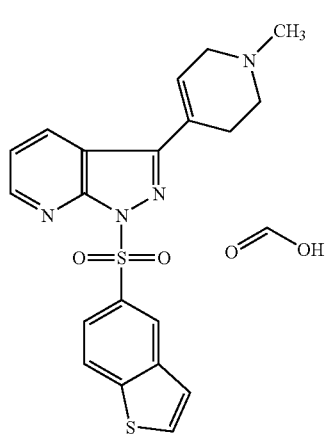
276)
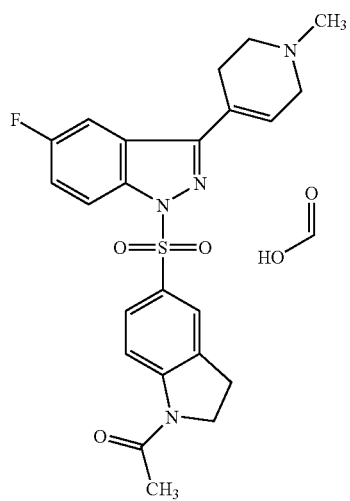
277)
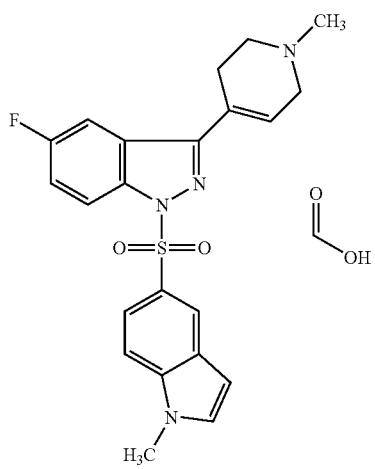
278)
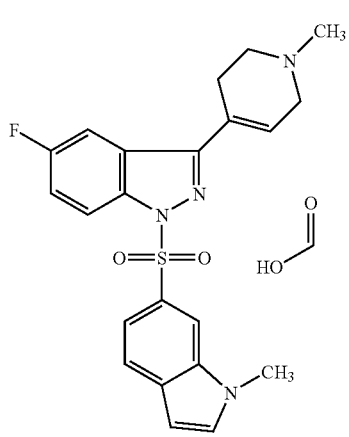
279)
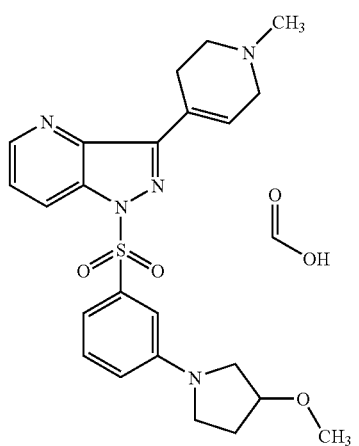

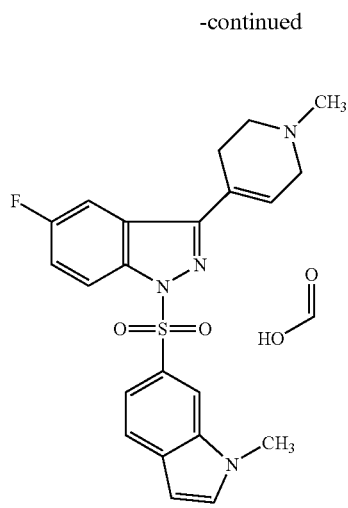
280)
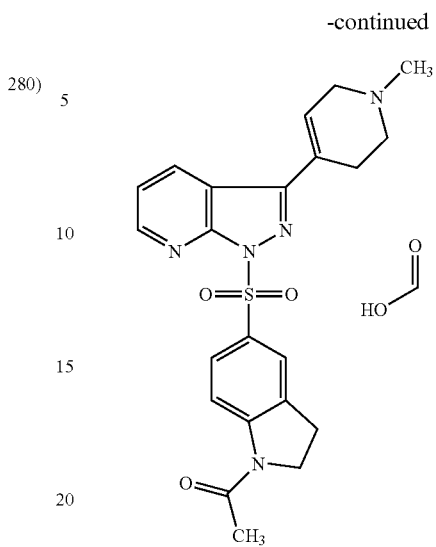
281)
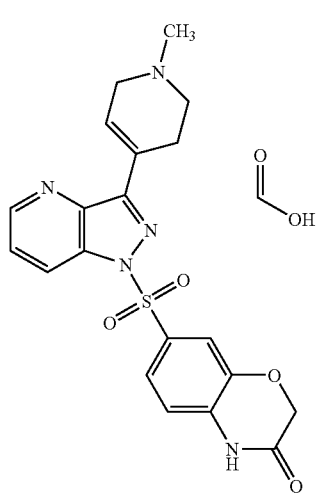
283)
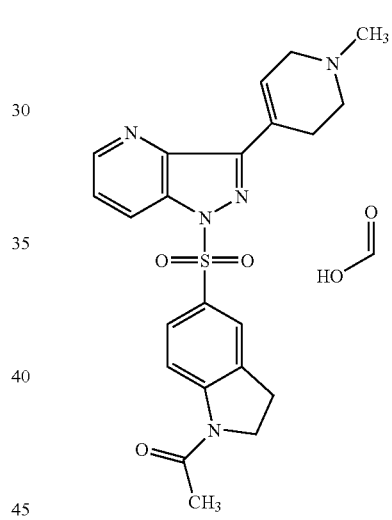
282)
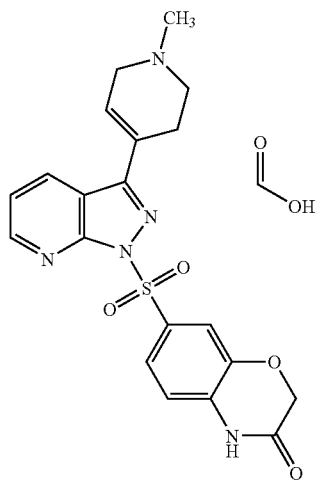
284)
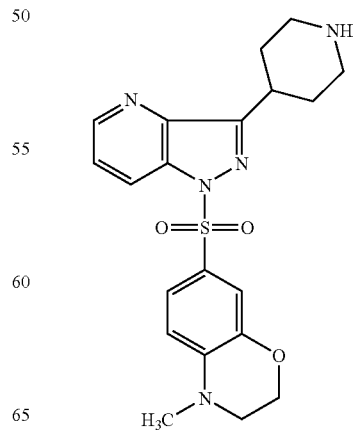
285)

127 128
-continued
286)
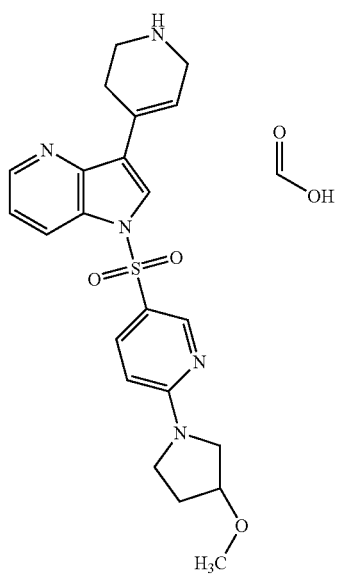
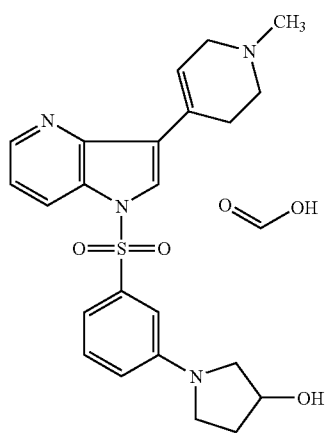 
287)
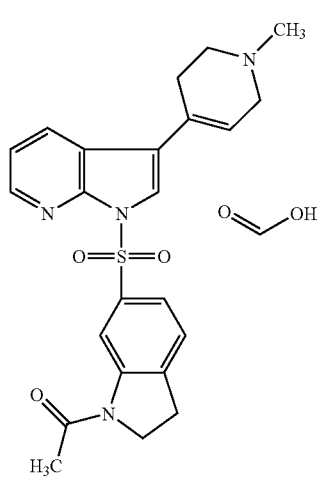 
289)
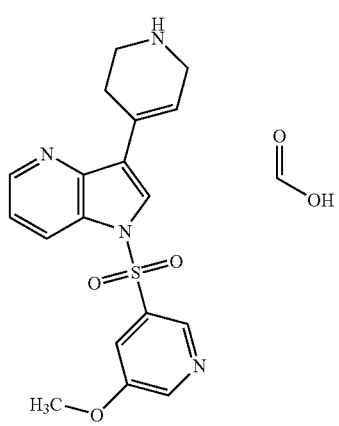
290)
288)
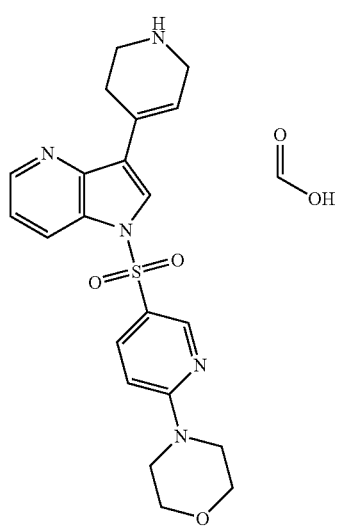 
291)
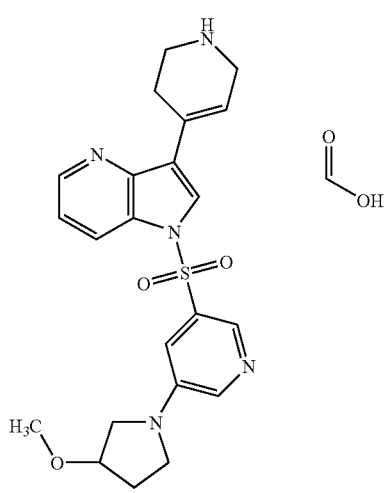

292)
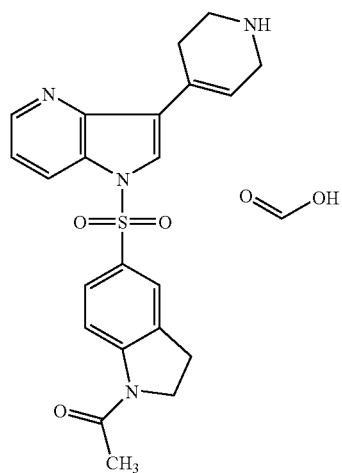
293)
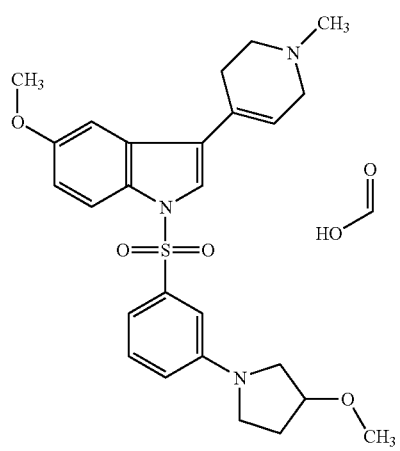
294)
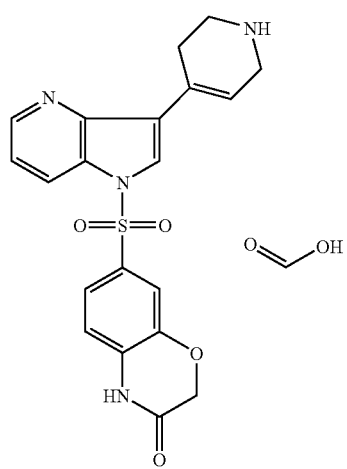
295)
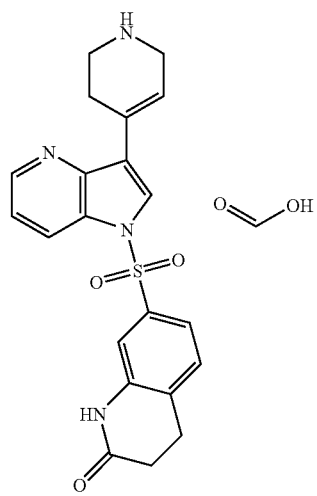
296)
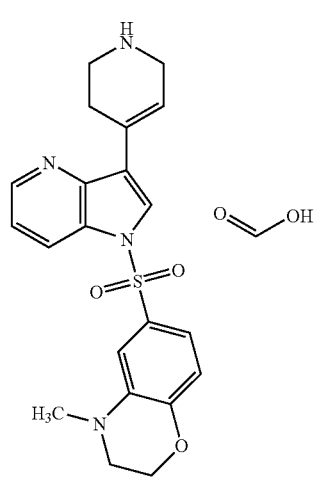
297)
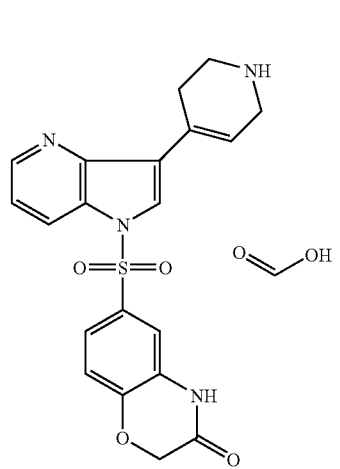

298)
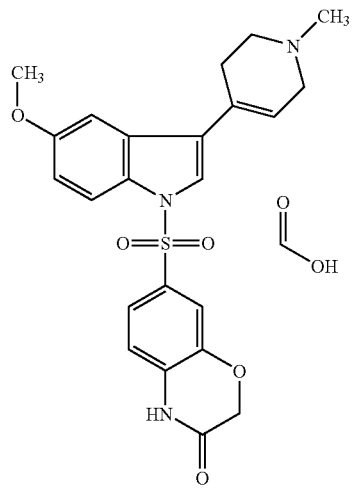
299)
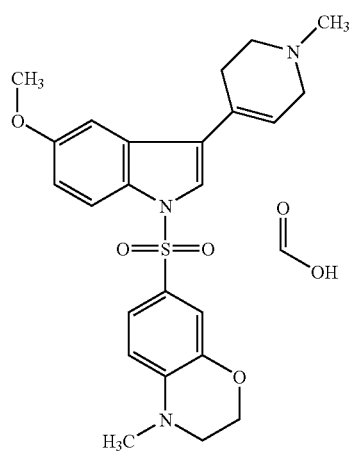
300)
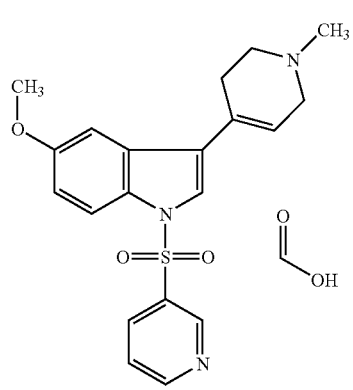
301)
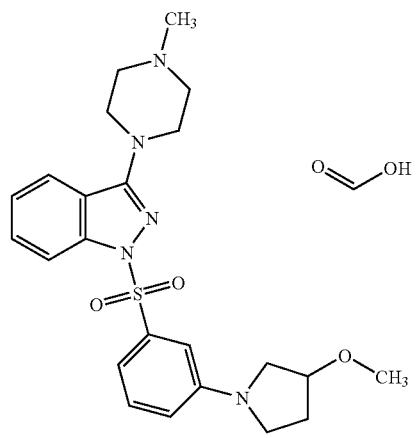
302)
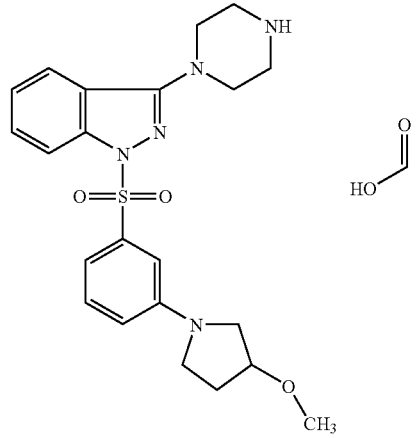
303)
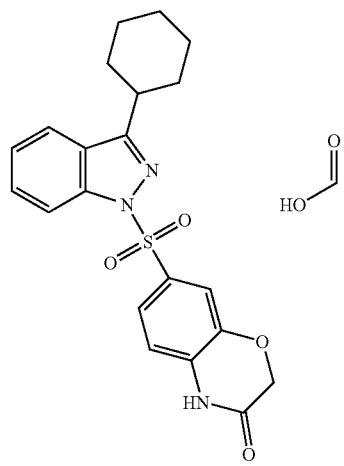

304)
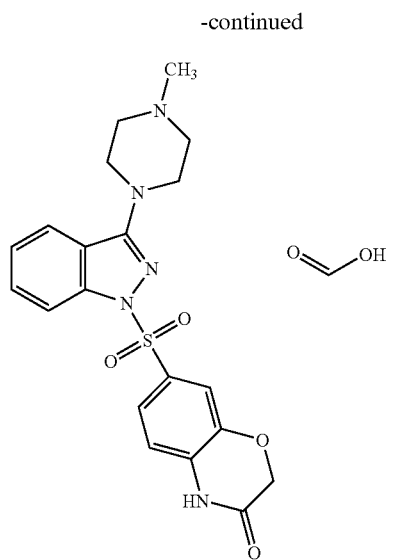
305)
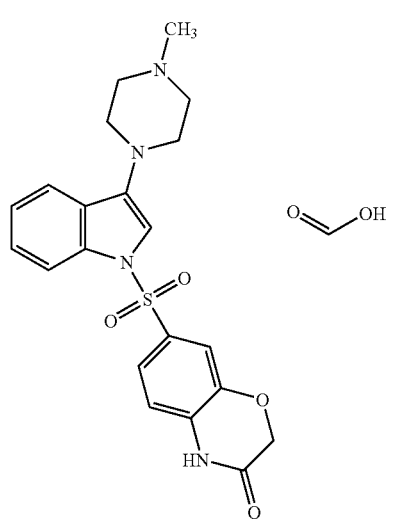
306)
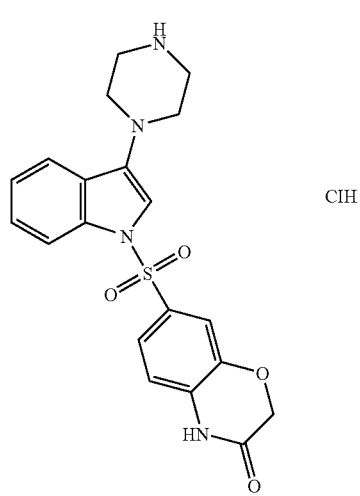
307)
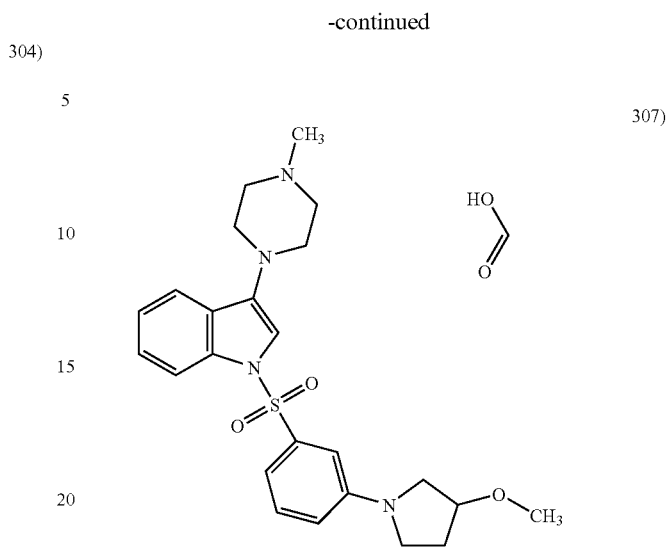
308)
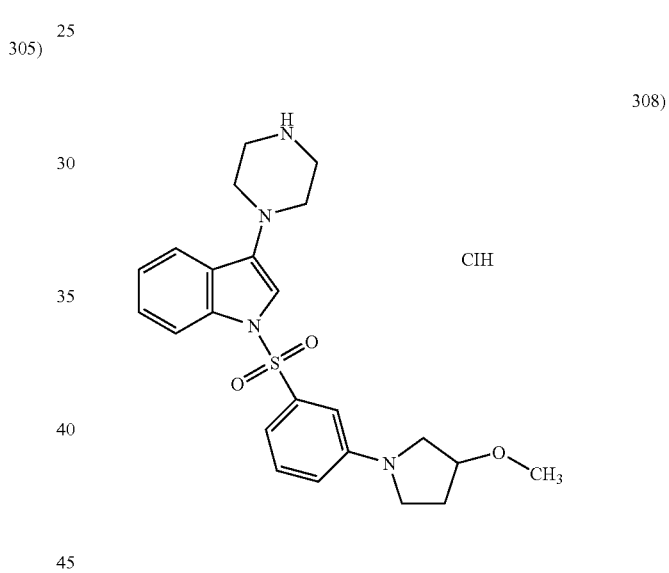
309)
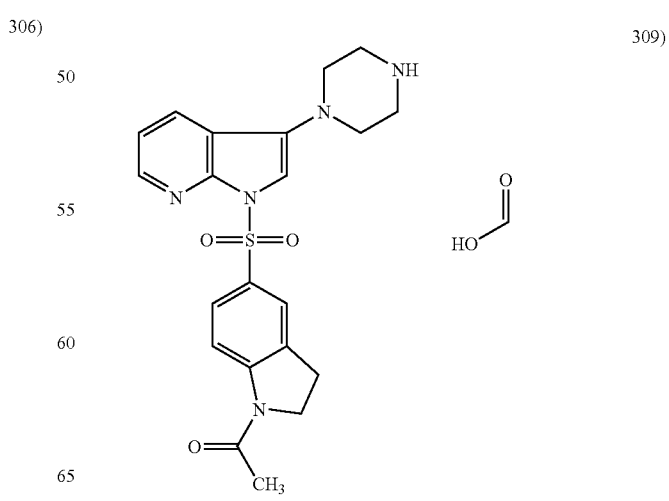

135
-continued
310)
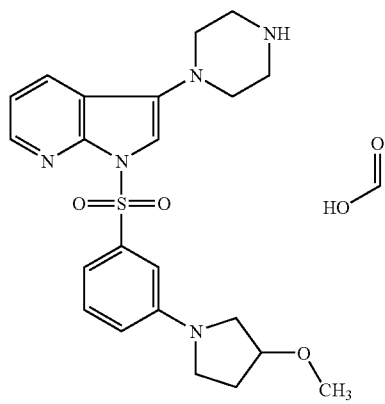
311)
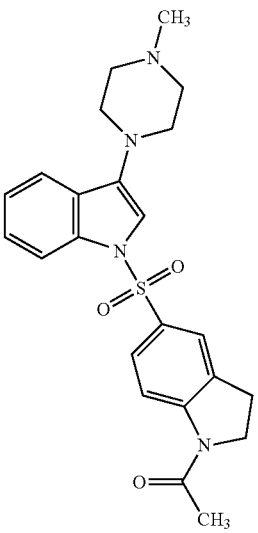
312)
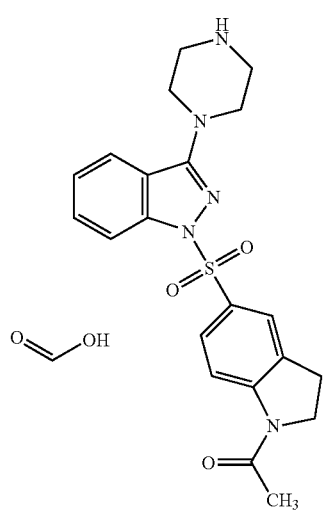
136
-continued
313)
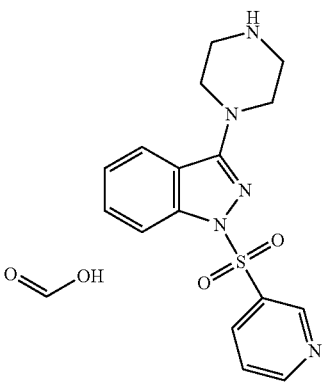
314)
315)
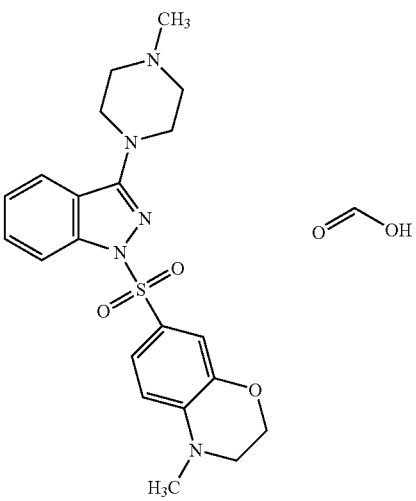

137
-continued
316)
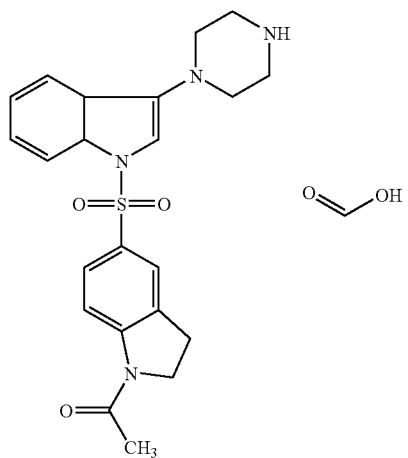
317)
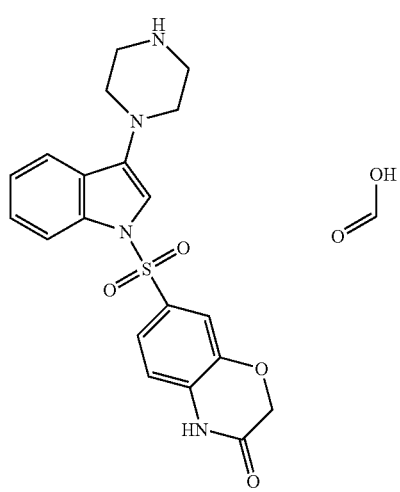
318)
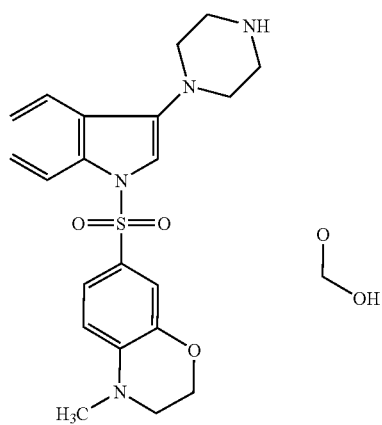
138
-continued
319)
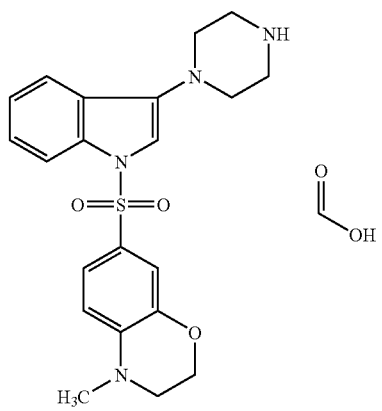
320)
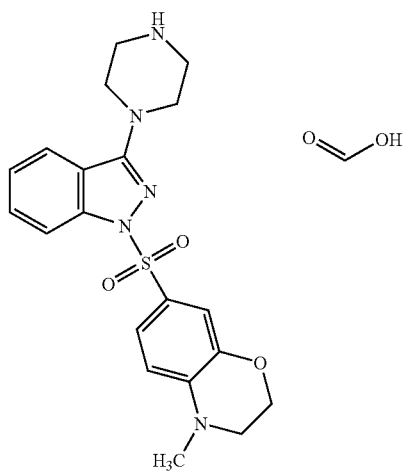
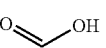
321)
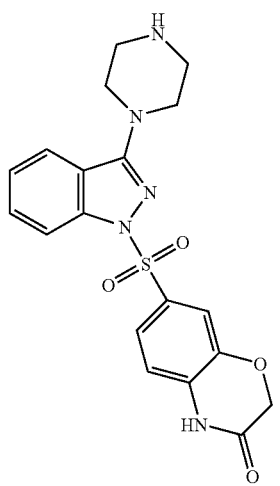

322)
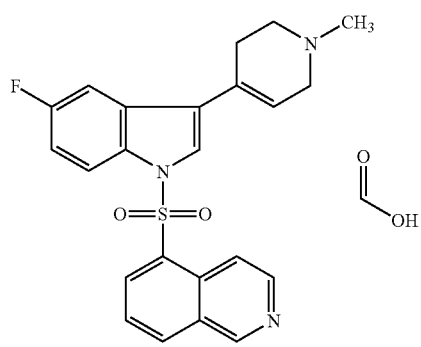
323)
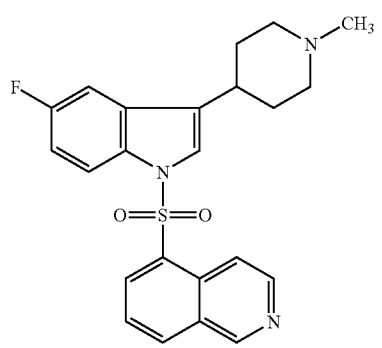
324)
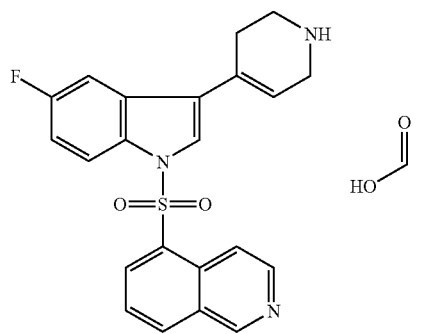
325)
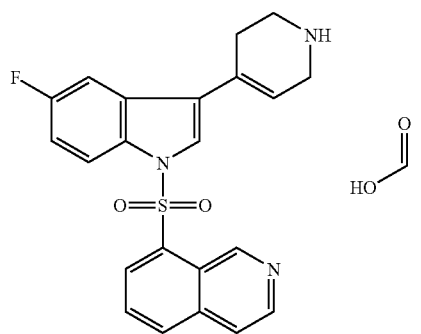
326)
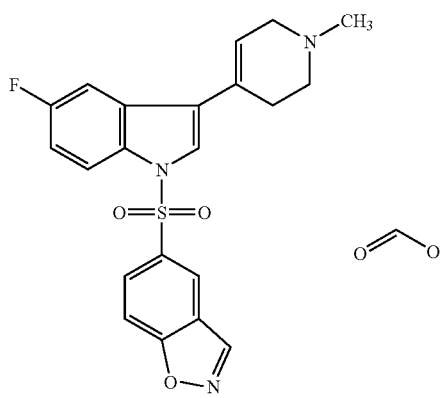
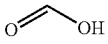
327)
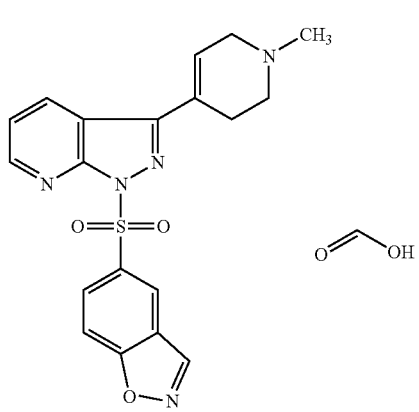
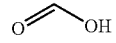
328)
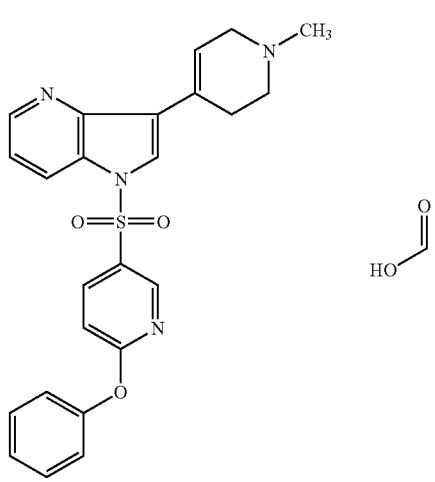
329)
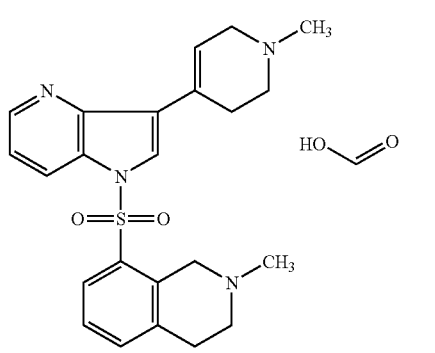
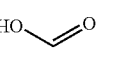

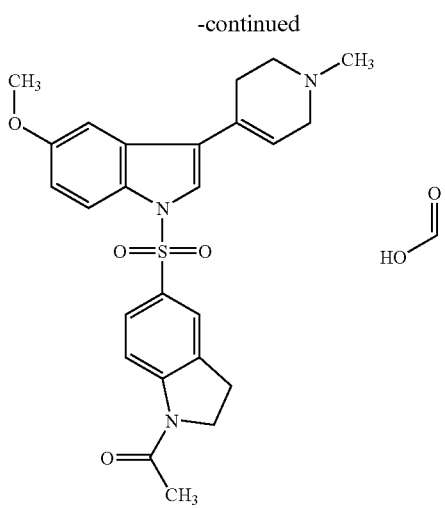

330)

Additional aspects of the present invention include pharmaceutical compositions comprising a compound of this invention and a pharmaceutically acceptable carrier and, optionally, one or more additional active agent(s) as discussed below. Further aspects include methods of treating a disease state related to or modulated by the 5HT6 receptor, in a patient, such as a mammal, e.g., a human, e.g., those disease states mentioned herein.

The compounds of the present invention are effective in inhibiting, or modulating the activity of the 5HT6 receptor in animals, e.g., mammals, especially humans. These compounds exhibit activity, especially where such activity affects states associated with CNS disorders including motor, mood, personality, behavioral, psychiatric, cognitive, and neurodegenerative disorders, such as, but not limited to, Alzheimer's disease (enhancement of cognitive memory), Parkinson's disease, Huntington's disease, anxiety, depression, manic depression, epilepsy, obsessive compulsive disorders, migraine, sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, psychoses, such as schizophrenia, bipolar disorder, and also disorders associated with spinal trauma and/or head injury such as hydrocephalus. Such compounds are also useful for the treatment of memory/cognitive impairment associated with Alzheimer's disease, schizophrenia, Parkinson's disease, Huntington's disease Pick's disease, Creutzfeld Jakob disease, HIV, cardiovascular disease, head trauma or age-related cognitive decline. In addition, such compounds are also expected to be of use in the treatment of certain gastrointestinal (GI) disorders such as, but not limited to, functional bowel disorder, constipation, including chronic constipation, gastroesophageal reflux disease (GERD), nocturnal-GERD, and irritable bowel syndrome (IBS), including diarrhea-predominant IBS (IBS-c), constipation-predominant IBS (IBS-c) and alternating constipation/diarrhea IBS.

All methods comprise administering to the patient in need of such treatment an effective amount of one or more compounds of the invention.

A subject or patient in whom administration of the therapeutic compound is an effective therapeutic regimen for a disease or disorder is preferably a human, but can be any animal, including a laboratory animal in the context of a clinical trial or screening or activity experiment. Thus, as can be readily appreciated by one of ordinary skill in the art, the methods, compounds and compositions of the present invention are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc., avian species, such as chickens, turkeys, songbirds, etc., i.e., for veterinary medical use.

The compounds of the present invention may be prepared using conventional synthetic methods analogous to those established in the art, and, if required, standard separation or isolation techniques. Suitable synthetic procedures that may be used to prepare the compounds of the present invention are described in, for example, U.S. Pat. Nos. 6,133,217, 6,191,141, and 6,903,112. All starting materials are either commercially available, or can be conventionally prepared from known starting materials without undue experimentation.

One of ordinary skill in the art will recognize that some of the compounds of Formula I can exist in different geometrical isomeric forms. In addition, some of the compounds of the present invention possess one or more asymmetric atoms and are thus capable of existing in the form of optical isomers, as well as m the form of racemic or nonracemic mixtures thereof, and in the form of diastereomers and diastereomeric mixtures inter alia. All of these compounds, including cis isomers, trans isomers, diastereomeric mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereomeric salts using an optically active acid or base or formation of covalent diastereomers. Examples of appropriate acids include, but are not limited to, tartaric, diacetyltartaric, dibenzoyltartaric, ditoluoyltartaric and camphorsulfonic acid. Mixtures of diastereomers can be separated into their individual diastereomers on the basis of their physical and/or chemical differences by methods known to those skilled in the art, for example, by chromatography or fractional crystallization. The optically active bases or acids are then liberated from the separated diastereomeric salts.

A different process for separation of optical isomers involves the use of chiral chromatography (e.g., chiral HPLC or SFC columns), with or without conventional derivation, optimally chosen to maximize the separation of the enantiomers. Suitable chiral HPLC or SFC columns are manufactured by Diacel, e.g., Chiracel OD and Chiracel OJ among many others, all routinely selectable. Enzymatic separations, with or without derivatization, are also useful. The optically active compounds of Formulas I-II can likewise be obtained by utilizing optically active starting materials in chiral syntheses processes under reaction conditions which do not cause racemization.

In addition, one of ordinary skill in the art will recognize that the compounds can be used in different enriched isotopic forms, e.g., enriched in the content of $^2H$, $^3H$, $^{11}C$, $^{13}C$ and/or $^{14}C$. In one particular embodiment, the compounds are deuterated. Such deuterated forms can be made by the procedure described in U.S. Pat. Nos. 5,846,514 and 6,334,997. As described in U.S. Pat. Nos. 5,846,514 and 6,334,997, deuteration can improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] (2000), 110 pp. CAN 133:68895 AN 2000:473538 CAPLUS; Kabalka, George W.; Varma, Rajender S. The Synthesis of Radiolabeled Compounds via Organometallic Intermediates. Tetrahedron (1989), 45(21), 6601-21, CODEN: TETRAB ISSN: 0040-4020. CAN 112:20527 AN 1990:20527 CAPLUS; and Evans, E. Anthony. Synthesis of radiolabeled compounds, J. Radioanal. Chem. (1981), 64(1-2), 9-32. CODEN: JRACBN ISSN:0022-4081, CAN 95:76229 AN 1981:476229 CAPLUS.

The present invention also relates to useful forms of the compounds as disclosed herein, including free base forms, as well as pharmaceutically acceptable salts or prodrugs of all the compounds of the present invention for which salts or prodrugs can be prepared. Pharmaceutically acceptable salts include those obtained by reacting the main compound, functioning as a base, with an inorganic or organic acid to form a salt, for example, but not limited to, salts of hydrochloric acid, sulfuric acid, phosphoric acid, methanesulfonic acid, camphorsulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

The following are further non-limiting examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, fydroiodides, 2-hydroxyethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

For example, the pharmaceutically acceptable salt can be a hydrochloride, hydroformate, hydrobromide, or maleate.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

One of ordinary skill in the art will also recognize that some of the compounds of Formula I can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

One of ordinary skill in the art will further recognize that compounds of Formula I can exist in different solvate forms. Solvates of the compounds of the invention may also form when solvent molecules are incorporated into the crystalline lattice structure of the compound molecule during the crystallization process. For example, suitable solvates include hydrates, e.g., monohydrates, dihydrates, sesquihydrates, and hemihydrates.

The compounds of the invention can be administered alone or as an active ingredient of a formulation. Thus, the present invention also includes pharmaceutical compositions of one or more compounds of Formula I containing, for example, one or more pharmaceutically acceptable carriers.

Numerous standard references are available that describe procedures for preparing various formulations suitable for administering the compounds according to the invention.

Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their high degree of selective 5HT6 receptor activity, the compounds of the present invention can be administered to anyone requiring modulation of the 5HT6 receptor. Administration may be accomplished according to patient needs, for example, orally, nasally, parenterally (subcutaneously, intravenously, intramuscularly, intrasternally and by infusion) by inhalation, rectally, vaginally, topically and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration, the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds of the present invention are effective in inhibiting, or modulating the activity of the 5HT6 receptor in animals, e.g., mammals, especially humans. These compounds exhibit activity, especially where such activity affects states associated with CNS disorders including motor, mood, personality, behavioral, psychiatric, cognitive, and neurodegenerative disorders, such as, but not limited to, Alzheimer's disease (enhancement of cognitive memory), Parkinson's disease, Huntington's disease, anxiety, depression, manic depression, epilepsy, obsessive compulsive disorders, migraine, sleep disorders, feeding disorders such as anorexia and bulimia, panic attacks, attention deficit hyperactivity disorder (ADHD), attention deficit disorder (ADD), withdrawal from drug abuse such as cocaine, ethanol, nicotine and benzodiazepines, psychoses, such as schizophrenia, bipolar disorder, and also disorders associated with spinal trauma and/or head injury such as hydrocephalus. Such compounds are also useful for the treatment of memory/cognitive impairment associated with Alzheimer's disease, schizophrenia, Parkinson's disease, Huntington's disease, Pick's disease, Creutzfeld Jakob disease, HIV, cardiovascular disease, head trauma or age-related cognitive decline. In addition, such compounds are also expected to be of use in the treatment of certain gastrointestinal (GI) disorders such as functional bowel disorder and irritable bowel syndrome.

Assays for determining 5HT6 receptor activity, and selectivity of 5HT6 receptor activity are known within the art. See, for example, U.S. Pat. Nos. 6,133,287, 6,686,374, and 6,903,112, and Example 13 described below. Compounds of the invention show 5-HT6 binding activity with receptor Ki values of typically less than 1-100 nM. Preferably, the binding activity will be less than 1-50 nM, and more preferably, the activity will be less than 1-10 nM. Compounds of the invention show 5-HT6 functional activity with pA2 values of greater than 6 ($IC_{50}$ less than 1 µM). Preferably, the pA2 value will be greater than 7 ($IC_{50}$ less than 500 nM), and more preferably the pA2 value will be greater than 8 ($IC_{50}$ less than 100 nM).

The preferred pharmacokinetic profile of the compounds may be further shown with measurements to determine hERG and Cyp3A4, inhibition. The hERG inhibition may be measured as described by Dubin, A. (2004). hERG Potassium Channel Activity Assayed with the PatchXpress Planar Patch Clamp. Inaugural PatchXpress User's Meeting, Feb. 12, 2004 (Baltimore, Md.). The Cyp inhibition may be measured as described by Miller V P, Stresser D M, Blanchard A P, Turner S, Crespi C L: Fluorometric high-throughput screening for inhibitors of cytochrome P450. Ann N Y Acad Sci 200; 919: 26-32. In one preferred embodiment, the compounds show hERG inhibition with an $IC_{50}$ greater than 1 µM, preferably greater than 3 µM, and more preferably greater than 10 µM. In another preferred embodiment, the compounds show Cyp3A4 inhibition with an $IC_{50}$ greater than 1 µM, preferably greater than 3 µM, and more preferably greater than 10 µM.

High hERG inhibition and Cyp3A4 inhibition is potentially linked with adverse cardiac action potential and drug metabolism, respectively.

According to a method aspect, the invention includes a method for the treatment of a disorder of the central nervous system (CNS) related to or affected by the 5HT6 receptor in a patient in need thereof by administering to the patient a therapeutically effective amount of a compound selected from formula I, as described herein above.

The compounds can be administered as the sole active agent or in combination with other pharmaceutical agents such as other agents used in the treatment of CNS disorders, such as psychoses, especially schizophrenia and bipolar disorder, obsessive-compulsive disorder, Parkinson's disease, cognitive impairment and/or memory loss, e.g., nicotinic α-7 agonists, PDE4 inhibitors, PDE10 inhibitors, other 5HT6 receptor ligands, calcium channel blockers, muscarinic m1 and m2 modulators, adenosine receptor modulators, ampakines, NMDA-R modulators, mGluR modulators, doparine modulators, serotonin modulators, canabinoid modulators, and cholinesterase inhibitors (e.g., donepezil, rivastigimine, and galanthanamine). In such combinations, each active ingredient can be administered either in accordance with their usual dosage range or in accordance with a dose below their usual dosage range.

The compounds can be administered in combination with other pharmaceutical agents used in the treatment of schizophrenia, e.g., Clozaril, Zyprexa, Risperidone, and Seroquel. Thus, the invention also includes methods for treating schizophrenia, including memory impairment associated with schizophrenia, comprising administering to a patient, simultaneously or sequentially, the compound of the invention and one or more additional agents used in the treatment of schizophrenia such as, but not limited to, Clozaril, Zyprexa, Risperidone, and Seroquel. In methods using simultaneous administration, the agents can be present in a combined composition or can be administered separately. As a result, the invention also includes compositions comprising a compound according to Formula I and one or more additional pharmaceutical agents used in the treatment of schizophrenia, e.g., Clozaril, Zyprexa, Risperidone, and Seroquel. Similarly, the invention also includes kits containing a composition comprising a compound according to Formula I and another composition comprising one or more additional pharmaceutical agents used in the treatment of schizophrenia, e.g., Clozaril, Zyprexa, Risperidone, and Seroquel.

In addition, the compounds can be administered in combination with other pharmaceutical agents used in the treatment bipolar disorder such as Lithium, Zyprexa, Depakote, and Zyprexa. Thus, the invention also includes methods for treating bipolar disorder, including treating memory and/or cognitive impairment associated with the disease, comprising administering to a patient, simultaneously or sequentially, the compound of the invention and one or more additional agents used in the treatment of bipolar disorder such as, but not limited to, Lithium, Zyprexa, and Depakote. In methods using simultaneous administration, the agents can be present in a combined composition or can be administered separately. As a result, the invention also includes compositions comprising a compound according to Formula I and one or more additional pharmaceutical agents used in the treatment of bipolar disorder such as, but not limited to, Lithium, Zyprexa, and Depakote. Similarly, the invention also includes kits containing a composition comprising a compound according to Formula I and another composition comprising one or more additional pharmaceutical agents used in the treatment of bipolar disorder such as Lithium, Zyprexa, and Depakote.

In one preferred embodiment, the compounds of the invention can be administered in combination with a nicotinic acetylcholine subtype α-7 receptor ligand (α-7 receptor ligand).

Nicotinic acetylcholine subtype α-7 receptor ligands modulate the function of nicotinic acetylcholine subtype α-7 receptors by altering the activity of the receptor. Suitable compounds also can be partial agonists that partially block or partially activate the α-7 receptor or agonists that activate the receptor. Positive allosteric modulators are compounds that potentiate the receptor response to acetylcholine without themselves triggering receptor activation or desensitization, or either, of the receptor. Nicotinic acetylcholine subtype α7 receptor ligands that can be combined with the 5HT6 ligand of the present invention can include full agonists, partial agonists, or positive allosteric modulators.

α-7 receptor ligands typically demonstrate $K_i$ values from about 1 nM to about 10 μM when tested by the [$^3$H]-MLA assay. Many having a binding value ("$K_i$ MLA") of less than 1 μM. According to one embodiment, [$^3$H]-Cytisine binding values ("$K_i$ Cyt") of the α-7 receptor ligand range from about 50 nM to greater than 100 μM. According to another embodiment, preferred α-7 receptor ligands have $K_i$ MLA value (as measured by MLA assay in view of the $K_i$ Cyt value as measured by [$^3$H]-cytisine binding, such that in the formula D=$K_i$ Cyt/$K_i$ MLA) of at least 50. For example, preferred compounds typically exhibit greater potency at α-7 receptors compared to α4β2 receptors. Although the MLA and [$^3$H]-cytisine binding assays are well known, further details for carrying out the assays are provided in International Publication Nos. WO 2005/028477; WO 2005/066168; US 20050137184; US20050137204; US20050245531; WO 2005/066166; WO 2005/066167; and WO 2005/077899.

Positive allosteric modulators, at concentrations ranging from 1 nM to 10 μM, enhance responses of acetylcholine at α-7 nicotinic receptors expressed endogenously in neurons or cell lines, or via expression of recombinant protein in Xenopus oocytes or in cell lines. α-7 receptor ligands can be used to improve efficacy of 5HT6 ligands without exaggerating the side effect profile of such agents.

Accordingly, α-7 receptor ligands that may be combined with the 5HT6 ligand can be compounds of various chemical classes. Particularly, some examples of α-7 receptor ligands suitable for the invention include, but are not limited to, diazabicycloalkane derivatives, for example as described in International Publication No. WO 2005/028477; spirocyclic quinuclidinic ether derivatives, for example as described in International Publication No. WO 2005/066168; fused bicycloheterocycle substituted quinuclidine derivatives, for example as described in US Publication Nos. US20050137184; US20050137204; and US20050245531; 3-quinuclidinyl aminosubstituted biaryl derivatives, for example as described in International Publication No. WO 2005/066166; 3-quinuclidinyl heteroatom-bridged biaryl derivatives, for example as described in International Publication No. WO 2005/066167; and aminosubstituted tricyclic derivatives, for example as described in International Publication No. WO 2005/077899, all of which are hereby incorporated by reference in their entirety.

Examples of compounds reported as α-7 agonists or partial agonists are quinuclidine derivatives, for example as described in WO 2004/016608 and WO 2004/022556; and tilorone derivatives, for example also as described in WO 2004/016608.

Examples of compounds reported as positive allosteric modulators are 5-hydroxyindole analogs, for example as described in WO 01/32619, WO 01/32620, and WO 01/32622; tetrahydroquinoline derivatives, for examples as described in WO 04/098600; amino-thiazole derivatives; and diarylurea derivatives, for example as described in WO 04/085433.

Specific examples of compounds that are suitable neuronal nicotinic subtype α-7 receptor ligands include, for example, 5-(6-[(3R)-1-azabicyclo[2.2.2]oct-3-yloxy]pyridazin-3-yl)-1H-indole; 2-(6-phenylpyridazine-3-yl)octahydropyrrolo[3,4-c]pyrrole; 5-[5-{(1R,5R)-6-methyl-3,6-diaza-bicyclo[3.2.0]hept-3-yl}-pyridin-2-yl]-1H-indole; and 5-[6-(cis-5-methyl-hexahydro-pyrrolo[3,4-c]pyrrol-2-yl)-pyridazin-3-yl-1H-indole. Other suitable α-7 ligands are described in WO2006/101745, which is hereby incorporated by reference.

Compounds modulating activity of nicotinic acetylcholine receptor α-7 subtype are suitable for the invention regardless of the manner in which they affect the receptor. Other compounds reported as demonstrating α-7 activity include, but are not limited to, quinuclidine amide derivatives, for example PNU-282987, N-[(3R)-1-azabicyclo[2.2.2]oct-3-yl]-4-chlorobenzamide TC-5619, varanicline, and others as described in WO 04/052894, and MEM-3454. Additional compounds can include, but are not limited to, AR R17779, AZD0328, WB-56203, SSR-180711A, GTS21, and OH-GTS-21, which are all described in the publicly available literature.

The invention also includes methods for treating Parkinson's disease, including treating memory and/or cognitive impairment associated with Parkinson's disease, comprising administering to a patient, simultaneously or sequentially, the compound of the invention and one or more additional agents used in the treatment of Parkinson's disease such as, but not limited to, Levodopa, Parlodel, Permax, Mirapex, Tasmar, Contan, Kemadin, Artane, and Cogentin. In methods using simultaneous administration, the agents can be present in a combined composition or can be administered separately. As a result, the invention also includes compositions comprising a compound according to Formula I and one or more additional pharmaceutical agents used in the treatment of Parkinson's disease, such as, but not limited to, Levodopa, Parlodel, Permax, Mirapex, Tasmar, Contan, Kemadin, Artane, and Cogentin. Similarly, the invention also includes kits containing a composition comprising a compound according to Formula I and another composition comprising one or more additional pharmaceutical agents gent used in the treatment of Parkinson's disease such as, but not limited to, Levodopa, Parlodel, Permax, Mirapex, Tasmar, Contan, Kemadin, Artane, and Cogentin.

In addition, the invention includes methods for treating memory and/or cognitive impairment associated with Alzheimer's disease comprising administering to a patient, simultaneously or sequentially, the compound of the invention and one or more additional agents used in the treatment of Alzheimer's disease such as, but not limited to, Reminyl, Cognex, Aricept, Exelon, Akatinol, Neotropin, Eldepryl, Estrogen and Cliquinol. In methods using simultaneous administration, the agents can be present in a combined composition or can be administered separately. As a result, the invention also includes compositions comprising a compound according to Formula I and one or more additional pharmaceutical agents used in the treatment of Alzheimer's disease such as, but not limited to, Reminyl, Cognex, Aricept, Exelon, Akatinol, Neotropin, Eldepryl, Estrogen and Cliquinol. Similarly, the invention also includes kits containing a composition comprising a compound according to Formula I and another composition comprising one or more additional pharmaceutical agents used in the treatment of Alzheimer's disease such as, but not limited to Reminyl, Cognex, Aricept, Exelon, Akatinol, Neotropin, Eldepryl, Estrogen and Cliquinol.

Another aspect of the invention includes methods for treating memory and/or cognitive impairment associated with dementia comprising administering to a patient, simultaneously or sequentially, the compound of the invention and one or more additional agents used in the treatment of dementia such as, but not limited to, Thioridazine, Haloperidol, Risperidone, Cognex, Aricept, and Exelon. In methods using simultaneous administration, the agents can be present in a combined composition or can be administered separately. As a result, the invention also includes compositions comprising a compound according to Formula I and one or more additional pharmaceutical agents used in the treatment of dementia such as, but not limited to, Thioridazine, Haloperidol, Risperidone, Cognex, Aricept, and Exelon. Similarly, the invention also includes kits containing a composition comprising a compound according to Formula I and another composition comprising one or more additional pharmaceutical agents used in the treatment of dementia such as, but not limited to, Thioridazine, Haloperidol, Risperidone, Cognex, Aricept, and Exelon.

A further aspect of the invention includes methods for treating memory and/or cognitive impairment associated with epilepsy comprising administering to a patient, simultaneously or sequentially, the compound of the invention and one or more additional agents used in the treatment of epilepsy such as, but not limited to, Dilantin, Luminol, Tegretol, Depakote, Depakene, Zarontin, Neurontin, Barbita, Solfeton, and Felbatol. In methods using simultaneous administration, the agents can be present in a combined composition or can be administered separately. As a result, the invention also includes compositions comprising a compound according to Formula I and one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol. Similarly, the invention also includes kits containing a composition comprising a compound according to Formula I and another composition comprising one or more additional pharmaceutical agents used in the treatment of epilepsy such as, but not limited to, Dilantin, Luminol, Tegretol, Depakote, Depakene, Zarontin, Neurontin, Barbita, Solfeton, and Felbatol.

A further aspect of the invention includes methods for treating memory and/or cognitive impairment associated with multiple sclerosis comprising administering to a patient, simultaneously or sequentially, the compound of the invention and one or more additional agents used in the treatment of multiple sclerosis such as, but not limited to, Detrol, Ditropan XL, OxyContin, Betaseron, Avonex, Azothioprine, Methotrexate, and Copaxone. In methods using simultaneous administration, the agents can be present in a combined composition or can be administered separately. As a result, the invention also includes compositions comprising a compound according to Formula I and one or more additional pharmaceutical agents used in the treatment of multiple sclerosis such as, but not limited to, Detrol, Ditropan XL, OxyContin, Betaseron, Avonex, Azothioprine, Methotrexate, and Copaxone. Similarly, the invention also includes kits containing a composition comprising a compound according to Formula I and another composition comprising one or more additional pharmaceutical agents used in the treatment of multiple sclerosis such as, but not limited to, Detrol, Ditropan XL, OxyContin, Betaseron, Avonex, Azothioprine, Methotrexate, and Copaxone.

The invention further includes methods for treating Huntington's disease, including treating memory and/or cognitive impairment associated with Huntington's disease, comprising administering to a patient, simultaneously or sequentially, the compound of the invention and one or more additional agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. In methods using simultaneous administration, the agents can be present in a combined composition or can be administered separately. As a result, the invention also includes compositions comprising a compound according to Formula I and one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone. Similarly, the invention also includes kits containing a composition comprising a compound according to Formula I and another composition comprising one or more additional pharmaceutical agents used in the treatment of Huntington's disease such as, but not limited to, Amitriptyline, Imipramine, Despiramine, Nortriptyline, Paroxetine, Fluoxetine, Setraline, Terabenazine, Haloperidol, Chloropromazine, Thioridazine, Sulpride, Quetiapine, Clozapine, and Risperidone.

Indications that may be treated with 5HT6 ligands, either alone or in combination with other drugs, include, but are not limited to, those diseases thought to be mediated in part by the basal ganglia, prefrontal cortex and hippocampus. These indications include psychoses, Parkinson's disease, dementias, obsessive compulsion disorder, tardive dyskinesia, choreas, depression, mood disorders, impulsivity, drug addiction, attention deficit/hyperactivity disorder (ADHD), depression with parkinsonian states, personality changes with caudate or putamen disease, dementia and mania with caudate and pallidal diseases, and compulsions with pallidal disease.

Psychoses are disorders that affect an individual's perception of reality. Psychoses are characterized by delusions and hallucinations. The present invention includes methods for treating patients suffering from all forms of psychoses, including but not limited to schizophrenia, late-onset schizophrenia, schizoaffective disorders, prodromal schizophrenia, and bipolar disorders. Treatment may be for the positive symptoms of schizophrenia as well as for the cognitive deficits and negative symptoms. Other indications for 5HT6 ligands include psychoses resulting from drug abuse (including amphetamines and PCP), encephalitis, alcoholism, epilepsy, Lupus, sarcoidosis, brain tumors, multiple sclerosis, dementia with Lewy bodies, or hypoglycemia. Other psychiatric disorders, like posttraumatic stress disorder (PTSD), and schizoid personality may also be treated with 5HT6 ligands.

Dementias are diseases that include memory loss and additional intellectual impairment separate from memory. The present invention includes methods for treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (Down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The condition of memory impairment is manifested by impairment of the ability to learn new information and/or the inability to recall previously learned information. The present invention includes methods for dealing with memory loss separate from dementia, including mild cognitive impairment (MCI) and age-related cognitive decline. The present invention includes methods of treatment for memory impairment as a result of disease. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. In another application, the invention includes methods for dealing with memory loss resulting from the use of general anesthetics, chemotherapy, radiation treatment, post-surgical trauma, and therapeutic intervention. Thus, in accordance with a preferred embodiment, the present invention includes methods of treating patients suffering from memory impairment due to, for example, Alzheimer's disease, multiple sclerosis, amylolaterosclerosis (ALS), multiple systems atrophy (MSA), schizophrenia, Parkinson's disease, Huntington's disease, Pick's disease, Creutzfeld-Jakob disease, depression, aging, head trauma, stroke, spinal cord injury, CNS hypoxia, cerebral senility, diabetes associated cognitive impairment, memory deficits from early exposure of anesthetic agents, multiinfarct dementia and other neurological conditions including acute neuronal diseases, as well as HIV and cardiovascular diseases. The invention also relates to agents and/or methods to stimulate the formation of memory in "normal" subjects (i.e., subjects who do not exhibit an abnormal or pathological decrease in a memory function), e.g., ageing middle-aged subjects.

The invention is also suitable for use in the treatment of a class of disorders known as polyglutamine-repeat diseases. These diseases share a common pathogenic mutation. The expansion of a CAG repeat, which encodes the amino acid glutamine, within the genome leads to production of a mutant protein having an expanded polyglutamine region. For example, Huntington's disease has been linked to a mutation of the protein huntingtin. In individuals who do not have Huntington's disease, huntingtin has a polyglutamine region containing about 8 to 31 glutamine residues. For individuals who have Huntington's disease, huntingtin has a polyglutamine region with over 37 glutamine residues. Aside from Huntington's disease (HD), other known polyglutamine-repeat diseases and the associated proteins are: dentatorubral-pallidoluysian atrophy, DRPLA (atrophin-1); spinocerebellar ataxia type-1 (ataxin-1); spinocerebellar ataxia type-2 (ataxin-2); spinocerebellar ataxia type-3 also called Machado-Joseph disease, MJD (ataxin-3); spinocerebellar ataxia type-6 (alpha 1a-voltage dependent calcium channel); spinocerebellar ataxia type-7 (ataxin-7); and spinal and bulbar muscular atrophy, SBMA, also know as Kennedy disease (androgen receptor). Thus, in accordance with a further aspect of the invention, there is provided a method of treating a polyglutamine-repeat disease or CAG repeat expansion disease comprising administering to a patient, such as a mammal, especially a human, a therapeutically effective amount of a compound. In accordance with a further embodiment, there is provided a method of treating Huntington's disease (HD), dentatorubral-pallidoluysian atrophy (DRPLA), spinocerebellar ataxia type-1, spinocerebellar ataxia type-2, spinocerebellar ataxia type-3 (Machado-Joseph disease), spinocerebellar ataxia type-6, spinocerebellar ataxia type-7, or spinal and bulbar muscular atrophy, comprising administering to a patient, such as a mammal, especially a human, a therapeutically effective amount of a compound of the invention.

The basal ganglia are important for regulating the function of motor neurons; disorders of the basal ganglia result in movement disorders. Most prominent among the movement disorders related to basal ganglia function is Parkinson's disease (Obeso J A et al., Neurology., 2004 Jan. 13; 62(1 Suppl 1):S17-30). Other movement disorders related to dysfunction of the basla ganglia include tardive dyskinesia, progressive supranuclear palsy and cerebral palsy, corticobasal degeneration, multiple system atrophy, Wilson disease, and dystonia, tics, and chorea. In one embodiment, the compounds of the invention may be used to treat movement disorders related to dysfunction of basal ganglia neurons.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations. One of ordinary skill in the art of treating such diseases will be able, without undue experimentation and in reliance upon personal knowledge and the disclosure of this Application, to ascertain a therapeutically effective amount of the compounds of the present invention for a given disease.

The compounds of the invention are typically administered at dosage levels and in a mammal customary for 5HT6 ligands, such as those known compounds mentioned above. For example, the compounds can be administered, in single or multiple doses, by oral administration at a dosage level of generally 0.001-100 mg/kg/day, for example, 0.01-100 mg/kg/day, preferably 0.1-70 mg/kg/day, especially 0.5-10 mg/kg/day. Unit dosage forms can contain generally 0.01-1000 mg of active compound, for example, 0.1-50 mg of active compound. For intravenous administration, the compounds can be administered, in single or multiple dosages, at a dosage level of, for example, 0.001-50 mg/kg/day, preferably 0.001-10 mg/kg/day, especially 0.01-1 mg/kg/day. Unit dosage forms can contain, for example, 0.1-10 mg of active compound.

In carrying out the procedures of the present invention, it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference in their entirety.

EXAMPLES

All spectra were recorded at 300 MHz on a Bruker Instruments NMR unless otherwise stated. Coupling constants (J) are in Hertz (Hz) and peaks are listed relative to TMS (δ 0.00 ppm).

Analytical HPLC was performed on 4.0 mm×50 mm WATERS YMC ODS-A Cartridge 120A S3u 4 column using (i) a gradient of 0/100 to 100/0 acetonitrile (0.05% TFA)/water (0.05% TFA) over 4 min (for all compounds except 1-[(1-acetyl-2,3-dihydro-1H-indol-5-yl)sulfonyl]-3-(1-methyl-1,2,3,6-tetrahydropyridin-4-yl)-1H-indole, or (ii) a 4.6 mm×100 mm Waters Sunfire RP C18 5 mm column using a gradient of 20/80 to 80/20 acetonitrile (0.1% formic acid)/water (0.1% formic acid) over 8 min (for 1-[(1-acetyl-2,3-dihydro-1H-indol-5-yl)sulfonyl]-3-(1-methyl-1,2,3,6-tetrahydropyridin-4-yl)-1H-indole).

Preparative HPLC was performed on 30 mm×100 mm Xterra Prep RP$_{18}$ 5μ columns using an 8 min gradient of 95/5 to 20/80 water (0.1% formic acid)/acetonitrile (0.1% formic acid).

General Procedure A

Synthesis of 5-bromo-3-(1-methyl-1,2,3,6-tetrahydropyridin-4-yl)-1-(phenylsulfonyl)-1H-indole

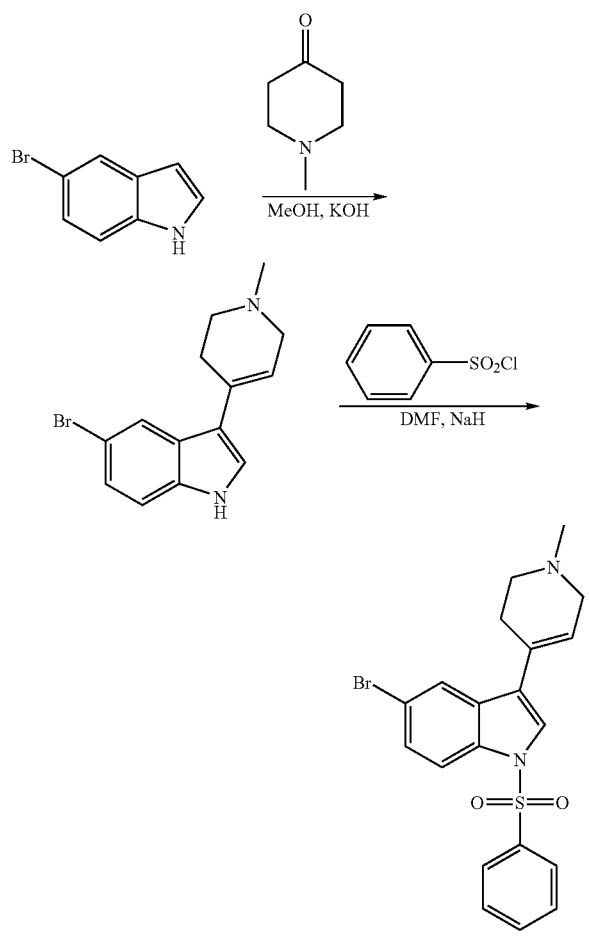

1) Synthesis of 5-bromo-3-(1-methyl-1,2,3,6-tetrahydropyridin-4-yl)-1H-indole

A solution of KOH (6.7 g, 118.45 mmol) in methanol (60 mL) was added to 5-bromo-1H-indole (10 g, 50.51 mmol) in a 250 mL 3-necked round bottom flask. 1-methylpiperidin-4-one (7.7 g, 67.46 mmol) was then added dropwise with stirring, while cooling to a temperature of 20° C. The resulting solution was allowed to react, with stirring, for 4 hours while the temperature was maintained at 73° C. The reaction mixture was then cooled to 15° C. and filtered. The filter cake was washed with water (3×50 mL). The product was purified by recrystallization from ethanol to afford 12.3 g (83%) of 5-bromo-3-(1-methyl-1,2,3,6-tetrahydropyridin-4-yl)-1H-indole as a white solid.

2) Synthesis of 5-bromo-3-(1-methyl-1,2,3,6-tetrahydropyridin-4-yl)-1-(phenylsulfonyl)-1H-indole NaH (600 mg, 15.00 mmol) was added (in several batches) to a solution of 5-bromo-3-(1-methyl-1,2,3,6-tetrahydropyridin-4-yl)-1H-indole (3 g, 9.79 mmol) in DMF (60 mL) while cooling to a temperature of 0-5° C. The resulting solution was stirred for 1 hour while the temperature was maintained at room temperature. Benzenesulfonyl chloride (2.3 g, 12.89 mmol) was then added dropwise and the reaction was stirred for an additional 4 hours at room temperature. After filtration, the filter cake was washed with ethanol (2×50 mL) and the resulting solid was dried to afford 0.4 g (10%) of 5-bromo-3-(1-methyl-1,2,3,6-tetrahydropyridin-4-yl)-1-phenylsulfonyl)-1H-indole as a white solid. $^1$H NMR (DMSO) δ 8.04 (4H), 7.95 (1H), 7.73 (1H), 7.32-7.63 (3H), 6.29 (s, 1H), 3.98 (2H), 3.68 (2H), 2.72-2.89 (5H). m/z 434.1 (M$^+$+1)

Split Patterns Needed Above

Using this general procedure, the following compounds were prepared using different starting materials:

2) N-(4-{[3-(1-methyl-1,2,3,6-tetrahydropyridin-4-yl)-1H-indol-1-yl]sulfonyl}phenyl)acetamide, LC/MS (EI) t$_R$ 1.87, m/z 410.2 (M$^+$+1)

3) N-(4-{[3-(1-methyl-1,2,3,6-tetrahydropyridin-4-yl)-1H-pyrrolo[2,3-b]pyridin-1-yl]sulfonyl}phenyl)acetamide, LC/MS (EI) t$_R$ 1.69, m/z 411.2 (M$^+$+1)

4) N-(4-{[5-fluoro-3-(1-methyl-1,2,3,6-tetrahydropyridin-4-yl)-H1-indol-1-yl]sulfonyl}phenyl)acetamide, LC/MS (EI) t$_R$ 1.87, m/z 428.1 (M$^+$+1)

5) N-(4-{[3-(1-methyl-1,2,3,6-tetrahydropyridin-4-yl)-5-(trifluoromethyl)-1H-indol-1-yl]sulfonyl}phenyl)acetamide, LC/MS (EI) t$_R$ 1.94, m/z 178.2 (M$^+$+1)

6) 1-(2,3-dihydro-1-benzofuran-5-ylsulfonyl)-3-(1-methyl-1,2,3,6-tetrahydropyridin-4-yl)-1H-indole, LC/MS (EI) t$_R$ 1.97, m/z 395.2 (M$^+$+1)

7) 1-(2,3-dihydro-1-benzofuran-5-ylsulfonyl)-3-(1-methyl-1,2,3,6-tetrahydropyridin-4-yl)-1H-pyrrolo[2,3-b]pyridine, LC/MS (EI) t$_R$ 1.83, m/z 396.2 (M$^+$+1)

8) 1-(2,3-dihydro-1-benzofuran-5-ylsulfonyl)-5-fluoro-3-(1-methyl-1,2,3,6-tetrahydropyridin-4-yl)-1H-indole, LC/MS (EI) t$_R$ 1.97, m/z 413.2 (M$^+$+1)

9) 1-(2,3-dihydro-1-benzofuran-5-ylsulfonyl)-3-(1-methyl-1,2,3,6-tetrahydropyridin-4-yl)-5-(trifluoromethyl)-1H-indole, LC/MS (EI) t$_R$ 2.04, m/z 463.2 (M$^+$+1)

10) 1-(3,4-dihydro-2H-1,5-benzodioxepin-7-ylsulfonyl)-3-(1-methyl-1,2,3,6-tetrahydropyridin-4-yl)-1H-indole, LC/MS (EI) t$_R$ 1.97, m/z 425.2 (M$^+$+1)

11) 1-(3,4-dihydro-2H-1,5-benzodioxepin-7-ylsulfonyl)-3-(1-methyl-1,2,3,6-tetrahydropyridin-4-yl)-1H-pyrrolo[2,3-b]pyridine, LC/MS (EI) t$_R$ 1.81, m/z 426.2 (M$^+$+1)

12) 1-(3,4-dihydro-2H-1,5-benzodioxepin-7-ylsulfonyl)-5-fluoro-3-(1-methyl-1,2,3,6-tetrahydropyridin-4-yl)-1H-indole, LC/MS (EI) $t_R$ 2.01, m/z 443.2 (M$^+$+1)

13) 1-(3,4-dihydro-2H-1,5-benzodioxepin-7-ylsulfonyl)-3-(1-methyl-1,2,3,6-tetrahydropyridin-4-yl)-5-(trifluoromethyl)-1H-indole, LC/MS (EI) $t_R$ 2.08, m/z 493.2 (M$^+$+1)

14) 1-[(4-methyl-2-phenyl-1,3-thiazol-5-yl)sulfonyl]-3-(1-methyl-1,2,3,6-tetrahydropyridin-4-yl)-1H-indole, LC/MS (EI) $t_R$ 2.11, m/z 450.2 (M$^+$+1)

15) 1-[(4-methyl-2-phenyl-1,3-thiazol-5-yl)sulfonyl]-3-(1-methyl-1,2,3,6-tetrahydropyridin-4-yl)-1H-pyrrolo[2,3-b]pyridine, LC/MS (EI) $t_R$ 2.01, m/z 451.2 (M$^+$+1)

16) 5-fluoro-1-[(4-methyl-2-phenyl-1,3-thiazol-5-yl)sulfonyl]-3-(1-methyl-1,2,3,6-tetrahydropyridin-4-yl)-1H-indole, LC/MS (EI) $t_R$ 2.11, m/z 468.2 (M$^+$+1)

17) 1-[(4-methyl-2-phenyl-1,3-thiazol-5-yl)sulfonyl]-3-(1-methyl-1,2,3,6-tetrahydropyridin-4-yl)-5-(trifluoromethyl)-1H-indole, LC/MS (EI) $t_R$ 2.22, m/z 518.2 (M$^+$+1)

18) 1-[(5-methyl-1-phenyl-1H-pyrazol-4-yl)sulfonyl]-3-(1-methyl-1,2,3,6-tetrahydropyridin-4-yl)-1H-indole, LC/MS (EI) $t_R$ 1.97, m/z 433.3 (M$^+$+1)

19) 1-[(5-methyl-1-phenyl-1H-pyrazol-4-yl)sulfonyl]-3-(1-methyl-1,2,3,6-tetrahydropyridin-4-yl)-1H-pyrrolo[2,3-b]pyridine, LC/MS (EI) $t_R$ 1.87, m/z 434.2 (M$^+$+1)

20) 5-fluoro-1-[(5-methyl-1-phenyl-1H-pyrazol-4-yl)sulfonyl]-3-(1-methyl-1,2,3,6-tetrahydropyridin-4-yl)-1H-indole, LC/MS (EI) $t_R$ 2.01, m/z 451.2 (M$^+$+1)

21) 1-[(5-methyl-1-phenyl-1H-pyrazol-4-yl)sulfonyl]-3-(1-methyl-1,2,3,6-tetrahydropyridin-4-yl)-5-(trifluoromethyl)-1H-indole, LC/MS (EI) $t_R$ 2.08, m/z 501.2 (M$^+$+1)

22) 1-(1-benzothien-2-ylsulfonyl)-3-(1-methyl-1,2,3,6-tetrahydropyridin-4-yl)-1H-indole, LC/MS (EI) $t_R$ 2.04, m/z 409.1 (M$^+$+1)

23) 1-(1-benzothien-2-ylsulfonyl)-5-fluoro-3-(1-methyl-1,2,3,6-tetrahydropyridin-4-yl)-1H-indole, LC/MS (EI) $t_R$ 2.04, m/z 427.1 (M$^+$+1)

24) 1-(1-benzothien-2-ylsulfonyl)-3-(1-methyl-1,2,3,6-tetrahydropyridin-4-yl)-5-(trifluoromethyl)-1H-indole, LC/MS (EI) $t_R$ 2.11, m/z 477.1 (M$^+$+1)

25) 3-(1-methyl-1,2,3,6-tetrahydropyridin-4-yl)-1-{[1-methyl-3-(trifluoromethyl)-1H-pyrazol-4-yl]sulfonyl}-1H-indole, LC/MS (EI) $t_R$ 1.94, m/z 425.2 (M$^+$+1)

26) 5-fluoro-3-(1-methyl-1,2,3,6-tetrahydropyridin-4-yl)-1-{[1-methyl-3-(trifluoromethyl)-1H-pyrazol-4-yl]sulfonyl}-1H-indole, LC/MS (EI) $t_R$ 1.97, m/z 443.2 (M$^+$+1)

27) 3-(1-methyl-1,2,3,6-tetrahydropyridin-4-yl)-1-{[1-methyl-3-(trifluoromethyl)-1H-pyrazol-4-yl]sulfonyl}-5-(trifluoromethyl)-1H-indole, LC/MS (EI) $t_R$ 2.01, m/z 493.2 (M$^+$+1)

28) methyl 5-{[3-(1-methyl-1,2,3,6-tetrahydropyridin-4-yl)-1H-indol-1-yl]sulfonyl}-2-furoate, LC/MS (EI) $t_R$ 1.90, m/z 401.2 (M$^+$+1)

29) methyl 5-{[5-fluoro-3-(1-methyl-1,2,3,6-tetrahydropyridin-4-yl)-1H-indol-1-yl]sulfonyl}-2-furoate, LC/MS (EI) $t_R$ 1.94, m/z 419.1 (M$^+$+1)

30) methyl 5-{[3-(1-methyl-1,2,3,6-tetrahydropyridin-4-yl)-5-(trifluoromethyl)-1H-indol-1-yl]sulfonyl}-2-furoate, LC/MS (EI) $t_R$ 2.01, m/z 469.2 (M$^+$+1)

31) methyl 5-{[3-(1-methyl-1,2,3,6-tetrahydropyridin-4-yl)-1H-pyrrolo[2,3-b]pyridin-1-yl]sulfonyl}-2-furoate, LC/MS (EI) $t_R$ 1.80, m/z 402.1 (M$^+$+1)

32) 1-[(1-methyl-1H-imidazol-4-yl)sulfonyl]-3-(1-methyl-1,2,3,6-tetrahydropyridin-4-yl)-1H-indole, LC/MS (EI) $t_R$ 1.83, m/z 357.2(M$^+$+1)

33) 5-fluoro-1-[(1-methyl-1H-imidazol-4-yl)sulfonyl]-3-(1-methyl-1,2,3,6-tetrahydropyridin-4-yl)-1H-indole, LC/MS (EI) $t_R$ 1.83, m/z 375.2 (M$^+$+1)

34) 1-[(1-methyl-1H-imidazol-4-yl)sulfonyl]-3-(1-methyl-1,2,3,6-tetrahydropyridin-4-yl)-5-(trifluoromethyl)-1H-indole, LC/MS (EI) $t_R$ 1.90, m/z 425.2 (M$^+$+1)

35) 1-(2,3-dihydro-1,4-benzodioxin-6-ylsulfonyl)-3-(1-methyl-1,2,3,6-tetrahydropyridin-4-yl)-1H-pyrrolo[2,3-b]pyridine, LC/MS (EI) $t_R$ 1.83, m/z 412.2 (M$^+$+1)

36) 1-[(1,2-dimethyl-1H-imidazol-4-yl)sulfonyl]-3-(1-methyl-1,2,3,6-tetrahydropyridin-4-yl)-1H-indazole, LC/MS (EI) $t_R$ 1.83, m/z 372.2 (M$^+$+1)

37) 1-[(1,2-dimethyl-1H-imidazol-4-yl)sulfonyl]-5-fluoro-3-(1-methyl-1,2,3,6-tetrahydropyridin-4-yl)-1H-indazole, LC/MS (EI) $t_R$ 1.83, m/z 390.2 (M$^+$+1)

38) 1-[(1,2-dimethyl-1H-imidazol-4-yl)sulfonyl]-3-(1-methyl-1,2,3,6-tetrahydropyridin-4-yl)-5-(trifluoromethyl)-1H-indazole, LC/MS (EI) $t_R$ 1.94, m/z 440.4 (M$^+$+1)

39) 1-[(2,5-dimethyl-3-furyl)sulfonyl]-3-(1-methyl-1,2,3,6-tetrahydropyridin-4-yl)-1H-indole, LC/MS (EI) $t_R$ 1.97, m/z 371.1 (M$^+$+1)

40) 1-[(2,5-dimethyl-3-furyl)sulfonyl]-5-fluoro-3-(1-methyl-1,2,3,6-tetrahydropyridin-4-yl)-1H-indole, LC/MS (EI) $t_R$ 1.97, m/z 389.1 (M$^+$+1)

41) 1-[(2,5-dimethyl-3-furyl)sulfonyl]-3-(1-methyl-1,2,3,6-tetrahydropyridin-4-yl)-5-(trifluoromethyl)-1H-indole, LC/MS (EI) $t_R$ 2.04, m/z 439.7 (M$^+$+1)

42) 1-(1-benzothien-3-ylsulfonyl)-3-(1-methyl-1,2,3,6-tetrahydropyridin-4-yl)-1H-indole, LC/MS (EI) $t_R$ 2.01, m/z 409.0 (M$^+$+1)

43) 1-(1-benzothien-3-ylsulfonyl)-5-fluoro-3-(1-methyl-1,2,3,6-tetrahydropyridin-4-yl)-1H-indole, LC/MS (EI) $t_R$ 2.01, m/z 427.4 (M$^+$+1)

44) 1-(1-benzothien-3-ylsulfonyl)-3-(1-methyl-1,2,3,6-tetrahydropyridin-4-yl)-5-(trifluoromethyl)-1H-indole, LC/MS (EI) $t_R$ 2.08, m/z 477.0 (M$^+$+1)

45) 1-(1,3-benzodioxol-5-ylsulfonyl)-3-(1-methyl-1,2,3,6-tetrahydropyridin-4-yl)-1H-pyrrolo[2,3-b]pyridine, LC/MS (EI) $t_R$ 1.83, m/z 398.4 (M$^+$+1)

46) 1-(1-benzofuran-2-ylsulfonyl)-3-(1-methyl-1,2,3,6-tetrahydropyridin-4-yl)-1H-indole, LC/MS (EI) $t_R$ 2.08, m/z 393.4 (M$^+$+1)

47) 1-(1-benzofuran-2-ylsulfonyl)-5-fluoro-3-(1-methyl-1,2,3,6-tetrahydropyridin-4-yl)-1H-indole, LC/MS (EI) $t_R$ 2.08, m/z 411.4 (M$^+$+1)

48) 1-(1-benzofuran-2-ylsulfonyl)-3-(1-methyl-1,2,3,6-tetrahydropyridin-4-yl)-5-(trifluoromethyl)-1H-indole, LC/MS (EI) $t_R$ 2.15, m/z 461.4 μM$^+$+1)

49) 1-{[3-(2-methylpyrimidin-4-yl)phenyl]sulfonyl}-3-(1-methyl-1,2,3,6-tetrahydropyridin-4-yl)-1H-indole, LC/MS (EI) $t_R$ 2.01, m/z 445.5 (M$^+$+1)

50) 5-fluoro-1-{[3-(2-methylpyrimidin-4-yl)phenyl]sulfonyl}-3-(1-methyl-1,2,3,6-tetrahydropyridin-4-yl)-1H-indole, LC/MS (EI) $t_R$ 2.01, m/z 463.5 (M$^+$+1)

51) 1-{[3-(2-methylpyrimidin-4-yl)phenyl]sulfonyl}-3-(1-methyl-1,2,3,6-tetrahydropyridin-4-yl)-5-(trifluoromethyl)-1H-indole, LC/MS (EI) $t_R$ 2.08, m/z 513.4 (M$^+$+1)

52) 1-{[3-(2-methylpyrimidin-4-yl)phenyl]sulfonyl}-3-(1-methyl-1,2,3,6-tetrahydropyridin-4-yl)-1H-pyrrolo[2,3-b]pyridine, LC/MS (EI) $t_R$ 1.90, m/z 446.4 (M$^+$+1)

53) 1-[(3,5-dimethylisoxazol-4-yl)sulfonyl]-3-(1-methyl-1,2,3,6-tetrahydropyridin-4-yl)-1H-indole, LC/MS (EI) $t_R$ 1.95, m/z 372.0 (M$^+$+1)

54) 1-[(3,5-dimethylisoxazol-4-yl)sulfonyl]-5-fluoro-3-(1-methyl-1,2,3,6-tetrahydropyridin-4-yl)-1H-indole, LC/MS (EI) $t_R$ 1.98, m/z 390.4 (M$^+$+1)

55) 1-[(3,5-dimethylisoxazol-4-yl)sulfonyl]-3-(1-methyl-1,2,3,6-tetrahydropyridin-4-yl)-5-(trifluoromethyl)-1H-indole, LC/MS (EI) $t_R$ 2.08, m/z 440.0 (M$^+$+1)

56) 6-{[3-(1-methyl-1,2,3,6-tetrahydropyridin-4-yl)-1H-indol-1-yl]sulfonyl}-1,3-benzothiazole, LC/MS (EI) t$_R$ 1.95, m/z 410.0 (M$^+$+1)

57) 6-{[5-fluoro-3-(1-methyl-1,2,3,6-tetrahydropyridin-4-yl)-1H-indol-1-yl]sulfonyl}-1,3-benzothiazole, LC/MS (EI) t$_R$ 1.97, m/z 428 (M$^+$+1)

58) 6-{[3-(1-methyl-1,2,3,6-tetrahydropyridin-4-yl)-5-(trifluoromethyl)-1H-indol-1-yl]sulfonyl}-1,3-benzothiazole, LC/MS (EI) t$_R$ 2.04, m/z 478.6 (M$^+$+1)

59) 3-(1-methyl-1,2,3,6-tetrahydropyridin-4-yl)-1-[(1,3,5-trimethyl-1H-pyrazol-4-yl)sulfonyl]-1H-indole, LC/MS (EI) t$_R$ 1.90, m/z 385.5 (M$^+$+1)

60) 5-fluoro-3-(1-methyl-1,2,3,6-tetrahydropyridin-4-yl)-1-[(1,3,5-trimethyl-1H-pyrazol-4-yl)sulfonyl]-1H-indole, LC/MS (EI) t$_R$ 1.94, m/z 403.4 (M$^+$+1)

61) 3-(1-methyl-1,2,3,6-tetrahydropyridin-4-yl)-5-(trifluoromethyl)-1-[(1,3,5-trimethyl-1H-pyrazol-4-yl)sulfonyl]-1H-indole, LC/MS (EI) t$_R$ 2.01, m/z 453.4 (M$^+$+1)

62) 1-[(4-chloro-1,2-dimethyl-1H-pyrrol-3-yl)sulfonyl]-3-(1-methyl-1,2,3,6-tetrahydropyridin-4-yl)-1H-indole, LC/MS (EI) t$_R$ 1.94, m/z 404.7 (M$^+$+1)

63) 1-[(4-chloro-1,2-dimethyl-1H-pyrrol-3-yl)sulfonyl]-5-fluoro-3-(1-methyl-1,2,3,6-tetrahydropyridin-4-yl)-1H-indole, LC/MS (EI) t$_R$ 1.97, m/z 422.6 (M$^+$+1)

64) 1-[(4-chloro-1,2-dimethyl-1H-pyrrol-3-yl)sulfonyl]-3-(1-methyl-1,2,3,6-tetrahydropyridin-4-yl)-5-(trifluoromethyl)-1H-indole, LC/MS (EI) t$_R$ 2.04, m/z 472.8 (M$^+$+1)

65) 1-[(1-acetyl-2,3-dihydro-1H-indol-5-yl)sulfonyl]-3-(1-methyl-1,2,3,6-tetrahydropyridin-4-yl)-1H-indole, LC/MS (EI) t$_R$ 3.60, m/z 436 (M$^+$+1)

66) 1-[(1-acetyl-2,3-dihydro-1H-indol-5-yl)sulfonyl]-5-fluoro-3-(1-methyl-1,2,3,6-tetrahydropyridin-4-yl)-1H-indole, LC/MS (EI) t$_R$ 3.12, m/z 454.0 (M$^+$+1)

67) 1-[(1-acetyl-2,3-dihydro-1H-indol-5-yl)sulfonyl]-3-(1-methyl-1,2,3,6-tetrahydropyridin-4-yl)-5-(trifluoromethyl)-1H-indole, LC/MS (EI) t$_R$ 3.13, m/z 504.0 (M$^+$+1)

68) 1-[(1-acetyl-2,3-dihydro-1H-indol-5-yl)sulfonyl]-3-(1-methyl-1,2,3,6-tetrahydropyridin-4-yl)-1H-pyrrolo[2,3-b]pyridine, LC/MS (EI) t$_R$ 2.85, m/z 437.0 (M$^+$+1)

69) 3-(1-methyl-1,2,3,6-tetrahydropyridin-4-yl)-1-[(6-morpholin-4-ylpyridin-3-yl)sulfonyl]-1H-indole, LC/MS (EI) t$_R$ 2.30, m/z 439.0 (M$^+$+1)

70) 5-fluoro-3-(1-methyl-1,2,3,6-tetrahydropyridin-4-yl)-1-[(6-morpholin-4-ylpyridin-3-yl)sulfonyl]-1H-indole, LC/MS (ED) t$_R$ 2.32, m/z 457.0 (M$^+$+1)

71) 3-(1-methyl-1,2,3,6-tetrahydropyridin-4-yl)-1-[(6-morpholin-4-ylpyridin-3-yl)sulfonyl]-5-(trifluoromethyl)-1H-indole, LC/MS (EI) t$_R$ 2.48, m/z 507.0 (M$^+$+1)

72) 3-(1-methyl-1,2,3,6-tetrahydropyridin-4-yl)-1-[(6-morpholin-4-ylpyridin-3-yl)sulfonyl]-1H-pyrrolo[2,3-b]pyridine, LC/MS (EI) t$_R$ 1.95, m/z 440.0 (M$^+$+1)

73) 1-(2,3-dihydro-1H-indol-5-ylsulfonyl)-3-(1-methyl-1,2,3,6-tetrahydropyridin-4-yl)-1H-indole, LC/MS (EI) t$_R$ 2.06, m/z 394.0 (M$^+$+1)

74) 1-(2,3-dihydro-1H-indol-5-ylsulfonyl)-5-fluoro-3-(1-methyl-1,2,3,6-tetrahydropyridin-4-yl)-1H-indole, LC/MS (EI) t$_R$ 2.09, m/z 412.0 (M$^+$+1)

75) 1-(2,3-dihydro-1H-indol-5-ylsulfonyl)-3-(1-methyl-1,2,3,6-tetrahydropyridin-4-yl)-5-(trifluoromethyl)-1H-indole, LC/MS (EI) t$_R$ 2.13, m/z 395.0 (M$^+$+1)

76) 1-(2,3-dihydro-1H-indol-5-ylsulfonyl)-3-(1-methyl-1,2,3,6-tetrahydropyridin-4-yl)-1H-pyrrolo[2,3-b]pyridine, LC/MS (EI) t$_R$ 1.92, m/z 395.0 (M$^+$+1)

82) 4-{[3-(1-methyl-1,2,3,6-tetrahydropyridin-4-yl)-5-(trifluoromethyl)-1H-indol-1-yl]sulfonyl}aniline, LC/MS (EI) t$_R$ 2.09, m/z 436.0 (M$^+$+1)

83) 4-{[3-(1-methyl-1,2,3,6-tetrahydropyridin-4-yl)-1H-pyrrolo[2,3-b]pyridin-1-yl]sulfonyl}aniline, LC/MS (EI) t$_R$ 1.85, m/z 369.0 (M$^+$+1)

87) 3-(1-methyl-1,2,3,6-tetrahydropyridin-4-yl)-1-[(4-morpholin-4-ylphenyl)sulfonyl]-1H-indole, LC/MS (ED) t$_R$ 2.06, m/z 438.0 (M$^+$+1)

88) 5-fluoro-3-(1-methyl-1,2,3,6-tetrahydropyridin-4-yl)-1-[(4-morpholin-4-ylphenyl)sulfonyl]-1H-indole, LC/MS (EI) t$_R$ 2.06, m/z 456.0 (M$^+$+1)

89) 3-(1-methyl-1,2,3,6-tetrahydropyridin-4-yl)-1-[(4-morpholin-4-ylphenyl)sulfonyl]-5-(trifluoromethyl)-1H-indole, LC/MS (EI) t$_R$ 2.16, m/z 506.0 (M$^+$+1)

90) 3-(1-methyl-1,2,3,6-tetrahydropyridin-4-yl)-1-[(4-morpholin-4-ylphenyl)sulfonyl]-1H-pyrrolo[2,3-b]pyridine, LC/MS (ED) t$_R$ 1.95, m/z 439.0 (M$^+$+1)

91) N,N-dimethyl-4-{[3-(1-methyl-1,2,3,6-tetrahydropyridin-4-yl)-1H-indol-1-yl]sulfonyl}aniline, LC/MS (EI) t$_R$ 2.13, m/z 396.0 (M$^+$+1)

92) 4-{[5-fluoro-3-(1-methyl-1,2,3,6-tetrahydropyridin-4-yl)-1H-indol-1-yl]sulfonyl}-N,N-dimethylaniline, LC/MS (EI) t$_R$ 2.13, m/z 414.0 (M$^+$+1)

93) N,N-dimethyl-4-{[3-(1-methyl-1,2,3,6-tetrahydropyridin-4-yl)-5-(trifluoromethyl)-1H-indol-1-yl]sulfonyl}aniline, LC/MS (ED) t$_R$ 2.16, m/z 464.0 (M$^+$+1)

94) N,N-dimethyl-4-{[3-(1-methyl-1,2,3,6-tetrahydropyridin-4-yl)-1H-pyrrolo[2,3-b]pyridin-1-yl]sulfonyl}aniline, LC/MS (ED) t$_R$ 1.99, m/z 397.0 (M$^+$+1)

95) N,N-dimethyl-3-{[3-(1-methyl-1,2,3,6-tetrahydropyridin-4-yl)-1H-indol-1-yl]sulfonyl}aniline, LC/MS (EI) t$_R$ 2.13, m/z 396.0 (M$^+$+1)

96) 3-{[5-fluoro-3-(1-methyl-1,2,3,6-tetrahydropyridin-4-yl)-1H-indol-1-yl]sulfonyl}-N,N-dimethylaniline, LC/MS (EI) t$_R$ 2.16, m/z 414.0 (M$^+$+1)

97) N,N-dimethyl-3-{[3-(1-methyl-1,2,3,6-tetrahydropyridin-4-yl)-5-(trifluoromethyl)-1H-indol-1-yl]sulfonyl}aniline, LC/MS (EI) t$_R$ 2.20, m/z 464.0 (M$^+$+1)

98) N,N-dimethyl-3-{[3-(1-methyl-1,2,3,6-tetrahydropyridin-4-yl)-1H-pyrrolo[2,3-b]pyridin-1-yl]sulfonyl}aniline, LC/MS (EI) t$_R$ 1.99, m/z 397.0 (M$^+$+1)

107) 1-[(1-methyl-2,3-dihydro-1H-indol-6-yl)sulfonyl]-3-(1-methyl-1,2,3,6-tetrahydropyridin-4-yl)-1H-indole, LC/MS (EI) t$_R$ 2.14, m/z 408.0 (M$^+$+1)

108) 5-fluoro-1-[(1-methyl-2,3-dihydro-1H-indol-6-yl)sulfonyl]-3-(1-methyl-1,2,3,6-tetrahydropyridin-4-yl)-1H-indole, LC/MS (EI) t$_R$ 2.13, m/z 426.0 (M$^+$+1)

109) 1-[(1-methyl-2,3-dihydro-1H-indol-6-yl)sulfonyl]-3-(1-methyl-1,2,3,6-tetrahydropyridin-4-yl)-5-(trifluoromethyl)-1H-indole, LC/MS (EI) t$_R$ 2.23, m/z 476.0 (M$^+$+1)

110) 1-[(1-methyl-2,3-dihydro-1H-indol-6-yl)sulfonyl]-3-(1-methyl-1,2,3,6-tetrahydropyridin-4-yl)-1H-pyrrolo[2,3-b]pyridine, LC/MS (EI) t$_R$ 1.99, m/z 409.0 (M$^+$+1)

111) 1-[(1-ethyl-2,3-dihydro-1H-indol-6-yl)sulfonyl]-3-(1-methyl-1,2,3,6-tetrahydropyridin-4-yl)-1H-indole, LC/MS (EI) t$_R$ 2.16, m/z 422.0 (M$^+$+1)

112) 1-[(1-ethyl-2,3-dihydro-1H-indol-6-yl)sulfonyl]-5-fluoro-3-(1-methyl-1,2,3,6-tetrahydropyridin-4-yl)-1H-indole, LC/MS (EI) t$_R$ 2.20, m/z 440.0 (M$^+$+1)

113) 1-[(1-ethyl-2,3-dihydro-1H-indol-6-yl)sulfonyl]-3-(1-methyl-1,2,3,6-tetrahydropyridin-4-yl)-5-(trifluoromethyl)-1H-indole, LC/MS (EI) t$_R$ 2.27, m/z 490.0 (M$^+$+1)

114) 1-[(1-ethyl-2,3-dihydro-1H-indol-6-yl)sulfonyl]-3-(1-methyl-1,2,3,6-tetrahydropyridin-4-yl)-1H-pyrrolo[2,3-b]pyridine, LC/MS (EI) $t_R$ 2.06, m/z 423.0 (M$^+$+1)

115) N-methyl-N-(4-{[3-(1-methyl-1,2,3,6-tetrahydropyridin-4-yl)-1H-indol-1-yl]sulfonyl}phenyl)acetamide, LC/MS (EI) $t_R$ 2.02, m/z 424 (M$^+$+1)

116) N-(4-{[5-fluoro-3-(1-methyl-1,2,3,6-tetrahydropyridin-4-yl)-1H-indol-1-yl]sulfonyl}phenyl)-N-methylacetamide, LC/MS (EI) $t_R$ 2.02, m/z 441.5 (M$^+$+1)

117) N-methyl-N-(4-{[3-(1-methyl-1,2,3,6-tetrahydropyridin-4-yl)-5-(trifluoromethyl)-1H-indol-1-yl]sulfonyl}phenyl)acetamide, LC/MS (EI) $t_R$ 2.13, m/z 492 (M$^+$+1)

118) N-methyl-N-(4-{[3-(1-methyl-1,2,3,6-tetrahydropyridin-4-yl)-1H-pyrrolo[2,3-b]pyridin-1-yl]sulfonyl}phenyl)acetamide, LC/MS (EI) $t_R$ 1.95, m/z 425 (M$^+$+1)

119) 7-{[3-(1-methyl-1,2,3,6-tetrahydropyridin-4-yl)-1H-indol-1-yl]sulfonyl}-1,2,3,4-tetrahydroquinoline, LC/MS (EI) $t_R$ 2.13, m/z 408 (M$^+$+1)

120) 7-{[5-fluoro-3-(1-methyl-1,2,3,6-tetrahydropyridin-4-yl)-1H-indol-1-yl]sulfonyl}-1,2,3,4-tetrahydroquinoline, LC/MS (EI) $t_R$ 2.20, m/z 426 (M$^+$+1)

121) 7-{[3-(1-methyl-1,2,3,6-tetrahydropyridin-4-yl)-5-(trifluoromethyl)-1H-indol-1-yl]sulfonyl}-1,2,3,4-tetrahydroquinoline, LC/MS (EI) $t_R$ 2.23, m/z 476 (M$^+$+1)

122) 7-{[3-(1-methyl-1,2,3,6-tetrahydropyridin-4-yl)-1H-pyrrolo[2,3-b]pyridin-1-yl]sulfonyl}-1,2,3,4-tetrahydroquinoline, LC/MS (EI) $t_R$ 2.09, m/z 409 (M$^+$+1)

123) 1-methyl-7-{[3-(1-methyl-1,2,3,6-tetrahydropyridin-4-yl)-1H-indol-1-yl]sulfonyl}-1,2,3,4-tetrahydroquinoline, LC/MS (EI) $t_R$ 2.27, m/z 422 (M$^+$+1)

124) 7-{[5-fluoro-3-(1-methyl-1,2,3,6-tetrahydropyridin-4-yl)-1H-indol-1-yl]sulfonyl}-1-methyl-1,2,3,4-tetrahydroquinoline, LC/MS (EI) $t_R$ 2.27, m/z 440 (M$^+$+1)

125) 1-methyl-7-{[3-(1-methyl-1,2,3,6-tetrahydropyridin-4-yl)-5-(trifluoromethyl)-1H-indol-1-yl]sulfonyl}-1,2,3,4-tetrahydroquinoline, LC/MS (EI) $t_R$ 2.34, m/z 490 (M$^+$+1)

126) 1-methyl-7-{[3-(1-methyl-1,2,3,6-tetrahydropyridin-4-yl)-1H-pyrrolo[2,3-b]pyridin-1-yl]sulfonyl}-1,2,3,4-tetrahydroquinoline, LC/MS (EI) $t_R$ 2.13, m/z 423 (M$^+$+1)

127) 1-methyl-6-{[3-(1-methyl-1,2,3,6-tetrahydropyridin-4-yl)-1H-indol-1-yl]sulfonyl}-1,2,3,4-tetrahydroquinoline, LC/MS (EI) $t_R$ 2.20, m/z 422 (M$^+$+1)

128) 6-{[5-fluoro-3-(1-methyl-1,2,3,6-tetrahydropyridin-4-yl)-1H-indol-1-yl]sulfonyl}-1-methyl-1,2,3,4-tetrahydroquinoline, LC/MS (EI) $t_R$ 2.20, m/z 440 (M$^+$+1)

129) 1-methyl-6-{[3-(1-methyl-1,2,3,6-tetrahydropyridin-4-yl)-5-(trifluoromethyl)-1H-indol-1-yl]sulfonyl}-1,2,3,4-tetrahydroquinoline, LC/MS (EI) $t_R$ 2.27, m/z 490 (M$^+$+1)

130) 1-methyl-6-{[3-(1-methyl-1,2,3,6-tetrahydropyridin-4-yl)-1H-pyrrolo[2,3-b]pyridin-1-yl]sulfonyl}-1,2,3,4-tetrahydroquinoline, LC/MS (EI) $t_R$ 2.06, m/z 423 (M$^+$+1)

131) 3-(1-methyl-1,2,3,6-tetrahydropyridin-4-yl)-1-[(4-pyrrolidin-1-ylphenyl)sulfonyl]-1H-indole, LC/MS (EI) $t_R$ 2.20, m/z 422(M$^+$+1)

132) 5-fluoro-3-(1-methyl-1,2,3,6-tetrahydropyridin-4-yl)-1-[(4-pyrrolidin-1-ylphenyl)sulfonyl]-1H-indole, LC/MS (EI) $t_R$ 2.20, m/z 440 (M$^+$+1)

133) 3-(1-methyl-1,2,3,6-tetrahydropyridin-4-yl)-1-[(4-pyrrolidin-1-ylphenyl)sulfonyl]-5-(trifluoromethyl)-1H-indole, LC/MS (EI) $t_R$ 2.27, m/z 490 (M$^+$+1)

134) 3-(1-methyl-1,2,3,6-tetrahydropyridin-4-yl)-1-[(4-pyrrolidin-1-ylphenyl)sulfonyl]-1H-pyrrolo[2,3-b]pyridine, LC/MS (EI) $t_R$ 2.09, m/z 423 (M$^+$+1)

135) 3-(1-methyl-1,2,3,6-tetrahydropyridin-4-yl)-1-[(3-pyrrolidin-1-ylphenyl)sulfonyl]-1H-indole, LC/MS (EI) $t_R$ 2.23, m/z 422 (M$^+$+1)

136) 5-fluoro-3-(1-methyl-1,2,3,6-tetrahydropyridin-4-yl)-1-[(3-pyrrolidin-1-ylphenyl)sulfonyl]-1H-indole, LC/MS (EI) $t_R$ 2.20, m/z 440 (M$^+$+1)

137) 3-(1-methyl-1,2,3,6-tetrahydropyridin-4-yl)-1-[(3-pyrrolidin-1-ylphenyl)sulfonyl]-5-(trifluoromethyl)-1H-indole, LC/MS (EI) $t_R$ 2.30, m/z 490 (M$^+$+1)

138) 3-(1-methyl-1,2,3,6-tetrahydropyridin-4-yl)-1-[(3-pyrrolidin-1-ylphenyl)sulfonyl]-1H-pyrrolo[2,3-b]pyridine, LC/MS (EI) $t_R$ 2.09, m/z 423 (M$^+$+1)

139) 1-[(1-ethyl-3-methyl-1H-pyrazol-4-yl)sulfonyl]-3-(1-methyl-1,2,3,6-tetrahydropyridin-4-yl)-1H-indole, LC/MS (EI) $t_R$ 2.06, m/z 385 (M$^+$+1)

140) 1-[(1-ethyl-3-methyl-1H-pyrazol-4-yl)sulfonyl]-5-fluoro-3-(1-methyl-1,2,3,6-tetrahydropyridin-4-yl)-1H-indole, LC/MS (EI) $t_R$ 2.09, m/z 403 (M$^+$+1)

141) 1-[(1-ethyl-3-methyl-1H-pyrazol-4-yl)sulfonyl]-3-(1-methyl-1,2,3,6-tetrahydropyridin-4-yl)-5-(trifluoromethyl)-1H-indole, LC/MS (EI) $t_R$ 2.16, m/z 453 (M$^+$+1)

142) 1-{[1-(difluoromethyl)-5-methyl-1H-pyrazol-4-yl]sulfonyl}-3-(1-methyl-1,2,3,6-tetrahydropyridin-4-yl)-1H-indole, LC/MS (EI) $t_R$ 2.09, m/z 407 (M$^+$+1)

143) 1-{[1-(difluoromethyl)-5-methyl-1H-pyrazol-4-yl]sulfonyl}-5-fluoro-3-(1-methyl-1,2,3,6-tetrahydropyridin-4-yl)-1H-indole, LC/MS (EI) $t_R$ 2.09, m/z 425 (M$^+$+1)

144) 1-{[1-(difluoromethyl)-5-methyl-1H-pyrazol-4-yl]sulfonyl}-3-(1-methyl-1,2,3,6-tetrahydropyridin-4-yl)-5-(trifluoromethyl)-1H-indole, LC/MS (EI) $t_R$ 2.13, m/z 475 (M$^+$+1)

145) 1-[(1-ethyl-5-methyl-1H-pyrazol-4-yl)sulfonyl]-3-(1-methyl-1,2,3,6-tetrahydropyridin-4-yl)-1H-indole, LC/MS (EI) $t_R$ 2.09, m/z 385 (M$^+$+1)

146) 1-[(1-ethyl-5-methyl-1H-pyrazol-4-yl)sulfonyl]-5-fluoro-3-(1-methyl-1,2,3,6-tetrahydropyridin-4-yl)-1H-indole, LC/MS (EI) $t_R$ 2.09, m/z 403 (M$^+$+1)

147) 1-[(1-ethyl-5-methyl-1H-pyrazol-4-yl)sulfonyl]-3-(1-methyl-1,2,3,6-tetrahydropyridin-4-yl)-5-(trifluoromethyl)-1H-indole, LC/MS (EI) $t_R$ 2.13, m/z 453 (M$^+$+1)

148) 1-[(1-ethyl-1H-pyrazol-4-yl)sulfonyl]-3-(1-methyl-1,2,3,6-tetrahydropyridin-4-yl)-1H-indole, LC/MS (EI) $t_R$ 1.99, m/z, 371 (M$^+$+1)

149) 1-[(1-ethyl-1H-pyrazol-4-yl)sulfonyl]-5-fluoro-3-(1-methyl-1,2,3,6-tetrahydropyridin-4-yl)-1H-indole, LC/MS (EI) $t_R$ 2.02, m/z 389 (M$^+$+1)

150) 1-[(1-ethyl-1H-pyrazol-4-yl)sulfonyl]-3-(1-methyl-1,2,3,6-tetrahydropyridin-4-yl)-5-(trifluoromethyl)-1H-indole, LC/MS (EI) $t_R$ 2.09, m/z 439 (M$^+$+1)

151) 1-[(1-ethyl-3,5-dimethyl-1H-pyrazol-4-yl)sulfonyl]-3-(1-methyl-1,2,3,6-tetrahydropyridin-4-yl)-1H-indole, LC/MS (EI) $t_R$ 2.03, m/z 399 (M$^+$+1)

152) 1-[(1-ethyl-3,5-dimethyl-1H-pyrazol-4-yl)sulfonyl]-5-fluoro-3-(1-methyl-1,2,3,6-tetrahydropyridin-4-yl)-1H-indole, LC/MS (EI) $t_R$ 2.09, m/z 417 (M$^+$+1)

153) 1-[(1-ethyl-3,5-dimethyl-1H-pyrazol-4-yl)sulfonyl]-3-(1-methyl-1,2,3,6-tetrahydropyridin-4-yl)-5-(trifluoromethyl)-1H-indole, LC/MS (EI) $t_R$ 2.16, m/z 467 (M$^+$+1)

154) 1-[(1-methyl-1H-pyrazol-4-yl)sulfonyl]-3-(1-methyl-1,2,3,6-tetrahydropyridin-4-yl)-1H-indole, LC/MS (EI) $t_R$ 1.95, m/z 357 (M$^+$+1)

155) 5-fluoro-1-[(1-methyl-1H-pyrazol-4-yl)sulfonyl]-3-(1-methyl-1,2,3,6-tetrahydropyridin-4-yl)-1H-indole, LC/MS (EI) $t_R$ 2.02, m/z 375 (M$^+$+1)

156) 1-[(1-methyl-1H-pyrazol-4-yl)sulfonyl]-3-(1-methyl-1,2,3,6-tetrahydropyridin-4-yl)-5-(trifluoromethyl)-1H-indole, LC/MS (EI) $t_R$ 2.06, m/z 425 (M$^+$+1)

157) 1-[(1,5-dimethyl-1H-pyrazol-4-yl)sulfonyl]-3-(1-methyl-1,2,3,6-tetrahydropyridin-4-yl)-1H-indole, LC/MS (EI) $t_R$ 1.99, m/z 371 (M$^+$+1)

158) 1-[(1,5-dimethyl-1H-pyrazol-4-yl)sulfonyl]-5-fluoro-3-(1-methyl-1,2,3,6-tetrahydropyridin-4-yl)-1H-indole, LC/MS (EI) $t_R$ 2.02, m/z 389 (M$^+$+1)

159) 1-[(1,5-dimethyl-1H-pyrazol-4-yl)sulfonyl]-3-(1-methyl-1,2,3,6-tetrahydropyridin-4-yl)-5-(trifluoromethyl)-1H-indole, LC/MS (EI) $t_R$ 2.09, m/z 439 (M$^+$+1)

160) 1-[(1,3-dimethyl-1H-pyrazol-4-yl)sulfonyl]-3-(1-methyl-1,2,3,6-tetrahydropyridin-4-yl)-1H-indole, LC/MS (ED) $t_R$ 2.02, m/z 371 (M$^+$+1)

161) 1-[(1,3-dimethyl-1H-pyrazol-4-yl)sulfonyl]-5-fluoro-3-(1-methyl-1,2,3,6-tetrahydropyridin-4-yl)-1H-indole, LC/MS (EI) $t_R$ 2.02, m/z 389 (M$^+$+1)

162) 1-[(1,3-dimethyl-1H-pyrazol-4-yl)sulfonyl]-3-(1-methyl-1,2,3,6-tetrahydropyridin-4-yl)-5-(trifluoromethyl)-1H-indole, LC/MS (EI) $t_R$ 2.09, m/z 439 (M$^+$+1) 163) 1-[(1-methyl-2,3-dihydro-1H-indol-5-yl)sulfonyl]-3-(1-methyl-1,2,3,6-tetrahydropyridin-4-yl)-1H-indole, LC/MS (EI) $t_R$ 2.13, m/z 408 (M$^+$+1)

164) 5-fluoro-1-[(1-methyl-2,3-dihydro-1H-indol-5-yl)sulfonyl]-3-(1-methyl-1,2,3,6-tetrahydropyridin-4-yl)-1H-indole, LC/MS (ED) $t_R$ 2.13, m/z 426 (M$^+$+1)

165) 1-[(1-methyl-2,3-dihydro-1H-indol-5-yl)sulfonyl]-3-(1-methyl-1,2,3,6-tetrahydropyridin-4-yl)-5-(trifluoromethyl)-1H-indole, LC/MS (ED) $t_R$ 2.18, m/z 476 (M$^+$+1)

166) 1-[(1-methyl-2,3-dihydro-1H-indol-5-yl)sulfonyl]-3-(1-methyl-1,2,3,6-tetrahydropyridin-4-yl)-1H-pyrrolo[2,3-b]pyridine, LC/MS (EI) $t_R$ 2.02, m/z 409 (M$^+$+1)

167) 1-(2,2-dimethylpropanoyl)-5-{[3-(1-methyl-1,2,3,6-tetrahydropyridin-4-yl)-1H-indol-1-yl]sulfonyl}-1H-indazole, LC/MS (EI) $t_R$ 2.3, m/z 477 (M$^+$+1)

168) 1-(2,2-dimethylpropanoyl)-5-{[5-fluoro-3-(1-methyl-1,2,3,6-tetrahydropyridin-4-yl)-1H-indol-1-yl]sulfonyl}-1H-indazole, LC/MS (ED) $t_R$ 2.3, m/z 495 (M$^+$+1)

169) 1-(2,2-dimethylpropanoyl)-5-{[3-(1-methyl-1,2,3,6-tetrahydropyridin-4-yl)-5-(trifluoromethyl)-1H-indol-1-yl]sulfonyl}-1H-indazole, LC/MS (EI) $t_R$ 2.37, m/z 545 (M$^+$+1)

170) 1-{[1-(difluoromethyl)-3-methyl-1H-pyrazol-4-yl]sulfonyl}-3-(1-methyl-1,2,3,6-tetrahydropyridin-4-yl)-1H-indole, LC/MS (EI) $t_R$ 2.09, m/z 407 (M$^+$+1)

171) 1-{[1-(difluoromethyl)-3-methyl-1H-pyrazol-4-yl]sulfonyl}-5-fluoro-3-(1-methyl-1,2,3,6-tetrahydropyridin-4-yl)-1H-indole, LC/MS (EI) $t_R$ 2.13, m/z 425 (M$^+$+1)

172) 1-{[1-(difluoromethyl)-3-methyl-1H-pyrazol-4-yl]sulfonyl}-3-(1-methyl-1,2,3,6-tetrahydropyridin-4-yl)-5-(trifluoromethyl)-1H-indole, LC/MS (ED) $t_R$ 2.16, m/z 475 (M$^+$+1)

Similarly, using this general procedure, with different starting materials, and where the 1-methylpiperidin-4-one can be replaced with 1-methyl-1,4-piperazine, additional compounds of the present invention wherein Q is N can be synthesized.

General Procedure B 81) 3-(1-methyl-1,2,3,6-tetrahydropyridin-4-yl)-1-(phenylsulfonyl)-5-(pyridin-4-yl)-1H-indole

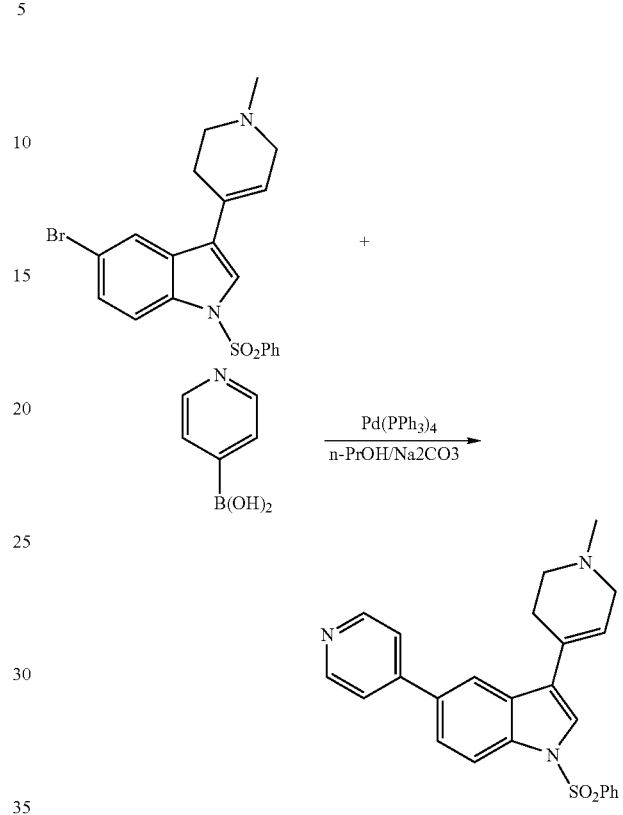

Into a 100 mL 3-necked round bottom flask was placed pyridin-3-ylboronic acid (200 mg, 1.63 mmol), 5-bromo-3-(1-methyl-1,2,3,6-tetrahydropyridin-4-yl)-1-(phenylsulfonyl)-1H-indole (470 mg, 1.08 mmol), and n-propanol (140 mL). The mixture was stirred at room temperature for 30 min during which time the solids dissolved. A solution of Na$_2$CO$_3$ (430 mg, 4.06 mmol) in water (5 mL) was then added, followed by the addition of Pd(PPh$_3$)$_4$ (130 mg, 0.108 mmol). The resulting solution was stirred at reflux temperature overnight, and then concentrated. The residue was dissolved in water (10 mL), and the resulting solution was extracted diethylether (2×50 mL). The organic layers were combined and the residue was purified by column chromatography using a 1:5 dichloromethane/methanol solvent system to afford 200 mg (42.5%) of 3-(1-methyl-1,2,3,6-tetrahydropyridin-4-yl)-1-(phenylsulfonyl)-5-(pyridin-4-yl)-1H-indole as a deep yellow solid. $^1$H NMR (CDCl$_3$) δ 8.69 (d, 2H), 8.12 (d, 1H), 7.93 (t, 3H), 7.60 (d, 3H), 7.48 (d×d, 4H), 6.18 (s, 1H), 2.85 (2H), 1.52 (2H), 1.25 (3H), 0.87 (2H). LC/MS (EI) $t_R$ 2.18, m/z 430.0 (M$^+$+1)

Using this general procedure, the following compounds were prepared using different starting materials:

84) 3-(1-methyl-1,2,3,6-tetrahydropyridin-4-yl)-1-(phenylsulfonyl)-5-pyridin-3-yl-1H-indole, LC/MS (EI) $t_R$ 1.92, m/z 430.0 (M$^+$+1)

85) 3-(1-methyl-1,2,3,6-tetrahydropyridin-4-yl)-1-(phenylsulfonyl)-6-pyridin-3-yl-1H-indole, LC/MS (EI) $t_R$ 1.88, m/z 430.0 (M$^+$+1)

86) 3-(1-methyl-1,2,3,6-tetrahydropyridin-4-yl)-1-(phenylsulfonyl)-6-pyridin-4-yl-1H-indole, LC/MS (EI) $t_R$ 1.85, m/z 430.0 (M$^+$+1)

105) 3-(1-methyl-1,2,3,6-tetrahydropyridin-4-yl)-1-(phenyl-sulfonyl)-5-pyridin-2-yl-1H-indole dihydrochloride, LC/MS (EI) $t_R$ 1.99, m/z 444.0 (M$^+$+1)

106) 3-(1-methyl-1,2,3,6-tetrahydropyridin-4-yl)-1-(phenyl-sulfonyl)-6-pyridin-2-yl-1H-indole dihydrochloride, LC/MS (EI) $t_R$ 1.99, m/z 444.0 (M$^+$+1)

General Procedure C 79) 5-(2,5-dimethyl-1H-pyrrol-t-yl)-3-(1-methyl-1,2,3,6-tetrahydropyridin-4-yl)-1-(phenylsulfonyl)-1H-indole

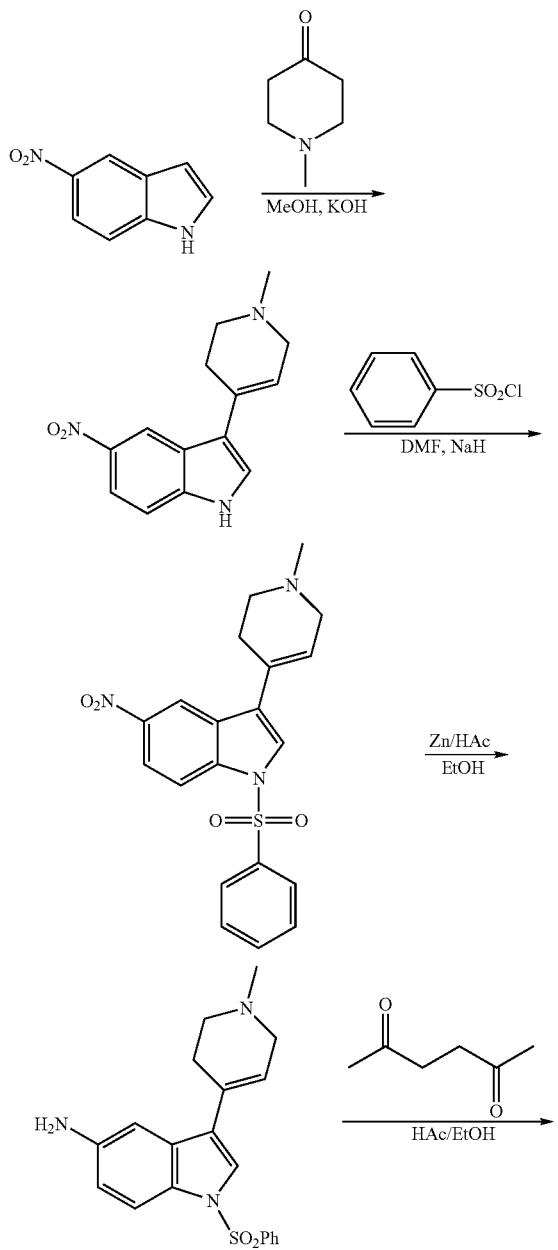

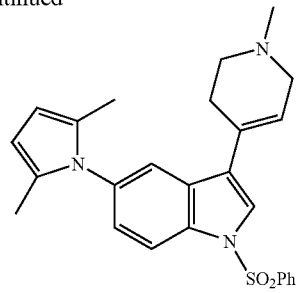

1) Synthesis of 3-(1-methyl-1,2,3,6-tetrahydropyridin-4-yl)-5-nitro-1H-indole

A solution of KOH (12 g, 213.21 mmol) in methanol (100 mL) was added to 5-nitro-1H-indole (15 g, 92.04 mmol) in a 250 mL flask. 1-methylpiperidin-4-one (13.7 g, 120.46 mmol) was then added dropwise with stirring, while cooling the reaction to 20° C. The resulting solution was stirred for 4 hours, while the temperature was maintained at 72° C. The reaction mixture was then cooled to 15° C., and the product was precipitated by the addition of water (100 mL). Filtration, followed by recrystallization of the residue from ethanol afforded 11 g (46%) of 3-(1-methyl-1,2,3,6-tetrahydropyridin-4-yl)-5-nitro-1H-indole as a yellow solid.

2) Synthesis of 3-(1-methyl-1,2,3,6-tetrahydropyridin-4-yl)-5-nitro-1-(phenylsulfonyl)-1H-indole NaH (330 mg, 8.25 mmol) was added in several batches, to a solution of 3-(1-methyl-1,2,3,6-tetrahydropyridin-4-yl)-5-nitro-1H-indole (1.4 g, 5.42 mmol) in DMF (25 mL) while cooling to 0-5° C. The resulting solution was stirred at room temperature for 0.5 hours, and then benzenesulfonyl chloride (1.5 g, 8.41 mmol) was added dropwise. The reaction was stirred for an additional 4 hours at room temperature, and then filtered. The filter cake was washed with ethanol (3×50 mL) and dried to afford 1.2 g (55%) of 3-(1-methyl-1,2,3,6-tetrahydropyridin-4-yl)-5-nitro-1-(phenylsulfonyl)-1H-indole as a light yellow solid. $^1$H NMR (DMSO) δ 8.62 (s, 1H), 8.17-8.27 (3H), 8.10 (d, 2H), 7.74 (1H), 7.61 (2H), 6.32 (s, 1H), 3.84 (s, 2H), 3.38 (2H), 2.83-2.87 (5H).

3) Synthesis of 3-(1-methyl-1,2,3,6-tetrahydropyridin-4-yl)-1-(phenylsulfonyl)-1H-indol-5-amine Zinc (3.28 g, 50.46 mmol) was added to a solution of 3-(1-methyl-1,2,3,6-tetrahydropyridin-4-yl)-5-nitro-1-(phenylsulfonyl)-1H-indole (2 g, 5.04 mmol) in ethanol (500 mL). Acetic acid (30 mL) was then added dropwise with stirring while the reaction was cooled in a ice water bath. The resulting solution was stirred for 2 hours at room and then filtered. The filtrate cake was washed with ethanol, and the collected filtrate was concentrated in vacuo. The residue was purified by column chromatography using a 10:1 methanol/ammonia solvent system to afford 1 g (54%) of 3-(1-methyl-1,2,3,6-tetrahydropyridin-4-yl)-1-(phenylsulfonyl)-1H-indol-5-amine as a yellow solid.

4) Synthesis of 5-(2,5-dimethyl-1H-pyrrol-1-yl)-3-(1-methyl-1,2,3,6-tetrahydropyridin-4-yl)-1-(phenylsulfonyl)-1H-indole Hexane-2,5-dione (2 mL) was added to a solution of 3-(1-methyl-1,2,3,6-tetrahydropyridin-4-yl)-1-(phenylsulfonyl)-1H-indol-5-amine (300 mg, 0.82 mmol) in ethanol (50 mL). Acetic acid (2 mL) was added, and the resulting solution was stirred at room temperature overnight. The solvent was concentrated, followed by column chromatography purification using a 1:10 methanol/dichloromethane solvent system provided 30 mg (8%) of 5-(2,5-dimethyl-1H-pyrrol-1-yl)-3-(1-methyl-1,2,3,6-tetrahydropyridin-4-yl)-1-phenylsulfonyl)-1H-indole as a yellow solid. $^1$H NMR (CDCl$_3$) δ 8.05 (d, 1H), 7.95 (d, 2H), 7.62 (s, 1H), 7.50 (d, 2H), 7.26 (2H), 6.84 (d, 2H), 6.11 (s, 1H), 5.90 (s, 2H), 3.46 (d, 2H), 3.07 (t, 2H), 2.74 (s, 2H), 2.62 (s, 2H), 1.98 (s, 6H). LC/MS (EI) $t_R$ 2.46, m/z 446.0 (M$^+$+1)

Using this general procedure the following compound was prepared using different starting materials:

77) 3-(1-methyl-1,2,3,6-tetrahydropyridin-4-yl)-5-nitro-1-(phenylsulfonyl)-1H-indole, LC/MS (EI) $t_R$ 2.27, m/z 398.0 (M$^+$+1).

General Procedure D 80) 6-(2,5-dimethyl-1H-pyrrol-1-yl)-3-(1-methyl-1,2,3,6-tetrahydropyridin-4-yl)-1-(phenylsulfonyl)-1H-indole

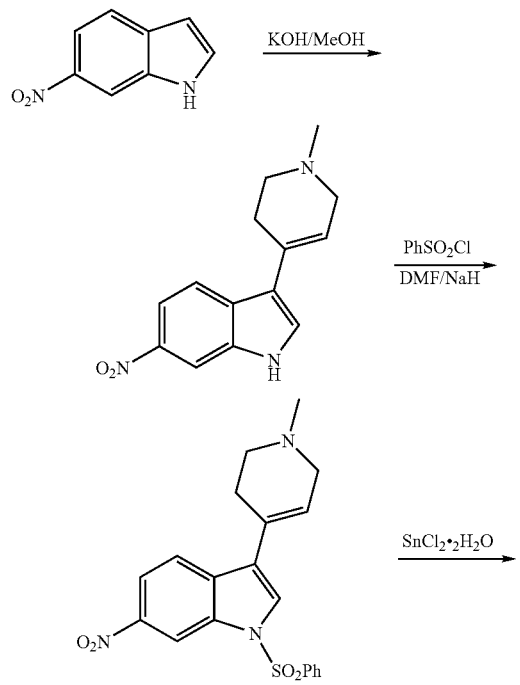

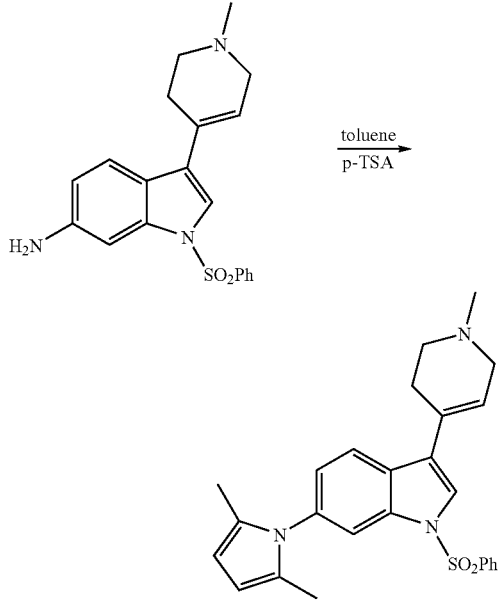

1) Synthesis of 3-(1-methylpiperidin-4-yl)-6-nitro-1H-indole

KOH (3.96 g, 70.71 mmol) was added to a solution of 6-nitro-1H-indole (5 g, 30.86 mmol) in methanol (50 mL). 1-methylpiperidin-4-one (4.53 g, 40.09 mmol) was then added, and the resulting solution was stirred for 6 hours at 90° C. After cooling, the mixture was concentrated and the residue was recrystallized from ethanol (20 mL) to afford 3.0 g (36%) of 3-(1-methylpiperidin-4-yl)-6-nitro-1H-indole as a yellow powder.

2) Synthesis of 3-(1-methyl-1,2,3,6-tetrahydropyridin-4-yl)-6-nitro-1-(phenylsulfonyl)-1H-indole Sodium hydride (50 mg, 2.08 mmol) was added in several batches to a solution of 3-(1-methyl-1,3,6-tetrahydropyridin-4-yl)-6-nitro-1H-indole (300 mg, 1.11 mmol) in DMF (30 mL) chilled in an ice water bath. The reaction was then placed under an atmosphere of nitrogen and maintained at 0° C. for 1 hour. Benzenesulfonyl chloride (214 mg, 1.21 mmol) was then added at 0° C., and the resulting solution was stirred for 2 hours at room temperature. The mixture was quenched by the addition of 35 mL of ice water (with external cooling by ice/water). After filtration, the residue was purified by column chromatography using a 50:1 dichloromethane/methanol solvent system to afford 0.13 g (30%) of 3-(1-methyl-1,2,3,6-tetrahydropyridin-4-yl)-6-nitro-1-(phenylsulfonyl)-1H-indole as a light yellow solid. $^1$H NMR (CDCl$_3$) δ 9.3 (s, 1H), 7.93 (d, 2H), 7.9 (d, 2H), 7.54 (d, 1H), 7.3 (s, 1H), 6.13 (s, 1H), 2.83 (t, 2H), 2.45 (t, 2H), 2.27 (t, 3H), 2.07 (t, 2H).

3) Synthesis of 3-(1-methyl-1,2,3,6-tetrahydropyridin-4-yl)-1-(phenylsulfonyl)-1H-indol-6-amine Tin (II) chloride (2 g, 9.35 mmol) was added to a solution of 3-(1-methyl-1,2,3,6-tetrahydropyridin-4-yl)-6-nitro-1-(phenylsulfonyl)-1H-indole (100 mg, 0.25 mmol) in methanol (30 mL). The resulting solution was stirred for 2 hours at reflux temperature After cooling to room temperature, the mixture was concentrated by evaporation to provide 3-(1-methyl-1,2,3,6-tetrahydropyridin-4-yl)-1-(phenylsulfonyl)-1H-indol-6-amine, which was used in the next stage without further purification.

4) Synthesis of 6-(2,5-dimethyl-1H-pyrrol-1-yl)-3-(1-methyl-1,2,3,6-tetrahydropyridin-4-yl)-1-(phenylsulfonyl)-1H-indole Hexane-2,5-dione (930 mg, 8.16 mmol) was added to a solution of 3-(1-methyl-1,2,3,6-tetrahydropyridin-4-yl)-1-(phenylsulfonyl)-1H-indol-6-amine (1.66 g, 1.13 mmol) in toluene (80 mL). Para-toluenesulfonic acid (30 mg, 0.17 mmol) was then added, and the resulting solution was stirred for 4 hours at 130° C. After filtration, the filtrate was concentrated and the residue was purified by column chromatography using a 30:1 dichloromethane/methanol solvent system. The product was washed with petroleum ether to afford 170 mg (32%) of 6-(2,5-dimethyl-1H-pyrrol-1-yl)-3-(1-methyl-1,2,3,6-tetrahydropyridin-4-yl)-1-(phenylsulfonyl)-1H-indole as a yellow solid. $^1$H NMR (DMSO) δ 8.3 (s, 1H), 8.3 (s, 1H), 8.1 (s, 1H), 8.0 (s, 1H), 7.8 (s, 1H), 7.6 (s, 1H), 7.4 (s, 1H), 7.4 (s, 1H), 7.1 (s, 1H), 6.3 (s, 1H), 5.8 (s, 1H), 5.8 (s, 1H), 3.0 (s, 2H), 2.27 (s, 3H), 2.6 (d, 2H), 2.6 (d, 2H), 1.8 (d, 3H), 1.8 (d, 3H). LC/MS (EI) $t_R$ 2.48, m/z 446.0 (M$^+$+1)

Using this general procedure the following compound was prepared using different starting materials:
78) 3-(1-methyl-1,2,3,6-tetrahydropyridin-4-yl)-6-nitro-1-(phenylsulfonyl)-1H-indole, LC/MS (EI) $t_R$ 2.17, m/z 398.0 (M$^+$+1).

General Procedure E

Synthesis of 3-(1-methyl-1,2,3,6-tetrahydropyridin-4-yl)-1-(phenylsulfonyl)-1H-indole-5-carbonitrile

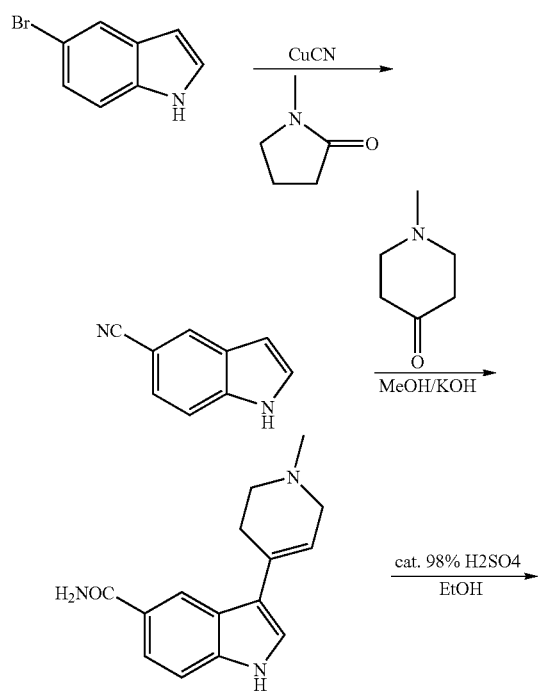

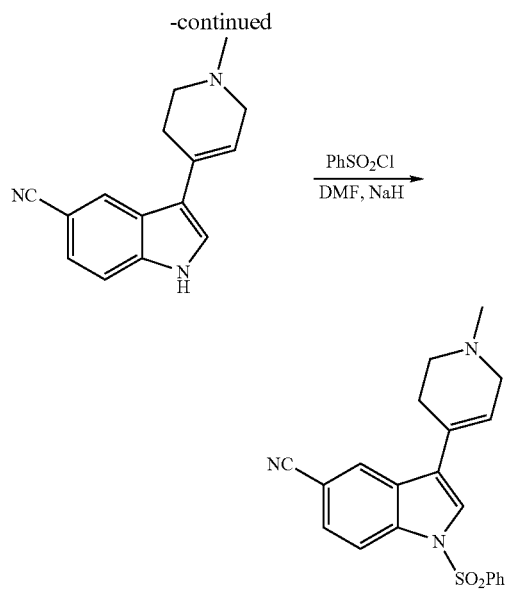

1) Synthesis of 1H-indole-5-carbonitrile

CuCN (3.7 g, 40.70 mmol) was added to a solution of 5-bromo-1H-indole (5 g, 25.26 mmol) in 1-methylpyrrolidin-2-one (25 mL), and the resulting solution was stirred at reflux for 18 hours. The reaction mixture was then added to 200 g of ice and the mixture was filtered. The filter cake was washed with ammonium hydroxide (3×50 mL). The residue was dissolved in chloroform (600 mL) and then filtered. The organic layer was washed with water (200 mL), and dried (MgSO$_4$). After a further filtration, the filtrate was concentrated to yield 3.7 g (82%) of 1H-indole-5-carbonitrile as brown oil.

2) Synthesis of 3-(1-methyl-1,2,3,6-tetrahydropyridin-4-yl)-1H-indole-5-carboxamide A solution of KOH (1.0 g, 17.68 mmol) in methanol (20 mL) was added to 1H-indole-5-carbonitrile (1.0 g, 6.96 mmol). 1-methylpiperidin-4-one (1.0 g, 8.75 mmol) was then added dropwise with stirring, while cooling to 0-5° C. and the resulting solution was stirred for 1 hour at 50° C. The reaction mixture was then cooled to room temperature, concentrated, and the residue was purified by column chromatography using ethanol solvent system to give 200 mg of 3-(1-methyl-1,2,3,6-tetrahydropyridin-4-yl)-1H-indole-5-carboxamide as a white solid.

3) 3-(1-methyl-1,2,3,6-tetrahydropyridin-4-yl)-1H-indole-5-carbonitrile

H$_2$SO$_4$ (0.1 mL) was added to a solution of 3-(1-methyl-1,2,3,6-tetrahydropyridin-4-yl)-1H-indole-5-carboxamide (130 mg, 0.41 mmol) in ethanol (4 mL) and the resulting solution was stirred at room temperature for 1 hour. Filtration and subsequent concentration afforded 20 mg (18.6%) of 3-(1-methyl-1,2,3,6-tetrahydropyridin-4-yl)-1H-indole-5-carbonitrile as a white solid.

4) Synthesis of 3-(1-methyl-1,2,3,6-tetrahydropyridin-4-yl)-1-(phenylsulfonyl)-1H-indole-5-carbonitrile NaH (26 mg, 1.07 mmol) was added in several batches to a solution of 3-(1-methyl-1,2,3,6-tetrahydropyridin-4-yl)-1H-indole-5-carbonitrile (200 mg, 0.76 mmol) in DMF (2 mL) at 0-5° C., and the mixture was maintained for 1 hour at room temperature. Benzenesulfonyl chloride (222 mg, 1.24 mmol) was then added, and the resulting solution was maintained at room temperature for an additional 4 hours. The mixture was filtered, and the filter cake was washed with ethanol (2×10 mL) and diethylether (2×10 mL) to afford 250 mg (86%) of 3-(1-methyl-1,2,3,6-tetrahydropyridin-4-yl)-1-(phenylsulfonyl)-1H-indole-5-carbonitrile as a white solid. $^1$H NMR (DMSO) δ 8.41 (s, 1H), 8.14 (d, 2H), 8.07 (d, 2H), 7.78 (d, 1H), 7.71 (d, 2H), 7.61 (t, 1H), 6.35 (s, 1H), 3.79 (2H), 3.34 (s, 2H), 2.80-2.87 (m, 5H).

General Procedure F

Synthesis of 3-(1-methyl-1,2,3,6-tetrahydropyridin-4-yl)-5-(pyrro-lidin-1-yl)-1H-indole

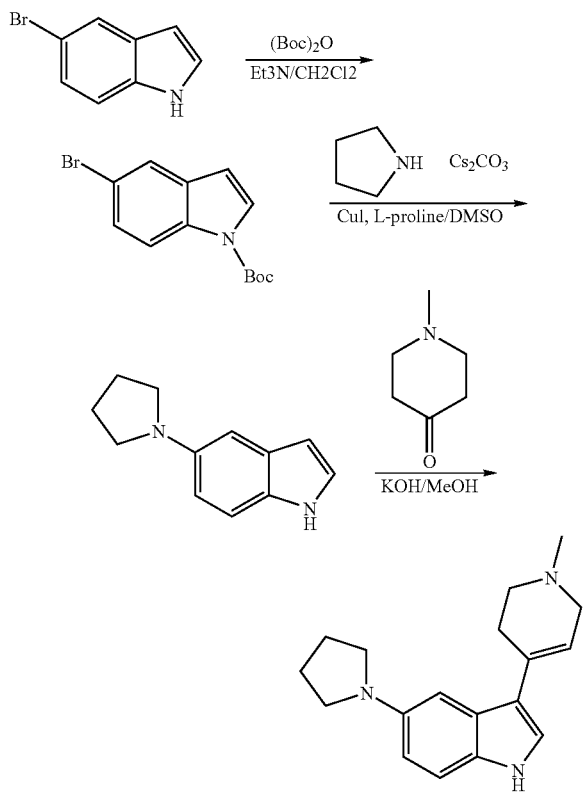

1) Synthesis of tert-butyl 5-bromo-1H-indole-1-carboxylate (Boc)$_2$O (23.35 g, 107.11 mmol) was added to a solution of 5-bromo-1H-indole (20 g, 102.04 mmol) in dichloromethane (120 mL). Et$_3$N (10.302 g, 102.00 mmol) was then added, and the resulting solution was stirred at room temperature overnight, then for 6 hours at reflux temperature. The residue was purified by column chromatography using petroleum ether solvent to afford 7.21 g (23%) of tert-butyl 5-bromo-1H-indole-1-carboxylate as a white solid.

2) Synthesis of 5-(pyrrolidin-1-yl)-1H-indole t-Butyl 5-bromo-1H-indole-1-carboxylate (200 mg, 0.68 mmol) was placed in a 10 mL sealed tube. Cs$_2$CO$_3$ (440 g, 1.35 mol) was then added, followed by CuI (13 mg, 0.07 mmol), L-proline (16 mg, 0.14 mmol), DMSO (3 mL), and pyrrolidine (480 g, 6.75 mol). After sparging with nitrogen, the resulting solution was stirred at 95° C. for 18 hours. The mixture was extracted with ethyl acetate (3×40 mL), and the organic layers were combined and washed with brine. The residue was purified by column chromatography using 1:5 and 1:2 ethyl acetate/petroleum ether solvent systems. The collected fractions were combined and concentrated to give 100 mg (80%) of 5-(pyrrolidin-1-yl)-1H-indole as brown oil.

3) Synthesis of 3-(1-methyl-1,2,3,6-tetrahydropyridin-4-yl)-5-(pyrro-lidin-1-yl)-1H-indole 1-methylpiperidin-4-one (1.2 g, 10.62 mmol) was added to a solution of 5-(pyrrolidin-1-yl)-1H-indole (200 mg, 1.08 mmol) in methanol (20 mL). KOH (600 mg, 10.71 mmol) was then added, and the resulting solution was stirred at reflux temperature overnight. The mixture was concentrated, quenched by the addition of water and filtered. The filter cake was washed with water and ether to afford 120 mg (37%) of 3-(1-methyl-1,2,3,6-tetrahydropyridin-4-yl)-5-(pyrro-lidin-1-yl)-1H-indole as a yellow solid. $^1$H NMR (CDCl$_3$) δ 7.85 (s, 1H), 7.09 (d, 1H), 6.98 (s, 1H), 6.69 (d, 1H), 6.12 (s, 1H), 3.32 (t, 4H), 3.25 (s, 2H), 2.75 (t, 2H), 2.66 (t, 2H), 2.47 (s, 3H), 1.71 (t, 4H).

Using this general procedure, followed by procedure A (2), the following compounds were prepared using different starting materials:

99) 3-(1-methyl-1,2,3,6-tetrahydropyridin-4-yl)-1-(phenylsulfonyl)-5-pyrrolidin-1-yl-1H-indole, LC/MS (EI) t$_R$ 2.02, m/z 422.0 (M$^+$+1)

101) 3-(1-methyl-1,2,3,6-tetrahydropyridin-4-yl)-1-(phenylsulfonyl)-5-piperidin-1-yl-1H-indole, LC/MS (EI) t$_R$ 1.88, m/z 436.0 (M$^+$+1)

103) 3-(1-methyl-1,2,3,6-tetrahydropyridin-4-yl)-5-morpholin-4-yl-1-(phenylsulfonyl)-1H-indole, LC/MS (EI) t$_R$ 2.02, m/z 438.0 (M$^+$+1)

General Procedure G

Synthesis of 3-(1-methyl-1,2,3,6-tetrahydropyridin-4-yl)-6-(pyrrolidin-1-yl)-1H-indole

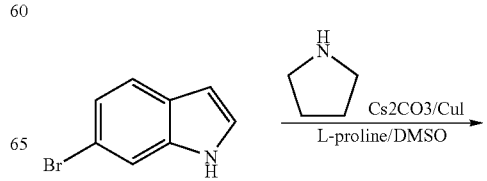

General Procedure H

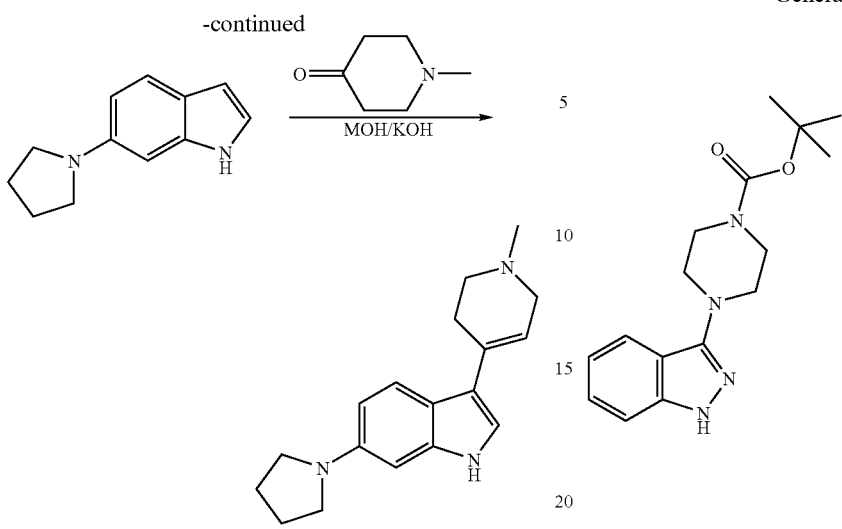
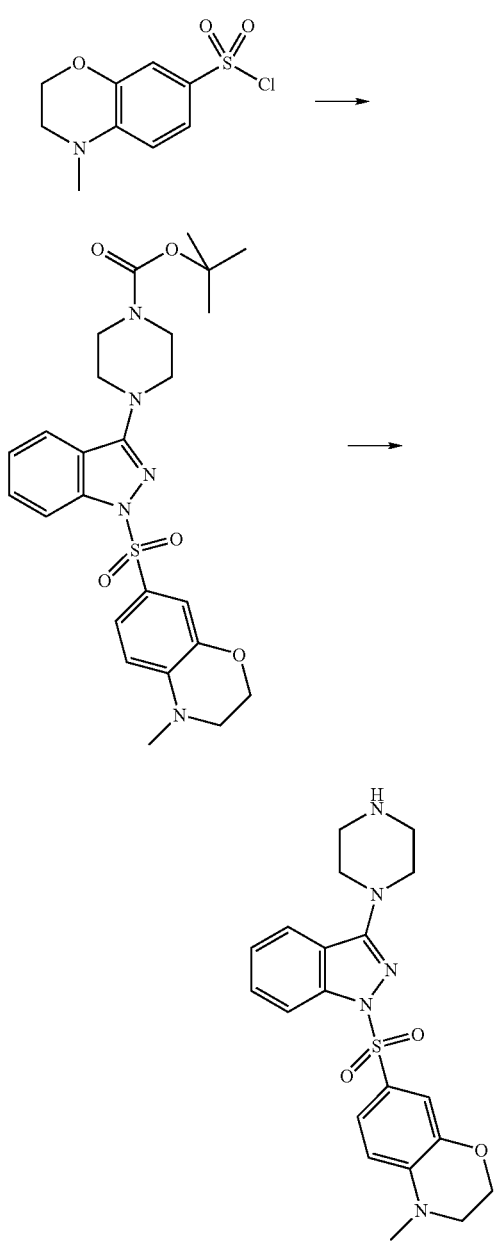

1). Synthesis of 6-(pyrrolidin-1-yl)-1H-indole

A solution of 6-bromo-1H-indole (300 mg, 1.53 mmol) in DMSO (2 mL) was placed in a 10 mL sealed tube and sparged with nitrogen. Pyrrolidine (1.09 g, 15.33 mmol) was then added, followed by the addition of cesium carbonate (1 g, 3.07 mmol), copper (I) iodide (30 mg, 0.16 mmol), and L-proline (200 mg, 1.74 mmol). The resulting solution was stirred for 20 hours at 94° C. The reaction mixture was then quenched by the addition of iced water (30 mL). The resulting solution was extracted with ethyl acetate (3×100 mL) and the organic layers were combined, dried (MgSO$_4$) and concentrated. The residue was purified by column chromatography using a 1:2 ethyl acetate/petroleum ether solvent system to give 160 mg (47%) of 6-(pyrrolidin-1-yl)-1H-indole as a tan crystalline solid.

2) Synthesis of 3-(1-methyl-1,2,3,6-tetrahydropyridin-4-yl)-6-(pyrrolidin-1-yl)-1H-indole 6-(pyrrolidin-1-yl)-1H-indole (500 mg, 2.68 mmol) was added to a solution of potassium hydroxide (1.55 g, 27.62 mmol) in methanol (20 mL). 1-methylpiperidin-4-one (610 mg, 5.39 mmol) was then added, and the resulting solution was stirred at 72° C. overnight. The mixture was concentrated and the residue was poured into water (40 mL). After filtration, the filter cake was washed with water (1×50 mL) and diethylether (1×50 mL), to afford 400 mg (47.6%) of 3-(1-methyl-1,2,3,6-tetrahydropyridin-4-yl)-6-(pyrrolidin-1-yl)-1H-indole as a white solid.

Using this general procedure, followed by procedure A (2), the following compounds were prepared using different starting materials:

100) 3-(1-methyl-1,2,3,6-tetrahydropyridin-4-yl)-1-(phenylsulfonyl)-6-pyrrolidin-1-yl-1H-indole, LC/MS (EI) t$_R$ 2.13, m/z 422.0 (M$^+$+1)

102) 3-(1-methyl-1,2,3,6-tetrahydropyridin-4-yl)-1-(phenylsulfonyl)-6-piperidin-1-yl-1H-indole, LC/MS (EI) t$_R$ 1.88, m/z 436.0 (M$^+$+1)

104) 3-(1-methyl-1,2,3,6-tetrahydropyridin-4-yl)-6-morpholin-4-yl-1-(phenylsulfonyl)-1H-indole, LC/MS (EI) t$_R$ 2.03, m/z 438.0 (M$^+$+1).

Ha: (319) Synthesis of 4-methyl-7-[(3-piperazin-1-yl-1H-indazol-1-yl)sulfonyl]-3,4-dihydro-2H-1,4-benzoxazine Into a vial, tert-butyl 4-(1H-indazol-3-yl)piperazine-1-carboxylate (85 mg, 0.00028 mol) was added to tetrahydrofuran (2 mL, 0.03 mol) and N,N-dimethylformamide (2 mL, 0.03 mol). The flask was cooled at 5° C. and 1.0 M of sodium bis(trimethylsilyl)amide in tetrahydrofuran (422 µL) was added and was stirred under an atmosphere of nitrogen for 30 minutes. The solution was drawn up and was added at 5° C. with 4-methyl-3,4-dihydro-2h-1,4-benzoxazine-7-sulfonyl chloride (104 mg, 0.000422 mol) and N,N-dimethylethylamine (45.7 µL, 0.000422 mol) and tetrahydrofuran (2 mL, 0.03 mol) into a 1-neck round-bottom flask. The reaction was stirred for 30 minutes and was extracted with ethyl acetate and then was washed with water twice and brine once. The solvent was rotovaped to 190 mg of crude material.

The crude was adsorbed onto silica gel and was flash chromatographed on silica gel on a 12 g cartridge using a hexane: ethyl acetate gradient (10-50%) over 8 minutes at a flow rate of 20 mL/min and UV detection at 240 nm. 50 mg was recovered.

Alternatively, if the Boc group is methyl group, the residue was purified on a C18 Sunfire column (30×100 mm) using a gradient of (5-80%)acetonitrile:water (with 0.1% formic acid) and a flow rate of 45 mL/min, gave the corresponding formic salt, or the crude was adsorbed onto silica gel and was flash chromatographed on silica gel on a 12 g cartridge using a ethyl acetate:methanol:$Et_3N$ gradient (70:30:1) over 8 minutes at a flow rate of 20 mL/min and UV detection at 240 nm, gave the corresponding free base).

Using this general procedure the following compound s were prepared using different starting materials:

174) 1-(2,3-dihydro-1,4-benzodioxin-6-ylsulfonyl)-5-fluoro-3-(1-methyl-1,2,3,6-tetrahydropyridin-4-yl)-1H-indole 187) 3-(1-methyl-1,2,3,6-tetrahydropyridin-4-yl)-6-(1,3-oxazol-2-yl)-1-(pyridin-3-ylsulfonyl)-1H-indole, 200) 4-methyl-7-{[3-(1-methyl-1,2,3,6-tetrahydropyridin->4-yl)-1H-pyrrolo[2,3-b]pyridin-1-yl]sulfonyl}-3,4->dihydro-2H-1,4-benzoxazine 203) 4-methyl-7-{[3-(1-methyl-1,2,3,6-tetrahydropyridin-4-yl)-1H-pyrrolo[3,2-b]pyridin-1-yl]sulfonyl}-3,4-dihydro-2H-1,4-benzoxazine 204) 3-(1-methyl-1,2,3,6-tetrahydropyridin-4-yl)-5-(1,3-oxazol-2-yl)-1-(pyridin-3-ylsulfonyl)-1H-indole 206) 3-(1-methyl-1,2,3,6-tetrahydropyridin-4-yl)-1-pyridin-3-ylsulfonyl)-5-(1,3-thiazol-2-yl)-1H-indole 217) 7-{[5-fluoro-3-(1-methylpiperidin-4-yl)-1H-indol-1-yl]sulfonyl}-4-methyl-3,4-dihydro-2H-1,4-benzoxazine, 225) 7-{[6-(3-methoxypyrrolidin-1-yl)-3-(1-methyl-1,2,3,6-tetrahydropyridin-4-yl)-1H-indol-1-yl]sulfonyl}-4-methyl-3,4-dihydro-2H-1,4-benzoxazine, 226) 6-(3-methoxypyrrolidin-1-yl)-3-(1-methyl-1,2,3,6-tetrahydropyridin-4-yl)-1-(pyridin-3-ylsulfonyl)-1H-indole 228) 7-{[4-fluoro-3-(1-methyl-1,2,3,6-tetrahydropyridin-4-yl)-1H-indol-1-yl]sulfonyl}-4-methyl-3,4-dihydro-2H-1,4-benzoxazine, 229) 7-[5-Fluoro-3-(1-methyl-1,2,3,6-tetrahydro-pyridin-4-yl)-indole-1-sulfonyl]-4-methyl-3,4-dihydro-2H-benzo[1,4]oxazine 230) 7-{[6-fluoro-3-(1-methyl-1,2,3,6-tetrahydropyridin-4-yl)-1H-indol-1-yl]sulfonyl}-4-methyl-3,4-dihydro-2H-1, 4-benzoxazine; compound with formic acid 231) 7-{[7-fluoro-3-(1-methyl-1,2,3,6-tetrahydropyridin-4-yl)-1H-indol-1-yl]sulfonyl}-4-methyl-3,4-dihydro-2H-1, 4-benzoxazine; compound with formic acid 234) 4-methyl-6-{[3-(1-methyl-1,2,3,6-tetrahydropyridin-4-yl)-1H-pyrrolo[3,2-b]pyridin-1-yl]sulfonyl}-3,4-dihydro-2H-1,4-benzoxazine 236) 7-{[3,5-bis(1-methyl-1,2,3,6-tetrahydropyridin-4-yl)-1H-indol-1-yl]sulfonyl}-4-methyl-3,4-dihydro-2H-1,4-benzoxazine, 242) 7-{[3,5-bis(1-methylpiperidin-4-yl)-1H-indol-1-yl]sulfonyl}-4-methyl-3,4-dihydro-2H-1,4-benzoxazine 245) 4-methyl-7-{[3-(1-methylpiperidin-4-yl)-1H-pyrrolo[3,2-b]pyridin-1-yl]sulfonyl}-3,4-dihydro-2H-1,4-benzoxazine; compound with formic acid 248) 4-methyl-7-{[3-(1-methyl-1,2,3,6-tetrahydropyridin-4-yl)-1H-indazol-1-yl]sulfonyl}-3,4-dihydro-2H-1,4-benzoxazine; compound with formic acid 261) 3-(1-methyl-1,2,3,6-tetrahydropyridin-4-yl)-5-(1H-pyrazol-1-yl)-1-(pyridin-3-ylsulfonyl)-1H-indole; compound with formic acid 262) 4-methyl-7-{[3-(1-methyl-1,2,3,6-tetrahydropyridin-4-yl)-5-(1H-pyrazol-1-yl)-1H-indol-1-yl]sulfonyl}-3,4-dihydro-2H-1,4-benzoxazine; compound with formic acid 263) 5-(1H-imidazol-1-yl)-3-(1-methyl-1,2,3,6-tetrahydropyridin-4-yl)-1-(pyridin-3-ylsulfonyl)-1H-indole; compound with formic acid 264) 7-{[5-(1H-imidazol-1-yl)-3-(1-methyl-1,2,3,6-tetrahydropyridin-4-yl)-1H-indol-1-yl]sulfonyl}-4-methyl-3,4-dihydro-2H-1,4-benzoxazine; compound with formic acid 279) 1-{[3-(3-methoxypyrrolidin-1-yl)phenyl]sulfonyl}-3-(1-methyl-1,2,3,6-tetrahydropyridin-4-yl)-1H-pyrazolo[4,3-b]pyridine 299) 7-{[5-methoxy-3-(1-methyl-1,2,3,6-tetrahydropyridin-4-yl)-1H-indol-1-yl]sulfonyl}-4-methyl-3,4-dihydro-2H-1,4-benzoxazine, 300) 5-methoxy-3-(1-methyl-1,2,3,6-tetrahydropyridin-4-yl)-1-(pyridin-3-ylsulfonyl)-1H-indole, 318) 4-methyl-7-[(3-piperazin-1-yl-1H-indol-1-yl)sulfonyl]-3,4-dihydro-2H-1,4-benzoxazine; compound with formic acid 322) 5-{[5-fluoro-3-(1-methyl-1,2,3,6-tetrahydropyridin-4-yl)-1H-indol-1-yl]sulfonyl} isoquinoline hydroformate, 323) 5-{[5-fluoro-3-(1-methylpiperidin-4-yl)-1H-indol-1-yl]sulfonyl} isoquinoline hydroformate 325) 8-[5-Fluoro-3-(1-methyl-1,2,3,6-tetrahydro-pyridin-4-yl)-indole-1-sulfonyl]-isoquinoline; compound with formic acid 329) 2-methyl-8-{[3-(1-methyl-1,2,3,6-tetrahydropyridin-4-yl)-1H-pyrrolo[3,2-b]pyridin-1-yl]sulfonyl}-1,2,3,4-tetrahydroisoquinoline Hb: Tert-butyl-4-{1-[(4-methyl-3,4-dihydro-2H-1,4-benzoxazin-7-yl)sulfonyl]-1H-indazol-3-yl}piperazine-1-carboxylate (50 mg, 0.0001 mol) was used in one of three ways.

1). The carboxylate was stirred in acetonitrile (2 mL, 0.04 mol) and iodotrimethylsilane (28 uL, 0.00019 mol) was added and was stirred for 10 minutes. LC-MS (1080_8 min) shows M+H=414. The reaction was diluted with water/acetonitrile (1.0 mL) and filtered through a 0.45 um filter. The filtrate was purified on a C18 Sunfire column (30×100 mm) using a gradient of (10-80%) acetonitrile:water (with 0.1% formic acid) and a flow rate of 45 mL/min. Detection was performed by z/z=413.2. Fractions of interest were pooled and lyophilized. 20 mg was recovered as a an amorphous white solid. LC-MS (2080_8 min) M+H 414.1 at 4.36 minutes. $^1$H NMR ($CD_3OD$) δ 2.82 (3H, s), 3.22 (6H, m), 3.4-3.6

(4H, m), 4.25 (2H, m), 6.56 (1H, d), 6.95 (1H, d), 7.08 (1H, m), 7.35 (1H, t), 7.58 (1H, t), 7.80 (1H, d), 8.15 (1H, d), 8.53 (1H, br s).

2). The carboxylate was treated with $CF_3CO_2H$ and concentrated to form the corresponding $CF_3CO_2H$ salt, 3) The carboxylate was treated with HCl in dioxane and concentrated to form the corresponding HCl salt.

Using the synthesis described in Ha and Hb the following compound was prepared using different starting materials:

246) 4-methyl-7-{[3-(1,2,3,6-tetrahydropyridin-4-yl)-1H-pyrrolo[3,2-b]pyridin-1-yl]sulfonyl}-3,4-dihydro-2H-1,4-benzoxazine; compound with formic acid 247) 4-methyl-7-[(3-piperidin-4-yl-1H-pyrrolo[3,2-b]pyridin-1-yl)sulfonyl]-3,4-dihydro-2H-1,4-benzoxazine; compound with formic acid 285) 4-Methyl-7-(3-piperidin-4-yl-pyrrolo[3,2-b]pyridine-1-sulfonyl)-3,4-dihydro-2H-benzo[1,4]oxazine 296) 4-methyl-6-{[3-(1,2,3,6-tetrahydropyridin-4-yl)-1H-pyrrolo[3,2-b]pyridin-1-yl]sulfonyl}-3,4-dihydro-2H-1,4-benzoxazine 313) 3-piperazin-1-yl-1-(pyridin-3-ylsulfonyl)-1H-indazole 318) 4-methyl-7-[(3-piperazin-1-yl-1H-indol-1-yl)sulfonyl]-3,4-dihydro-2H-1,4-benzoxazine; compound with formic acid 319) 4-methyl-7-[(3-piperazin-1-yl-1H-indazol-1-yl)sulfonyl]-3,4-dihydro-2H-1,4-benzoxazine 324) 5-{[5-fluoro-3-(1,2,3,6-tetrahydropyridin-4-yl)-1H-indol-1-yl]sulfonyl}isoquinoline hydroformate General Procedure I

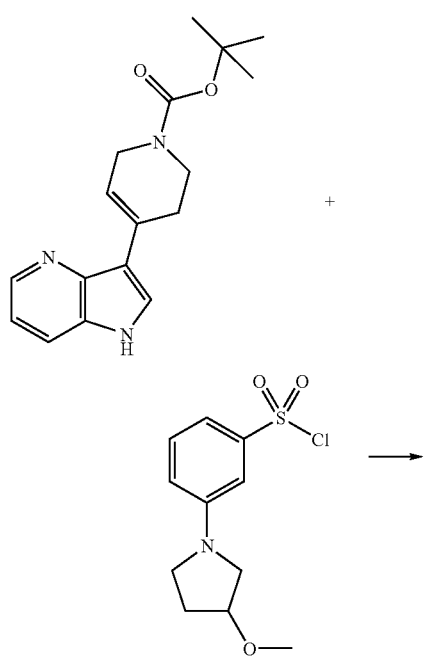

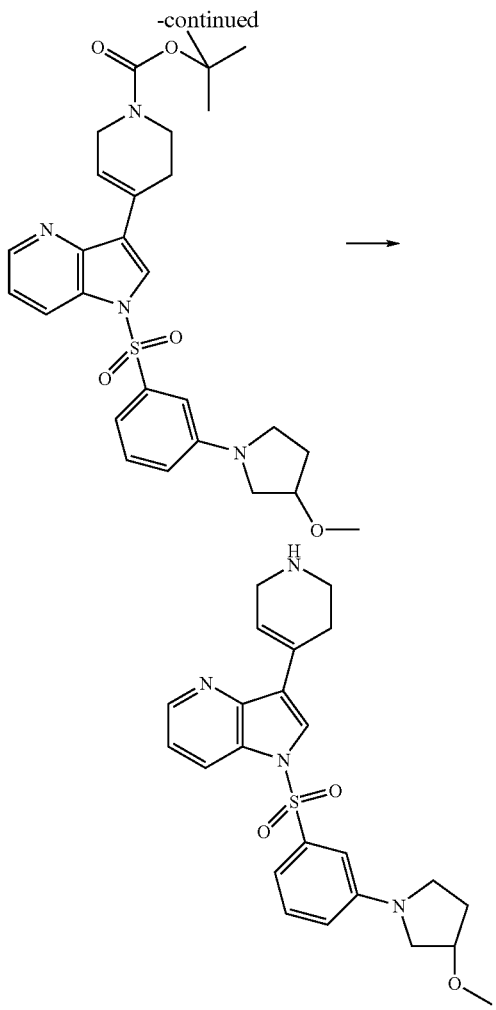

Ia: Synthesis of tert-butyl 4-(1-{[3-(3-methoxypyrrolidin-1-yl)phenyl]sulfonyl}-1H-pyrrolo[3,2-b]pyridin-3-yl)-3,6-dihydropyridine-1(2H)-carboxylate Into a 1-Neck round-bottom flask tert-butyl 4-(1H-pyrrolo[3,2-b]pyridin-3-yl)-3,6-dihydropyridine-1(2H)-carboxylate (100 mg, 0.000334 mol) was stirred in tetrahydrofuran (3 mL, 0.04 mol) and N,N-dimethylformamide (3 mL, 0.04 mol) at 5° C. and 1.0 M of sodium bis(trimethylsilyl)amide in tetrahydrofuran (0.50 mL) was added. The reaction was stirred for 20 minutes at 5° C. 3-(3-Methoxypyrrolidin-1-yl)benzenesulfonyl chloride (138 mg, 0.000501 mol) in tetrahydrofuran (3 mL, 0.04 mol) was added by syringe at 5° C. and the reaction was stirred for 30 minutes. The reaction was extracted with ethyl acetate and was washed with water and brine. The solvent was rotovaped.

The crude was adsorbed onto silica gel and was flash chromatographed on silica gel on a 12 g cartridge using a hexane:ethyl acetate gradient (10-50%) over 10 minutes at a flow rate of 20 mL/min and UV detection at 254 nm. 137 mg recovered as an oil. LC-MS (80% acetonitrile/water with 0.1% formic acid) M+H=539 at 8.00 minutes If the Boc group was a methyl group, the residue was purified on a C18 Sunfire column (30×100 mm) using a gradient of (5-80%) acetonitrile:water (with 0.1% formic acid) and a flow rate of 45 mL/min, gave the corresponding formic salt, or the crude was adsorbed onto silica gel and was flash chromatographed on silica gel on a 12 g cartridge using a ethyl acetate: methanol: Et$_3$N gradient (70:30:1) over 8 minutes at a flow rate of 20 mL/min and UV detection at 240 nm, gave the corresponding free base.

Using this general procedure the following compound was prepared using different starting materials:

173) 1-(2,3-dihydro-1,4-benzodioxin-6-ylsulfonyl)-3-(1-methyl-1,2,3,6-tetrahydropyridin-4-yl)-1H-indole
175) 1-(2,3-dihydro-1,4-benzodioxin-6-ylsulfonyl)-3-(1-methyl-1,2,3,6-tetrahydropyridin-4-yl)-5-(trifluoromethyl)-1H-indole
176) 4-{[3-(1-methyl-1,2,3,6-tetrahydropyridin-4-yl)-1H-indol-1-yl]sulfonyl}aniline
178) 1-(2,2-dimethylpropanoyl)-5-{[3-(1-methyl-1,2,3,6-tetrahydropyridin-4-yl)-1H-pyrrolo[2,3-b]pyridin-1-yl]sulfonyl}-1H-indazole
179) 6-{[3-(1-methyl-1,2,3,6-tetrahydropyridin-4-yl)-1H-pyrrolo[2,3-b]pyridin-1-yl]sulfonyl}-3,4-dihydroquinolin-2(1H)-one
180) 1-methyl-6-{[3-(1-methyl-1,2,3,6-tetrahydropyridin-4-yl)-1H-pyrrolo[2,3-b]pyridin-1-yl]sulfonyl}-3,4-dihydroquinolin-2(1H)-one
181) 1-methyl-6-{[3-(1-methyl-1,2,3,6-tetrahydropyridin-4-yl)-5-(trifluoromethyl)-1H-indol-1-yl]sulfonyl}-3,4-dihydroquinolin-2(1H)-one
182) 6-{[5-fluoro-3-(1-methyl-1,2,3,6-tetrahydropyridin-4-yl)-1H-indol-1-yl]sulfonyl}-1-methyl-3,4-dihydroquinolin-2(1H)-one
183) 1-methyl-6-{[3-(1-methyl-1,2,3,6-tetrahydropyridin-4-yl)-1H-indol-1-yl]sulfonyl}-3,4-dihydroquinolin-2(1H)-one
184) 1-(2,3-dihydro-1,4-benzodioxin-6-ylsulfonyl)-3-(1-methylpiperidin-4-yl)-1H-pyrrolo[2,3-b]pyridine
186) 5-fluoro-1-[(1-methyl-1H-indol-5-yl)sulfonyl]-3-(1-methyl-1,2,3,6-tetrahydropyridin-4-yl)-1H-indole
189) 1-[(1-ethyl-1H-pyrazol-4-yl)sulfonyl]-3-(1-methyl-1,2,3,6-tetrahydropyridin-4-yl)-6-(1,3-oxazol-2-yl)-1H-indole
190) 1-[(1-ethyl-1H-pyrazol-4-yl)sulfonyl]-3-(1-methyl-1,2,3,6-tetrahydropyridin-4-yl)-5-(1,3-oxazol-2-yl)-1H-indole
191) 1-(2,3-dihydro-1,4-benzodioxin-6-ylsulfonyl)-3-(1-methyl-1,2,3,6-tetrahydropyridin-4-yl)-5-(1,3-oxazol-2-yl)-1H-indole
192) 5-(3,6-dihydro-2H-pyran-4-yl)-3-(1-methyl-1,2,3,6-tetrahydropyridin-4-yl)-1-(phenylsulfonyl)-1H-indole
193) 3-(1-methyl-1,2,3,6-tetrahydropyridin-4-yl)-1-(phenylsulfonyl)-6-(1,3-thiazol-2-yl)-1H-indole
194) 5-fluoro-1-{[6-(3-methoxypyrrolidin-1-yl)pyridin-3-yl]sulfonyl}-3-(1-methyl-1,2,3,6-tetrahydropyridin-4-yl)-1H-indole
195 1-{[6-(3-methoxypyrrolidin-1-yl)pyridin-3-yl]sulfonyl}-3-(1-methyl-1,2,3,6-tetrahydropyridin-4-yl)-1H-pyrrolo[2,3-b]pyridine
196) 7-{[5-fluoro-3-(1-methyl-1,2,3,6-tetrahydropyridin-4-yl)-1H-indol-1-yl]sulfonyl}-2H-1,4-benzoxazin-3(4H)-one
197) 7-{[3-(1-methyl-1,2,3,6-tetrahydropyridin-4-yl)-1H-pyrrolo[2,3-b]pyridin-1-yl]sulfonyl}-2H-1,4-benzoxazin-3(4H)-one
198) 1-[(1-acetyl-2,3-dihydro-1H-indol-6-yl)sulfonyl]-5-fluoro-3-(1-methyl-1,2,3,6-tetrahydropyridin-4-yl)-1H-indole
199) 1-[(1-acetyl-2,3-dihydro-1H-indol-6-yl)sulfonyl]-3-(1-methyl-1,2,3,6-tetrahydropyridin-4-yl)-1H-pyrrolo[2,3-b]pyridine
201) 1-(2,3-dihydro-1,4-benzodioxin-6-ylsulfonyl)-5-fluoro-3-(1-methylpiperidin-4-yl)-1H-indole hydroformate
202) 1-(2,3-dihydro-1,4-benzodioxin-6-ylsulfonyl)-3-(1-methyl-1,2,3,6-tetrahydropyridin-4-yl)-1H-pyrrolo[3,2-b]pyridine
205) 1-(2,3-dihydro-1,4-benzodioxin-6-ylsulfonyl)-3-(1-methyl-1,2,3,6-tetrahydropyridin-4-yl)-5-(1,3-thiazol-2-yl)-1H-indole
207) 1-[(1-ethyl-1H-pyrazol-4-yl)sulfonyl]-3-(1-methyl-1,2,3,6-tetrahydropyridin-4-yl)-5-(1,3-thiazol-2-yl)-1H-indole
208) 1-[(1-methyl-2,3-dihydro-1H-indol-5-yl)sulfonyl]-3-(1-methyl-1,2,3,6-tetrahydropyridin-4-yl)-1H-pyrrolo[3,2-b]pyridine
209) 1-[(1-acetyl-2,3-dihydro-1H-indol-5-yl)sulfonyl]-3-(1-methyl-1,2,3,6-tetrahydropyridin-4-yl)-1H-pyrrolo[3,2-b]pyridine
210) 1-(4-{[3-(1-methyl-1,2,3,6-tetrahydropyridin-4-yl)-1H-pyrrolo[2,3-b]pyridin-1-yl]sulfonyl}phenyl)pyrrolidin-2-one
211) 3-methyl-6-{[3-(1-methyl-1,2,3,6-tetrahydropyridin-4-yl)-1H-pyrrolo[2,3-b]pyridin-1-yl]sulfonyl}-1,3-benzoxazol-2(3H)-one
212) 1-[(1-methyl-2,3-dihydro-1H-indol-5-yl)sulfonyl]-3-(1-methyl-1,2,3,6-tetrahydropyridin-4-yl)-1H-pyrrolo[2,3-b]pyridine
213) 1-[(1-acetyl-2,3-dihydro-1H-indol-5-yl)sulfonyl]-3-(1-methyl-1,2,3,6-tetrahydropyridin-4-yl)-1H-pyrrolo[2,3-b]pyridine
214) 1-(4-{[3-(1-methyl-1,2,3,6-tetrahydropyridin-4-yl)-1H-pyrrolo[3,2-b]pyridin-1-yl]-sulfonyl}phenyl)pyrrolidin-2-one
215) 3-methyl-6-{[3-(1-methyl-1,2,3,6-tetrahydropyridin-4-yl)-1H-pyrrolo[3,2-b]pyridin-1-yl]sulfonyl}-1,3-benzoxazol-2(3H)-one
219) 6-{[3-(1-methyl-1,2,3,6-tetrahydropyridin-4-yl)-1H-pyrrolo[2,3-b]pyridin-1-yl]sulfonyl}-2H-1,4-benzoxazin-3(4H)-one
220) 5-{[3-(1-methyl-1,2,3,6-tetrahydropyridin-4-yl)-1H-pyrrolo[3,2-b]pyridin-1-yl]sulfonyl}-1,3-dihydro-2H-benzimidazol-2-one
221) 7-{[3-(1-methyl-1,2,3,6-tetrahydropyridin-4-yl)-1H-pyrrolo[3,2-b]pyridin-1-yl]sulfonyl}-2H-1,4-benzoxazin-3(4H)-one
222) 6-{[3-(1-methyl-1,2,3,6-tetrahydropyridin-4-yl)-1H-pyrrolo[3,2-b]pyridin-1-yl]sulfonyl}-2H-1,4-benzoxazin-3(4H)-one
227) 6-(3-methoxypyrrolidin-1-yl)-1-[((1-methyl-1H-indol-5-yl)sulfonyl]-3-(1-methyl-1,2,3,6-tetrahydropyridin-4-yl)-1H-indole
233) 1-(3,4-dihydro-2H-1,5-benzodioxepin-7-ylsulfonyl)-3-(1-methyl-1,2,3,6-tetrahydropyridin-4-yl)-1H-pyrrolo[3,2-b]pyridine
235) 1-[(1-acetyl-2,3-dihydro-1H-indol-5-yl)sulfonyl]-3-(1-methylpiperidin-4-yl)-1H-pyrrolo[2,3-b]pyridine
237) 7-{[3-(1-methyl-1,2,3,6-tetrahydropyridin-4-yl)-1H-indazol-1-yl]sulfonyl}-2H-1,4-benzoxazin-3(4H)-one
238) 1-[(1-methyl-1H-indol-5-yl)sulfonyl]-3-(1-methyl-1,2,3,6-tetrahydropyridin-4-yl)-1H-indazole
239) 1-[(1-methyl-1H-indol-5-yl)sulfonyl]-3,5-bis(1-methyl-1,2,3,6-tetrahydropyridin-4-yl)-1H-indole 243) 1-[(1-acetyl-2,3-dihydro-1H-indol-5-yl)sulfonyl]-3-(1-methyl-1,2,3,6-tetrahydropyridin-4-yl)-1H-pyrrolo[2,3-b]pyridine
249) 1-{[3-(3-methoxypyrrolidin-1-yl)phenyl]sulfonyl}-3-(1-methyl-1,2,3,6-tetrahydropyridin-4-yl)-1H-pyrrolo[2,3-b]pyridine
250) 1-(3-{[3-(1-methyl-1,2,3,6-tetrahydropyridin-4-yl)-1H-pyrrolo[2,3-b]pyridin-1-yl]sulfonyl}phenyl)pyrrolidin-2-one
251) 1-[(5-bromo-2,3-dihydro-1-benzofuran-7-yl)sulfonyl]-3-(1-methyl-1,2,3,6-tetrahydropyridin-4-yl)-1H-pyrrolo[2,3-b]pyridine
252) 1-{[3-(3-methoxypyrrolidin-1-yl)phenyl]sulfonyl}-3-(1-methyl-1,2,3,6-tetrahydropyridin-4-yl)-1H-pyrrolo[3,2-b]pyridine
253) 1-(3-{[3-(1-methyl-1,2,3,6-tetrahydropyridin-4-yl)-1H-pyrrolo[3,2-b]pyridin-1-yl]sulfonyl}phenyl)pyrrolidin-2-one
254) 1-[(5-bromo-2,3-dihydro-1-benzofuran-7-yl)sulfonyl]-3-(1-methyl-1,2,3,6-tetrahydropyridin-4-yl)-1H-pyrrolo[3,2-b]pyridine
255) 6-ethyl-1-[(1-methyl-1H-indol-5-yl)sulfonyl]-3-(1-methyl-1,2,3,6-tetrahydropyridin-4-yl)-1H-pyrrolo[2,3-b]pyridine
256) 6-ethyl-1-[(1-methyl-1H-indol-6-yl)sulfonyl]-3-(1-methyl-1,2,3,6-tetrahydropyridin-4-yl)-1H-pyrrolo[2,3-b]pyridine
257) 6-ethyl-3-(1-methyl-1,2,3,6-tetrahydropyridin-4-yl)-1-[(3-pyrrolidin-1-ylphenyl)sulfonyl]-1H-pyrrolo[2,3-b]pyridine
258) 6-ethyl-1-{[3-(3-methoxypyrrolidin-1-yl)phenyl]sulfonyl}-3-(1-methyl-1,2,3,6-tetrahydropyridin-4-yl)-1H-pyrrolo[2,3-b]pyridine
259) 1-(3-{[6-ethyl-3-(1-methyl-1,2,3,6-tetrahydropyridin-4-yl)-1H-pyrrolo[2,3-b]pyridin-1-yl]sulfonyl}phenyl)pyrrolidin-2-one
260) 1-[(5-bromo-2,3-dihydro-1-benzofuran-7-yl)sulfonyl]-6-ethyl-3-(1-methyl-1,2,3,6-tetrahydropyridin-4-yl)-1H-pyrrolo[2,3-b]pyridine
265) 1-[(1-acetyl-2,3-dihydro-1H-indol-5-yl)sulfonyl]-3-(1-methyl-1,2,3,6-tetrahydropyridin-4-yl)-1H-indazole
266) 4-acetyl-6-{[3-(1-methyl-1,2,3,6-tetrahydropyridin-4-yl)-1H-indazol-1-yl]sulfonyl}-3,4-dihydro-2H-1,4-benzoxazine
267) 5-{[3-(1-methyl-1,2,3,6-tetrahydropyridin-4-yl)-1H-indazol-1-yl]sulfonyl}-1,2-benzisoxazole
268) 1-(1-benzothien-5-ylsulfonyl)-3-(1-methyl-1,2,3,6-tetrahydropyridin-4-yl)-1H-indazole
269) 1-(1-benzofuran-5-ylsulfonyl)-3-(1-methyl-1,2,3,6-tetrahydropyridin-4-yl)-1H-indazole
270) 1-[(1-acetyl-2,3-dihydro-1H-indol-5-yl)sulfonyl]-6-ethyl-3-(1-methyl-1,2,3,6-tetrahydropyridin-4-yl)-1H-pyrrolo[2,3-b]pyridine
271) 6-{[3-(1-methyl-1,2,3,6-tetrahydropyridin-4-yl)-1H-indazol-1-yl]sulfonyl}-2H-1,4-benzoxazin-3(4H)-one
272) 1-(1-benzofuran-5-ylsulfonyl)-3-(1-methyl-1,2,3,6-tetrahydropyridin-4-yl)-1H-pyrazolo[4,3-b]pyridine
273) 1-(1-benzothien-5-ylsulfonyl)-3-(1-methyl-1,2,3,6-tetrahydropyridin-4-yl)-1H-pyrazolo[4,3-b]pyridine
274) 1-(1-benzofuran-5-ylsulfonyl)-3-(1-methyl-1,2,3,6-tetrahydropyridin-4-yl)-1H-pyrazolo[3,4-b]pyridine
275) 1-(1-benzothien-5-ylsulfonyl)-3-(1-methyl-1,2,3,6-tetrahydropyridin-4-yl)-1H-pyrazolo[3,4-b]pyridine
276) 1-[(1-acetyl-2,3-dihydro-1H-indol-5-yl)sulfonyl]-5-fluoro-3-(1-methyl-1,2,3,6-tetrahydropyridin-4-yl)-1H-indazole; compound with formic acid
277) 5-fluoro-1-[(1-methyl-1H-indol-5-yl)sulfonyl]-3-(1-methyl-1,2,3,6-tetrahydropyridin-4-yl)-1H-indazole; compound with formic acid
278) 5-fluoro-1-[(1-methyl-1H-indol-6-yl)sulfonyl]-3-(1-methyl-1,2,3,6-tetrahydropyridin-4-yl)-1H-indazole; compound with formic acid
279) 1-{[3-(3-methoxypyrrolidin-1-yl)phenyl]sulfonyl}-3-(1-methyl-1,2,3,6-tetrahydropyridin-4-yl)-1H-pyrazolo[4,3-b]pyridine
280) 1-{[3-(3-methoxypyrrolidin-1-yl)phenyl]sulfonyl}-3-(1-methyl-1,2,3,6-tetrahydropyridin-4-yl)-1H-pyrazolo[3,4-b]pyridine
281) 7-{[3-(1-methyl-1,2,3,6-tetrahydropyridin-4-yl)-1H-pyrazolo[4,3-b]pyridin-1-yl]sulfonyl}-2H-1,4-benzoxazin-3(4H)-one
282) 7-{[3-(1-methyl-1,2,3,6-tetrahydropyridin-4-yl)-1H-pyrazolo[3,4-b]pyridin-1-yl]sulfonyl}-2H-1,4-benzoxazin-3(4H)-one
283) 1-[(1-acetyl-2,3-dihydro-1H-indol-5-yl)sulfonyl]-3-(1-methyl-1,2,3,6-tetrahydropyridin-4-yl)-1H-pyrazolo[3,4-b]pyridine
284) 1-[(1-acetyl-2,3-dihydro-1H-indol-5-yl)sulfonyl]-3-(1-methyl-1,2,3,6-tetrahydropyridin-4-yl)-1H-pyrazolo[4,3-b]pyridin
286) 1-(3-{[3-(1-methyl-1,2,3,6-tetrahydropyridin-4-yl)-1H-pyrrolo[3,2-b]pyridin-1-yl]sulfonyl}phenyl)pyrrolidin-3-ol
287) 1-[(1-acetyl-2,3-dihydro-1H-indol-6-yl)sulfonyl]-3-(1-methyl-1,2,3,6-tetrahydropyridin-4-yl)-1H-pyrrolo[2,3-b]pyridine
293) 5-methoxy-1-{[3-(3-methoxypyrrolidin-1-yl)phenyl]sulfonyl}-3-(1-methyl-1,2,3,6-tetrahydropyridin-4-yl)-1H-indole
298) 7-{[5-methoxy-3-(1-methyl-1,2,3,6-tetrahydropyridin-4-yl)-1H-indol-1-yl]sulfonyl}-2H-1,4-benzoxazin-3(4H)-one
301) 1-{[3-(3-methoxypyrrolidin-1-yl)phenyl]sulfonyl}-3-(4-methylpiperazin-1-yl)-1H-indazole
304) 7-{[3-(4-methylpiperazin-1-yl)-1H-indazol-1-yl]sulfonyl}-2H-1,4-benzoxazin-3(4H)-one
305) 7-{[3-(4-methylpiperazin-1-yl)-1H-indol-1-yl]sulfonyl}-2H-1,4-benzoxazin-3(4H)-one
306) 7-[(3-piperazin-1-yl-1H-indol-1-yl)sulfonyl]-2H-1,4-benzoxazin-3(4H)-one
3107) 1-{[3-(3-methoxypyrrolidin-1-yl)phenyl]sulfonyl}-3-(4-methylpiperazin-1-yl)-1H-indole
311) 1-[(1-acetyl-2,3-dihydro-1H-indol-5-yl)sulfonyl]-3-(4-methylpiperazin-1-yl)-1H-indazole
314) 1-[(1-acetyl-2,3-dihydro-1H-indol-5-yl)sulfonyl]-3-(4-methylpiperazin-1-yl)-1H-indole
315) 4-methyl-7-{[3-(4-methylpiperazin-1-yl)-1H-indazol-1-yl]sulfonyl}-3,4-dihydro-2H-1,4-benzoxazine
326) 1-(1,2-benzisoxazol-5-ylsulfonyl)-3-(1-methyl-1,2,3,6-tetrahydropyridin-4-yl)-1H-pyrazolo[4,3-b]pyridine
327) 1-(1,2-benzisoxazol-5-ylsulfonyl)-3-(1-methyl-1,2,3,6-tetrahydropyridin-4-yl)-1H-pyrazolo[3,4-b]pyridine
328) 3-(1-methyl-1,2,3,6-tetrahydropyridin-4-yl)-1-[(6-phenoxypyridin-3-yl)sulfonyl]-1H-pyrrolo[3,2-b]pyridine
330) 1-[(1-acetyl-2,3-dihydro-1H-indol-5-yl)sulfonyl]-5-methoxy-3-(1-methyl-1,2,3,6-tetrahydropyridin-4-yl)-1H-indole Ib: Synthesis of 1-{[3-(3-methoxypyrrolidin-1-yl)phenyl]sulfonyl}-3-(1,2,3,6-tetrahydropyridin-4-yl)-1H-pyrrolo[3,2-b]pyridine Tert-butyl 4-(1-{[3-(3-methoxypyrrolidin-1-yl)phenyl]sulfonyl}-1H-pyrrolo[3,2-b]pyridin-3-yl)-3,6-dihydropyridine-1(2H)-carboxylate (0.137 g, 0.000254 mol) was put into a 1-neck round-bottom flask in one of the two reactions.

1.) The carboxylate was combined with acetonitrile (4 mL, 0.08 mol) and stirred and iodotrimethylsilane (72 μL, 0.00051 mol) was added and was stirred for 20 minutes. The solvent was rotovaped. The reaction was diluted with water/acetonitrile (3.0 mL) and filtered through a 0.45 um filter. The filtrate was purified on a C18 Sunfire column (30×100 mm) using a gradient of (10-80%) acetonitrile-water (with 0.1% formic acid) and a flow rate of 45 mL/min. Detection was performed by m/z=439. Fractions of interest were pooled and concentrated on a freeze drier. 48.5 mg recovered as a white amorphous solid. LC-MS (10-80% acetonitrile/water with 0.1% formic acid over 8 min) M+H=439.0 at 4.86 minutes $^1$H NMR (CD$_3$OD) δ 2.12 (m, 2H), 2.81 (m, 2H), 3.4-3.5 (m, 6H), 3.60 (m, 3H), 3.82 (m, 2H), 4.14 (m, 1H), 6.22 (m, 1H), 6.99 (s, 1H), 7.15 (m, 1H), 7.42 (m, 3H), 8.03 (s, 1H), 8.41 (m, 1H), 8.62 (m, 2H), 2) The carboxylate was treated with CF$_3$CO$_2$H and concentrated to form the corresponding CF$_3$CO$_2$H salt, 3) or was treated with HCl in dioxane and concentrated to form the corresponding HCl salt.

Using the synthesis described in Ia and Ib, the following compound was prepared using different starting materials:

177) 4-{[5-fluoro-3-(1-methyl-1,2,3,6-tetrahydropyridin-4-yl)-1H-indol-1-yl]sulfonyl}aniline,
185) 1-(2,3-dihydro-1,4-benzodioxin-6-ylsulfonyl)-3-(1,2,3,6-tetrahydropyridin-4-yl)-1H-pyrrolo[2,3-b]pyridine
188) 1-(2,3-dihydro-1,4-benzodioxin-6-ylsulfonyl)-3-(1-methyl-1,2,3,6-tetrahydropyridin-4-yl)-6-(1,3-oxazol-2-yl)-1H-indole
218) 1-(2,3-dihydro-1,4-benzodioxin-6-ylsulfonyl)-5-fluoro-3-(1,2,3,6-tetrahydropyridin-4-yl)-1H-indole hydroformate
223) 6-{[5-fluoro-3-(1-methyl-1,2,3,6-tetrahydropyridin-4-yl)-1H-indol-1-yl]sulfonyl}-2H-1,4-benzoxazin-3(4H)-one; compound with formic acid
224) 6-{[5-fluoro-3-(1-methyl-1,2,3,6-tetrahydropyridin-4-yl)-1H-indol-1-yl]sulfonyl}-3-methyl-1,3-benzoxazol-2(3H)-one; compound with formic acid
232) 1-[(1-acetyl-2,3-dihydro-1H-indol-5-yl)sulfonyl]-3-(1,2,3,6-tetrahydropyridin-4-yl)-1H-pyrrolo[2,3-b]pyridine
240) 1-(2,3-dihydro-1,4-benzodioxin-6-ylsulfonyl)-3-piperidin-4-yl-1H-pyrrolo[2,3-b]pyridine; compound with formic acid
241) 1-(2,3-dihydro-1,4-benzodioxin-6-ylsulfonyl)-5-fluoro-3-piperidin-4-yl-1H-indole hydroformate
244) 1-[(1-acetyl-2,3-dihydro-1H-indol-5-yl)sulfonyl]-3-piperidin-4-yl-1H-pyrrolo[2,3-b]pyridine
288) 1-[(6-morpholin-4-ylpyridin-3-yl)sulfonyl]-3-(1,2,3,6-tetrahydropyridin-4-yl)-1H-pyrrolo[3,2-b]pyridine; compound with formic acid
289) 1-{[6-(3-methoxypyrrolidin-1-yl)pyridin-3-yl]sulfonyl}-3-(1,2,3,6-tetrahydropyridin-4-yl)-1H-pyrrolo[3,2-b]pyridine; compound with formic acid
290) 1-[(5-methoxypyridin-3-yl)sulfonyl]-3-(1,2,3,6-tetrahydropyridin-4-yl)-1H-pyrrolo[3,2-b]pyridine; compound with formic acid
291) 1-{[5-(3-methoxypyrrolidin-1-yl)pyridin-3-yl]sulfonyl}-3-(1,2,3,6-tetrahydropyridin-4-yl)-1H-pyrrolo[3,2-b]pyridine; compound with formic acid
292) 1-[(1-acetyl-2,3-dihydro-1H-indol-5-yl)sulfonyl]-3-(1,2,3,6-tetrahydropyridin-4-yl)-1H-pyrrolo[3,2-b]pyridine
294) 7-{[3-(1,2,3,6-tetrahydropyridin-4-yl)-1H-pyrrolo[3,2-b]pyridin-1-yl]sulfonyl}-2H-1,4-benzoxazin-3(4H)-one
295) 7-{[3-(1,2,3,6-tetrahydropyridin-4-yl)-1H-pyrrolo[3,2-b]pyridin-1-yl]sulfonyl}-3,4-dihydroquinolin-2(1H)-one
297) 6-{[3-(1,2,3,6-tetrahydropyridin-4-yl)-1H-pyrrolo[3,2-b]pyridin-1-yl]sulfonyl}-2H-1,4-benzoxazin-3(4H)-one
302) 1-{[3-(3-methoxypyrrolidin-1-yl)phenyl]sulfonyl}-3-piperazin-1-yl-1H-indazole
303) 7-[(3-piperazin-1-yl-1H-indazol-1-yl)sulfonyl]-2H-1,4-benzoxazin-3(4H)-one
308) 1-{[3-(3-methoxypyrrolidin-1-yl)phenyl]sulfonyl}-3-piperazin-1-yl-1H-indole
309) 1-[(1-acetyl-2,3-dihydro-1H-indol-5-yl)sulfonyl]-3-piperazin-1-yl-1H-pyrrolo[2,3-b]pyridine; compound with formic acid
310) 1-{[3-(3-methoxypyrrolidin-1-yl)phenyl]sulfonyl}-3-piperazin-1-yl-1H-pyrrolo[2,3-b]pyridine; compound with formic acid
312) 1-[(1-acetyl-2,3-dihydro-1H-indol-5-yl)sulfonyl]-3-piperazin-1-yl-1H-indazole
316) 1-[(1-acetyl-2,3-dihydro-1H-indol-5-yl)sulfonyl]-3-piperazin-1-yl-1H-indole
317) 7-[(3-piperazin-1-yl-1H-indol-1-yl)sulfonyl]-2H-1,4-benzoxazin-3(4H)-one
320) 7-[(3-piperazin-1-yl-1H-indol-1-yl)sulfonyl]-2H-1,4-benzoxazin-3(4H)-one
321) 7-[(3-piperazin-1-yl-1H-indazol-1-yl)sulfonyl]-2H-1,4-benzoxazin-3(4H)-one

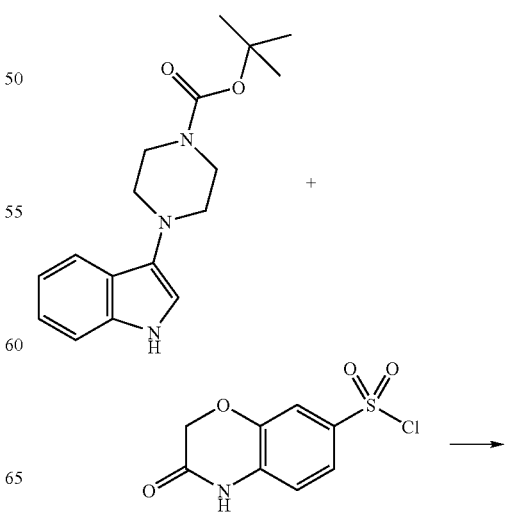

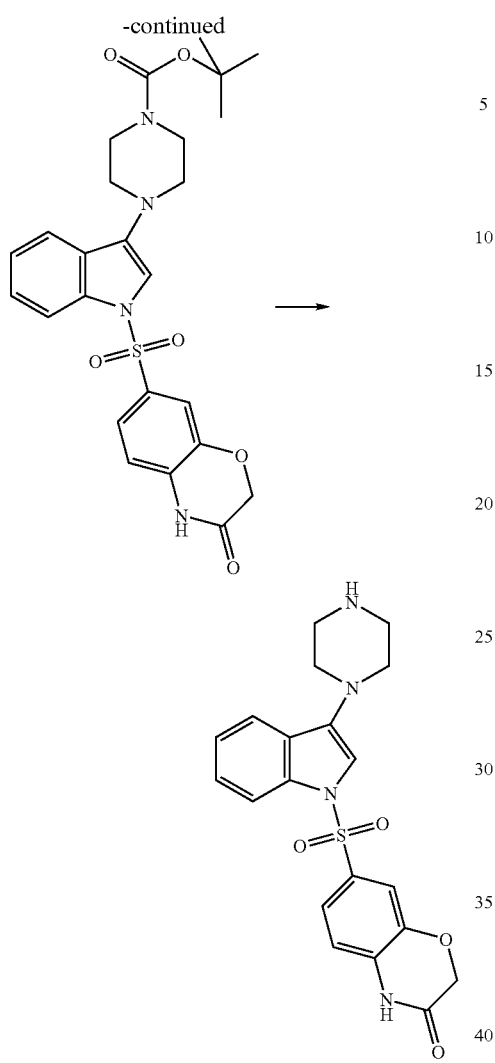

Ia and Ib (306) Synthesis of 7-[(3-piperazin-1-yl-1H-indol-1-ylsulfonyl]-2H-1,4-benzoxazin-3(4H)-one In a vial was placed a solution of tert-butyl 4-(1H-indol-3-yl)piperazine-1-carboxylate (70 mg, 0.0002 mol) N,N-Dimethylformamide (1.5 mL, 0.019 mol). Sodium bis(trimethylsilyl)amide (0.08 mL, 0.0005 mol) was then added. The mixture was allowed to stir at 5° C. for 30 min. 3-oxo-3,4-dihydro-2H-1,4-benzoxazine-7-sulfonyl chloride (76.5 mg, 0.000309 mol) in tetrahydrofuran (1 mL) was then added, and the resulting mixture was stirred at room temperature for 60 minutes, and was concentrated followed by FCC, the obtained fraction was treated with 4.0 M HCl in dioxane. The obtained residue was purified by HPLC. The reaction mixture was diluted with water/acetonitrile (1.0 mL) and filtered through a 0.45 um filter. The filtrate was purified on a C18 Sunfire column (30×100 mm) using a gradient of (5-80%) acetonitrile:water (with 0.1% formic acid) and a flow rate of 45 mL/min. Detection was performed by m/z=413. Fractions of interest were pooled and concentrated on a Genevac. A tan solid was recovered. LC-MS (2080_8 min) M+H=413 at 4.13 minutes. $^1$H NMR (CD$_3$OD) δ 3.3 (4H, m), 3.7 (4H, m), 4.7 (2H, s), 7.0 (1H, t), 7.2 (1H, d), 7.4 (1H, t), 7.5 (1H, d), 7.6 (1H, t), 7.9 (1H, d), 8.1 (1H, d), 8.5 (1H, br s).

Synthesis of tert-butyl-4-(1H-indol-3-yl)-piperazine-1-carboxylate

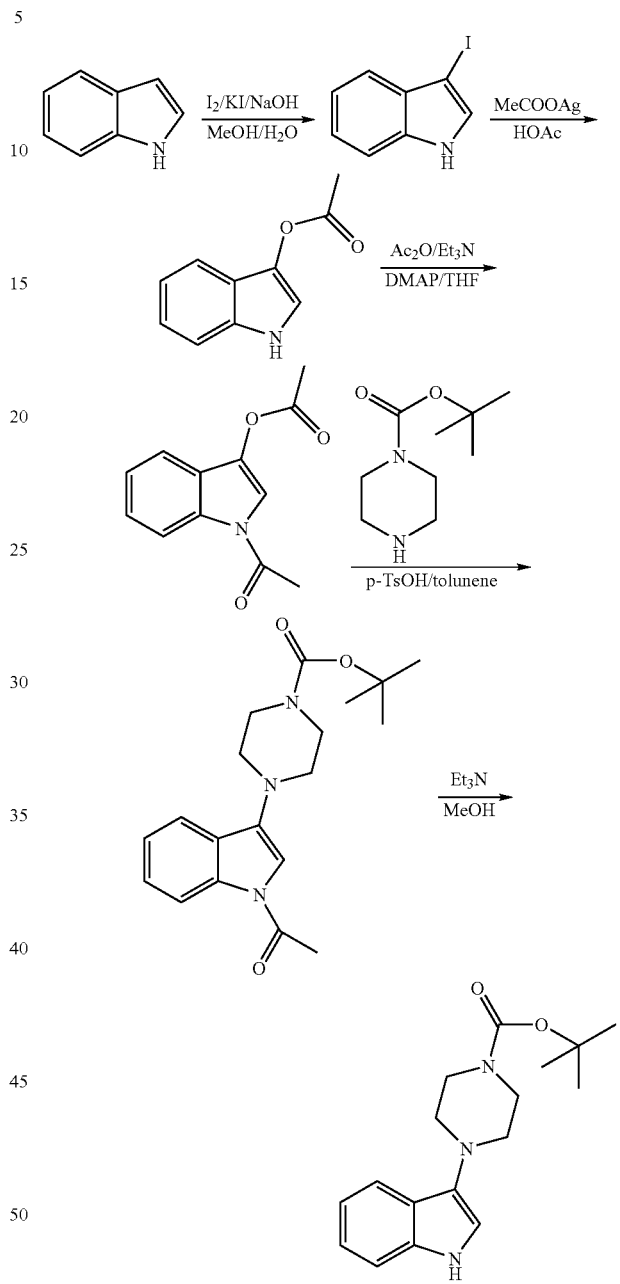

1. Synthesis of 3-iodo-1H-indole

Into a 500 mL 3-necked round bottom flask, was placed a solution of 1H-indole (10 g, 85.40 mmol) in MeOH/H$_2$O (150/30 mL). To this was added potassium iodide (15.6 g, 93.98 mmol). To the mixture was added sodium hydroxide (3.76 g, 94.00 mmol). To the above was added I2 (23.88 g, 94.02 mmol) in several batches. The resulting solution was allowed to react, with stirring, for 3 hours while the temperature was maintained at room temperature. The reaction progress was monitored by TLC (ethyl acetate/petroleum ether=1:10). The reaction mixture was then quenched by the adding 100 mL of H₂O. A filtration was performed. The filter cake was washed 3 times with 200 mL of water. This resulted in 18 g (84%) of 3-iodo-1H-indole as a light yellow solid.

2. Synthesis of 1H-indol-3-yl acetate

Into a 500 mL round bottom flask was placed a solution of 3-iodo-1H-indole (23 g, 94.65 mmol) in acetic acid (300 mL). To the mixture was added CH3COOAg (31.6 g, 189.22 mmol). The resulting solution was allowed to react, with stirring, for 1 hour while the temperature was maintained at 90° C. in a bath of oil. The reaction progress was monitored by TLC (ethyl acetate/petroleum ether=1:1). A filtration was performed. The filtrate was concentrated by evaporation under vacuum using a rotary evaporator. The resulting solution was dissolved with 100 mL of ethyl acetate. The resulting mixture was washed 2 times with 100 mL of NaCl(aq.). The final product was purified by recrystallization from MeOH/H₂O in the ratio 2:3. This resulted in 8.5 g (41%) of 1H-indol-3-yl acetate as a dark purple solid.

3. Synthesis of 1-acetyl-1H-indol-3-yl acetate

Into a 500 mL round bottom flask was placed a solution of 1H-indol-3-yl acetate (8 g, 45.69 mmol) in tetrahydrofuran (150 mL). To this was added acetic anhydride (46.6 g, 456.86 mmol). Addition of triethylamine (9.25 g, 91.49 mmol) was next. To the mixture was added DMAP (1.11 g, 9.10 mmol). The resulting solution was allowed to react, with stirring, for 3 hours while the temperature was maintained at reflux in a bath of oil. The reaction progress was monitored by TLC (ethyl acetate/petroleum ether=1:2). The mixture was concentrated by evaporation under vacuum using a rotary evaporator. The resulting solution was diluted with 300 mL of ethyl acetate The resulting mixture was washed 2 times with 150 mL of NaCl(aq.). The mixture was dried over Na₂SO₄. The residue was purified by eluting through a column with a 20:1 petroleum ether/ethyl acetate solvent system. This resulted in 6.6 g (67%) of 1-acetyl-1H-indol-3-yl acetate as a white solid.

4. Synthesis of tert-butyl 4-(1-acetyl-1H-indol-3-yl)piperazine-1-carboxylate

Into a 150 mL sealed tube was placed a solution of 1-acetyl-1H-indol-3-yl acetate (2.5 g, 11.51 mmol) in toluene (80 mL). To this was added tert-butyl piperazine-1-carboxylate (10.71 g, 57.55 mmol). To the mixture was added p-toluenesulfonic acid (400 mg, 2.33 mmol). The resulting solution was allowed to react, with stirring, overnight while the temperature was maintained at 120° C. in a bath of oil. The reaction progress was monitored by TLC (ethyl acetate/petroleum ether=1:1). The mixture was concentrated by evaporation under vacuum using a rotary evaporator. The resulting solution was diluted with 200 mL of ethyl acetate. The resulting mixture was washed 3 times with 200 mL of NaCl(aq.). The mixture was dried over Na₂SO₄. The residue was purified by eluting through a column with a 10:1 petroleum ether/ethyl acetate solvent system. This resulted in 2.9 g (72%) of tert-butyl 4-(1-acetyl-1H-indol-3-yl)piperazine-1-carboxylate as a purple solid.

5. tert-butyl-4-(1H-indol-3-yl)-piperazine-1-carboxylate

Into a 250 mL round bottom flask was placed a solution of tert-butyl 4-(1-acetyl-1H-indol-3-yl)piperazine-1-carboxylate (2.6 g, 7.58 mmol) in methanol (80 mL). To the mixture was added Et₃N (2.3 g, 22.73 mmol). The resulting solution was allowed to react, with stirring, for 1 hour while the temperature was maintained at reflux in a bath of oil. The reaction progress was monitored by LCMS and TLC (ethyl acetate/petroleum ether=1:1). The mixture was concentrated by evaporation under vacuum using a rotary evaporator. The resulting solution was diluted with 200 mL of ethyl acetate. The resulting mixture was washed 3 times with 150 mL of NaCl(aq.). The residue was purified by eluting through a column with a 10:1 petroleum ether/ethyl acetate solvent system. This resulted in 2.1 g (89%) of tert-butyl 4-(1H-indol-3-yl)piperazine-1-carboxylate as a light pink solid.

¹H NMR (400 MHz, CDCl₃) δ 1.55 (9H, s), 3.1 (4H, s), 3.7 (4H, s), 6.7 (1H, s), 7.21 (1H, t), 7.32 (1H, t), 7.34 (1H, d), 7.68 (1H, d), 7.7 (1H, d). m/z 302 (M⁺+1).

Synthesis of tert-butyl 4-(1H-indazol-3-yl)piperazine-1-carboxylate

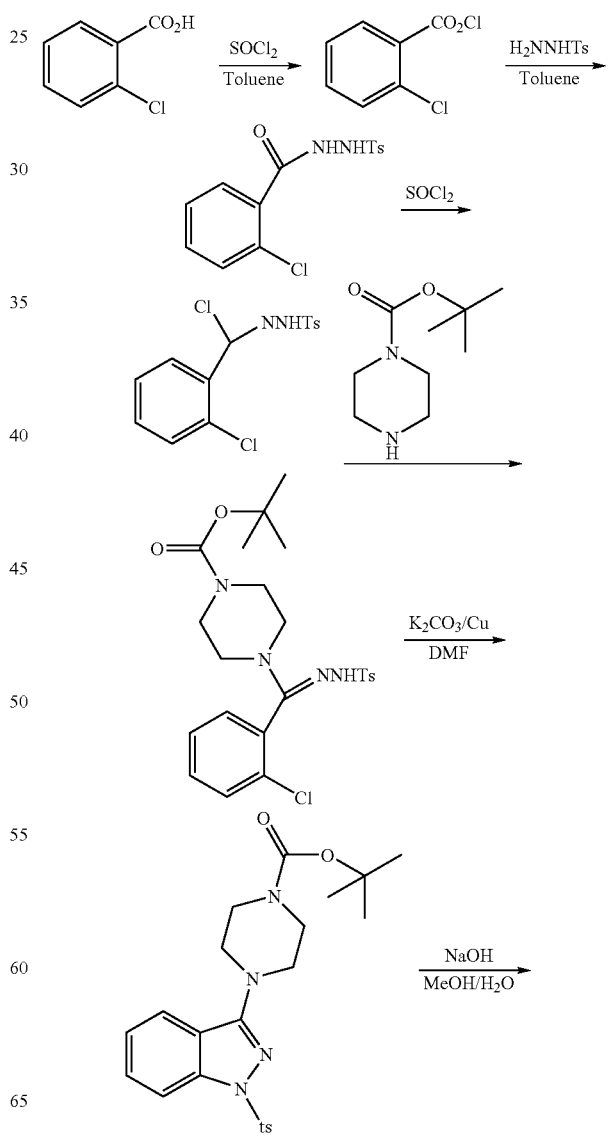

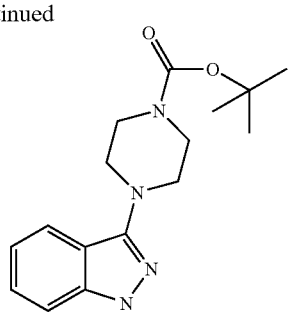

1. Synthesis of 2-chlorobenzoyl chloride

Into a 500 mL round bottom flask was placed a solution of 2-chlorobenzoic acid (20 g, 127.80 mmol) in toluene (150 mL). To the mixture was added $SOCl_2$ (16 g, 134.45 mmol). The resulting solution was allowed to react, with stirring, overnight while the temperature was maintained at 75° C. in a bath of oil. The mixture was concentrated by evaporation under vacuum using a rotary evaporator. This resulted in 22.3 g (100%) of 2-chlorobenzoyl chloride as yellow oil.

2. Synthesis of 2-chloro-N'-tosylbenzohydrazide

Into a 500 mL round bottom flask was placed a solution of 2-chlorobenzoyl chloride (22.3 g, 127.43 mmol) in toluene (200 mL). To the mixture was added 4-methylbenzenesulfonohydrazide (23.3 g, 125.27 mmol). The resulting solution was allowed to react, with stirring, overnight while the temperature was maintained at 75° C. in a bath of oil. A filtration was performed. The filter cake was dried in an oven under reduced pressure. This resulted in 37.7 g (91%) of 2-chloro-N'-tosylbenzohydrazide as a white solid.

3. Synthesis of N'-(chloro(2-chlorophenyl)methylene)-4-methylbenzenesulfonohydrazide Into a 500 mL round bottom flask was placed 2-chloro-N'-tosylbenzohydrazide (10 g, 30.79 mmol). To this was added $SOCl_2$ (36.6 g, 307.56 mmol). The resulting solution was allowed to react, with stirring, for 1.5 hours while the temperature was maintained at 75° C. in a bath of oil. To the mixture was added 2-chloro-N'-tosylbenzohydrazide (10 g, 30.79 mmol), while cooling to a temperature of 60° C. The resulting solution was allowed to react, with stirring, for an additional 2 hours while the temperature was maintained at 75° C. in a bath of oil. The reaction mixture was then quenched by the adding 100 mL of n-hexane. A filtration was performed. The filter cake was washed with n-hexane. The solid was dried in an oven under reduced pressure. This resulted in 19.6 g (74%) of N'-(chloro(2-chlorophenyl)methylene)-4-methylbenzenesulfonohydrazide as a white solid.

4. Synthesis of tert-butyl 4-(1-tosyl-1H-indazol-3-yl)piperazine-1-carboxylate Into a 500 mL round bottom flask was placed a solution of tert-butyl piperazine-1-carboxylate (11.9 g, 63.98 mmol) in NMP (100 mL). This was followed by the addition of a solution of N'-(chloro(2-chlorophenyl)methylene)-4-methylbenzenesulfonohydrazide (11 g, 32.07 mmol) in NMP (100 mL), which was added dropwise with stirring. The resulting solution was allowed to react, with stirring, for 40 minutes while the temperature was maintained at room temperature. To the mixture was added $K_2CO_3$ (6.2 g, 44.93 mmol). The resulting solution was allowed to react, with stirring, for an additional 4 hours while the temperature was maintained at 40° C. in a bath of oil. The reaction progress was monitored by TLC (ethyl acetate/petroleum ether=1:1). The reaction mixture was then quenched by the adding 100 mL of $H_2O$/ice. The reaction was filtered. The filter cake was washed with water. This resulted in 13.8 g (87%) of piperazine analog as a white solid.

Into a 500 mL round bottom flask was placed the obtained piperazine analog (13.8 g, 27.99 mmol). To this was added Cu (900 mg, 14.06 mmol). Addition of $K_2CO_3$ (3.8 g, 27.54 mmol) was next. To the mixture was added DMF (200 mL). The resulting solution was allowed to react, with stirring, for 1.5 hours while the temperature was maintained at reflux in a bath of oil. The reaction progress was monitored by TLC (ethyl acetate/petroleum ether=1:2). The reaction mixture was then quenched by the adding 100 mL of $H_2O$. The resulting solution was extracted one time with 200 mL of ethyl acetate and the organic layers combined and dried over $MgSO_4$ and concentrated by evaporation under vacuum using a rotary evaporator. This resulted in 7 g (55%) of tert-butyl 4-(1-tosyl-1H-indazol-3-yl)piperazine-1-carboxylate as a white solid.

5. Synthesis of tert-butyl 4-(1-indazol-3-yl)piperazine-1-carboxylate

Into a 500 mL 3-necked round bottom flask purged and maintained with an inert atmosphere of nitrogen was placed tert-butyl 4-(1-tosyl-1H-indazol-3-yl)piperazine-1-carboxylate (6 g, 13.16 mmol). To this was added NaOH (1.3 g, 32.50 mmol). Addition of methanol (100 mL) was next. To the mixture was added $H_2O$ (40 mL). The resulting solution was allowed to react, with stirring, for 4 hours while the temperature was maintained at 90° C. in a bath of oil. The reaction progress was monitored by TLC (ethyl acetate/petroleum ether=1:1). The mixture was concentrated by evaporation under vacuum using a rotary evaporator. The resulting solution was extracted one time with 200 mL of ethyl acetate and the organic layers combined and dried over $Na_2SO_4$. The residue was purified by eluting through a column with a 1:5 ethyl acetate/petroleum ether solvent system. This resulted in 3.0 g (60%) of tert-butyl 4-(1H-indazol-3-yl)piperazine-1-carboxylate as a white solid.

$^1$HNMR (400 Hz, $CDCl_3$) δ 1.5 (s, 9H) 3.4 (m, 4H) 3.6 (m, 4H) 7.10 (m, 1H) 7.39 (m, 2H) 7.73 (m, 1H). m/z: 303 ($M^+$+1).

Synthesis of tert-butyl 4-(1H-pyrrolo[2,3-b]pyridin-3-yl)piperazine-1-carboxylate

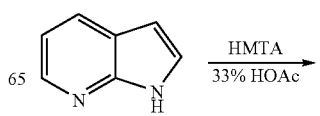

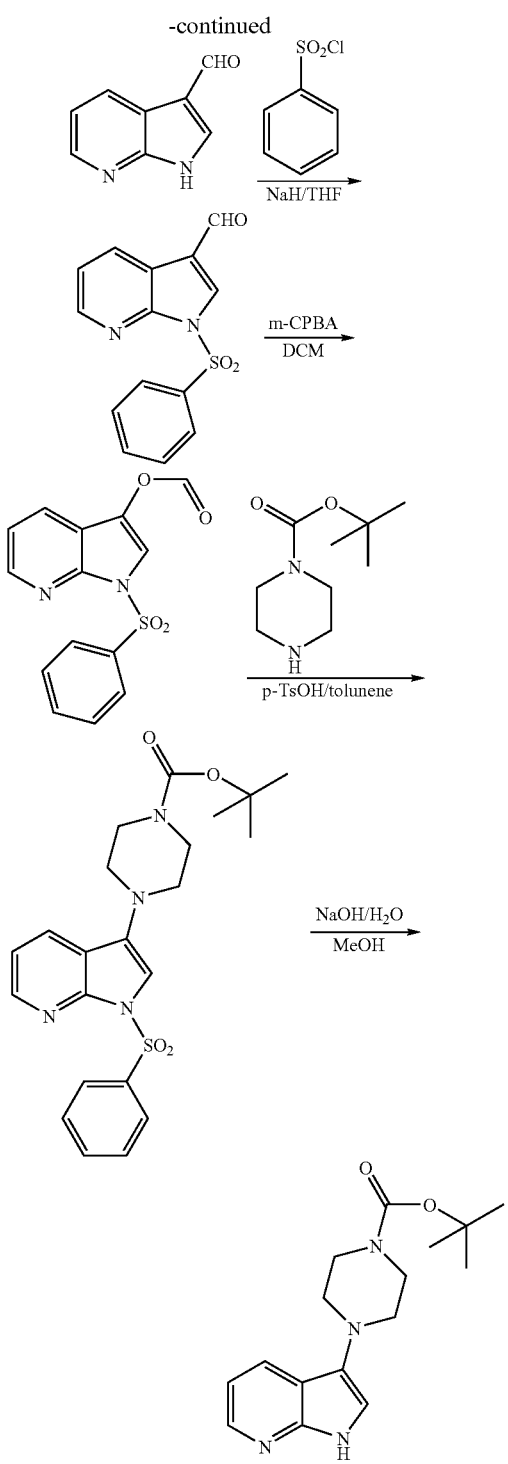

1. Synthesis of 1H-pyrrolo[2,3-b]pyridine-3-carbaldehyde

Into a 250 mL round bottom flask was placed 1H-pyrrolo[2,3-b]pyridine (10 g, 84.75 mmol). To this was added HMTA (hexamethylenetetramine) (17.8 g, 126.99 mmol). Addition of acetic acid (36 mL) was next. To the mixture was added H$_2$O (70 mL). The resulting solution was allowed to react, with stirring, for 4 hours while the temperature was maintained at reflux in a bath of oil. The resulting solution was diluted with 200 mL of H$_2$O. The reaction mixture was cooled. A filtration was performed and the filtrate cake was washed with H$_2$O. This resulted in 7.5 g (61%) of 1H-pyrrolo[2,3-b]pyridine-3-carbaldehyde as a white solid.

2. Synthesis of 1-(phenylsulfonyl)-1H-pyrrolo[2,3-b]pyridine-3-carbaldehyde

Into a 100 ni 3-necked round bottom flask was placed tetrahydrofuran (50 mL). To the above was added NaH (2.19 g, 54.75 mmol) in several batches, while cooling to a temperature of 0° C. This was followed by the addition of a solution of 1H-pyrrolo[2,3-b]pyridine-3-carbaldehyde (2 g, 13.70 mmol) in tetrahydrofuran (400 mL), which was added dropwise with stirring, while cooling to a temperature of 0° C. The resulting solution was allowed to react, with stirring, for 30 minutes while the temperature was maintained at room temperature. This was followed by the addition of a solution of benzenesulfonyl chloride (3.63 g, 20.55 mmol) in tetrahydrofuran (50 mL), which was added dropwise with stirring, while cooling to a temperature of 0° C. The resulting solution was allowed to react, with stirring, for 3 hours while the temperature was maintained at room temperature. The reaction mixture was then quenched by the adding of H$_2$O. The mixture was concentrated by evaporation under vacuum using a rotary evaporator. The residue was dissolved in 300 mL of ethyl acetate. The resulting mixture was washed two times with 200 mL of brine and the organic layers combined. The mixture was dried over Na$_2$SO$_4$ and concentrated by evaporation under vacuum using a rotary evaporator. The resulting mixture was washed with ethyl acetate/petroleum ether=1:40. This resulted in 3.4 g (82%) of 1-(phenylsulfonyl)-1H-pyrrolo[2,3-b]pyridine-3-carbaldehyde as a light yellow solid.

3. Synthesis of 1-(phenylsulfonyl)-1H-pyrrolo[2,3-b]pyridin-3-yl formate

Into a 250 mL 3-necked round bottom flask was placed dichloromethane (30 mL). To the mixture was added mCPBA (m-chloroperbenzoic acid) (2.78 g, 13.69 mmol), while cooling to a temperature of 0° C. This was followed by the addition of a solution of 1-(phenylsulfonyl)-1H-pyrrolo[2,3-b]pyridine-3-carbaldehyde (3 g, 10.49 mmol) in dichloromethane (100 mL), which was added dropwise with stirring, while cooling to a temperature of 0° C. The resulting solution was allowed to react, with stirring, 2 hours while the temperature was maintained at 0° C. Then the resulting solution was allowed to react, with stirring, overnight while the temperature was maintained at 30° C. in a bath of oil. The reaction progress was monitored by LC-MS. The residue was purified by eluting through a column with a 1:10 ethyl acetate/petroleum ether solvent system. This resulted in 2 g (63%) of 1-(phenylsulfonyl)-1H-pyrrolo[2,3-b]pyridin-3-yl formate as a light yellow solid.

4. Synthesis of tert-butyl 4-(1-(phenylsulfonyl)-1H-pyrrolo[2,3-b]pyridin-3-yl)piperazine-1-carboxylate Into a 150 mL sealed tube was placed 1-(phenylsulfonyl)-1H-pyrrolo[2,3-b]pyridin-3-yl formate (1.5 g, 4.97 mmol). To this was added tert-butyl piperazine-1-carboxylate (9.24 g, 49.68 mmol). Addition of p-toluenesulfonic acid (171 mg, 0.99 mmol) was next. To the mixture was added toluene (70 mL). After nitrogen bubbled, the resulting solution was allowed to react, with stirring, overnight while the temperature was maintained at 120° C. in a bath of oil. The mixture was concentrated by evaporation under vacuum using a rotary evaporator. The residue was dissolved in 300 mL of ethyl acetate. The resulting mixture was washed 2 times with 150 mL of brine. The mixture was dried over $Na_2SO_4$. The residue was purified by eluting through a column with a 1:2 ethyl acetate/petroleum ether solvent system. This resulted in 420 mg (18%) of tert-butyl 4-(1-(phenylsulfonyl)-1H-pyrrolo[2,3-b]pyridin-3-yl)piperazine-1-carboxylate as a yellow solid.

5. Synthesis of tert-butyl 4-(1H-pyrrolo[2,3-b]pyridin-3-yl)piperazine-1-carboxylate Into a 50 mL round bottom flask purged and maintained with an inert atmosphere of nitrogen was placed tert-butyl 4-(1-(phenylsulfonyl)-1H-pyrrolo[2,3-b]pyridin-3-yl)piperazine-1-carboxylate (400 mg, 0.90 mmol). To this was added NaOH (90 mg, 2.25 mmol). Addition of methanol (20 mL) was next. To the mixture was added $H_2O$ (8 mL). The resulting solution was allowed to react, with stirring, for 4 hours while the temperature was maintained at 90° C. in a bath of oil. The mixture was concentrated by evaporation under vacuum using a rotary evaporator. A filtration was performed and the filter cake was washed with $H_2O$. This resulted in 180 mg (66%) of tert-butyl 4-(1H-pyrrolo[2,3-b]pyridin-3-yl)piperazine-1-carboxylate as a light yellow solid. $^1$H NMR (400 MHz, $CDCl_3$) δ 1.40 (s, 9H), 2.96 (m, 4H), 3.56 (m, 4H), 6.73 (s, 1H), 6.97 (d, 1H), 7.88 (d, 1H), 8.22 (d, 1H), 8.97 (s, 1H). m/z 303 ($M^+$+1).

Example 1

Synthesis of 1-methylindoline-6-sulfonyl chloride

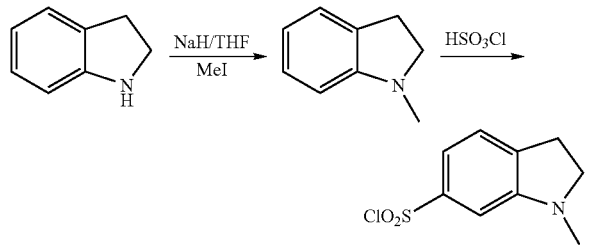

1) Synthesis of 1-methylindoline

NaH (15 g, 375.00 mmol) was added in several batches to a chilled (0° C.) solution of indoline (30 g, 252.10 mmol) in tetrahydrofuran (400 mL). Methyl iodide (53 g, 373.24 mmol) was then added dropwise with stirring, while maintaining the temperature of 0° C. The resulting solution was stirred at room temperature for 15 hours, then quenched by the addition of ethanol (200 mL). The mixture was concentrated, water (400 mL) was added, and the product was extracted with methylene chloride (3×200 mL). The organics were combined, dried ($Na_2SO_4$), filtered and concentrated to provide 20.4 g (60%) of 1-methylindoline as a brown liquid.

2) Synthesis of 1-methylindoline-6-sulfonyl chloride $ClSO_3H$ (400 g, 3.45 mol) was cooled to 0° C. and 1-methylindoline (35 g, 263.16 mmol) was added dropwise with stirring, maintaining the temperature at 0° C. The resulting solution was then warmed to room temperature and stirred for 20 hours. The reaction mixture was added carefully then dropwise to 3 L of iced water and the resulting solution was extracted using dichloromethane (3×400 mL). The organic layers were combined, dried ($Na_2SO_4$) and concentrated. The resulting residue was purified by column chromatography using a 1:30 ethyl acetate/petroleum ether solvent system. The collected fractions were combined and concentrated to give 4.2 g (7%) of 1-methylindoline-6-sulfonyl chloride as a brown solid. $^1$H NMR ($CDCl_3$) δ 7.34 (d, 1H), 7.20 (d, 1H), 6.95 (s, 1H), 3.52 (t, 2H), 3.08 (t, 2H), 2.86 (s, 3H).

Example 2

Synthesis of 3-(Dimethylamino) benzene-1-sulfonyl chloride

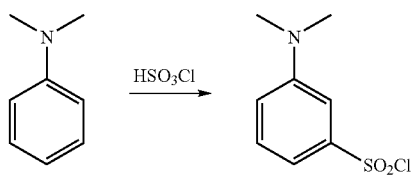

Sulfurochloridic acid (100 g, 862.07 mmol) was cooled to 0° C. and N,N-dimethylbenzenamine (20 g, 165.29 mmol) was added dropwise with stirring, maintaining a temperature of 0° C. The resulting solution was then heated to 120° C. and stirred for 3 hours. After cooling to room temperature, dichloromethane (40 mL) was added and the resulting mixture was added dropwise to 100 mL of ice/salt water. The resulting solution was extracted with dichloromethane (3×500 mL) and the organic layers combined, dried ($Na_2SO_4$) and filtered. The filtrate was concentrated and the residue was purified by column chromatography using a 1:100 ethyl acetate/petroleum ether solvent system. The collected fractions were combined and concentrated to give 4.1 g (11%) of 3-(dimethylamino) benzene-1-sulfonyl chloride as a yellow solid. $^1$H NMR ($CDCl_3$) δ 7.41 (t, 1H), 7.31 (d, 1H), 7.23 (s, 1H), 6.98 (m, 1H), 3.05 (s, 6H).

Example 3

Synthesis of 4-morpholinobenzene-1-sulfonyl chloride

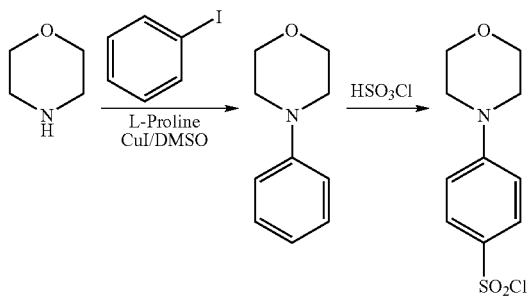

1) Synthesis of 4-phenylmorpholine 1-iodobenzene (28.12 g, 137.84 mmol) was added to morpholine (12.0 g, 137.93 mmol). L-Proline (3.12 g, 27.13 mmol) was then added, followed by the addition of CuI (2.6 g, 13.68 mmol) and DMSO (120 mL). The resulting solution was stirred at 90° C. for 4 hours, and then the reaction mixture was then quenched by the addition of 300 mL of iced water. The resulting solution was extracted using dichloromethane (2×200 mL), and the organic layers combined, dried (Na$_2$SO$_4$) and concentrated. The residue was purified by column chromatography using a petroleum ether solvent system. The collected fractions were combined and concentrated to give 10 g (42%) of 4-phenylmorpholine as a white solid.

2) Synthesis of 4-morpholinobenzene-1-sulfonyl chloride

Sulfurochloridic acid (71.0 g, 612.07 mmol) was cooled to 0° C. and 4-phenylmorpholine (20.0 g, 122.53 mmol) was added in several batches, while keeping the temperature at 0° C. The resulting solution was then stirred at 90° C. for 20 hours. The reaction mixture was then added dropwise to 200 mL of ice/salt. The resulting solution was extracted with ethyl acetate (2×200 mL) and the organic layers were combined, dried (MgSO$_4$) and filtered. The filtrate was concentrated, and the residue was purified by column chromatography using a 20:1 ethyl acetate/petroleum ether solvent system to give 4.7 g of 4-morpholinobenzene-1-sulfonyl chloride as a yellow solid. $^1$H NMR (CDCl$_3$) δ 7.9 (d, 2H), 6.9 (d, 1H), 7.5 (d, 2H), 3.87 (t, 2H), 3.4 (t, 2H).

Example 4

Synthesis of 1-ethylindoline-5-sulfonyl chloride

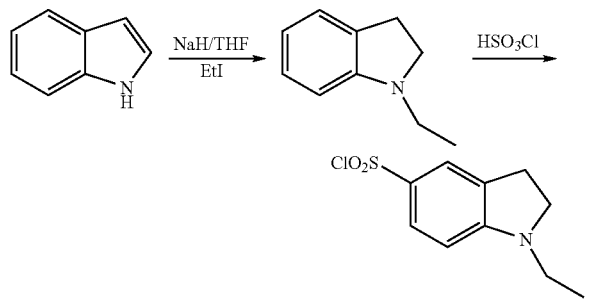

1) Synthesis of 1-ethylindoline

NaH (10 g) was added to a chilled (0° C.) solution of indoline (30 g, 252.10 mmol) in tetrahydrofuran (300 mL). The resulting solution was then stirred at room temperature for 30 minutes. Iodoethane (50 g, 322.58 mmol) was then added dropwise and the resulting solution was maintained at room temperature for an additional 3 hours. The reaction mixture was then quenched by adding ethanol (100 mL). The resulting solution was extracted with dichloromethane (3×500 mL), and the organic layers were combined and concentrated. The residue was purified by column chromatography using a 100:1 ethyl acetate/petroleum ether solvent system to give 29 g (78%) of 1-ethylindoline as yellow oil.

2) Synthesis of 1-ethylindoline-5-sulfonyl chloride 1-ethylindoline (15 g, 102.04 mmol) was added at 0° C. to ClSO$_3$H (60 g). The resulting solution was stirred at 50° C. overnight, then the reaction was quenched by adding 300 g iced water. The resulting solution was extracted with dichloromethane (3×600 mL) and the organic layers were combined, dried (MgSO$_4$) and concentrated. The residue was then purified by column chromatography using a 1:100 ethyl acetate/petroleum ether solvent system to give 1.5 g (6%) of 1-ethylindoline-5-sulfonyl chloride as a yellow solid. $^1$H NMR (CDCl$_3$) δ 7.28 (d, 1H), 7.18 (d, 1H), 7.11 (s, 1H), 3.39 (q, 2H), 3.52 (t, 2H), 3.06 (t, 2H), 1.23 (t, 3H).

Example 5

Synthesis of 2-oxo-2,3-dihydrobenzo[d]oxazole-6-sulfonyl chloride

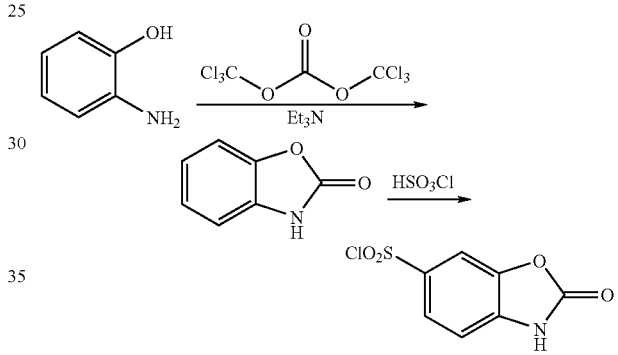

1) Synthesis of benzo[d]oxazol-2(3H)-one

Triethylamine (27.0 mL) was added to a mixture of 2-aminophenol (10 g, 91.74 mmol) in dichloromethane (200 μL) at 5° C. This was followed by the addition of a solution of bis(trichloromethyl) carbonate (9.35 g, 31.48 mmol) in dichloromethane (40 mL), while maintaining the temperature below 10° C. The resulting solution was then maintained below 10° C. for 6 hours. The reaction mixture was then quenched by the addition of water (50 mL) and ethanol (20 mL). After 0.5 hours, the mixture was concentrated and then poured into 400 mL of water. After filtration, the filter cake was washed with hydrochloric acid (10%) and water to afford 10 g (48%) of benzo[d]oxazol-2(3H)-one as an off-white solid.

2) Synthesis of 2-oxo-2,3-dihydrobenzo[d]oxazole-6-sulfonyl chloride

Sulfurochloridic acid (70 g, 603.45 mmol) was cooled to 0° C. and benzo[d]oxazol-2(3H)-one (1.8 g, 13.33 mmol) was added in several batches, maintaining the temperature at about 0° C. The resulting solution was stirred at room temperature for 3 hours, then quenched by the addition 400 mL of iced water. The resulting solution was extracted with ethyl acetate (3×100 mL) and the organic layers were combined, dried (Na$_2$SO$_4$), filtered and concentrated. The residue was purified by column chromatography using a 1:10 ethyl acetate/petroleum ether solvent system to afford 0.8 g (26%) of 2-oxo-2,3-dihydrobenzo[d]oxazole-6-sulfonyl chloride as a white solid. $^1$H NMR (CDCl$_3$) δ 8.26 (s, 1H), 8.00 (d, 1H), 7.98 (d, 1H), 7.32 (s, 1H).

Example 6

Synthesis of 3-methyl-2-oxo-2,3-dihydrobenzo[d]oxazole-6-sulfonyl chloride

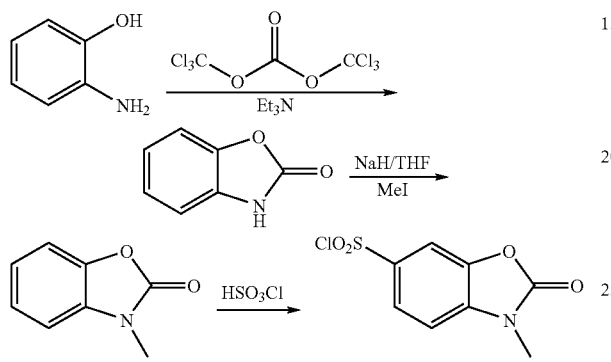

1) Synthesis of benzo[d]oxazol-2(3H)-one

Triethylamine (27.0 mL) was added to a mixture of 2-aminophenol (10 g, 91.74 mmol) in CH$_2$Cl$_2$ (200 mL) at 5° C. A solution of bis(trichloromethyl) carbonate (9.35 g, 31.48 mmol) in dichloromethane (40 mL) was then added, maintaining the temperature below 10° C. The resulting solution was then maintained below 10° C. for 6 hours. The reaction mixture was then quenched by the addition of water (50 mL) and ethanol (20 mL). After 0.5 hours, the mixture was concentrated and then poured into 400 mL of H$_2$O. After filtration, the filter cake was washed with hydrochloric acid (10%) and water to afford 10 g (48%) of benzo[d]oxazol-2(3H)-one as an off-white solid.

2) Synthesis of 3-methylbenzo[d]oxazol-2-(3H)-one

NaH (280 mg, 7.00 mmol) was added to a chilled (0° C.) solution of benzo[d]oxazol-2(3H)-one (650 mg, 4.81 mmol) in tetrahydrofuran (20 mL). After 0.5 hours, methyl iodide (1.03 g, 7.25 mmol) was added dropwise with stirring, maintaining a temperature of 0° C. The resulting solution was then stirred for 6 hours at room temperature. The reaction mixture was then quenched by the addition of ethanol (10 mL), and the mixture was concentrated. Water (50 mL) was then added and the resulting solution was extracted with dichloromethane (3×20 mL). The organic layers were combined, dried (Na$_2$SO$_4$), filtered and concentrated to afford 0.62 g (82%) of 3-methylbenzo[d]oxazol-2(3H)-one as a light red solid.

3) Synthesis of 3-methyl-2-oxo-2,3-dihydrobenzo[d]oxazole-6-sulfonyl chloride 3-methylbenzo[d]oxazol-2(3H)-one (620 mg, 4.16 mmol) was added, in several batches, to chilled sulfurochloridic acid (17.5 g, 150.86 mmol) at 0° C. The resulting solution was stirred at room temperature for 3 hours, then quenched by adding it slowly to 200 mL of ice/salt. The resulting solution was extracted with ethyl acetate (3×40 mL). The organic layers were combined, dried (Na$_2$SO$_4$), filtered and concentrated to afford 0.5 g (46%) of 3-methyl-2-oxo-2,3-dihydrobenzo[d]oxazole-6-sulfonyl chloride as a light brown solid. $^1$H NMR (CDCl$_3$) δ 8.00 (d, 1H), 7.97 (s, 1H), 7.16 (d, 1H), 3.52 (s, 3H).

Example 7

Synthesis of 4-(pyrrolidin-1-yl)benzene-1-sulfonyl chloride

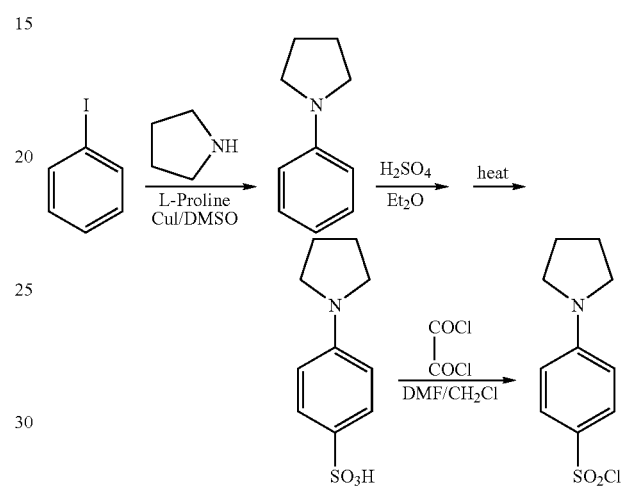

1) Synthesis of 1-phenylpyrrolidine

Pyrrolidine (21.6 g, 304.23 mmol), L-proline (1.12 g, 9.74 mmol), and CuI (960 mg, 5.05 mmol) were added sequentially to 1-iodobenzene (10.0 g, 49.02 mmol). DMSO (40 mL) was then added, and the resulting solution was stirred at 60° C. for 20 hours. The reaction mixture was then quenched by adding 400 mL of iced water. The resulting solution was extracted with ethyl acetate (3×150 mL), and the organic layers were combined, dried (Na$_2$SO$_4$), filtered and concentrated. The residue was purified by column chromatography using a 1:100 ethyl acetate/petroleum ether solvent system to afford 4.3 g (57%) of 1-phenylpyrrolidine as brown oil.

2) Synthesis of 4-(pyrrolidin-1-yl)benzenesulfonic acid

A solution of H$_2$SO$_4$ (6.8 g, 68.00 mmol) in diethylether (80 mL) was added to 1-phenylpyrrolidine (10 g, 68.03 mmol) in diethylether (20 mL) at 0° C. The diethylether was decanted, and the resulting solution was stirred for 3 hours at 170° C., then concentrated in vacuo to afford 7.3 g (43%) of 4-(pyrrolidin-1-yl)benzenesulfonic acid as a white solid.

3) Synthesis of 4-(pyrrolidin-1-yl)benzene-1-sulfonyl chloride

DMF (0.5 mL) was added to solution of 4-(pyrrolidin-1-yl)benzenesulfonic acid (7.3 g, 32.16 mmol) in dichloromethane (40 mL). Oxalyl chloride (10 g, 78.74 mmol) was then dropwise and the resulting solution was maintained at room temperature for 1 hour. The reaction mixture was then quenched by the addition of 40 mL of iced water. The resulting solution was extracted using dichloromethane (3×20 mL), and the organic layers were combined, dried (Na$_2$SO$_4$), filtered and concentrated. The residue was purified by column chromatography using a 1:100 ethyl acetate/petroleum ether solvent system to afford 1.5 g (19%) of 4-(pyrrolidin-1-yl)benzene-1-sulfonyl chloride as a yellow solid. $^1$H NMR (CDCl$_3$) δ 7.78 (d, 2H), 6.55 (d, 2H), 3.41 (t, 4H), 2.03 (t, 4H).

Example 8

Synthesis of 3-(pyrrolidin-1-yl)benzene-1-sulfonyl chloride

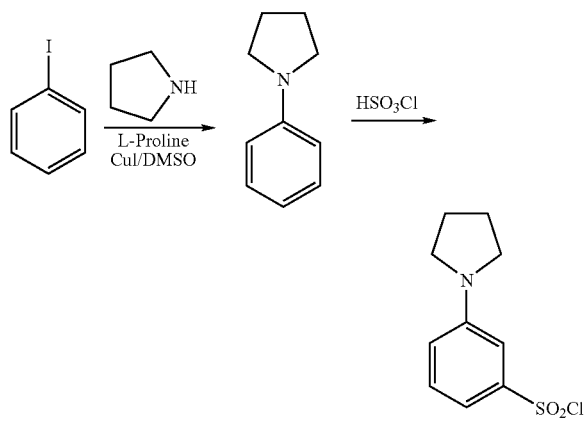

1) Synthesis of 1-phenylpyrrolidine

Pyrrolidine (21.6 g, 304.23 mmol), L-proline (1.12 g, 9.74 mmol), and CuI (960 mg, 5.05 mmol) were added sequentially to 1-iodobenzene (10.0 g, 49.02 mmol). Dimethyl sulfoxide (40 mL) was then added, and the resulting solution was stirred at 60° C. for 20 hours. The reaction mixture was then quenched by adding 400 mL of iced water. The resulting solution was extracted with ethyl acetate (3×150 mL), and the organic layers were combined, dried (Na$_2$SO$_4$), filtered and concentrated. The residue was purified by column chromatography using a 1:100 ethyl acetate/petroleum ether solvent system to afford 4.3 g (57%) of 1-phenylpyrrolidine as brown oil.

2) Synthesis of 3-(pyrrolidin-1-yl)benzene-1-sulfonyl chloride 1-phenylpyrrolidine (4.3 g, 29.25 mmol) was added dropwise to sulfurochloridic acid (20 mL) at 0° C. and the resulting solution was then maintained at 60° C. overnight. The reaction mixture was then quenched by adding 200 mL of ice/salt. The resulting solution was extracted with ethyl acetate (3×100 mL), and the organic layers were combined, dried over Na$_2$SO$_4$, filtered and concentrated. The residue was purified by column chromatography using a 1:500 ethyl acetate/petroleum ether solvent system. The collected fractions were combined and concentrated to give 0.5 g (7%) of 3-(pyrrolidin-1-yl)benzene-1-sulfonyl chloride as a yellow solid. $^1$H NMR (CDCl$_3$) δ 7.36 (m, 1H), 7.24 (d, 1H), 7.07 (s, 1H), 6.82 (d, 1H), 3.34 (t, 4H), 2.05 (t, 4H).

Example 9

Synthesis of 4-(N-methylacetamido)benzene-1-sulfonyl chloride

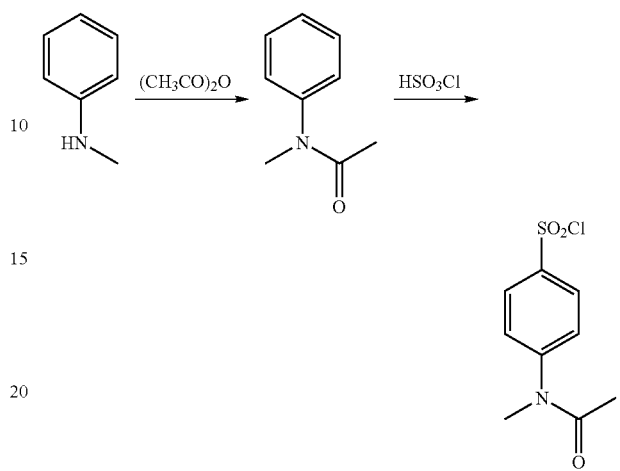

1) Synthesis of N-methyl-N-phenylacetamide (CH$_3$CO)$_2$O (50 g, 480.77 mmol) was added to N-methylbenzenamine (10.7 g, 100.00 mmol), and the resulting solution was stirred at room temperature for 15 hours. The reaction mixture was then quenched by adding 200 mL of iced water. The resulting solution was extracted with dichloromethane (2×100 mL), and the organic layers were combined and concentrated to afford 11 g (70%) of N-methyl-N-phenylacetamide as a white solid.

2) Synthesis of 4-(N-methylacetamido)benzene-1-sulfonyl chloride

A solution of N-methyl-N-phenylacetamide (11 g, 73.83 mmol) in dichloromethane (20 mL) was added dropwise to HSO$_3$Cl (80 g, 689.66 mmol) at 5° C. The resulting solution was then stirred at room temperature overnight. The reaction mixture was then quenched by adding 100 mL of iced water. The resulting solution was extracted using dichloromethane (2×50 mL) and the organic layers were combined. The residue was purified by column chromatography using a 10:1 ethyl acetate/petroleum ether solvent system to give 2.2 g (11%) of 4-(N-methylacetamido)benzene-1-sulfonyl chloride as a white solid. $^1$H NMR (CDCl$_3$) δ 8.09 (d, 2H), 7.48 (d, 2H), 3.38 (s, 3H), 2.17 (s, 3H).

Example 10

Synthesis of 1-(2,2,2-trifluoroacetyl)-1,2,3,4-tetrahydroquinoline-6-sulfonyl chloride

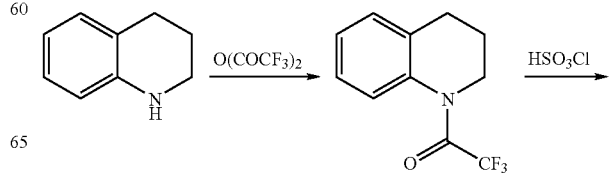

-continued

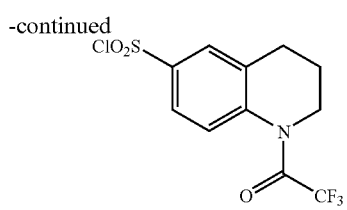

1) Synthesis 1-(3,4-dihydroquinolin-1(2H)-yl)-2,2,2-trifluoroethanone

A solution of O(COCF$_3$)$_2$ (6.3 g, 29.95 mmol) in CHCl$_3$ (30 mL) was added dropwise to a solution of 1,2,3,4-tetrahydroquinoline (2.66 g, 19.97 mmol) in chloroform (20 mL) at 5° C., and the resulting mixture was stirred for 2 hours at room temperature. The mixture was concentrated, and the residue was purified by column chromatography using a 1:10 ethyl acetate/petroleum ether solvent system to afford 4 g (87%) of 1-(3,4-dihydroquinolin-1(2H)-yl)-2,2,2-trifluoroethanone as a yellow liquid.

2) Synthesis of 1-(2,2,2-trifluoroacetyl)-1,2,3,4-tetrahydroquinoline-6-sulfonyl chloride 1-(3,4-dihydroquinolin-1(2H)-yl)-2,2,2-trifluoroethanone (4 g, 17.45 mmol) was added to HSO$_3$Cl (30 g, 258.62 mmol) at 0° C. The resulting solution was maintained at room temperature overnight. The reaction mixture was then quenched by adding 100 mL of iced water and the resulting solution was extracted with dichloromethane (3×50 mL). The residue was purified by column chromatography using a 1:10 ethyl acetate/petroleum ether solvent system to afford 1.2 g (21.4%) of 1-(2,2,2-trifluoroacetyl)-1,2,3,4-tetrahydroquinoline-6-sulfonyl chloride as a white solid. $^1$H NMR (CDCl$_3$) δ 8.01 (d, 1H), 7.89 (s, 1H), 7.87 (s, 1H), 3.91 (t, 2H), 3.01 (t, 2H), 2.16 (m, 2H).

Example 11

Synthesis of 1-methyl-1,2,3,4-tetrahydroquinoline-7-sulfonyl chloride

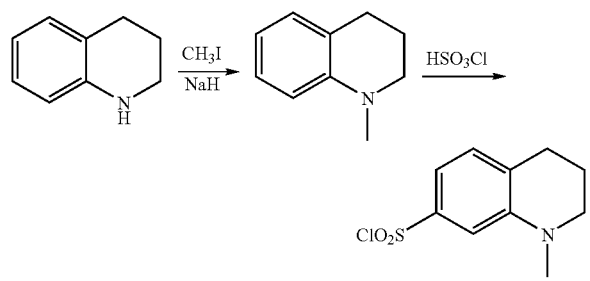

1) Synthesis of 1-methyl-1,2,3,4-tetrahydroquinoline

NaH (12 g, 60%, 300.00 mmol) was added in several batches, to a solution of 1,2,3,4-tetrahydroquinoline (26.6 g, 199.70 mmol) in tetrahydrofuran (150 mL) at 0-5° C. The resulting solution was maintained at 0-5° C. for 30 minutes, then iodomethane (50 g, 352.11 mmol) was added dropwise (at 0-5° C.). The resulting solution was then stirred at room temperature overnight. The mixture was filtered, and the filtrate was purified by column chromatography using a 1:100 ethyl acetate/petroleum ether solvent system to afford 19 g (61%) of 1-methyl-1,2,3,4-tetrahydroquinoline as a yellow liquid.

2) Synthesis of 1-methyl-1,2,3,4-tetrahydroquinoline-7-sulfonyl chloride

A solution of 1-methyl-1,2,3,4-tetrahydroquinoline (10 g, 68.03 mmol) in dichloromethane (20 mL) was added dropwise to HSO$_3$Cl (80 g, 689.66 mmol) at 0-5° C., and the resulting solution was maintained at room temperature overnight. The reaction mixture was then quenched by adding 300 mL of iced water. The resulting solution was extracted using ethyl acetate (3×150 mL). The organic layers were combined, concentrated, and the residue was purified by column chromatography using a 1:20 ethyl acetate/petroleum ether solvent system to afford 1-methyl-1,2,3,4-tetrahydroquinoline-7-sulfonyl chloride as a yellow liquid in 8% yield. $^1$H NMR (CDCl$_3$) δ 7.19 (d, 1H), 7.10 (d, 1H), 7.06 (s, 1H), 3.33 (t, 2H), 2.97 (s, 3H), 2.81 (d, 2H), 1.99 (m, 2H).

Example 12

Synthesis of 1-methyl-1,2,3,4-tetrahydroquinoline-6-sulfonyl chloride

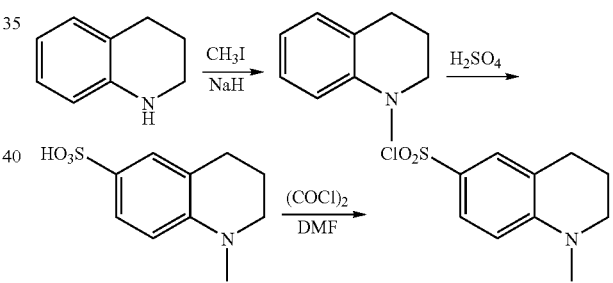

1) Synthesis of 1-methyl-1,2,3,4-tetrahydroquinoline

NaH (12 g, 60%, 300.00 mmol) was added in several batches, to a solution of 1,2,3,4-tetrahydroquinoline (26.6 g, 199.70 mmol) in tetrahydrofuran (150 mL) at 0-5° C. The resulting solution was maintained at 0-5° C. for 30 minutes, then iodomethane (50 g, 352.11 mmol) was added dropwise (at 0-5° C.). The resulting solution was stirred at room temperature overnight. The mixture was filtered, and the filtrate was purified by column chromatography using a 1:100 ethyl acetate/petroleum ether solvent system to give 19 g (61%) of 1-methyl-1,2,3,4-tetrahydroquinoline as a yellow liquid.

2) Synthesis of 1-methyl-1,2,3,4-tetrahydroquinoline-6-sulfonic acid

A solution of H$_2$SO$_4$ (6 g, 60.00 mmol) in ether (40 mL) was added dropwise to a solution of 1-methyl-1,2,3,4-tetrahydroquinoline (9 g, 61.14 mmol) in diethylether (10 mL) at 5° C. The resulting solution was maintained at room temperature for 30 minutes, then under vacuum, with stirring, for an additional 3 hours at 170° C. The resulting mixture was washed with methanol (1×100 mL) and filtered to afford 5 g (34%) of 1-methyl-1,2,3,4-tetrahydroquinoline-6-sulfonic acid as a white solid.

3) Synthesis of 1-methyl-1,2,3,4-tetrahydroquinoline-6-sulfonyl chloride

Oxalyl chloride (20 g, 157.60 mmol) was added dropwise at room temperature to a solution of 1-methyl-1,2,3,4-tetrahydroquinoline-6-sulfonic acid (5 g, 22.00 mmol) in dichloromethane (100 mL) and DMF (10 mL). The resulting solution was stirred for 2 hours, then quenched by adding 200 mL of iced water. The resulting solution was extracted using dichloromethane (2×100 mL), and the combined organics were dried ($Na_2SO_4$), filtered and concentrated. The residue was purified by column chromatography using a 1:4 ethyl acetate/petroleum ether solvent system to afford 1.1 g (20.1%) of 1-methyl-1,2,3,4-tetrahydroquinoline-6-sulfonyl chloride as a yellow solid. $^1$H NMR ($CDCl_3$) δ 7.69 (d, 1H), 7.51 (s, 1H), 6.54 (d, 1H), 3.57 (t, 2H), 3.02 (s, 3H), 2.78 (d, 2H), 1.98 (m, 2H).

Example 13

Synthesis of 2-methyl-1,2,3,4-tetrahydroisoquinoline-8-sulfonyl chloride

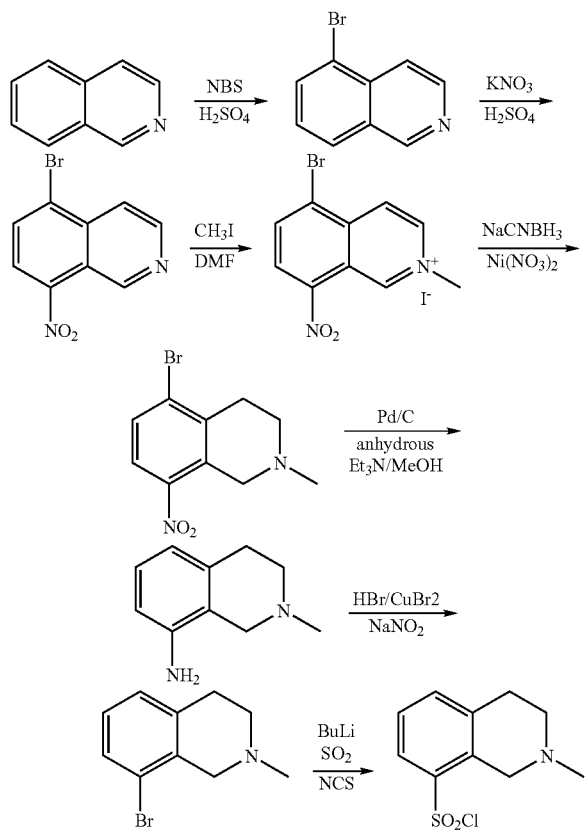

1. Synthesis of 5-bromoisoquinoline

Into a 250 mL 3-necked round bottom flask was placed $H_2SO_4$ (150 mL). To the above was added isoquinoline (17 g, 131.62 mmol) in several batches, while cooling to a temperature of 0° C. To the above was added NBS (29.2 g, 164.04 mmol) in several batches, while cooling to a temperature of −25--22° C. The resulting solution was allowed to react, with stirring, for 2 hours while the temperature was maintained at −25--22° C. The resulting solution was allowed to react, with stirring, overnight while the temperature was maintained at room temperature. The reaction progress was monitored by TLC (ethyl acetate/petroleum ether=1:5). The reaction mixture was then quenched by the adding 1000 mL of $H_2O$/ice. Adjustment of the pH to 8-10 was accomplished by the addition of $NH_3 \cdot H_2O$ (30%). The resulting solution was extracted four times with 500 mL of ethyl acetate and the organic layers combined and dried over $Na_2SO_4$. The residue was purified by eluting through a column with a 1:5 ethyl acetate/petroleum ether solvent system. This resulted in 22.24 g (81%) of 5-bromoisoquinoline as a white solid.

2. Synthesis of 5-bromo-8-nitroisoquinoline

Into a 500 mL 3-necked round bottom flask was placed a solution of 5-bromoisoquinoline (22.24 g, 106.87 mmol) in $H_2SO_4$ (120 mL). This was followed by the addition of a solution of $KNO_3$ (15.1 g, 149.36 mmol) in $H_2SO_4$ (100 mL), which was added dropwise with stirring, while cooling to a temperature of 20° C. over a time period of 1 hour. The resulting solution was allowed to react, with stirring, for 1 hour while the temperature was maintained at room temperature. The reaction progress was monitored by TLC (ethyl acetate/petroleum ether=1:5). The reaction mixture was then quenched by the adding 600 mL of $H_2O$/ice. Adjustment of the pH to 8-10 was accomplished by the addition of $NH_3 \cdot H_2O$ (30%). A filtration was performed. The filter cake was washed 2 times with 500 mL of $H_2O$. The solid was dried in an oven under reduced pressure. This resulted in 25.59 g (90%) of 5-bromo-8-nitroisoquinoline as a yellow solid.

3. Synthesis of 5-bromo-8-nitro-N-methylisoquinolinium iodide

Into a 500 mL round bottom flask, was placed a solution of 5-bromo-8-nitroisoquinoline (25.59 g, 101.11 mmol) in DMF (200 mL). To the mixture was added iodomethane (71.8 g, 505.99 mmol). The resulting solution was allowed to react, with stirring, overnight while the temperature was maintained at 40° C. A filtration was performed. The filter cake was washed 2 times with 250 mL of ether. This resulted in 33.33 g (83%) of 5-bromo-8-nitro-N-methylisoquinolinium iodide as a red solid.

4. Synthesis of 5-bromo-2-methyl-8-nitro-1,2,3,4-tetrahydroisoquinoline

Into a 500 mL 3-necked round bottom flask was placed a solution of $Ni(NO_3)_2 \cdot 6H_2O$ (12.6 g, 43.33 mmol) in $CH_3OH$ (200 mL). To the mixture was added 5-bromo-8-nitro-N-methylisoquinolinium iodide (33.33 g, 84.38 mmol). To the above was added $NaCNBH_3$ (10.6 g, 168.68 mmol) in several batches. The resulting solution was allowed to react, with stirring, for 5 hours while the temperature was maintained at room temperature. The reaction progress was monitored by TLC (ethyl acetate/petroleum ether=1:5). The resulting solution was concentrated by evaporation under vacuum using a rotary evaporator. The residue was dissolved with 800 mL of H₂O. Adjustment of the pH to 8-10 was accomplished by the addition of NaOH (5%). A filtration was performed. The resulting solution was extracted 2 times with 800 mL of ethyl acetate and the organic layers combined and dried over Na₂SO₄. The residue was purified by eluting through a column with a 1:5 ethyl acetate/petroleum ether solvent system. This resulted in 19.3 g (83%) of 5-bromo-2-methyl-8-nitro-1,2,3,4-tetrahydroisoquinoline as a yellow solid.

5. Synthesis of 2-methyl-1,2,3,4-tetrahydroisoquinolin-8-amine

Into a 250 mL 3-necked round bottom flask was added a solution of 5-bromo-2-methyl-8-nitro-1,2,3,4-tetrahydroisoquinoline (4.85 g, 17.89 mmol) in CH₃OH/Et₃N(anhydrous) (150/15 mL). To the mixture was added Pd/C (4.5 g). Hydrogen gas was bubbled into the mixture The resulting solution was allowed to react, with stirring, for 3 hours while the temperature was maintained at room temperature. The reaction progress was monitored by TLC (ethyl acetate/petroleum ether=1:1). A filtration was performed. The filtrate was concentrated by evaporation under vacuum using a rotary evaporator. The resulting solution was diluted with 50 mL of Na₂CO₃ (10%). The resulting solution was extracted four times with 50 mL of ethyl acetate and the organic layers combined and dried over Na₂SO₄. The residue was purified by eluting through a column with a 50:1 CH₂Cl₂/MeOH solvent system. This resulted in 2.57 g (89%) of 2-methyl-1,2,3,4-tetrahydroisoquinolin-8-amine as a light yellow oil.

6. Synthesis of 8-bromo-2-methyl-1,2,3,4-tetrahydroisoquinoline

Into a 50 mL 3-necked round bottom flask (named A), was placed 2-methyl-1,2,3,4-tetrahydroisoquinolin-8-amine (500 mg, 3.08 mmol). This was followed by the addition of a solution of HBr (5 mL) in H₂O (5 mL), which was added dropwise with stirring, while cooling to a temperature of 0° C. To the above was added NaNO₂ (230 mg, 3.33 mmol) in several batches, while cooling to a temperature of 0° C. and the mixture was stirred for 30 mins at that temperature. Then into another 50 mL 3-necked round bottom flask (named B), was purged and maintained with an inert atmosphere of nitrogen, was placed a solution of CuBr (550 mg, 3.83 mmol) in HBr/H₂O (3 mol/L) (10 mL), while cooling to a temperature of 0° C. The mixture was stirred for 10 minutes. Then was followed by the addition of the reaction solution of flask A with dropwise while the temperature was maintained at 0° C. The resulting solution was allowed to react, with stirring, for 30 minutes while the temperature was maintained at 0° C. The resulting solution was allowed to react, with stirring, for an additional 2 hours at room temperature. The reaction progress was monitored by TLC(ethyl acetate:petroleum ether=1:1). Adjustment of the pH to 9 was accomplished by the addition of NaOH (10%). The resulting solution was extracted three times with 50 mL of CH₂Cl₂ and the organic layers combined and dried over K₂CO₃. A filtration was performed. The filtrate was concentrated by evaporation under vacuum using a rotary evaporator. The residue was purified by eluting through a column with a 1:1 ethyl acetate; petroleum ether solvent system. This resulted in 0.45 g (65%) of 8-bromo-2-methyl-1,2,3,4-tetrahydroisoquinoline as light yellow oil.

7. Synthesis of 2-methyl-1,2,3,4-tetrahydroisoquinoline-8-sulfonyl chloride

Into a 100 mL 3-necked round bottom flask purged and maintained with an inert atmosphere of nitrogen was placed a solution of 8-bromo-2-methyl-1,2,3,4-tetrahydroisoquinoline (3 g, 13.27 mmol) in tetrahydrofuran (30 mL). To the above was added 2.5M n-BuLi/hexane (6.9 mL), while cooling to a temperature of −78° C. over a time period of 15 minutes. The resulting solution was allowed to react, with stirring, for 40 minutes while the temperature was maintained at −78° C. Addition of SO₂ (890 mg, 13.91 mmol) was next, while cooling to a temperature of −100° C. The resulting solution was allowed to react, with stirring, for 20 minutes while the temperature was maintained at −78° C. The resulting solution was allowed to react, with stirring, for an additional 1 hour while the temperature was maintained at room temperature. This was followed by the addition of n-hexane (60 mL). Then a filtration was performed. A light yellow solid was obtained. In another 250 mL 3-necked round bottom flask was placed the above filter cake and CH₂Cl₂ (80 mL). To the above was added NCS (2.7 g, 20.22 mmol) in several batches, while cooling to a temperature of −10-0° C. The resulting solution was allowed to react, with stirring, for an additional 1 hour while the temperature was maintained at room temperature. The reaction progress was monitored by TLC(ethyl acetate:petroleum ether=3:2). The resulting mixture was washed 2 times with 100 mL of saturated NaHSO₃ and 2 times with 50 mL of saturated NaCl. The mixture was dried over Na₂SO₄. A filtration was performed. The filtrate was concentrated by evaporation under vacuum using a rotary evaporator. This resulted in 1.44 g (44%) of 2-methyl-1,2,3,4-tetrahydroisoquinoline-8-sulfonyl chloride as a light yellow solid.

¹HNMR (300 MHz, DMSO) δ 7.63 (d, 1H), 7.22 (m, 2H), 5.03 (d, 1H), 4.4 (m, 1H), 3.6 (d, 1H), 3.34 (d, 1H), 2.94 (m, 2H), 2.49 (s, 3H). m/z 246 [M+1]⁺

Example 14

Synthesis of 4-methyl-3,4-dihydro-2H-benzo[b][1,4]oxazine-6-sulfonyl chloride

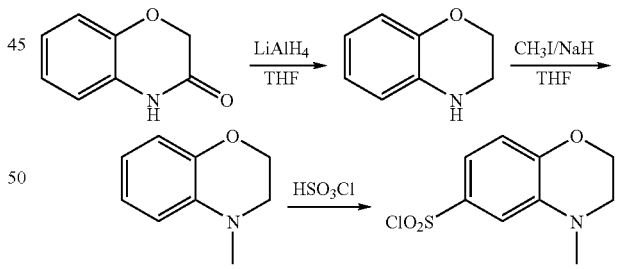

1. Synthesis of 3,4-dihydro-2H-benzo[b][1,4]oxazine

Into a 250 mL 3-necked round bottom flask was placed a solution of lithium aluminum hydride (3.6 g, 94.74 mmol) in tetrahydrofuran (80 ml). The mixture was stirred for 15 minutes. This was followed by the addition of a solution of 2H-benzo[b][1,4]oxazin-3(4H)-one (5.7 g, 38.22 mmol) in tetrahydrofuran (21 mL), which was added dropwise with stirring. The resulting solution was allowed to react, with stirring, overnight while the temperature was maintained at reflux in a bath of oil. The reaction progress was monitored by TLC (ethyl acetate/petroleum ether=1:1). The reaction mixture was then quenched by the adding 3.6 mL of H₂O and 10.8 mL 15% NaOH. A filtration was performed. The filter cake was washed with 30 mL of tetrahydrofuran. The resulting solution was extracted two times with 100 mL of ethyl acetate and the organic layers combined and dried over Na₂SO₄ and concentrated by evaporation under vacuum using a rotary evaporator. This resulted in 4.8 g (79%) of 3,4-dihydro-2H-benzo[b][1,4]oxazine as red oil.

2. Synthesis of 4-methyl-3,4-dihydro-2H-benzo[b][1,4]oxazine

Into a 250 mL 3-necked round bottom flask was placed a solution of 3,4-dihydro-2H-benzo[b][1,4]oxazine (4.8 g, 35.51 mmol) in tetrahydrofuran (50 mL). To the above was added NaH (2.3 g, 57.50 mmol) in several batches, while cooling to a temperature of 0-5° C. The mixture was stirred for 30 minutes at 0-5° C. To the above was added iodomethane (9.0 g, 63.41 mmol) dropwise with stirring, white cooling to a temperature of 0-5° C. The resulting solution was allowed to react, with stirring, overnight while the temperature was maintained at room temperature. The reaction progress was monitored by TLC (ethyl acetate/petroleum ether=1:2). A filtration was performed. The filtrate was concentrated by evaporation under vacuum using a rotary evaporator. The residue was purified by eluting through a column with a 1:100 ethyl acetate/petroleum ether solvent system. This resulted in 3.0 g (50%) of 4-methyl-3,4-dihydro-2H-benzo[b][1,4]oxazine as yellow oil.

3. Synthesis of 4-methyl-3,4-dihydro-2H-benzo[b][1,4]oxazine-6-sulfonyl chloride Into a 250 n-L 3-necked round bottom flask was placed HSO₃Cl (25 mL). To the above was added 4-methyl-3,4-dihydro-2H-benzo[b][1,4]oxazine (5.8 g, 38.93 mmol) dropwise with stirring, while cooling to a temperature of 0-5° C. The resulting solution was allowed to react, with stirring, for 120 minutes while the temperature was maintained at room temperature. The reaction progress was monitored by TLC (ethyl acetate/petroleum ether=1:2). The reaction mixture was then quenched by the adding of H₂O/ice. The resulting solution was extracted three times with 200 mL of ethyl acetate and the organic layers combined and dried over Na₂SO₄ and concentrated by evaporation under vacuum using a rotary evaporator. The resulting mixture was washed 3 times with 15 mL of hexane. This resulted in 2.9 g (27%) of 4-methyl-3,4-dihydro-2H-benzo[b][1,4]oxazine-6-sulfonyl chloride as a light yellow solid.

¹H NMR (300 MHz, CDCl₃) δ 2.98 (s, 3H), 3.36 (m, 2H), 4.38 (m. 2H), 6.87 (d, 1H), 7.19 (s, 1H), 7.34 (d, 1H). m/z 319 [M+BnNH+H]⁺

Example 15

Synthesis of 2-oxo-1,2,3,4-tetrahydroquinoline-7-sulfonyl chloride

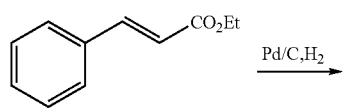

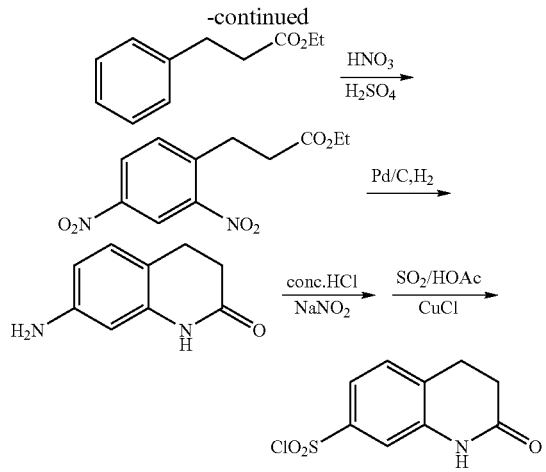

1. Synthesis of ethyl 3-phenylpropanoate

A 500 mL 3-necked round bottom flask was added a solution of ethyl cinnamate (10 g, 56.75 mmol) in methanol (200 mL). To the mixture was added Pd/C (2 g) followed by addition of hydrogen gas. The resulting solution was allowed to react, with stirring, overnight while the temperature was maintained at 35° C. in a bath of oil. A filtration was performed. The filtrate was concentrated by evaporation under vacuum using a rotary evaporator. This resulted in 10 g (99%) of ethyl 3-phenylpropanoate as a colorless oil.

2. Synthesis of ethyl 3-(2,4-dinitrophenyl)propanoate

Into a 250 mL 3-necked round bottom flask was placed a solution of fuming HNO₃ (25 mL) in conc. H₂SO₄ (50 mL). To the mixture was added ethyl 3-phenylpropanoate (5 g, 28.09 mmol) while cooling to a temperature of 0° C. The resulting solution was allowed to react, with stirring, for 1 hour while the temperature was maintained at 0° C. The resulting solution was allowed to react, with stirring, overnight while the temperature was maintained at 60° C. The reaction progress was monitored by TLC (ethyl acetate/petroleum ether=1:3). The reaction mixture was then quenched by the adding of H₂O/ice. The resulting solution was extracted two times with 50 mL of ethyl acetate and the organic layers combined. The resulting mixture was washed 2 times with 50 mL of NaHCO₃ (aq.). The mixture was dried over MgSO₄ and concentrated by evaporation under vacuum using a rotary evaporator. This resulted in 2 g (27%) of ethyl 3-(2,4-dinitrophenyl)propanoate as a yellow solid.

3. Synthesis of 7-amino-3,4-dihydroquinolin-2(1H)-one

Into a 100 mL 3-necked round bottom flask was placed a solution of ethyl 3-(2,4-dinitrophenyl)propanoate (1.5 g, 5.60 mmol) in methanol (20 mL). To the mixture was added Pd/C (0.5 g). Hydrogen gas was passed through. The resulting solution was allowed to react, with stirring, overnight while the temperature was maintained at 30° C. A filtration was performed. The filtrate was concentrated by evaporation under vacuum using a rotary evaporator. This resulted in 0.5 g (55%) of 7-amino-3,4-dihydroquinolin-2(1H)-one as a green-yellow solid.

4. Synthesis of 2-oxo-1,2,3,4-tetrahydroquinoline-7-sulfonyl chloride

Into a 50 mL 3-necked round bottom flask was placed a solution of 7-amino-3,4-dihydroquinolin-2(1H)-one (350 mg, 2.16 mmol) in conc.HCl (6 mL). This was followed by the addition of a solution of sodium nitrite (200 mg, 2.90 mmol) in H₂O (2 mL) at −5-0° C. The mixture was stirred for 30 minutes. Then the resulting solution was added into a solution of copper chloride (200 mg, 2.02 mmol) in CH₃COOH (10 mL) that was saturated with SO₂ gas. The resulting solution was allowed to react, with stirring, for 1 hour while the temperature was maintained at 10-30° C. The reaction progress was monitored by TLC (CH₂Cl₂/MeOH=10:1). The reaction mixture was then quenched by the adding of H₂O/ice. The resulting solution was extracted two times with 20 mL of ethyl acetate and the organic layers combined. The resulting mixture was washed 2 times with 10 mL of H₂O and 1 time with 10 mL of NaHCO₃/H₂O. The mixture was dried over Na₂SO₄. A filtration was performed. The filtrate was concentrated by evaporation under vacuum using a rotary evaporator. This resulted in 0.24 g (45%) of 2-oxo-1,2,3,4-tetrahydroquinoline-7-sulfonyl chloride as a brown solid.

¹HNMR (300 MHz, CDCl₃)) δ 2.89 (m, 2H), 2.95 (m, 2H), 7.41 (m, 1H), 7.43 (m, 1H), 7.47 (m, 1H). m/z 315 [M−H]⁻

Example 16

Synthesis of 3-(3-methoxypyrrolidin-1-yl)benzene-1-sulfonyl chloride

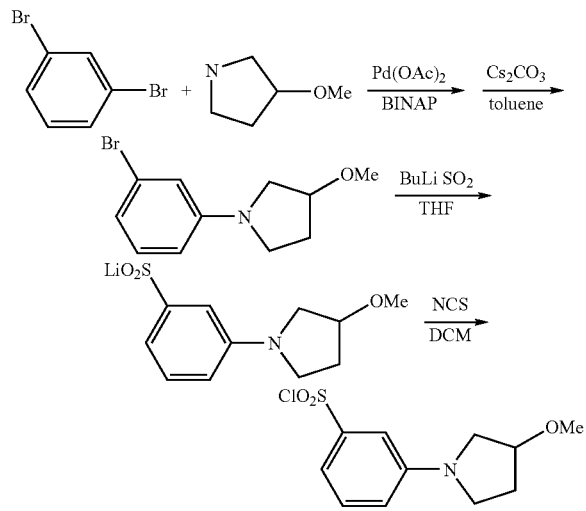

1. Synthesis of 1-(3-bromophenyl)-3-methoxypyrrolidine

Into a 250 mL 3-necked round bottom flask purged and maintained with an inert atmosphere of nitrogen, was placed a solution of 1,3-dibromobenzene (11.9 g, 50.42 mmol) in toluene (100 mL). To this was added 3-methoxypyrrolidine (6.1 g, 60.40 mmol). Addition of Pd(OAc)₂ (113 mg, 0.50 mmol) was next. This was followed by the addition of BINAP (940 mg, 1.51 mmol). To the mixture was added Cs₂CO₃ (40.9 g, 125.54 mmol). The resulting solution was allowed to react, with stirring, overnight while the temperature was maintained at reflux in a bath of oil. The reaction progress was monitored by TLC (ethyl acetate/petroleum ether=1:5). A filtration was performed. The filtrate was concentrated by evaporation under vacuum using a rotary evaporator. The residue was purified by eluting through a column with a 1:30 ethyl acetate/petroleum ether solvent system. This resulted in 8.3 g (64.3%) of 1-(3-bromophenyl)-3-methoxypyrrolidine as yellow oil.

2. Synthesis of lithium 3-(3-methoxypyrrolidin-1-yl)benzenesulfinate

Into a 250 mL 3-necked round bottom flask purged and maintained with an inert atmosphere of nitrogen, was placed a solution of 1-(3-bromophenyl)-3-methoxypyrrolidine (8.3 g, 32.42 mmol) in tetrahydrofuran (100 mL). To this was added BuLi (15.6 mL). The resulting solution was allowed to react, with stirring, for 1 hour while the temperature was maintained at −78° C. in a bath of liquid nitrogen. To the mixture was added SO₂ (4 mL). The resulting solution was allowed to react, with stirring, for an additional 2 hours while the temperature was maintained at −78° C. in a bath of liquid nitrogen. The reaction progress was monitored by TLC (ethyl acetate/petroleum ether=1:1). The mixture was concentrated by evaporation under vacuum using a rotary evaporator. The product was precipitated by the addition of hexane. A filtration was performed. The filter cake was washed 2 times with 50 mL of hexane. The solid was dried in an oven under reduced pressure. This resulted in 12 g (90%) of lithium 3-(3-methoxypyrrolidin-1-yl)benzenesulfinate as a yellow solid.

3. Synthesis of 3-(3-methoxypyrrolidin-1-yl)benzene-1-sulfonyl chloride

Into a 250 mL round bottom flask was placed a solution of lithium 3-(3-methoxypyrrolidin-1-yl)benzenesulfinate (12 g, 29.15 mmol) in dichloromethane (100 mL). To the above was added NCS (4.48 g, 33.56 mmol) in several batches, while cooling to a temperature of 0° C. over a time period of 10 minutes. The resulting solution was allowed to react, with stirring, for 15 minutes while the temperature was maintained at 0° C. in a bath of H₂O/ice, then the ice bath was removed and the solution was allowed to react for an additional 25 minutes at room temperature. The reaction progress was monitored by TLC (ethyl acetate/petroleum ether 5=1:1). The resulting mixture was washed 2 times with 50 mL of NaHSO₃ and 2 times with 50 mL of brine. The mixture was dried over Na₂SO₄ and concentrated by evaporation under vacuum using a rotary evaporator. The residue was purified by eluting through a column with a 2:3 ethyl acetate/petroleum ether solvent system. This resulted in 6.6 g (82.5%) of 3-(3-methoxypyrrolidin-1-yl)benzene-1-sulfonyl chloride as yellow oil.

¹HNMR (400 Hz, CDCl₃) δ 2.24 (1H, m), 2.30 (m, 1H); 3.54-3.45 (m, 2H) 3.61-3.56 (m, 2H), 4.2 (s, 3H), 6.90 (d, 1H, J=8 Hz), 7.34 (s, 1H, J=8 Hz), 7.367 (dd, 1H, J=8 Hz), 7.485 (dd, 1H, J=8, 8 Hz). m/z 347 [M+BnNH+H]⁺

Example 17

Synthesis of 3-oxo-3,4-dihydro-2H-benzo[b][1,4]oxazine-6-sulfonyl chloride

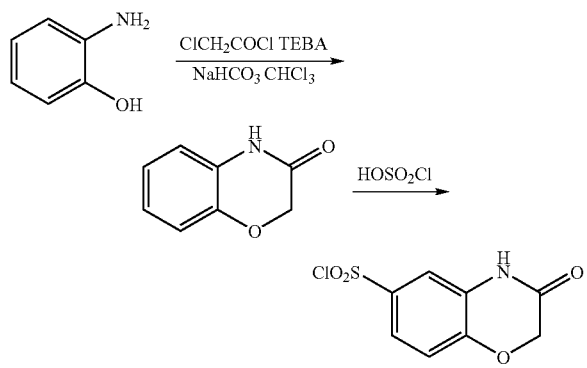

1. Synthesis of 2H-benzo[b][1,4]oxazin-3(4H)-one

Into a 100 mL round bottom flask was placed a solution of 2-aminophenol (5.45 g, 49.98 mmol) in CHCl$_3$ (30 mL). To this was added TEBA (11.4 g, 50.00 mmol). To the mixture was added NaHCO$_3$ (16.8 g, 200.00 mmol). This was followed by the addition of a solution of 2-chloroacetyl chloride (8.16 g, 72.21 mmol) in CHCl$_3$ (5 mL), which was added dropwise with stirring, while cooling to a temperature of 0° C. over a time period of 20 minutes. The resulting solution was allowed to react, with stirring, for 1 hour while the temperature was maintained at 0-5° C. The resulting solution was allowed to react, with stirring, overnight while the temperature was maintained at 55° C. The mixture was concentrated by evaporation under vacuum using a rotary evaporator. The product was precipitated by the addition of H$_2$O. A filtration was performed. The filter cake was washed 2 times with 50 mL of H$_2$O. The final product was purified by recrystallization from ethanol. This resulted in 4.5 g (60%) of 2H-benzo[b][1,4]oxazin-3(4H)-one as a white solid.

2. Synthesis of 3-oxo-3,4-dihydro-2H-benzo[b][1,4]oxazine-6-sulfonyl chloride Into a 100 mL round bottom flask, was placed HSO$_3$Cl (10 mL). To the above was added 2H-benzo[b][1,4]oxazin-3(4H)-one (2 g, 13.42 mmol) in several batches, while cooling to a temperature of 0-5° C. over a time period of 20 minutes. The resulting solution was allowed to react, with stirring, for 1 hour while the temperature was maintained at 5-10° C. The reaction mixture was poured into 100 g of ice carefully. The resulting solution was extracted one time with 100 mL of CH$_2$Cl$_2$ and the organic layers combined and dried over Na$_2$SO$_4$. A filtration was performed. The filtrate was concentrated by evaporation under vacuum using a rotary evaporator. This resulted in 2.2 g (66%) of 3-oxo-3,4-dihydro-2H-benzo[b][1,4]oxazine-6-sulfonyl chloride as a white solid. $^1$HNMR (400 MHz, CDCl$_3$) δ 9.29 (s, 1H), 7.71 (d, 2H), 7.52 (s, 1H), 7.16 (d, 2H), 4.80 (s, 2H). m/z 317 [M+BnNH–H]$^-$

Example 18

Synthesis of 3-(3-(tetrahydro-2H-pyran-2-yloxy)pyrrolidin-1-yl)benzene-1-sulfonyl chloride

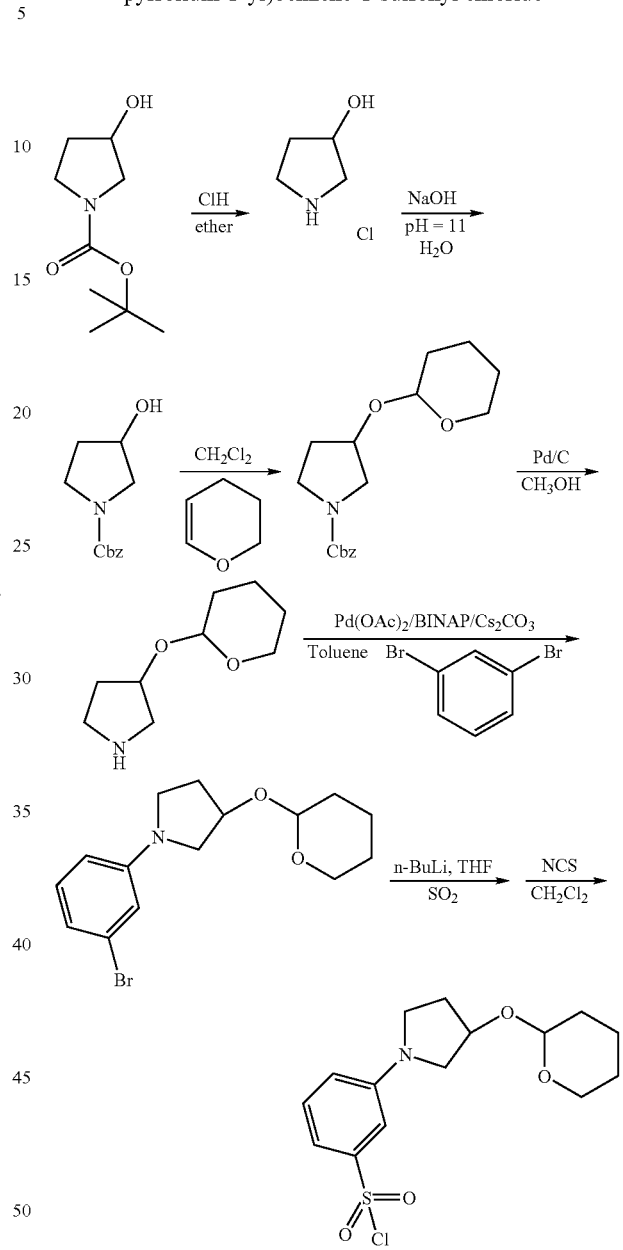

1. Synthesis of pyrrolidin-3-ol hydrochloride

Into a 500 mL 3-necked round bottom flask was placed a solution of tert-butyl 3-hydroxypyrrolidine-1-carboxylate (41 g, 218.97 mmol) in ethyl ether (300 mL). To the above was bubbled HCl (g), while maintaining at room temperature over a time period of 3 hours. The resulting solution was allowed to react, with stirring, overnight while the temperature was maintained at room temperature. The mixture was concentrated by evaporation under vacuum using a rotary evaporator. This resulted in 27 g (crude) of pyrrolidin-3-ol hydrochloride as a white solid.

2. Synthesis of benzyl 3-hydroxypyrrolidine-1-carboxylate

Into a 500 mL 3-necked round bottom flask was placed a solution of pyrrolidin-3-ol hydrochloride (20.2 g, 163.43 mmol) in H$_2$O (60 mL) while cooling to 5° C. Adjustment of the pH to 7 was accomplished by the NaOH (10%). This was followed by the addition of a solution of benzyl chloroformate (36.8 g, 216.47 mmol), which was added dropwise with stirring, while cooling to a temperature of 5° C. The resulting solution was allowed to react, with stirring, for 2 hours at 5° C. Then the resulting solution was allowed to react, with stirring, for 1 hour while the temperature was maintained at room temperature. The reaction progress was monitored by TLC (ethyl acetate/petroleum ether=1:2). The resulting solution was extracted three times with 100 mL of ethyl acetate and the organic layers combined and dried over MgSO$_4$ and concentrated by evaporation under vacuum using a rotary evaporator. This resulted in 30 g (crude) of benzyl 3-hydroxypyrrolidine-1-carboxylate as brown oil.

3. Synthesis of benzyl 3-(tetrahydro-2H-pyran-2-yloxy)pyrrolidine-1-carboxylate Into a 250 mL 3-necked round bottom flask was placed a solution of benzyl 3-hydroxypyrrolidine-1-carboxylate (10 g, 45.23 mmol) in CH$_2$Cl$_2$ (100 mL). To this was added 3,4-dihydro-2H-pyran (19 g, 226.19 mmol). To the mixture was added p-toluenesulfonic acid (389 mg, 2.26 mmol) and the resulting solution was allowed to react, with stirring, for 10 minutes while the temperature was maintained at 0° C. The resulting solution was allowed to react, with stirring, for an additional 1 hour at room temperature. The reaction progress was monitored by TLC (ethyl acetate/petroleum ether=1:2). The reaction mixture was then quenched by the adding 100 mL of NaHCO$_3$. The resulting mixture was washed with 100 mL of NaHCO$_3$ and 100 mL of brine. The mixture was dried over MgSO$_4$ and concentrated under vacuum using a rotary evaporator. This resulted in 15 g (98%) of benzyl 3-(tetrahydro-2H-pyran-2-yloxy)pyrrolidine-1-carboxylate as yellow oil.

4. Synthesis of 3-(tetrahydro-2H-pyran-2-yloxy)pyrrolidine

Into a 250 mL round bottom flask was placed a solution of benzyl 3-(tetrahydro-2H-pyran-2-yloxy)pyrrolidine-1-carboxylate (15 g, 44.26 mmol) and Pd/C (2.3 g) in CH$_3$OH (absolute) (100 mL). Hydrogen gas was bubbled. The resulting solution was allowed to react, with stirring, for 2 hours while the temperature was maintained at room temperature. A filtration was performed. The filtrate was concentrated by evaporation under vacuum using a rotary evaporator. This resulted in 5.6 g (67%) of 3-(tetrahydro-2H-pyran-2-yloxy)pyrrolidine as a yellow liquid.

5. Synthesis of 1-(3-bromophenyl)-3-(tetrahydro-2H-pyran-2-yloxy)pyrrolidine Into a 250 mL 3-necked round bottom flask purged and maintained with an inert atmosphere of nitrogen, was placed a solution of 1,3-dibromobenzene (7.0 g, 29.91 mmol) in toluene (100 mL). To this was added 3-(tetrahydro-2H-pyran-2-yloxy)pyrrolidine (5.6 g, 32.75 mmol). Addition of Pd(OAc)$_2$ (66.9 mg, 0.30 mmol) was next. This was followed by the addition of Cs$_2$CO$_3$ (24.27 g, 74.49 mmol). To the mixture was added BINAP (556 mg, 0.89 mmol). The resulting solution was allowed to react, with stirring, overnight while the temperature was maintained at reflux in a bath of oil. The reaction progress was monitored by TLC (ethyl acetate/petroleum ether=1:5). A filtration was performed. The filter cake was washed 3 times with 100 mL of brine. The mixture was dried over MgSO$_4$. The residue was purified by eluting through a column with a 1:100 ethyl acetate/petroleum ether solvent system. This resulted in 1.36 g (13%) of 1-(3-bromophenyl)-3-(tetrahydro-2H-pyran-2-yloxy)pyrrolidine as a yellow liquid.

6. Synthesis of 3-(3-(tetrahydro-2H-pyran-2-yloxy)pyrrolidin-1-yl)benzene-1-sulfonyl chloride Into a 100 mL 3-necked round bottom flask purged and maintained with an inert atmosphere of nitrogen, was placed a solution of 1-(3-bromophenyl)-3-(tetrahydro-2H-pyran-2-yloxy)pyrrolidine (1.4 g, 0.00429 mol) in tetrahydrofuran (50 mL). To the above was added n-BuLi (2.16 mL) dropwise with stirring, while cooling to a temperature of –78° C. The resulting solution was allowed to react, with stirring, for 40 minutes at –78 degree C. To the mixture was added SO$_2$ (450 mg, 0.00703 mol). The resulting solution was allowed to react, with stirring, for 60 minutes at –78-40 degree C. Then 50 mL of n-hexane was added, and the solid was collected by filtration. Then the solid was suspended in 50 mL of CH$_2$Cl$_2$. To the above was added NCS (930 mg, 0.00697 mol) in several batches, while cooling to a temperature of 0° C. The resulting solution was allowed to react, with stirring, for 40 minutes while the temperature was maintained at room temperature. The resulting mixture was washed 3 times with 100 mL of NaHSO$_3$ (2M) and 1 time with 100 mL of brine. The mixture was dried over MgSO$_4$. A filtration was performed. The filtrate was concentrated by evaporation under vacuum using a rotary evaporator. This resulted in 1.0 g (61%) of 3-(3-(tetrahydro-2H-pyran-2-yloxy)pyrrolidin-1-yl)benzene-1-sulfonyl chloride as yellow oil.

$^1$HNMR (300 MHz, CDCl$_3$) δ 7.38 (m, 1H), 7.30 (m, 1H), 7.10 (s, 1H), 6.82 (d, 1H), 4.75 (m, 1H), 4.52 (m, 1H), 3.90 (m, 1H) 3.38-3.57 (m, 5H), 2.18 (m, 1H), 2.05 (m, 1H), 1.70-1.80 (m, 2H), 1.55 (d, 4H). m/z 417 [M+BnNH2+H]$^+$.

Example 19

Synthesis of benzo[d]isoxazole-5-sulfonyl chloride

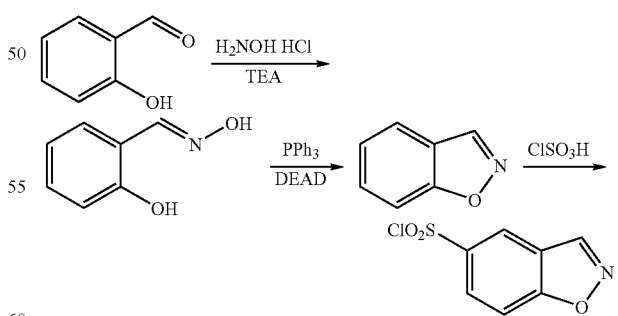

1. Synthesis of (E)-2-hydroxybenzaldehyde oxime

Into a 500 mL round bottom flask was placed a solution of 2-hydroxybenzaldehyde (20 g, 163.93 mmol) in ethanol (200 mL). To this was added (H$_2$NOH HCl) hydroxylamine hydrochloride (14 g, 197.18 mmol). To the mixture was added triethylamine (19.2 g, 190.10 mmol) slowly. The resulting solution was allowed to react, with stirring, for 5 hours while the temperature was maintained at 95° C. in a bath of oil. The reaction progress was monitored by TLC (ethyl acetate/petroleum ether=1:2). The mixture was concentrated by evaporation. The resulting solution was extracted two times with 150 mL of ethyl acetate and water. The resulting mixture was washed 3 times with 150 mL of water. The mixture was dried over $MgSO_4$ and concentrated by evaporator. The residue was purified by eluting through a column with a 1:100 ethyl acetate/petroleum ether solvent system. This resulted in 10 g (43%) of (E)-2-hydroxybenzaldehyde oxime as a white solid.

2. Synthesis of benzo[d]isoxazole

Into a 1 L 3-necked round bottom flask purged and maintained with an inert atmosphere of nitrogen, was placed a solution of (E)-2-hydroxybenzaldehyde oxime (3 g, 21.90 mmol) in tetrahydrofuran (300 mL). To the mixture was added $PPh_3$ (6.024 g, 22.99 mmol), while cooling to a temperature of 4° C. This was followed by the addition of a solution of DEAD (4 g, 22.99 mmol) in tetrahydrofuran (150 mL), while cooling to a temperature of 4° C. over a time period of 4 hours. The resulting solution was allowed to react, with stirring, for 1 hour while the temperature was maintained at 4° C. in a bath of $H_2O$/ice. The reaction progress was monitored by TLC (ethyl acetate/petroleum ether=1:2). The mixture was concentrated by evaporation under vacuum using a rotary evaporator. The residue was purified by eluting through a column with a 1:100 ethyl acetate/petroleum ether solvent system. This resulted in 1.8 g (66%) of benzo[d]isoxazole as yellow oil.

3. Synthesis of benzo[d]isoxazole-5-sulfonyl chloride

Into a 50 mL round bottom flask was placed $ClSO_3H$ (2.8 mL). To the mixture was added benzo[d]isoxazole (500 mg, 4.20) dropwise at 0° C. The resulting solution was allowed to react, with stirring, for 27 hours while the temperature was maintained at 100° C. in a bath of oil. The reaction progress was monitored by TLC (ethyl acetate/petroleum ether=1:5). The reaction mixture was diluted by $CH_2Cl_2$ and poured into 50 mL of $H_2O$/ice cautiously. The aqueous layer was extracted two times with 50 mL of $CH_2Cl_2$ and the organic layers combined. The resulting mixture was washed 2 times with 50 mL of water. The mixture was dried over $MgSO_4$ and concentrated by evaporation under vacuum using a rotary evaporator. This resulted in 500 mg (48%) of benzo[d]isoxazole-5-sulfonyl chloride as a red solid.

$^1$HNMR (300 MHz, $CDCl_3$) δ 8.93 (s, 1H), 8.54 (s, 1H), 8.26 (d, 1H), 7.87 (d, 1H). m/z 287 [M+BnNH−H]$^-$

Example 20

Synthesis of isoquinoline-8-sulfonyl chloride

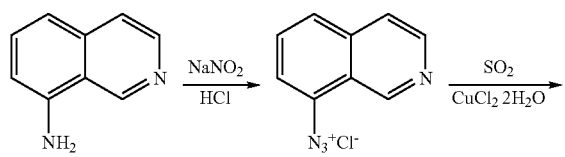

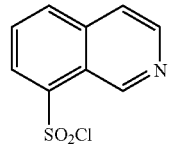

1. Synthesis of isoquinoline-8-sulfonyl chloride

Into a 500 mL 4-necked round bottom flask, was placed a solution of isoquinolin-8-amine (2.9 g, 16.09 mmol) in $CH_3CN$ (100 mL). To this was added acetic acid (12 g, 199.67 mmol), while cooling to a temperature of −5-0° C. To the above was added HCl (6.1 g, 60.16 mmol) dropwise with stirring, while cooling to a temperature of −5-0° C. This was followed by the addition of a solution of $NaNO_2$ (1.67 g, 24.20 mmol) in $H_2O$ (2 mL) and the mixture was stirred for 45 mins, while cooling to a temperature of −5-0° C. $SO_2$ gas was introduced for about 2 hours. This was followed by the addition of a solution of $CuCl_2.2H_2O$ (3.6 g, 21.11 mmol) in $H_2O$ (5 mL), while cooling to a temperature of −5-0° C. To the mixture was introduced with $SO_2$ gas for about 1 hour. The resulting solution was allowed to react, with stirring, overnight while the temperature was maintained at 0-5° C. in a bath of $H_2O$/ice. The reaction progress was monitored by TLC (ethyl acetate/petroleum ether=1:2). The reaction mixture was then quenched by the adding 400 mL of $H_2O$ lice. The resulting solution was extracted three times with 200 mL of $CH_2Cl_2$ and the organic layers combined and washed with brine and dried over $Na_2SO_4$ and concentrated by evaporation under vacuum using a rotary evaporator. The resulting mixture was washed 2 times with 10 mL of $CH_2Cl_2$. A filtration was performed. This resulted in 0.74 g (12%) of isoquinoline-8-sulfonyl chloride as a brown solid. m/z 228 [M+H]$^+$

Example 21

Synthesis of 4-(2-oxopyrrolidin-1-yl)benzene-1-sulfonyl chloride

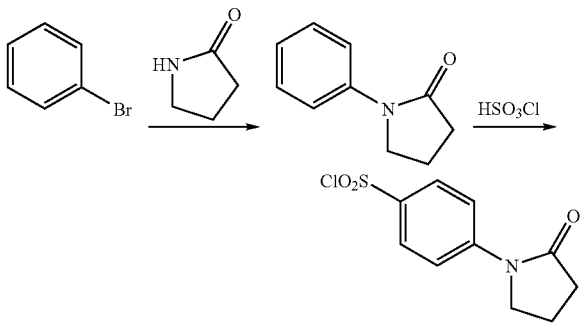

1. Synthesis of 1-phenylpyrrolidin-2-one

Into a 150 mL sealed tube purged and maintained with an atmosphere of nitrogen, was placed 1-bromobenzene (4 g, 25.48 mmol). To this was added pyrrolidin-2-one (2.18 g, 25.65 mmol). Addition of Pd(OAc)$_2$ (57 mg, 0.25 mmol) was next. This was followed by the addition of BINAP (240 mg, 0.39 mmol). This was followed by the addition of $Cs_2CO_3$ (12.5 g, 38.34=mol). To the mixture was added toluene (50 mL). The resulting solution was allowed to react, with stirring, overnight while the temperature was maintained at 120° C. in a bath of oil. The mixture was concentrated by evaporation under vacuum using a rotary evaporator. The residue was purified by eluting through a column with a 1:10 ethyl acetate/petroleum ether solvent system. This resulted in 1 g (24%) of 1-phenylpyrrolidin-2-one as yellow oil.

2. Synthesis of 4-(2-oxopyrrolidin-1-yl)benzene-1-sulfonyl chloride

Into a 50 mL round bottom flask was placed $HSO_3Cl$ (10 mL). To the mixture was added 1-phenylpyrrolidin-2-one (1 g, 6.21 mmol). The resulting solution was allowed to react, with stirring, overnight while the temperature was maintained at room temperature. The reaction mixture was then quenched by the adding 100 mL of $H_2O$/ice. The resulting solution was extracted one time with 100 mL of $CH_2Cl_2$ and the organic layers and dried over $MgSO_4$ and concentrated by evaporation under vacuum using a rotary evaporator. This resulted in 0.7 g (43%) of 4-(2-oxopyrrolidin-1-yl)benzene-1-sulfonyl chloride as a yellow solid. $^1HNMR$ (400 MHz, $CDCl_3$) δ 2.22 (m, 2H), 2.71 (t, 2H), 3.95 (t, 2H), 7.88 (t, 2H), 8.05 (t, 2H). m/z $[M+H]^+$ Example 22

Synthesis of 4-methyl-3,4-dihydro-2H-benzo[b][1,4]oxazine-6-sulfonyl chloride

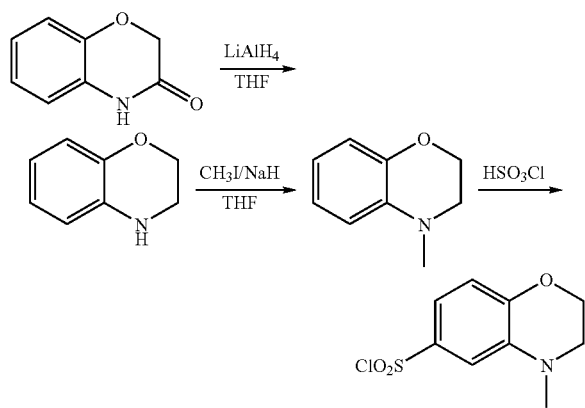

1. Synthesis of 3,4-dihydro-2H-benzo[b][1,4]oxazine

Into a 250 mL 3-necked round bottom flask was placed a solution of lithium aluminum hydride (3.6 g, 94.74 mmol) in tetrahydrofuran (80 mL). The mixture was stirred for 15 minutes. This was followed by the addition of a solution of 2H-benzo[b][1,4]oxazin-3(4H)-one (5.7 g, 38.22 mmol) in tetrahydrofuran (21 mL), which was added dropwise with stirring. The resulting solution was allowed to react, with stirring, overnight while the temperature was maintained at reflux in a bath of oil. The reaction progress was monitored by TLC (ethyl acetate/petroleum ether=1:1). The reaction mixture was then quenched by the adding 3.6 mL of $H_2O$ and 10.8 mL 15% NaOH. A filtration was performed. The filter cake was washed 1 time with 30 mL of tetrahydrofuran. The resulting solution was extracted two times with 100 mL of ethyl acetate and the organic layers combined and dried over $Na_2SO_4$ and concentrated by evaporation under vacuum using a rotary evaporator. This resulted in 4.8 g (79%) of 3,4-dihydro-2H-benzo[b][1,4]oxazine as red oil.

2. Synthesis of 4-methyl-3,4-dihydro-2H-benzo[b][1,4]oxazine

Into a 250 mL 3-necked round bottom flask was placed a solution of 3,4-dihydro-2H-benzo[b][1,4]oxazine (4.8 g, 35.51 mmol) in tetrahydrofuran (50 mL). To the above was added NaH (2.3 g, 57.50 mmol) in several batches, while cooling to a temperature of 0-5° C. The mixture was stirred for 30 minutes at 0-5° C. To the above was added iodomethane (9.0 g, 63.41 nm not) dropwise with stirring, while cooling to a temperature of 0-5° C. The resulting solution was allowed to react, with stirring, overnight while the temperature was maintained at room temperature. The reaction progress was monitored by TLC (ethyl acetate/petroleum ether=1:2). A filtration was performed. The filtrate was concentrated by evaporation under vacuum using a rotary evaporator. The residue was purified by eluting through a column with a 1:100 ethyl acetate/petroleum ether solvent system. This resulted in 3.0 g (50%) of 4-methyl-3,4-dihydro-2H-benzo[b][1,4]oxazine as yellow oil.

3. Synthesis of 4-methyl-3,4-dihydro-2H-benzo[b][1,4]oxazine-6-sulfonyl chloride Into a 250 mL 3-necked round bottom flask was placed $HSO_3Cl$ (25 mL). To the above was added 4-methyl-3,4-dihydro-2H-benzo[b][1,4]oxazine (5.8 g, 38.93 mmol) dropwise with stirring, while cooling to a temperature of 0-5° C. The resulting solution was allowed to react, with stirring, for 120 minutes while the temperature was maintained at room temperature. The reaction progress was monitored by TLC (ethyl acetate/petroleum ether=1:2). The reaction mixture was then quenched by the adding of $H_2O$ lice. The resulting solution was extracted three times with 200 mL of ethyl acetate and the organic layers combined and dried over $Na_2SO_4$ and concentrated by evaporation under vacuum using a rotary evaporator. The resulting mixture was washed 3 times with 15 mL of hexane. This resulted in 2.9 g (27%) of 4-methyl-3,4-dihydro-2H-benzo[b][1,4]oxazine-6-sulfonyl chloride as a light yellow solid. $^1H$ NMR (300 MHz, $CDCl_3$) δ 2.98 (s, 3H), 3.36 (m, 2H), 4.38 (m, 2H), 6.87 (d, 1H), 7.19 (s, 1H), 7.34 (d, 1H). m/z 319 $[M+BnNH+H]^+$ Example 23

Synthesis of 3-oxo-3,4-dihydro-2H-benzo[b][1,4]oxazine-7-sulfonyl chloride

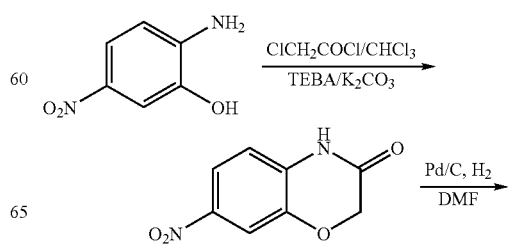

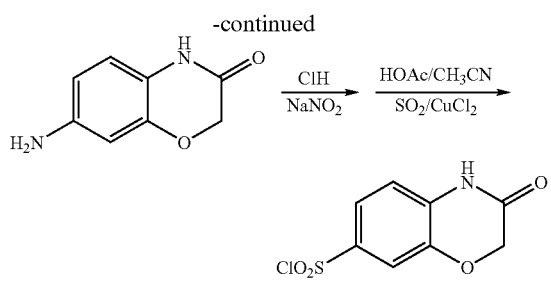

1. Synthesis of 7-amino-2H-benzo[b][1,4]oxazin-3(4H)-one

Into 500 mL 3-necked round bottom flask was added a solution of 7-nitro-2H-benzo[b][1,4]oxazin-3(4H)-one (12 g, 61.86 mmol) in DMF (150 mL). To the mixture was added Pd/C (5 g) followed by addition of hydrogen gas. The resulting solution was allowed to react, with stirring, overnight while the temperature was maintained at room temperature. The reaction progress was monitored by TLC (ethyl acetate/petroleum ether=1:1). A filtration was performed. The filtrate was concentrated by evaporation under vacuum using a rotary evaporator. The product was precipitated by the addition of $H_2O$. A filtration was performed. The filter cake was washed 3 times with 300 mL of hexane. This resulted in 7.3 g (68%) of 7-amino-2H-benzo[b][1,4]oxazin-3(4H)-one as a yellow solid.

2. Synthesis of 3-oxo-3,4-dihydro-2H-benzo[b][1,4]oxazine-7-sulfonyl chloride Into a 500 mL 3-necked round bottom flask was placed a solution of 7-amino-2H-benzo[b][1,4]oxazin-3(4H)-one (5 g, 28.96 mmol) in $CH_3CN$ (200 mL). To the above was added acetic acid (24.9 g) dropwise with stirring, while cooling to a temperature of 0° C. To the above was added HCl (16.2 g) dropwise with stirring, while cooling to a temperature of 0° C. This was followed by the addition of a solution of $NaNO_2$ (2.52 g, 36.52 mmol) in $H_2O$ (2 mL), which was added dropwise with stirring, while cooling to a temperature of 0° C. The resulting solution was allowed to react, with stirring, for 30 minutes while the temperature was maintained at 0-5° C. in a bath of $H_2O$/ice. This was followed by and maintained with an atmosphere of sulfur dioxide, the resulting solution was allowed to react, with stirring, for an additional 2 hours while the temperature was maintained at 0-5° C. in a bath of $H_2O$/ice. To the mixture was added $CuCl_2.2H_2O$ (5.11 g, 29.97 mmol), while cooling to a temperature of 0-5° C. The resulting solution was allowed to react, with stirring, maintained with an atmosphere of sulfur dioxide for an additional 2 hours while the temperature was maintained at 0-5° C. in a bath of $H_2O$/ice. The resulting solution was allowed to react, with stirring, overnight while the temperature was maintained at room temperature. The reaction progress was monitored by TLC (petroleum ether/ethyl acetate=1:1). The reaction mixture was then quenched by the adding 200 mL of $H_2O$/ice. The resulting solution was extracted one time with 500 mL of ethyl acetate and the organic layers combined. Then the mixture was washed 3 times with 200 mL of brine. The mixture was dried over $MgSO_4$ and concentrated by evaporation under vacuum using a rotary evaporator. The residue was dissolved in 100 mL of $CH_2Cl_2$. A filtration was performed. The filtrate was concentrated by evaporation under vacuum using a rotary evaporator. This resulted in 0.9 g (11%) of 3-oxo-3,4-dihydro-2H-benzo[b][1,4]oxazine-7-sulfonyl chloride as a yellow solid. $^1$HNMR (400 MHz, $CDCl_3$) δ 4.73 (s, 2H), 7.00 (m, 1H), 7.28 (d, 1H), 7.71 (d, 1H), 8.27 (s, 1H).

Example 24

Assays for determining $5HT_6$ receptor activity, and selectivity of $5HT_6$ receptor activity are known within the art (see. e.g., Example 58 of U.S. Pat. No. 6,903,112).

The assay protocol for determining $5\text{-}HT_6$ receptor activity generally entailed the incubation of membrane homogenates prepared from HeLa cells expressing the human 5-HT6 receptor with the radioligand $^3$H-lysergic acid diethylamide ($^3$H-LSD) at a concentration of 1.29 nM. Concentrations ranging from $10^{-10}$ M to $10^{-5}$ M of test compound were incubated with the radioligand and the membrane homogenates. After 60 minutes incubation at 37° C. the reaction was terminated by vacuum filtration. The filters were washed with buffer and were counted for radioactivity using a liquid scintillation counter. The affinity of the test compound was calculated by determining the amount of the compound necessary to inhibit 50% of the binding of the radioligand to the receptor. Ki values were determined based upon the following equation:

$$K_i = IC_{50}/(1 + L/K_D)$$

where L is the concentration of the radioligand used and $K_D$ is the dissociation constant of the ligand for the receptor (both expressed in nM).

Compounds of the invention show 5-HT6 binding activity with receptor Ki values of typically less than 1-100 nM. In addition, compounds of the invention show 5-HT6 functional activity with pA2 values of greater than 6 ($IC_{50}$ less than 1 μM).

In terms of selectivity, affinity for other serotonin receptors, specifically the 5-HT1A, 5-HT1B, 5-HT1D, 5-HT2A, 5-HT2B, 5-HT2C, 5-HT5A, and 5HT7 receptors, is expressed as the amount (in percent) of binding of the radioligand that is inhibited in the presence of 100 nM test compound. A lower percent inhibition indicates lower affinity for the serotonin receptor. Selected compounds show a percent inhibition of less than 50% for other serotonin receptors. In one embodiment, the compounds show a percent inhibition of less than 25% for other serotonin receptors The preceding procedures and examples can be repeated with similar success by substituting the generically or specifically described reactants and/or operating conditions of this invention for those used in the preceding procedures and examples.

While the invention has been illustrated with respect to the production and of particular compounds, it is apparent that variations and modifications of the invention can be made without departing from the spirit or scope of the invention. Upon further study of the specification, further aspects, objects and advantages of this invention will become apparent to those skilled in the art.

We claim:
1. A compound of formula I:

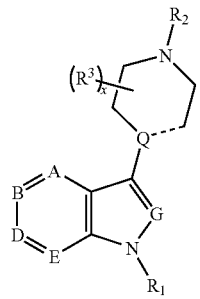

wherein
A, B, D, E and G, are each independently CH, or $CR^4$;
----- represents a single bond or a double bond;
Q is C when ---- is a double bond, and Q is CH or N when ----- is a single bond;
x is 0, 1, 2, 3, or 4;
$R^1$ is $SO_2Ar$, wherein
Ar is selected from formulas (a)-(i) and (k)-(r):

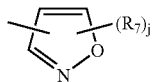 (g)

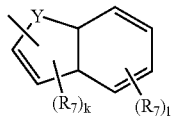 (h)

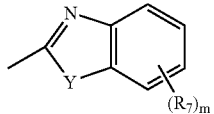 (i)

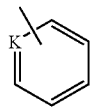 (j)

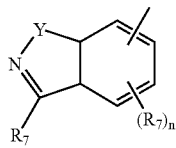 (k)

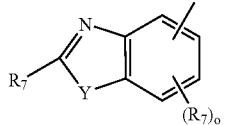 (l)

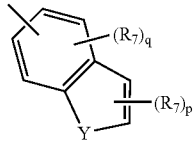 (m)

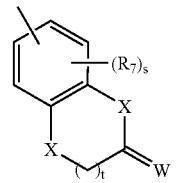 (n)

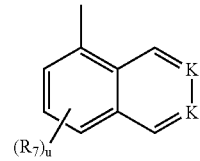 (o)

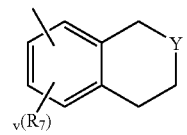 (p)

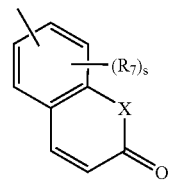 (q)

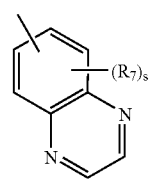 (r)

wherein
formula (a) is substituted at least by a substitued or unsubstituted heterocyclic group;
J is $CR^7$ or N;
in formula (o), one K is N and the other is CH;
W is O, S, or is absent;
X is, in each instance independently, O or $NR^7$;
Y is O, $NR^7$ or S;
Z is S or $NR^7$;
a is 1, 2, 3, 4 or 5;
b, l, m and v are independently 0, 1, 2, 3 or 4;
c, f, h, n, o, q, s, and u are independently 0, 1, 2 or 3;
d, and e are independently 1, 2 or 3;
g, i, j, and p are independently 0, 1 or 2;
k and t are 0 or 1;
$R^2$ is H or alkyl having 1 to 8 carbon atoms, cycloalkyl having 3 to 12 carbon atoms, or cycloalkylalkyl having 4 to 12 carbon atoms, each of which is branched or unbranched and each of which is unsubstituted or substituted one or more times with halogen, $C_{1-4}$-alkyl, $C_{1-4}$-alkoxy, oxo, or any combination thereof;
$R^3$ is H or alkyl having 1 to 8 carbon atoms, which is unsubstituted or substituted one or more times by halogen, $C_{1-4}$-alkyl, $C_{1-4}$-alkoxy, oxo, or any combination thereof;
$R^4$ is halogen, nitro, alkyl having 1 to 8 carbon atoms, cycloalkyl having 3 to 12 carbon atoms, or cycloalkylalkyl having 4 to 12 carbon atoms, each of which is branched or unbranched and which is unsubstituted or substituted one or more times with halogen, $C_{1-4}$-alkyl, $C_{1-4}$-alkoxy, oxo, or any combination thereof,
an alkoxy having 1 to 8 carbon atoms, or
a heterocyclic group, which is saturated, partially saturated or unsaturated, having 5 to 10 ring atoms in which at least 1 ring atom is an N, O or S atom, which is unsubstituted or substituted one or more times by halogen, hydroxy, $C_{5-7}$-aryl, $C_{1-4}$-alkyl, $C_{1-4}$-alkoxy, cyano, halogenated alkyl, nitro, or any combination thereof, $R^5$ is amino, $C_{1-4}$-alkylamino, $C_{1-4}$-dialkylamino, $NR^6C(O)R^8$,
a heterocyclic group, which is saturated, partially saturated or unsaturated, having 5 to 10 ring atoms in which at least 1 ring atom is an N, O or S atom, which is unsubstituted or substituted one or more times by halogen, hydroxy, $C_{5-7}$-aryl, $C_{1-4}$-alkyl, $C_{1-4}$-alkoxy, cyano, halogenated $C_{1-4}$-alkyl, or —O—Ar', wherein Ar' is an $C_{5-7}$-aryl;

$R^6$ is H or alkyl having 1 to 8 carbon atoms, which is branched or unbranched and which is unsubstituted or substituted one or more times with halogen, $C_{1-4}$-alkyl, $C_{1-4}$-alkoxy, oxo, or any combination thereof;

$R^7$ is, in each instance, independently H, halogen $C(O)R^8$, $CO_2R^8$, $NR^6COR^8$, an alkyl having 1 to 12 carbon atoms, which is branched or unbranched and which is unsubstituted or substituted one or more times by halogen, hydroxy, cyano, $C_{1-4}$-alkoxy, oxo or any combination thereof, and wherein optionally one or more —$CH_2CH_2$— groups is replaced in each instance by —CH=CH— or —C≡C—,
alkoxy having 1 to 8 carbon atoms, which is branched or unbranched and which is unsubstituted or substituted one or more times by halogen,
cycloalkyl having 3 to 10 carbon atoms, which is unsubstituted or substituted one or more times by halogen, hydroxy, oxo, cyano, $C_{1-4}$-alkyl, $C_{1-4}$-alkoxy, or any combination thereof,
cycloalkylalkyl having 4 to 16 carbon atoms, which is unsubstituted or substituted in the cycloalkyl portion and/or the alkyl portion one or more times by halogen, oxo, cyano, hydroxy, $C_{1-4}$-alkyl, $C_{1-4}$-alkoxy or any combination thereof,
aryl having 6 to 14 carbon atoms, which is unsubstituted or substituted one or more times by halogen, $CF_3$, $OCF_3$, $C_{1-4}$-alkyl, hydroxy, $C_{1-4}$-alkoxy, nitro, methylenedioxy, ethylenedioxy, cyano, or any combination thereof,
arylalkyl in which the aryl portion has 6 to 14 carbon atoms and the alkyl portion, which is branched or unbranched, has 1 to 5 carbon atoms, wherein the arylalkyl radical is unsubstituted, substituted in the aryl portion one or more times by halogen, $CF_3$, $OCF_3$, $C_{1-4}$-alkyl, hydroxy, $C_{1-4}$-alkoxy, nitro, cyano, methylenedioxy, ethylenedioxy, or any combination thereof, and/or substituted in the alkyl portion one or more times by halogen, oxo, hydroxy, cyano, or any combination thereof, and wherein in the alkyl portion one or more —$CH_2CH_2$— groups are each optionally replaced by —CH=CH— or —C≡C—, and one or more —$CH_2$— groups are each optionally replaced by —O— or —NH—,
a heterocyclic group, which is saturated, partially saturated or unsaturated, having 5 to 10 ring atoms in which at least 1 ring atom is an N, O or S atom, which is unsubstituted or substituted one or more times by halogen, hydroxy, $C_{5-7}$-aryl, $C_{1-4}$-alkyl, $C_{1-4}$-alkoxy, cyano, trifluoromethyl, nitro, oxo, or any combination thereof, or
a heterocycle-alkyl group, wherein the heterocyclic portion is saturated, partially saturated or unsaturated, and has 5 to 10 ring atoms in which at least 1 ring atom is an N, O or S atom, and the alkyl portion is branched or unbranched and has 1 to 5 carbon atoms, the heterocycle-alkyl group is unsubstituted, substituted one or more times in the heterocyclic portion by halogen, $OCF_3$, hydroxy, $C_{5-7}$-aryl, $C_{1-4}$-alkyl, $C_{1-4}$-alkoxy, cyano, trifluoromethyl, nitro, oxo, or any combination thereof, and/or substituted in the alkyl portion one or more times by halogen, oxo, hydroxy, cyano, or any combination thereof, and wherein in the alkyl portion one or more —$CH_2CH_2$— groups are each optionally replaced by —CH=CH— or —C≡C—, and one or more —$CH_2$— groups are each optionally replaced by —O— or —NH—;

$R^8$ is in each instance, independently, H or alkyl having 1 to 8, carbon atoms carbon atoms, which is branched or unbranched and which is unsubstituted or substituted one or more times by halogen;

or a pharmaceutically acceptable salt thereof;
with the following provisos:
(i) when A, B, D, E and G are CH, and Ar is represented by forumula (b), and each X is O, then d is 3;
(ii) said compound is not:
1-[(4-aminophenyl)sulfonyl]-5-nitro-3-(1,2,3,6-tetrahydro-4-pyridinyl)-1H indole,
1-[(4-aminophenyl)sulfonyl]-5-bromo-3-(1,2,3,6-tetrahydro-4-pyridinyl)-1H indole,
1-[(4-aminophenyl)sulfonyl]-5-fluoro-3-(1,2,3,6-tetrahydro-4-pyridinyl)-1H indole,
1-[(4-aminophenyl)sulfonyl]-6-chloro-3-(1,2,3,6-tetrahydro-4-pyridinyl)-1H indole,
1-[(4-aminophenyl)sulfonyl]-6-nitro-3-(1,2,3,6-tetrahydro-4-pyridinyl)-1H indole,
1-[(4-aminophenyl)sulfonyl]-3-(1,2,3,6-tetrahydro-4-pyridinyl)-1H indole,
5-(4-methyl-2-thiazolyl)-1-(phenylsulfonyl)-3-(1,2,3,6-tetrahydro-4-pyridinyl)-1H indole,
1-[(4-aminophenyl)sulfonyl]-5-fluoro-3-(4-piperidinyl)-1H indole,
1-[(4-aminophenyl)sulfonyl]-6-chloro-3-(4-piperidinyl)-1H indole, or
3,6-dihydro-4-[5(4-methyl-2-thiazolyl)-1-(phenylsulfonyl)-1H-indol-3-yl)-1,1-dimethylethylester.

2. The compound of claim 1, wherein $R_2$ is H.

3. The compound of claim 1, wherein ----- represents a single bond and Q is CH or N.

4. The compound of claim 1, wherein Ar is (a).

5. The compound of claim 1, wherein Ar is (c).

6. The compound of claim 1, wherein Ar is (k).

7. The compound of claim 1, wherein Ar is (n).

8. The compound of claim 7, wherein Ar is

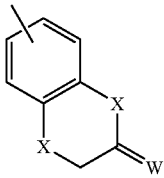

wherein W is O or is absent and X is, in each instance independently, O, NH, or N—CH$_3$.

9. The compound of claim 1, wherein
Q is N,
A, B, and D are CH,
E is CH,
R$_2$ is H or CH$_3$,
R$_3$ is H, and
R$^1$ is SO$_2$Ar wherein Ar is a heterocycle selected from formulas (a), (c) and (n).

10. The compound of claim 1, wherein
A, D, and E are CH,
B is CR$^4$ and R$^4$ is F
R$^1$ is SO$_2$Ar wherein Ar is a heterocycle having the formula (o),
R$_2$ is H or CH$_3$, and
R$_3$ is H.

11. The compound of claim 1, wherein
Q is N
A, B, D, E and G are CH,
R$^1$ is SO$_2$Ar wherein Ar is 2H-benzo[b][1,4]oxazin-3(4H)-one,
R$_2$ is H,
R$_3$ is H, and
----- represents a single bond.

12. The compound of claim 1, wherein the compound is selected from the group consisting of:
1-(2,3-dihydro-1-benzofuran-5-ylsulfonyl)-3-(1-methyl-1,2,3,6-tetrahydropyridin -4-yl)-1H-indole,
1-(2,3-dihydro-1-benzofuran-5-ylsulfonyl)-5-fluoro-3-(1-methyl-1,2,3,6-tetrahydropyridin-4-yl)-1H-indole,
1-(2,3-dihydro-1-benzofuran-5-ylsulfonyl)-3-(1-methyl-1,2,3,6-tetrahydropyridin -4-yl)-5-(trifluoromethyl)-1H-indole,
1-(3,4-dihydro-2H-1,5-benzodioxepin-7-ylsulfonyl)-3-(1-methyl-1,2,3,6-tetrahydropyridin-4-yl)-1H-indole,
1-(3,4-dihydro-2H-1,5-benzodioxepin-7-ylsulfonyl)-5-fluoro-3-(1-methyl-1,2,3,6-tetrahydropyridin-4-yl)-1H-indole,
1-(3,4-dihydro-2H-1,5-benzodioxepin-7-ylsulfonyl)-3-(1-methyl-1,2,3,6-tetrahydropyridin-4-yl)-5-(trifluoromethyl)-1H-indole,
1-[(4-methyl-2-phenyl-1,3-thiazol-5-yl)sulfonyl]-3-(1-methyl-1,2,3,6-tetrahydropyridin-4-yl)-1H-indole,
5-fluoro-1-[(4-methyl-2-phenyl-1,3-thiazol-5-yl)sulfonyl]-3-(1-methyl-1,2,3,6-tetrahydropyridin-4-yl)-1H-indole,
1-[(4-methyl-2-phenyl-1,3-thiazol-5-yl)sulfonyl]-3-(1-methyl-1,2,3,6-tetrahydropyridin-4-yl)-5-(trifluoromethyl)-1H-indole, and
1-[(5-methyl-1-phenyl-1H-pyrazol-4-yl)sulfonyl]-3-(1-methyl-1,2,3,6-tetrahydropyridin-4-yl)-1H-indole,
or a pharmaceutically acceptable salt thereof.

13. The compound of claim 1, wherein the compound is 7-[(3-piperazin-1-yl-1H-indol-1-yl)sulfonyl]-2H-1,4-benzoxazin-3(4H)-one or a pharmaceutically acceptable salt thereof.

14. The compound of claim 1, wherein the compound is 4-methyl-7-[(3-piperazin-1-yl-1H-indol-1-yl)sulfonyl]-3,4-dihydro-2H-1,4-benzoxazine or a pharmaceutically acceptable salt thereof.

15. A pharmaceutical compositon comprising a therapeutically effective amount of the compound of formula I:

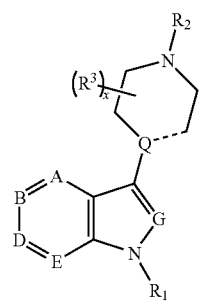

(I)

wherein

A, B, D, E and G, are each independently CH or CR$^4$;

----- represents a single bond or a double bond;

Q is C when ---- is a double bond, and Q is CH or N when ----- is a single bond;

x is 0, 1, 2, 3, or 4;

R$^1$ is SO$_2$Ar, wherein

Ar is selected from formulas (a)-(i) and (k)-(r):

(a)

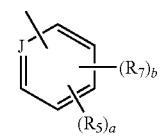

(b)

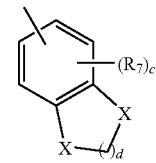

(c)

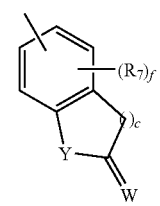

(d)

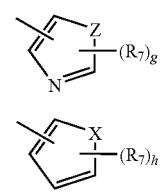

(e)

-continued (f)
(g)
(h)
(i)
(k)
(l)
(m)
(n)
(o)
(p)
(q)

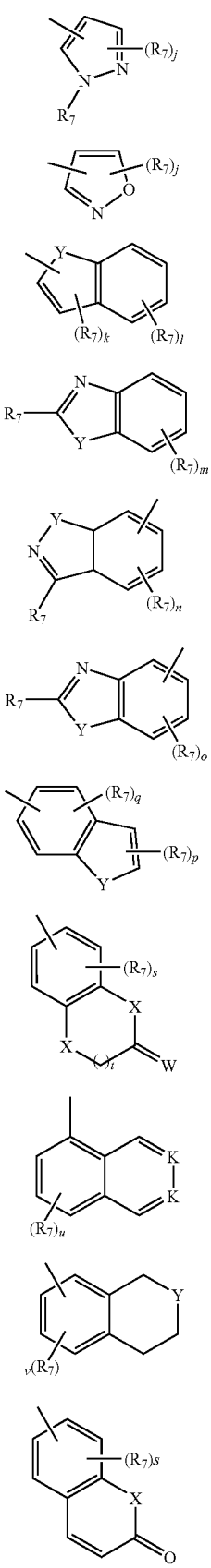

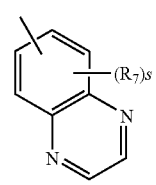

(r)

wherein
formula (a) is substituted at least once by a substituted or unsubstituted heterocyclic group;
J is $CR^7$ or N;
in formula (o), one K is N and the other is CH;
W is O, S, or is absent;
X is, in each instance independently, O or $NR^7$;
Y is O, $NR^7$ or S;
Z is S or $NR^7$;
a is 1, 2, 3, 4 or 5;
b, l, m and v are independently 0, 1, 2, 3 or 4;
c, f, h, n, o, q, s, and u are independently 0, 1, 2 or 3;
d, and e are independently 1, 2 or 3;
g, i, j, and p are independently 0, 1 or 2;
k and t are 0 or 1;
$R_2$ is H or alkyl having 1 to 8 carbon atoms, cycloalkyl having 3 to 12 carbon atoms, or cycloalkylalkyl having 4 to 12 carbon atoms, each of which is branched or unbranched and each of which is unsubstituted or substituted one or more times with halogen, $C_{1-4}$-alkyl, $C_{1-4}$-alkoxy, oxo, or any combination thereof;
$R_3$ is H is H or alkyl having 1 to 8 carbon atoms, which is unsubstituted or substituted one or more times by halogen, $C_{1-4}$-alkyl, $C_{1-4}$-alkoxy, oxo, or any combination thereof;
$R_4$ is halogen, nitro, alkyl having 1 to 8 carbon atoms, cycloalkyl having 3 to 12 carbon atoms, or cycloalkylalkyl having 4 to 12 carbon atoms, each of which is branched or unbranched and wherein the alkyl, cycloalkyl or cycloalkylalkyl is unsubstituted or substituted one or more times with halogen, $C_{1-4}$-alkyl, $C_{1-4}$-alkoxy oxo, or any combination thereof,
an alkoxy having 1 to 8 carbon atoms, or
a heterocyclic group, which is saturated, partially saturated or unsaturated, having 5 to 10 ring atoms in which at least 1 ring atom is an N, O or S atom, which is unsubstituted or substituted one or more times by halogen, hydroxy, $C_{5-7}$-aryl, $C_{1-4}$-alkyl, $C_{1-4}$-alkoxy, cyano, halogenated alkyl, nitro, or any combination thereof,
$R_5$ is amino, $C_{1-4}$-alkylamino, $C_{1-4}$-dialkylamino, $NR^6C(O)R^8$, a heterocyclic group, which is saturated, partially saturated or unsaturated, having 5 to 10 ring atoms in which at least 1 ring atom is an N, O or S atom, which is unsubstituted or substituted one or more times by halogen, hydroxy, $C_{5-7}$-aryl, $C_{1-4}$-alkyl, $C_{1-4}$-alkoxy, cyano, halogenated $C_{1-4}$-alkyl, or —O—Ar', wherein Ar' is an $C_{5-7}$-aryl;
$R_6$ is H or alkyl having 1 to 8 carbon atoms, which is branched or unbranched and which is unsubstituted or substituted one or more times with halogen, $C_{1-4}$-alkyl, $C_{1-4}$-alkoxy, oxo, or any combination thereof;
$R_7$ is, in each instance, independently H, halogen $C(O)R^8$, $CO_2R^8$, $NR^6COR^8$, an alkyl having 1 to 12 carbon atoms, which is branched or unbranched and which is unsubstituted or substituted one or more times by halogen, hydroxy, cyano, $C_{1-4}$alkoxy, oxo or any combination thereof, and wherein optionally one or more —CH$_2$CH$_2$— groups is replaced in each instance by —CH=CH— or —C≡C—, alkoxy having 1 to 8 carbon atoms, which is branched or unbranched and which is unsubstituted or substituted one or more times by halogen, cycloalkyl having 3 to 10 carbon atoms, which is unsubstituted or substituted one or more times by halogen, hydroxy, oxo, cyano, C$_{1-4}$-alkyl, C$_{1-4}$-alkoxy, or any combination thereof, cycloalkylalkyl having 4 to 16 carbon atoms, which is unsubstituted or substituted in the cycloalkyl portion and/or the alkyl portion one or more times by halogen, oxo, cyano, hydroxy, C$_{1-4}$-alkyl, C$_{1-4}$-alkoxy or any combination thereof, aryl having 6 to 14 carbon atoms, which is unsubstituted or substituted one or more times by halogen, CF$_3$, OCF$_3$, C$_{1-4}$-alkyl, hydroxy, C$_{1-4}$-alkoxy, nitro, methylenedioxy, ethylenedioxy, cyano, or any combination thereof, arylalkyl in which the aryl portion has 6 to 14 carbon atoms and the alkyl portion, which is branched or unbranched, has 1 to 5 carbon atoms, wherein the arylalkyl radical is unsubstituted, substituted in the aryl portion one or more times by halogen, CF$_3$, OCF$_3$, C$_{1-4}$-alkyl, hydroxy, C$_{1-4}$-alkoxy, nitro, cyano, methylenedioxy, ethylenedioxy, or any combination thereof, and/or substituted in the alkyl portion one or more times by halogen, oxo, hydroxy, cyano, or any combination thereof and wherein in the alkyl portion one or more —CH$_2$CH$_2$— groups are each optionally replaced by —CH=CH— or —C≡C—, and one or more —CH$_2$— groups are each optionally replaced by —O— or —NH—, a heterocyclic group, which is saturated, partially saturated or unsaturated, having 5 to 10 ring atoms in which at least 1 ring atom is an N, O or S atom, which is unsubstituted or substituted one or more times by halogen, hydroxy, C$_{5-7}$-aryl, C$_{1-4}$-alkyl, C$_{1-4}$-alkoxy, cyano, trifluoromethyl, nitro, oxo, or any combination thereof, or a heterocycle-alkyl group, wherein the heterocyclic portion is saturated, partially saturated or unsaturated, and has 5 to 10 ring atoms in which at least 1 ring atom is an N, O or S atom, and the alkyl portion is branched or unbranched and has 1 to 5 carbon atoms, the heterocycle-alkyl group is unsubstituted, substituted one or more times in the heterocyclic portion by halogen, OCF$_3$, hydroxy, C$_{5-7}$-aryl, C$_{1-4}$-alkyl, C$_{1-4}$-alkoxy, cyano, trifluoromethyl, nitro, oxo, or any combination thereof, and/or substituted in the alkyl portion one or more times by halogen, oxo, hydroxy, cyano, or any combination thereof, and wherein in the alkyl portion one or more —CH$_2$CH$_2$— groups are each optionally replaced by —CH=CH— or —C≡C—, and one or more —CH$_2$— groups are each optionally replaced by —O— or —NH—, R$_5$ is in each instance, independently, H or alkyl having 1 to 8, carbon atoms carbon atoms, which is branched or unbranched and which is unsubstituted or substituted one or more times by halogen;

or a pharmaceutically acceptable salt thereof;

with the following provisos:

(i) when A, B, D, B and G are CH, and Ar is represented by formula (b), and each X is O, then d is 3;

(ii) said compound is not:
1-[(4-aminophenyl)sulfonyl]-5-nitro-3-(1,2,3,6-tetrahydro-4-pyridinyl)-1H indole,
1-[(4-aminophenyl)sulfonyl]-5-bromo-3-(1,2,3,6-tetrahydro-4-pyridinyl)-1H indole,
1-[(4-aminophenyl)sulfonyl]-5-fluoro-3-(1,2,3,6-tetrahydro-4-pyridinyl)-1H indole,
1-[(4-aminophenyl)sulfonyl]-6-chloro-3-(1,2,3,6-tetrahydro-4-pyridinyl)-1H indole,
1-[(4-aminophenyl)sulfonyl]-6-nitro-3-(1,2,3,6-tetrahydro-4-pyridinyl)-1H indole,
1-[(4-aminophenyl)sulfonyl]-3-(1,2,3,6-tetrahydro-4-pyridinyl)-1H indole,
5-(4-methyl-2-thiazolyl)-1-(phenylsulfonyl)-3-(1,2,3,6-tetrahydro-4-pyridinyl)-1H indole,
1-[(4-aminophenyl)sulfonyl]-5-fluoro-3-(4-piperidinyl)-1H indole,
1-[(4-aminophenyl)sulfonyl]-6-chloro-3-(4-piperidinyl)-1H indole, or
3,6-dihydro-4-[5(4-methyl-2-thiazolyl)-1-(phenylsulfonyl)-1H-indol-3-yl)-1,1-dimethylethylester, and a pharmaceutically acceptable carrier.

16. A compound of formula I:

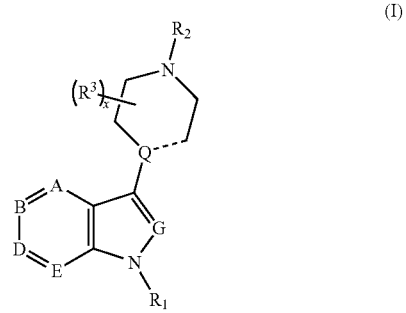

(I)

wherein

A, B, D, E and G, are each independently CH or CR$^4$;

at least one of A, B, D, or E is CR$^4$, where R$^4$ is a substituted or unsubstituted heterocyclic group;

----- represents a single bond or a double bond;

Q is C when ---- is a double bond, and Q is CH or N when ----- is a single bond;

x is 0, 1, 2, 3, or 4;

R$^1$ is SO$_2$Ar, wherein

Ar is unsubstituted phenyl or unsubstituted pyridinyl;

R$_2$ is H or alkyl having 1 to 8 carbon atoms, cycloalkyl having 3 to 12 carbon atoms, or cycloalkylalkyl having 4 to 12 carbon atoms, each of which is branched or unbranched and each of which is unsubstituted or substituted one or more times with halogen, C$_{1-4}$-alkyl, C$_{1-4}$-alkoxy oxo, or any combination thereof;

R$_3$ is H or alkyl having 1 to 8 carbon atoms, which is unsubstituted or substituted one or more times by halogen, C$_{1-4}$-alkyl, C$_{1-4}$-alkoxy, oxo, or any combination thereof; and R$^4$ is halogen, nitro, alkyl having 1 to 8 carbon atoms, cycloalkyl having 3 to 12 carbon atoms, or cycloalkylalkyl having 4 to 12 carbon atoms, each of which is branched or unbranched and which is unsubstituted or substituted one or more times with halogen, C$_{1-4}$-alkyl, C$_{1-4}$-alkoxy, oxo, or any combination thereof, an alkoxy having 1 to 8 carbon atoms, or a heterocyclic group, which is saturated, partially saturated or unsaturated, having 5 to 10 ring atoms in which at least 1 ring atom is an N, O or S atom, which is unsubstituted or substituted one or more times by halogen, hydroxy, $C_{5-7}$-aryl, $C_{1-4}$-alkyl, $C_{1-4}$-alkoxy cyano, halogenated alkyl, nitro, or any combination thereof, or a pharmaceutically acceptable salt thereof;
with the proviso that the compound is not
  5-(4-methyl-2-thiazolyl)-1-(phenylsulfonyl)-3-(1,2,3,6-tetrahydro-4-pyridinyl)-1H indole, or
  3,6-dihydro-4-[5(4-methyl-2-thiazolyl)-1-(phenylsulfonyl)-1H-indol-3-yl]-1,1-dimethylethylester.

17. The compound of claim 1, wherein the compound is selected from the group consisting of:
  5-fluoro-1-[(5-methyl-1-phenyl-1H-pyrazol4-yl)sulfonyl]-3-(1-methyl-1,2,3,6-tetrahydropyridin-4-yl)-1H-indole,
  1-[(5-methyl-1-phenyl-1H-pyrazol-4-yl)sulfonyl]-3-(1-methyl-1,2,3,6-tetrahydropyridin -4-yl)-5-(trifluoromethyl)-1H-indole,
  1-(1-benzothien-2-ylsulfonyl)-3-(1-methyl-1,2,3,6-tetrahydropyridin-4-yl)-1H-indole,
  1-(1-benzothien-2-ylsulfonyl)-5-fluoro-3-(1-methyl-1,2,3,6-tetrahydropyridin-4-yl)-1H -indole,
  1-(1-benzothien-2-ylsulfonyl)-3-(1-methyl-1,2,3,6-tetrahydropyridin-4-yl)-5-(trifluoromethyl)-1H-indole,
  3-(1-methyl-1,2,3,6-tetrahydropyridin-4-yl)-1-{[1-methyl-3-(trifluoromethyl)-1H -pyrazol-4-yl]sulfonyl}-1H-indole,
  5-fluoro-3-(1-methyl-1,2,3,6-tetrahydropyridin-4-yl)-1-{[1-methyl-3-(trifluoromethyl)-1H-pyrazol-4-yl]sulfonyl}-1H-indole,
  3-(1-methyl-1,2,3,6-tetrahydropyridin-4-yl)-1-{[1-methyl-3-(trifluoromethyl)-1H -pyrazol-4-yl]sulfonyl}-5-(trifluoromethyl)-1H-indole,
  Methyl 5-{[3-(1-methyl-1,2,3,6-tetrahydropyridin-4-yl)-1H-indol-1-yl]sulfonyl}-2-furoate, and
  Methyl 5-{[5-fluoro-3-(1-methyl-1,2,3,6-tetrahydropyridin-4-yl)-1H-indol-1-yl]sulfonyl}-2-furoate,
or a pharmaceutically acceptable salt thereof.

18. The compound of claim 1, wherein the compound is selected from the group consisting of:
  Methyl 5-{[3-(1-methyl-1,2,3,6-tetrahydropyridin-4-yl)-5-(trifluoromethyl)-1H-indol-1-yl]sulfonyl}-2-furoate,
  1[(1-methyl-1H-imidazol-4-yl)sulfonyl]-3-(1-methyl-1,2,3,6-tetrahydropyridin-4-yl) -1H-indole,
  5-fluoro-1-[(1-methyl-1H-imidazol-4-yl)sulfonyl]-3-(1-methyl-1,2,3,6-tetrahydropyridin-4-yl)-1H-indole,
  1-[(1-methyl-1H-imidazol-4-yl)sulfonyl]-3-(1-methyl-1,2,3,6-tetrahydropyridin-4-yl)-5-(trifluoromethyl) 1H-indole,
  1-[(2,5-dimethyl-3-furyl)sulfonyl]-3-(1-methyl-1,2,3,6-tetrahydropyridin-4-yl)-1H -indole,
  1-[(2,5-dimethyl-3-furyl)sulfonyl]-5-fluoro-3-(1-methyl-1,2,3,6-tetrahydropyridin-4-yl)-1H-indole,
  1-[(2,5-dimethyl-3-furyl)sulfonyl]-3-(1-methyl-1,2,3,6-tetrahydropyridin-4-yl)-5-(trifluoromethyl)-1H-indole,
  1-(1-benzothien-3-ylsulfonyl)-3-(1-methyl-1,2,3,6-tetrahydropyridin-4-yl)-1H-indole,
  1-(1-benzothien-3-ylsulfonyl)-5-fluoro-3-(1-methyl-1,2,3,6-tetrahydropyridin-4-yl)-1H -indole, and
  1-(1-benzothien-3-ylsulfonyl)-3-(1-methyl-1,2,3,6 -tetrahydropyridin-4-yl)-5-(trifluoromethyl)-1H-indole,
or a pharmaceutically acceptable salt thereof.

19. the compound of claim 1, wherein the compound is selected from the group consisting of:
  1-(1-benzofuran-2-ylsulfonyl)-3-(1-methyl-1,2,3,6-tetrahydropyridin-4-yl)-1H-indole,
  1-(1-benzofuran-2-ylsulfonyl)-5-fluoro-3-(1-methyl-1,2,3,6-tetrahydropyridin-4-yl)-1H -indole,
  1-(1-benzofuran-2-ylsulfonyl)-3-(1-methyl-1,2,3,6-tetrahydropyridin-4-yl)-5-(trifluoromethyl-1H-indole,
  1-[(3,5-dimethylisoxazol-4-yl)sulfonyl]-3-(1-methyl-1,2,3,6-tetrahydropyridin-4-yl)-1H-indole,
  1-[(3,5-dimethylisoxazol-4-yl)sulfonyl]-5-fluoro-3-(1-methyl-1,2,3,6-tetrahydropyridin-4-yl)-1H-indole,
  1-[(3,5-dimethylisoxazol-4-yl)sulfonyl]-3-(1-methyl-1,2,3,6-tetrahydropyridin-4-yl)-5-(trifluoromethyl)-1H-indole,
  6-{[3-(1-methyl-1,2,3,6-tetrahydropyridin-4-yl)-1H-indol-1-yl]sulfonyl}-1,3-benzothiazole,
  6-{[5-fluoro-3-(1-methyl-1,2,3,6-tetrahydropyridin-4-yl)-5-(trifluoromethyl)-1H-indol-1-yl]sulfonyl}-1,3-benzothiazole,
  6-{[3-(1-methyl-1,2,3,6-tetrahydropyridin-4-yl)-5-(trifluoromethyl)-1H-indol-1-yl]sulfonyl)}-1,3-benzothiazole, and
  3-(1-methyl-1,2,3,6-tetrahydropyridin-4-yl)-1-[(1,3,5-trimethyl-1H-pyrazol-4-yl)sulfonyl]-1H-indole,
or a pharmaceutically acceptable salt thereof.

20. The compound of claim 1, wherein the compound is selected from the group consisting of:
  5-fluoro-3-(1-methyl-1,2,3,6-tetrahydropyridin-4-yl)-1-[(1,3,5-trimethyl-1H-pyrazol-4-yl)sulfonyl]-1H-indole,
  3-(1-methyl-1,2,3,6-tetrahydropyridin-4-yl)-5-(trifluoromethyl)-1-[(1,3,5-trimethyl-1H -pyrazol-4-yl)sulfonyl]-1H-indole,
  1-[(4-chloro-1,2-dimethyl-1H-pyrrol-3-yl)sulfonyl]-3-(1-methyl-1,2,3,6-tetrahydropyridin-4-yl)-1H-indole,
  1-[(4-chloro-1,2-dimethyl-1H-pyrrol-3-yl)sulfonyl]-5-fluoro-3-(1-methyl-1,2,3,6-tetrahydropyridin-4-yl)-1H-indole,
  1-[(4-chloro-1,2-dimethyl-1H-pyrrol-3-yl)sulfonyl]-3-(1-methyl-1,2,3,6-tetrahydropyridin-4-yl)-5-(trifluoromethyl)-1H-indole,
  1-[(1-acetyl-2,3-dihydro-1H-indol-5-yl)sulfonyl]-3-(1-methyl-1,2,3,6-tetrahydropyridin-4-yl)-1H-indole,
  1-[(1-acetyl-2,3-dihydro-1H-indol-5-yl)sulfonyl]-5-fluoro-3-(1-methyl-1,2,3,6-tetrahydropyridin-4-yl)-1H-indole,
  1-[(1-acetyl-2,3-dihydro-1H-indol-5-yl)sulfonyl]-3-(1-methyl-1,2,3,6-tetrahydropyridin-4-yl)-5-(trifluoromethyl)-1H-indole,
  3-(1-methyl-1,2,3,6-tetrahydropyridin-4-yl)-1-[(6-morpholin-4-ylpyridin-3-yl)sulfonyl]-1H-indole, and
  5-fluoro-3-(1-methyl-1,2,3,6-tetrahydropyridin-4-yl)-1-[(6-morpholin-4-ylpyridin-3-yl)sulfonyl]-1H-indole,
or a pharmaceutically acceptable salt thereof.

21. the compound of claim 1, wherein the compound is selected from the group consisting of:
  3-(1-methyl-1,2,3,6-tetrahydropyridin-4-yl)-1-[(6-morpholin-4-ylpyridin-3-yl)sulfonyl]-5-(trifluoromethyl)-1H-indole,
  1-(2,3-dihydro-1H-indol-5-ylsulfonyl)-3-(1-methyl-1,2,3,6-tetrahydropyridin-4-yl)-1H -indole,
  1-(2,3-dihydro-1H-indol-5-ylsulfonyl)-5-fluoro-3-(1-methyl-1,2,3,6-tetrahydropyridin-4-yl)-1H-indole,
  1-(2,3-dihydro-1H-indol-5-ylsulfonyl)-3-(1-methyl-1,2,3,6-tetrahydropyridin-4-yl)-5-(trifluoromethyl)-1H-indole, 3-(1-methyl-1,2,3,6-tetrahydropyridin-4-yl)-1-[(4-morpholin-4-ylphenyl)sulfonyl]-1H-indole, 5-fluoro-3-(1-methyl-1,2,3,6-tetrahydropyridin-4-yl)-1-[(4-morpholin-4-ylphenyl)sulfonyl]-1H-indole, 3-(1-methyl-1,2,3,6-tetrahydropyridin-4-yl)-1-[(4-morpholin-4-ylphenyl)sulfonyl]-5-(trifluoromethyl)-1H-indole, 1-[(1-methyl-2,3-dihydro-1H-indol-6-yl)sulfonyl]-3-(1-methyl-1,2,3,6-tetrahydropyridin-4-yl)-1H-indole, 5-fluoro-1-[(1-methyl-2,3-dihydro-1H-indol-6-yl)sulfonyl]-3-(1-methyl-1,2,3,6-tetrahydropyridin-4-yl)-1H-indole, and 1-[(1-methyl-2,3-dihydro-1H-indol-6-yl)sulfonyl]-3-(1-methyl-1,2,3,6-tetrahydropyridin-4-yl)-5-(trifluoromethyl)-1H-indole, or a pharmaceutically acceptable salt thereof.

22. The compound of claim 1, wherein the compound is selected from the group consisting of:

1-[(1-ethyl-2,3-dihydro-1H-indol-6-yl)sulfonyl]-3-(1-methyl-1,2,3,6-tetrahydropyridin-4-yl)-1H-indole, 1-[(1-ethyl-2,3-dihydro-1H-indol-6-yl)sulfonyl]-5-fluoro-3-(1-methyl-1,2,3,6-tetrahydropyridin-4-yl)-1H-indole, 1-[(1-ethyl-2,3-dihydro-1H-indol-6-yl)sulfonyl]-3-(1-methyl-1,2,3,6-tetrahydropyridin-4-yl)-5-(trifluoromethyl 1H-indole, 7-{[3-(1-methyl-1,2,3,6-tetrahydropyridin-4-yl)-1H-indol-1-yl]sulfonyl}-1,2,3,4-tetrahydroquinoline, 7-{[5-fluoro-3-(1-methyl-1,2,3,6-tetrahydropyridin-4-yl)-1H-indol-1-yl]sulfonyl}-1,2,3,4-tetrahydroquinoline, -yl]sulfonyl}-1,2,3,4-tetrahydroquinoline, 7-{[3-(1-methyl-1,2,3,6-tetrahydropyridin-4-yl)-5-yl]sulfonyl}-1,2,3,4-tetrahydroquinoline, 1-methyl-7-{[3-(1-methyl-1,2,3,6-tetrahydropyridin-4-yl)-1H-indol-1-yl]sulfonyl}-1,2,3,4-tetrahydroquinoline, 7-{[3-(1-methyl-1,2,3,6-tetrahydropyridin-4-yl)-1H-indol-1-yl]sulfonyl}-1-methyl-1,2,3,4-tetrahydroquinoline, 1-methyl-7-{[3-(1-methyl-1,2,3,6-tetrahydropyridin-4-yl)-5-(trifluoromethyl)-1H-indol-1-yl]sulfonyl}-1,2,3,4-tetrahydroquinoline, and 1-methyl-6-{[3-(1-methyl-1,2,3,6-tetrahydropyridin-4-yl)-1H-indol-1-yl]sulfonyl}-1,2,3,4-tetrahydroquinoline, or a pharmaceutically acceptable salt thereof.

23. The compound of claim 1, wherein the compound is selected from the group consisting of:

6-{[5-fluoro-3-(1-methyl-1,2,3,6-tetrahydropyridin-4-yl)-1H-indol-1-yl]sulfonyl}-1-methyl-1,2,3,4-tetrahydroquinoline, 1-methyl-6-{[3-(1-methyl-1,2,3,6-tetrahydropyridin-4-yl)-5-(trifluoromethyl)-1H-indol-1-yl]sulfonyl}-1,2,3,4-tetrahydroquinoline, 3-(1-methyl-1,2,3,6-tetrahydropyridin-4-yl)-1-[(4-pyrrolidin-1-ylphenyl)sulfonyl]-1H-indole, 5-fluoro-3-(1-methyl-1,2,3,6-tetrahydropyridin-4-yl)-1-[(4-pyrrolidin-1-ylphenyl)sulfonyl]-1H-indole, 3-(1-methyl-1,2,3,6-tetrahydropyridin-4-yl)-1-[(4-pyrrolidin-1-ylphenyl)sulfonyl]-5-(trifluoromethyl)-1H-indole, 3-(1-methyl-1,2,3,6-tetrahydropyridin-4-yl)-1-[(3-pyrrolidin-1-ylphenyl)sulfonyl]-1H-indole, 5-fluoro-3-(1-methyl-1,2,3,6-tetrahydropyridin-4-yl)-1-[(3-pyrrolidin-1-ylphenyl)sulfonyl]-1H-indole, 3-(1-methyl-1,2,3,6-tetrahydropyridin-4-yl)-1-[(3-pyrrolidin-1-ylphenyl)sulfonyl]-5-(trifluoromethyl)-1H-indole, 1-[(1-ethyl-3-methyl-1H-pyrazol-4-yl)sulfonyl]-3-(1-methyl-1,2,3,6-tetrahydropyridin-4-yl)-1H-indole, and 1-[(1-ethyl-3-methyl-1H-pyrazol-4-yl)sulfonyl]-5-fluoro-3-(1-methyl-1,2,3,6-tetrahydropyridin-4-yl)-1H-indole, or a pharmaceutically acceptable salt thereof.

24. The compound of claim 1, wherein the compound is selected from the group consisting of:

1-[(1-ethyl-3-methyl-1H-pyrazol-4-yl)sulfonyl]-3-(1-methyl-1,2,3,6-tetrahydropyridin-4-yl)-5-(trifluoromethyl 1H-indole, 1-{[1-(difluoromethyl)-5-methyl-1H-pyrazol-4-yl]sulfonyl}-3-(1-methyl-1,2,3,6-tetrahydropyridin-4-yl)-1H-indole, 1-{[1-(difluoromethyl)-5-methyl-1H-pyrazol-4-yl]sulfonyl}-3-(1-methyl-1,2,3,6-tetrahydropyridin-4-yl)-1H-indole, 1-{[1-(difluoromethyl)-5-methyl-1H-pyrazol-4-yl]sulfonyl}-5-fluoro-3-(1-methyl-1,2,3,6-tetrahydropyridin-4-yl)-1H-indole, 1-{[1-(difluoromethyl)-5-methyl-1H-pyrazol-4-yl]sulfonyl}-3-(1-methyl-1,2,3,6-tetrahydropyridin-4-yl)-5-(trifluoromethyl)-1H-indole, 1-[(1-ethyl-5-methyl-1H-pyrazol-4-yl)sulfonyl]-3-(1-methyl-1,2,3,6-tetrahydropyridin-4-yl)-1H-indole, 1-[(1-ethyl-5-methyl-1H-pyrazol-4-yl)sulfonyl]-5-fluoro-3-(1-methyl-1,2,3,6-tetrahydropyridin-4-yl)-1H-indole, 1-[(1-ethyl-5-methyl-1H-pyrazol-4-yl)sulfonyl]-3-(1-methyl-1,2,3,6-tetrahydropyridin-4-yl)-5-(trifluoromethyl)-1H-indole, 1-[(1-ethyl-1H-pyrazol-4-yl)sulfonyl]-3-(1-methyl-1,2,3,6-tetrahydropyridin-4-yl)-1H-indole, 1-[(1-ethyl-1H-pyrazol-4-yl)sulfonyl]-5-fluoro-3-(1-methyl-1,2,3,6-tetrahydropyridin-4-yl)-1H-indole, and 1-[(1-ethyl-1H-pyrazol-4-yl)sulfonyl]-3-(1-methyl-1,2,3,6-tetrahydropyridin-4-yl)-5-(trifluoromethyl)-1H-indole, or a pharmaceutically acceptable salt thereof.

25. The compound of claim 1, wherein the compound is selected from the group consisting of:

1-[(1-ethyl-3,5-dimethyl-1H-pyrazol-4-yl)sulfonyl]-3-(1-methyl-1,2,3,6-tetrahydropyridin-4-yl)-1H-indole, 1-[(1-ethyl-3,5-dimethyl-1H-pyrazol-4-yl)sulfonyl]-5-fluoro-3-(1-methyl-1,2,3,6-tetrahydropyridin-4-yl)-1H-indole, 1-[(1-ethyl-3,5-dimethyl-1H-pyrazol-4-yl)sulfonyl]-3-(1-methyl-1,2,3,6-tetrahydropyridin-4-yl)-5-(trifluoromethyl)-1H-indole, 1-[(1-methyl-1H-pyrazol-4-yl)sulfonyl]-3-(1-methyl-1,2,3,6-tetrahydropyridin-4-yl)-1H-indole, 5-fluoro-1-[(1-methyl-1H-pyrazol-4-yl)sulfonyl]-3-(1-methyl-1,2,3,6-tetrahydropyridin-4-yl)-1H-indole, 1-[(1-methyl-1H-pyrazol-4-yl)sulfonyl]-3-(1-methyl-1,2,3,6-tetrahydropyridin-4-yl)-5-(trifluoromethyl)-1H-indole, 1-[(1,5-dimethyl-1H-pyrazol-4-yl)sulfonyl]-3-(1-methyl-1,2,3,6-tetrahydropyridin-4-yl)-1H-indole, 1-[(1,5-dimethyl-1H-pyrazol-4-yl)sulfonyl]-5-fluoro-3-(1-methyl-1,2,3,6-tetrahydropyridin-4-yl)-1H-indole, 1-[(1,5-dimethyl-1H-pyrazol-4-yl)sulfonyl]-3-(1-methyl-1,2,3,6-tetrahydropyridin-4-yl)-5-(trifluoromethyl)-1H-indole, and or a pharmaceutically acceptable salt thereof.

26. The compound of claim 1, wherein the compound is selected from the group consisting of:
- 1-[(1,3-dimethyl-1H-pyrazol-4-yl)sulfonyl]-3-(1-methyl-1,2,3,6-tetrahydropyridin-4-yl)-1H-indole,
- 1-[(1,3-dimethyl-1H-pyrazol-4-yl)sulfonyl]-5-fluoro-3-(1-methyl-1,2,3,6-tetrahydropyridin-4-yl)-1H-indole,
- 1-[(1,3-dimethyl-1H-pyrazol-4-yl)sulfonyl]-3-(1-methyl-1,2,3,6-tetrahydropyridin-4-yl)-5-(trifluoromethyl)-1H-indole,
- 1-[(1-methyl-2,3-dihydro-1H-indol-5-yl)sulfonyl]-3-(1-methyl-1,2,3,6-tetrahydropyridin-4-yl)-1H-indole,
- 5-fluoro-1-[(1-methyl-2,3-dihydro-1H-indol-5-yl)sulfonyl]-3-(1-methyl-1,2,3,6-tetrahydropyridin-4-yl)-1H-indole,
- 1-[(1-methyl-2,3-dihydro-1H-indol-5-yl)sulfonyl]-3-(1-methyl-1,2,3,6-tetrahydropyridin-4-yl)-5-(trifluoromethyl)-1H-indole,
- 1-{[1-(difluoromethyl)-3-methyl-1H-pyrazol-4-yl]sulfonyl}-3-(1-methyl-1,2,3,6-tetrahydropyridin-4-yl)-1H-indole,
- 1-{[1-(difluoromethyl)-3-methyl-1H-pyrazol-4-yl]sulfonyl}-5-fluoro-3-(1-methyl-1,2,3,6-tetrahydropyridin-4-yl)-1H-indole,
- 1-{[1-(difluoromethyl)-3-methyl-1H-pyrazol-4-yl]sulfonyl}-3-(1-methyl-1,2,3,6-tetrahydropyridin-4-yl)-5-(trifluoromethyl)-1H-indole,
- 1-(2,3-dihydro-1,4-benzodioxin-6-ylsulfonyl)-3-(1-methyl-1,2,3,6-tetrahydropyridin-4-yl)-1H-indole, and
- 1-(2,3-dihydro-1,4-benzodioxin-6-ylsulfonyl)-5-fluoro-3-(1-methyl-1,2,3,6-tetrahydropyridin-4-yl)-1H-indole, or a pharmaceutically acceptable salt thereof.

27. The compound of claim 1, wherein the compound is selected from the group consisting of:
- 1-(2,3-dihydro-1,4-benzodioxin-6-ylsulfonyl)-3-(1-methyl-1,2,3,6-tetrahydropyridin-4-yl)-5-(trifluoromethyl)-1H-indole,
- methyl-6-{[3-(1-methyl-1,2,3,6-tetrahydropyridin-4-yl)-5-(trifluoromethyl)-1H-indol-1-yl]sulfonyl}-3,4-dihydroquinolin-2(1H)-one,
- 6-{[5-fluoro-3-(1-methyl-1,2,3,6-tetrahydropyridin-4-yl)-1H-indol-1-1-yl]sulfonyl}-1-methyl-3,4-dihydroquinolin-2(1H)-one,
- 1-methyl-6-{[3-(1-methyl-1,2,3,6-tetrahydropyridin-4-yl)-1H-indol-1yl_9 sulfonyl}-3,4- dihydroquinolin-2(1H)-one,
- 5-fluoro-1-[(1-methyl-1H-indol-5-yl)sulfonyl]-3-(1-methyl-1,2,3,6-tetrahydropyridin-4-yl)-1H-indole,
- 1-[(1-ethyl-1H-pyrazol-4-yl)sulfonyl]-3-(1-methyl-1,2,3,6-tetrahydropyridin-4-yl)-6-(1,3-oxazol-2-yl)-1H-indole,
- 1-[(1-ethyl-1H-pyrazol-4-yl)sulfonyl]-3-(1-methyl-1,2,3,6-tetrahydropyridin-4-yl)-5-(1,3-oxazol-2-yl)-1H-indole,
- 1-(2,3-dihydro-1,4-benzodioxin-6-ylsulfonyl)-3-(1-methyl-1,2,3,6-tetrahydropyridin-4-yl)-5-(1,3-oxazol-2-yl)-1H-indole,
- 5-fluoro-1-{[6-(3-methoxypyrrolidin-1-yl)pyridin-3-yl]sulfonyl}-3-(1-methyl-1,2,3,6-tetrahydropyridin-4-yl)-1H-indole, and
- 7-{[5-fluoro-3-(1-methyl-1,2,3,6-tetrahydropyridin-4-yl)-1H-indol-1-yl]sulfonyl}-2H-1,4-benzoxazin-3(4H)-one, or a pharmaceutically acceptable salt thereof.

28. The compound of claim 1, wherein the compound is selected from the group consisting of:
- 1-[(1-acetyl-2,3-dihydro-1H-indol-6-yl)sulfonyl]-5-fluoro-3-(1-methyl-1,2,3,6-tetrahydropyridin-4-yl)-1H-indole,
- 1-(2,3-dihydro-1,4-benzodioxin-6-ylsulfonyl)-5-fluoro-3-(1-methylpiperidin-4-yl)-1H-indole hydroformate,
- 1-(2,3-dihydro-1,4-benzodioxin-6-ylsulfonyl)-3-(1-methyl-1,2,3,6-tetrahydropyridin-4-yl)-5-(1,3-thiazol-2-yl)-1H-indole,
- 1-[(1-ethyl-1H-pyrazol-4-yl)sulfonyl]-3-(1-methyl-1,2,3,6-tetrahydropyridin-4-yl)-5-(1,3-thiazol-2-yl)-1H-indole,
- 7-{[5-fluoro-3-(1-methyl-1,2,3,6-tetrahydropyridin-4-yl)-1H-indol-1-yl]sulfonyl}-4-methyl-3,4-dihydro-2H-1,4-benzoxazine,
- 7-{[5-fluoro-3-(1-methylpiperidin-4-yl)-1H-indol-1-yl]sulfonyl}-4-methyl-3,4-dihydro-2H-1,4-benzoxazine,
- 1-(2,3-dihydro-1,4-benzodioxin-6-ylsulfonyl)-5-fluoro-3-(1,2,3,6-tetrahydropyridin-4-yl)-1H-indole hydroformate,
- 6-{[3-(1-methyl-1,2,3,6-tetrahydropyridin-4-yl)-1H-indol-1-yl]sulfonyl}-2H-1,4-benzoxazin-3(4H)-one,
- 6-{[5-fluoro-3-(1-methyl-1,2,3,6-tetrahydropyridin-4-yl)-1H-indol-1-yl]sulfonyl}-3- methyl-1,3-benzoxazol-2(3H)-one, and
- 7-{[6-(3-methoxypyrrolidin-1-yl)-3-(1-methyl-1,2,3,6-tetrahydropyridin-4-yl)-1H-indol-1-yl]sulfonyl}-4-methyl-3,4-dihydro-2H-1,4-benzoxazine, or a pharmceutically acceptable salt thereof.

29. The compound of claim 1, wherein the compound is selected from the group consisting of:
- 6-(3-methoxypyrrolidin-1-yl)-1-[(1-methyl-1H-indol-5-yl)sulfonyl]-3-(1-methyl-1,2,3,6-tetrahydropyridin-4-yl)-1H-indole,
- 7-{[4-fluoro-3-(1-methyl-1,2,3,6-tetrahydropyridin-4-yl)-1H-indol-1-yl]sulfonyl}-4-methyl-3,4-dihydro-2H-1,4-benzoxazine,
- 7-[5-Fluoro-3-(1-methyl-1,2,3,6-tetrahydro-pyridin-4-yl)-indole-1-sulfonyl]-4-methyl-3,4-dihydro-2H-benzo[1,4]oxazine,
- 7-{[6-fluoro-3-(1-methyl-1,2,3,6-tetrahydropyridin-4-yl)-1H-indol-1-yl]sulfonyl}-4-methyl-3,4-dihydro-2H-1,4-benzoxazine,
- 7-{[7-fluoro-3-(1-methyl-1,2,3,6-tetrahydropyridin-4-yl)-1H-indol-1-yl]sulfonyl}-4-methyl-3,4-dihydro-2H-1,4-benzoxazine,
- 7-{[3,5-bis(1-methyl-1,2,3,6-tetrahydropyridin-4-yl)-1H-indol-1-yl]sulfonyl}-4-methyl-3,4-dihydro-2H-1,4-benzoxazine,
- 7-{[3-(1-methyl-1,2,3,6-tetrahydropyridin-4-yl)-1H-indazol-1-yl]sulfonyl}-2H-1,4-benzoxazin-3(4H)-one,
- 1-[(1-methyl-1H-indol-5-yl)sulfonyl]-3,5-bis(1-methyl-1,2,3,6-tetrahydropyridin-4-yl)-1H-indole,
- 1-(2,3-dihydro-1,4-benzodioxin-6-ylsulfonyl)-5-fluoro-3-piperidin-4-yl-1H-indole hydroformate,
- 7-{[3,5-bis(1-methylpiperidin-4-yl)-1H-indol-1-yl]sulfonyl}-4-methyl-3,4-dihydro-2H-1,4-benzoxazine,
- 4-methyl-7-{[3-(1-methyl-1,2,3,6-tetrahydropyridin-4-yl)-5-(1H-pyrazol-1-yl)-1H-indol-1-yl]sulfonyl}-3,4-dihydro-2H-1,4-benzoxazine,
- 7-{[5-(1H-imidazol-1-yl)-3-(1-methyl-1,2,3,6-tetrahydropyridin-4-yl)-1H-indol-1-yl]sulfonyl}-4-methyl-3,4-dihydro-2H-1,4-benzoxazine,
- 5-methoxy-1-{[3-(3-methoxypyrrolidin-1-yl)phenyl]sulfonyl}-3-(1-methyl-1,2,3,6-tetrahydropyridin-4-yl)-1H-indole, 7-{[5-methoxy-3-(1-methyl-1,2,3,6-tetrahydropyridin-4-yl)-1H-indol-1-yl]sulfonyl}-2H-1,4-benzoxazin-3(4H)-one, 7-{[5-methoxy-3-(1-methyl-1,2,3,6-tetrahydropyridin-4-yl)-1H-indol-1-yl]sulfonyl}-4-methyl-3,4-dihydro-2H-1,4-benzoxazine, 7-{[3-(4-methylpiperazin-1-yl)-1H-indol-1-yl]sulfonyl}-2H-1,4-benzoxazin-3(4H)-one, 7-[(3-piperazin-1-yl-1H-indol-1-yl)sulfonyl]-2H-1,4-benzoxazin-3(4H)-one, 1-{[3-(3-methoxypyrrolidin-1-yl)phenyl]sulfonyl}-3-(4-methylpiperazin-1-yl)-1H-indole, 1-{[3-(3-methoxypyrrolidin-1-yl)phenyl]sulfonyl}-3-piperazin-1-yl-1H-indole, and 1-[(1-acetyl-2,3-dihydro-1H-indol-5-yl)sulfonyl]-3-(4-methylpiperazin-1-yl)-1-yl-1H-indole, or a pharmaceutically acceptable salt thereof.

30. The compound of claim 1, wherein the compound is selected from the group consisting of:

1-[(1-acetyl-2,3-dihydro-1H-indol-5-yl)sulfonyl]-3-piperazin-1-yl-1H-indole,

7-[(3-piperazin-1-yl-1H-indol-1-yl)sulfonyl]-2H-1,4-benzoxazin-3(4H)-one, 4-methyl-7-[(3-piperazin-1-yl-1H-indol-1-yl)sulfonyl]-3,4-dihydro-2H-1,4-benzoxazine, 7-[(3-piperazin-1-yl-1H-indol-1-yl)sulfonyl]-2H-1,4-benzoxazin-3(4H)-one, 5-{[5-fluoro-3-(1-methyl-1,2,3,6-tetrahydropyridin-4-yl)-1H-indol-1-yl]sulfonyl}isoquinoline hydroformate, 5-{[5-fluoro-3-(1-methylpiperidin-4-yl)-1H-indol-1-yl]sulfonyl}isoquinoline hydroformate, 5-{[5-fluoro-3-(1,2,3,6-tetrahydropyridin-4-yl)-1H-indol-1-yl]sulfonyl}isoquinoline hydroformate, 8-[5-Fluoro-3-(1-methyl-1,2,3,6-tetrahydro-pyridin-4-yl)-indole-1-sulfonyl]-isoquinoline, and 1-[(1-acetyl-2,3-dihydro-1H-indol-5-yl)sulfonyl]-5-methoxy-3-(1-methyl-1,2,3,6-tetrahydropyridin-4-yl)-1H-indole, or a pharmaceutically acceptable salt thereof.

* * * * *